US 11,806,394 B2

United States Patent
Feldhaus et al.

(10) Patent No.: US 11,806,394 B2
(45) Date of Patent: Nov. 7, 2023

(54) PROTEIN-BASED NANOPARTICLE VACCINE FOR METAPNEUMOVIRUS

(71) Applicant: Icosavax, Inc., Seattle, WA (US)

(72) Inventors: Andrew Lawrence Feldhaus, Seattle, WA (US); Douglas Andrew Holtzman, Seattle, WA (US); Clancey Buchanan Wolf, Seattle, WA (US)

(73) Assignee: Icosavax, Inc., Seattle, WA (US)

( * ) Notice: Subject to any disclaimer, the term of this patent is extended or adjusted under 35 U.S.C. 154(b) by 0 days.

(21) Appl. No.: 18/126,140

(22) Filed: Mar. 24, 2023

(65) Prior Publication Data

US 2023/0241199 A1  Aug. 3, 2023

Related U.S. Application Data

(63) Continuation of application No. PCT/US2021/058989, filed on Nov. 11, 2021.

(60) Provisional application No. 63/113,686, filed on Nov. 13, 2020.

(51) Int. Cl.
| | |
|---|---|
| C07K 14/005 | (2006.01) |
| C07K 14/74 | (2006.01) |
| C07K 14/115 | (2006.01) |
| A61K 39/12 | (2006.01) |
| A61K 39/145 | (2006.01) |
| A61P 37/04 | (2006.01) |
| A61K 39/39 | (2006.01) |
| A61K 39/00 | (2006.01) |

(52) U.S. Cl.
CPC ............ *A61K 39/145* (2013.01); *A61K 39/39* (2013.01); *A61P 37/04* (2018.01); *A61K 2039/55505* (2013.01); *A61K 2039/55566* (2013.01)

(58) Field of Classification Search
CPC .............. C07K 14/005; C07K 2319/70; C07K 2319/03; C07K 2319/00; C07K 2319/735
See application file for complete search history.

(56) References Cited

U.S. PATENT DOCUMENTS

| | | | |
|---|---|---|---|
| 6,299,884 | B1 | 10/2001 | Van et al. |
| 7,285,289 | B2 | 10/2007 | Nagy et al. |
| 8,323,696 | B2 | 12/2012 | Hubbell et al. |
| 9,441,019 | B2 | 9/2016 | Nabel et al. |
| 9,630,994 | B2 | 4/2017 | Baker et al. |
| 2004/0038406 | A1 | 2/2004 | Unger et al. |
| 2008/0145373 | A1 | 6/2008 | Arumugham et al. |
| 2013/0274441 | A1 | 10/2013 | Baker et al. |
| 2015/0356240 | A1 | 12/2015 | Baker et al. |
| 2016/0122392 | A1 | 5/2016 | Baker et al. |
| 2018/0137234 | A1 | 5/2018 | Baker et al. |
| 2019/0155988 | A2 | 5/2019 | Baker et al. |

FOREIGN PATENT DOCUMENTS

| | | |
|---|---|---|
| EP | 2636413 A1 | 9/2013 |
| WO | 2011027222 A2 | 3/2011 |
| WO | 2012006380 A2 | 1/2012 |
| WO | 2014124301 A1 | 8/2014 |
| WO | 2016103238 A1 | 6/2016 |
| WO | 2018187325 A1 | 10/2018 |
| WO | 2020163719 A2 | 8/2020 |
| WO | 2020234300 A1 | 11/2020 |
| WO | 2021222639 A2 | 11/2021 |
| WO | 2022076669 A1 | 4/2022 |
| WO | 2022103967 A1 | 5/2022 |

OTHER PUBLICATIONS

Kawano, Y. et al., "Crystalstructureanalysisofthe4-hydroxy-2-Oxog1Aldolase2-Deydro-3-DeoxyphosphogluconateAldolaseTthb1", UNPUBLISHEDsubmitted, 2007, GENPEPT2YW3A.*
Altschul et al. (Oct. 5, 1990) "Basic Local Alignment Search Tool", Journal of Molecular Biology, 215(3):403-410.
Altschul et al. (Sep. 1, 1997) "Gapped BLAST and PSI-BLAST: A New Generation of Protein Database Search Programs", Nucleic Acids Research, 25(17):3389-3402.
Bale et al. (Jul. 22, 2016) "Accurate Design of Megadalton-Scale Two-Component Icosahedral Protein Complexes", Science, 353(6297):389-394.
Bar-Peled et al. (Sep. 12, 2019) "A Potent Neutralizing Site III-Specific Human Antibody Neutralizes Human Metapneumovirus In Vivo", 93(19):e00342-19(15 Pages).
Battles et al. (Nov. 16, 2017) "Structure and Immunogenicity of Pre-Ffusion-Stabilized Human Metapneumovirus F Glycoprotein", Nature, 8(1):1528(11 Pages).
Bode et al. (Apr. 2011) "CpG DNA as a Vaccine Adjuvant", Expert Review of Vaccines, 10(4):499-511.
Cseke et al. (Jan. 2007) "Human Metapneumovirus Fusion Protein Vaccines that are Immunogenic and Protective in Cotton Rats", Journal of Virology, 81(2):698-707.
Database Genbank (Oct. 8, 2003) "Human Metapneumovirus Isolate CAN00-12 Fusion Protein (F) Gene, Complete cds", GenBank Accession AY145297.1, 2 Pages.
Dowling, David J. (Jul. 2, 2018) "Recent Advances in the Discovery and Delivery of TLR7/8 Agonists as Vaccine Adjuvants", ImmunoHorizons, 2(6):185-197.

(Continued)

*Primary Examiner* — Barry A Chestnut
(74) *Attorney, Agent, or Firm* — Mintz Levin Cohn Ferris Glovsky and Popeo, P.C.; James Whittle; Anna Mirôn

(57) ABSTRACT

Provided are virus-like particle vaccines for human metapneumovirus (hMPV) in which the ectodomain of hMPV F protein is linked to, and thereby displayed on, a symmetric protein-based virus-like particle. For example, the vaccine antigen may be a N-terminal fusion of the ectodomain of hMPV F protein to a protein having a multimerization domain for a one- or two-component virus-like particle, such as a two-component icosahedral virus-like particle. Further provided are vaccine compositions, methods of manufacturing, and methods of use, e.g., immunizing a subject to generate a protective immune response to hMPV.

30 Claims, 10 Drawing Sheets
Specification includes a Sequence Listing.

(56) References Cited

OTHER PUBLICATIONS

Heinze et al. (2016) "Protein Nanocontainers From Nonviral Origin: Testing the Mechanics of Artificial and Natural Protein Cages by AFM", The Journal of Physical Chemistry, 120(26):5945-5952.

Hoeven et al. (Feb. 22, 2016) "A Novel Synthetic TLR-4 Agonist Adjuvant Increases the Protective Response to a Clinical-Stage West Nile Virus Vaccine Antigen in Multiple Formulations", PLOS One, 11(2):e0149610(20 Pages).

Huang et al. (Nov. 29, 2019) "Antibody Epitopes of Pneumovirus Fusion Proteins", Frontiers in Immunology, 10:2778(8 Pages).

King et al. (2014) "Accurate Design of Coassembling Multi-Component Protein Nanomaterials", Nature, 510 (7503):103-108.

King et al. (2012) "Computational Design of Self-Assembling Protein Nanomaterials with Atomic Level Accuracy", Science, 336(6085):1171-1174.

Ko et al. (2018) "Immunology and efficacy of MF59-adjuvanted vaccines", Hum Vaccin Immunother, 14(12):3041-3045.

Más et al. (Sep. 9, 2016) "Engineering, Structure and Immunogenicity of the Human Metapneumovirus F Protein in the Postfusion Conformation", PLOS Pathogens. 12(9):e1005859 (21 Pages).

Needleman et al. (Mar. 1970) "A General Method Applicable to the Search for Similarities in the Amino Acid Sequence of Two Proteins", Journal of Molecular Biology, 48(3):443-453.

Pearson et al. (Apr. 1988) "Improved Tools For Biological Sequence Comparison", Proceedings of the National Academy of Sciences, 85:2444-2448.

Quan et al. (Jan. 2, 2020) "Progress in the Development of Virus-like Particle Vaccines against Respiratory Viruses", Expert Review of Vaccines, 19(1):11-24.

Wen et al. (Jan. 30, 2017) "Structural Basis for Antibody Cross-neutralization of Respiratory Syncytial Virus and Human Metapneumovirus", Nature Microbiology, 2:16272 (7 Pages).

Wen et al. (Apr. 2012) "Structure of the Human Metapneumovirus Fusion Protein with Neutralizing Antibody Identifies a Pneumovirus Antigenic Site", Nature Structural & Molecular Biology, 19(4):461-483.

Zhu et al. (Apr. 2016) "QS-21: A Potent Vaccine Adjuvant", Natural Products Chemistry & Research, 3(4):e113(4 Pages).

\* cited by examiner

FIG. 3A
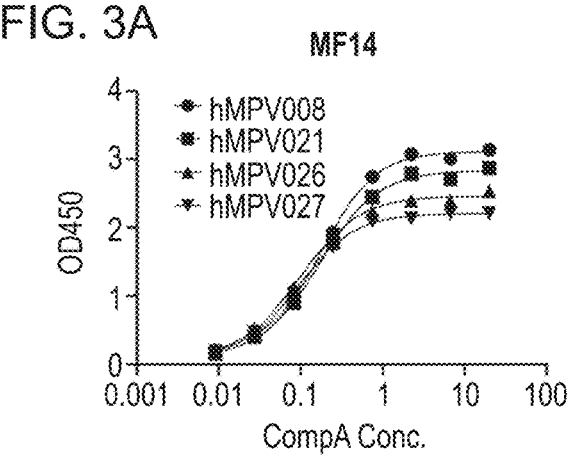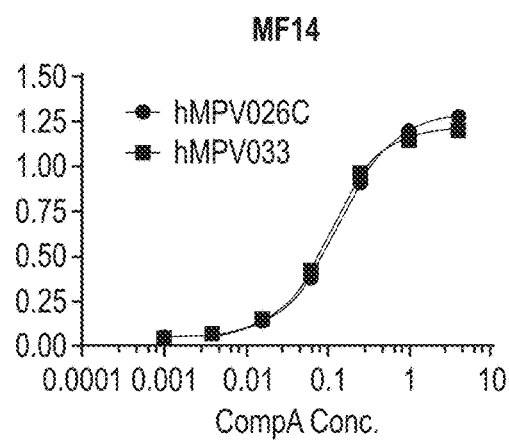
FIG. 3B
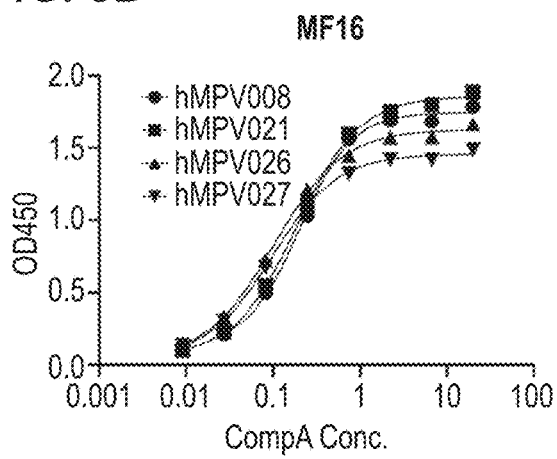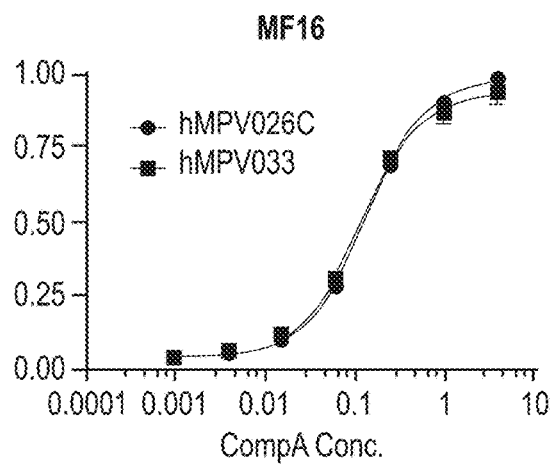
FIG. 3C
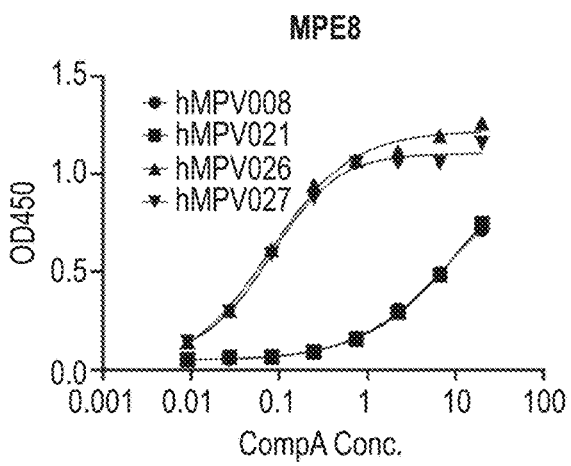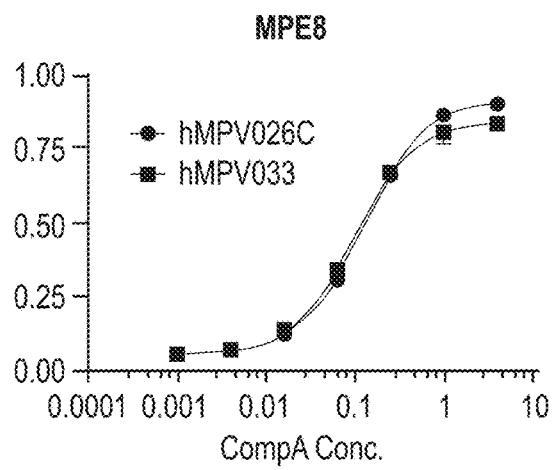

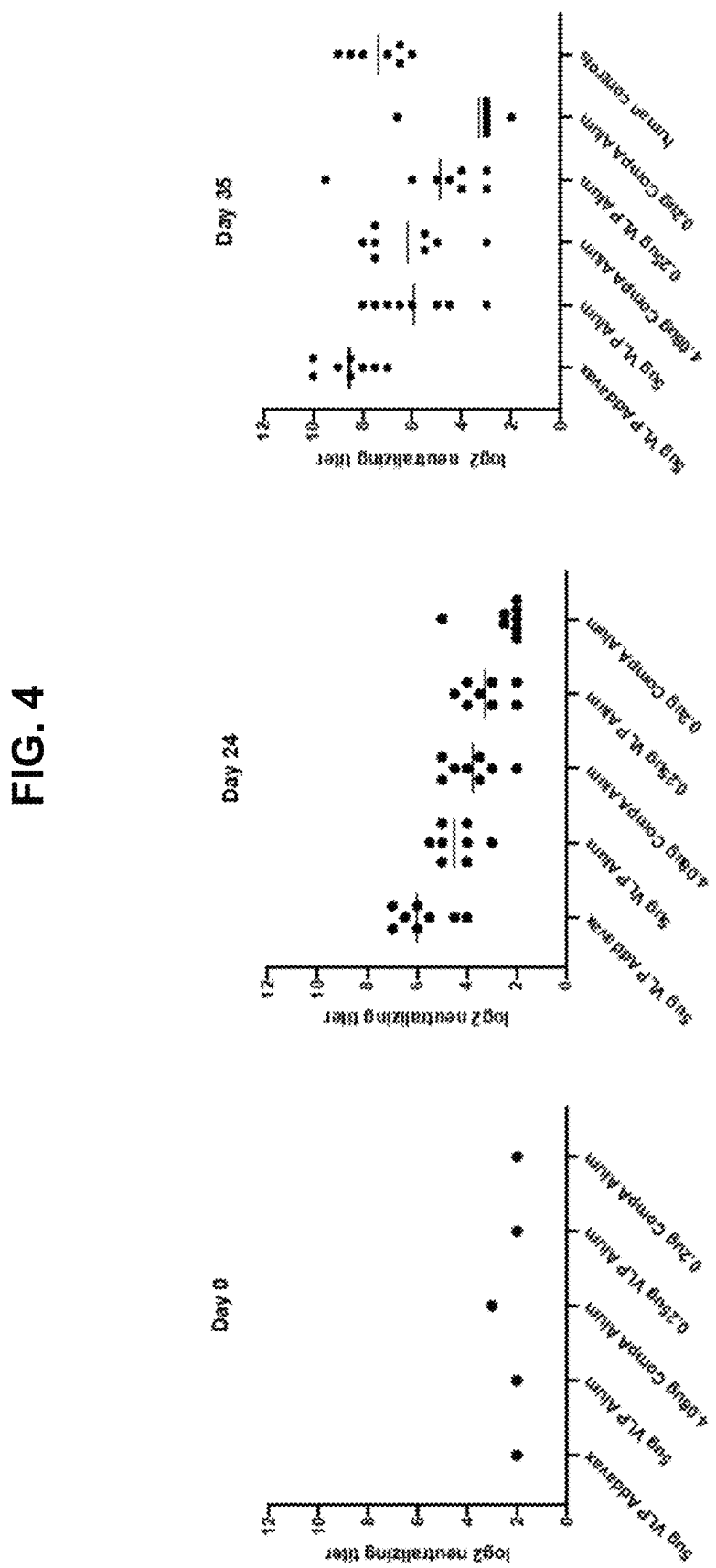

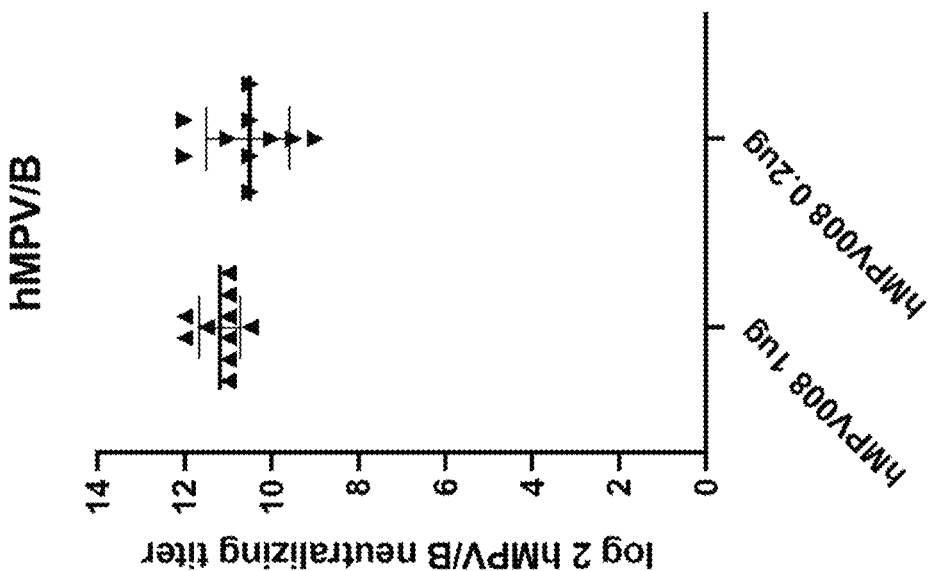

PROTEIN-BASED NANOPARTICLE VACCINE FOR METAPNEUMOVIRUS

CROSS REFERENCE TO RELATED APPLICATIONS

This application is a continuation of and claims priority to the International Patent Application No. PCT/US2021/058989, filed Nov. 11, 2021 and entitled "Protein-Based Nanoparticle Vaccine for Metapneumovirus," which claims the benefit of U.S. Provisional Application No. 63/113,686, filed on Nov. 13, 2020, the contents of each of which are incorporated herein by reference in their entireties.

INCORPORATION BY REFERENCE OF SEQUENCE LISTING

This application contains a Sequence Listing which has been submitted in ST26.XML format via EFS-WEB and is hereby incorporated by reference in its entirety. Said .XML copy, created on Mar. 24, 2023 is named 061291-504C01US_SeqList_ST26.xml and is 239 kilo bytes in size.

BACKGROUND

Human metapneumovirus (hMPV) causes upper and lower respiratory disease in people of all ages. The symptoms can include cough, fever, nasal congestion, and shortness of breath. In some cases, hMPV infection can progress to severe disease, such as bronchitis or pneumonia.

hMPV is single-stranded RNA virus in the paramyxovirus family, which also includes measles, mumps, and other respiratory tract infections such as respiratory syncytial virus (RSV). hMPV can be of two subtypes, A and B that are identified by genotyping the G and F genes in the viral genome. The F gene encodes hMPV fusion glycoprotein (hMPV F protein) and may be used as a target for vaccine development. However, to date there has been no approved vaccine for hMPV in humans despite the clinical need.

There is therefore a need for a vaccine against hMPV.

SUMMARY

Provided are protein-based virus-like particle (VLP) vaccines for human metapneumovirus in which the hMPV F protein ectodomain is linked to, and thereby displayed on, a protein-based VLP.

In one aspect, the disclosure provides a virus-like particle (VLP), comprising a first component and optionally a second component, wherein the first component is a fusion protein, comprising a human metapneumovirus (hMPV) F protein ectodomain or antigenic variant thereof, and a first multimerization domain; and wherein the second component, if present, is a protein comprising a second multimerization domain.

In some embodiments, first multimerization domain is a trimerization domain. In some embodiments, the multimerization domain is selected from SEQ ID NOS: 1, 4, 5, 7, 9, 18, 19, 21, 24, 25, 26, 29, 30, 31, 34, 36, 37, 39, 42, 43, 44, 45, 46, 47, 48, 49, 50, 51, 52, 53, 144, or 145, or functional variants thereof. In some embodiments, the multimerization domain is I53-50A (SEQ ID NO: 7 or SEQ ID NO: 144) or a functional variant or variant thereof. In some embodiments, the first multimerization domain shares at least 70%, at least 80%, at least 90%, at least 95%, at least 98%, at least 99%, or 100% identity to SEQ ID NO: 7, SEQ ID NO: 53, SEQ ID NO: 144, or SEQ ID NO: 145. In some embodiments, the first multimerization domain comprises: the amino acid substitutions C74A and C98A; the amino acid substitutions C163A and C201A; or the amino acid substitutions C74A, C98A, C163A, and C201A relative to SEQ ID NO: 144. In some embodiments, the first multimerization domain has a polypeptide sequence identical to SEQ ID NO: 7 or SEQ ID NO: 144. In some embodiments, the first multimerization domain has a polypeptide sequence identical to SEQ ID NO: 53 or SEQ ID NO: 145. In some embodiments, the first multimerization domain is a VLP-forming domain. In some embodiments, the first multimerization domain is adapted to drive assembly of an icosahedral particle or tetrahedral particle, optionally with a second multimerization domain.

In some embodiments, second multimerization domain is selected from SEQ ID NOs: 2, 3, 6, 8, 10, 11, 12, 13, 14, 15, 16, 17, 20, 22, 23, 27, 28, 32, 33, 35, 38, 40, and 41 or functional variants and fragments thereof. In some embodiments, the second multimerization domain is I53-50B (SEQ ID NO: 8), I53-50B.4PosT1 (SEQ ID NO: 34), or a functional variant thereof.

In some embodiments, the first component and the second component are joined by a linker sequence. In some embodiments, the linker sequence comprises a foldon, wherein the foldon sequence is EKAAKAEEAARK (SEQ ID NO: 125). In some embodiments, the linker sequence comprises GSGGSGSGSGGS (SEQ ID NO: 126).

In some embodiments, the hMPV F protein ectodomain contains one or more substitutions or deletions selected from A185P, Q100R, S101R, T127C, N153C, V84C, A140C, A147C, A249C, N97G, P98G, R99G, Q100G, S101G, R102G, A63C, K188C, K450C, S470C, G106 deletion, A113C, A120C, A339C, Q426C, T160F, Q100K, S101A, I177L, K450A, S470A, G294E, T365C, V463C, L219K, H368N, and/or V231I. In some embodiments, the hMPV F protein ectodomain contains one or more substitutions or deletions selected from V84C, A140C, A147C, N97G, P98G, Q100G, S101G, R102G, A63C, K188C, K450C, S470C, R99G, A113C, A120C, A339C, Q426C, T160F, Q100K, S101A, Q100R, S101R, G106 deletion, S101R, A185P, I177L, and/or G294E.

In some embodiments, the hMPV F protein ectodomain contains two or more substitutions or deletions selected from V84C, A140C, A147C, N97G, P98G, Q100G, S101G, R102G, A63C, K188C, K450C, S470C, R99G, A113C, A120C, A339C, Q426C, T160F, Q100K, S101A, Q100R, S101R, G106 deletion, S101R, A185P, I177L, and/or G294E. In some embodiments, the hMPV F protein ectodomain contains one or more substitutions selected from A185P, Q100R, S101R, T127C, N153C, T365C, V463C, L219K, V231I, G294E, N153C, N97G, P98G, R99G, Q100G, S101G, H368N, and/or R102G.

In some embodiments, the hMPV F protein ectodomain contains two or more of A185P, Q100R, S101R, T127C, N153C, T365C, V463C, L219K, V231I, G294E, N153C, N97G, P98G, R99G, Q100G, S101G, H368N, and/or R102G. In some embodiments, the hMPV F protein ectodomain comprises: the substitutions Q100R and S101R; the substitutions A185P, Q100R, and S101R; the substitutions A185P, T127C, N153C, Q100R, and S101R; the substitutions V84C, A140C, A147C, A249C, N97G, P98G, R99G, Q100G, S101G, and R102G; the substitutions A63C, A140C, A147C, K188C, K450C, S470C, N97G, P98G, R99G, Q100G, S101G, and R102G; the substitutions and deletion A63C, A140C, A147C, K188C, G106 deletion, N97G, P98G, R99G, Q100G, S101G, and R102G; the substitutions A113C, A120C, A339C, Q426C, T160F, I177L, Q100K, and S101A; the substitutions V84C, A140C, A147C, A249C, Q100R, and S101R; the substitutions A63C, A140C, A147C, K188C, K450C, S470C, Q100R, and S101R; the substitutions and deletion A63C, A140C, A147C, K188C, G106 deletion, Q100R, and S101R; the substitutions A113C, A120C, A339C, Q426C, T160F, I177L, Q100R, and S101R; the substitutions A185P, A113C, A339C, Q100R, and S101R; the substitutions A185P, T160F, I177L, Q100R, and S101R; the substitutions A185P, A113C, A339C, T160F, I177L, Q100R, and S101R; the substitutions A63C, K188C, N97G, P98G, R99G, Q100G, S101G, and R102G; the substitutions A63C, K188C, K450A, S470A, N97G, P98G, R99G, Q100G, S101G, and R102G; the substitutions A63C, A140C, A147C, K188C, G294E, N97G, P98G, R99G, Q100G, S101G, and R102G; the substitutions A63C, A140C, A147C, K188C, K450C, S470C, N97G, P98G, R99G, Q100G, S101G, R102G, and G294E; the substitutions A63C, K188C, N97G, P98G, R99G, Q100G, S101G, R102G, and G294E; the substitutions T127C, N153C, T365C, V463C, A185P, L219K, V231I, G294E, H368N, Q100R, and S101R; the substitutions A63C, A140C, A147C, K188C, K450C, S470C, N97G, P98G, R99G, Q100G, S101G, and R102G; the substitutions V84C, A140C, A147C, A249C, N97G, P98G, R99G, Q100G, S101G, and R102G; the substitutions T127C, N153C, T365C, V463C, A185P, L219K, V231I, G294E, H368N, N97G, P98G, R99G, Q100G, S101G, and R102G.

In some embodiments, the hMPV F protein ectodomain comprises a sequence that shares at least 95% or at least 99% identity to SEQ ID NOs: 58. In some embodiments, the hMPV F protein ectodomain comprises a sequence that shares at least 95% or at least 99% identity to SEQ ID NO: 59. In some embodiments, the hMPV F protein ectodomain comprises a sequence that shares at least 95% or at least 99% identity to SEQ ID NO: 60. In some embodiments, the hMPV F protein ectodomain comprises a sequence that shares at least 95% or at least 99% identity to SEQ ID NO: 61. In some embodiments, the hMPV F protein ectodomain comprises a sequence that shares at least 95% or at least 99% identity to SEQ ID NO: 62. In some embodiments, the hMPV F protein ectodomain comprises a sequence that shares at least 95% or at least 99% identity to SEQ ID NO: 63. In some embodiments, the hMPV F protein ectodomain comprises a sequence that shares at least 95% or at least 99% identity to SEQ ID NO: 64.

In some embodiments, the hMPV F protein ectodomain comprises a sequence that shares at least 95% or at least 99% identity to SEQ ID NO: 65. In some embodiments, the hMPV F protein ectodomain comprises a sequence that shares at least 95% or at least 99% identity to SEQ ID NO: 66. In some embodiments, the hMPV F protein ectodomain comprises a sequence that shares at least 95% or at least 99% identity to SEQ ID NO: 67. In some embodiments, the hMPV F protein ectodomain comprises a sequence that shares at least 95% or at least 99% identity to SEQ ID NO: 68. In some embodiments, the hMPV F protein ectodomain comprises a sequence that shares at least 95% or at least 99% identity to SEQ ID NO: 69. In some embodiments, the hMPV F protein ectodomain comprises a sequence that shares at least 95% or at least 99% identity to SEQ ID NO: 70. In some embodiments, the hMPV F protein ectodomain comprises a sequence that shares at least 95% or at least 99% identity to SEQ ID NO: 71. In some embodiments, the hMPV F protein ectodomain comprises a sequence that shares at least 95% or at least 99% identity to SEQ ID NO: 72. In some embodiments, the hMPV F protein ectodomain comprises a sequence that shares at least 95% or at least 99% identity to SEQ ID NO: 73. In some embodiments, the hMPV F protein ectodomain comprises a sequence that shares at least 95% or at least 99% identity to SEQ ID NO: 74. In some embodiments, the hMPV F protein ectodomain comprises a sequence that shares at least 95% or at least 99% identity to SEQ ID NO: 75. In some embodiments, the hMPV F protein ectodomain comprises a sequence that shares at least 95% or at least 99% identity to SEQ ID NO: 76. In some embodiments, the hMPV F protein ectodomain comprises a sequence that shares at least 95% or at least 99% identity to SEQ ID NO: 77. In some embodiments, the hMPV F protein ectodomain comprises a sequence that shares at least 95% or at least 99% identity to SEQ ID NO: 78. In some embodiments, the hMPV F protein ectodomain comprises a sequence that shares at least 95% or at least 99% identity to SEQ ID NO: 79. In some embodiments, the hMPV F protein ectodomain comprises a sequence that shares at least 95% or at least 99% identity to SEQ ID NO: 80. In some embodiments, the hMPV F protein ectodomain comprises a sequence that shares at least 95% or at least 99% identity to SEQ ID NO: 81. In some embodiments, the hMPV F protein ectodomain comprises a sequence that shares at least 95% or at least 99% identity to SEQ ID NO: 82. In some embodiments, the hMPV F protein ectodomain comprises a sequence that shares at least 95% or at least 99% identity to SEQ ID NO: 83. In some embodiments, the hMPV F protein ectodomain comprises a sequence that shares at least 95% or at least 99% identity to SEQ ID NO: 84. In some embodiments, the hMPV F protein ectodomain comprises a sequence that shares at least 95% or at least 99% identity to SEQ ID NO: 85. In some embodiments, the hMPV F protein ectodomain comprises a sequence that shares at least 95% or at least 99% identity to SEQ ID NO: 86. In some embodiments, the hMPV F protein ectodomain comprises a sequence that shares at least 95% or at least 99% identity to SEQ ID NO: 87. In some embodiments, the hMPV F protein ectodomain comprises a sequence that shares at least 95% or at least 99% identity to SEQ ID NO: 88. In some embodiments, the hMPV F protein ectodomain comprises a sequence that shares at least 95% or at least 99% identity to SEQ ID NO: 89. In some embodiments, the hMPV F protein ectodomain comprises a sequence that shares at least 95% or at least 99% identity to SEQ ID NO: 90. In some embodiments, the hMPV F protein ectodomain shares at least 85%, at least 90%, at least 95%, at least 99%, or 100% identity to SEQ ID NOs: 58, 60, 61, 77, 78, 86, 87, 88, or 89. In some embodiments, the hMPV F protein ectodomain shares at least 85%, at least 90%, at least 95%, at least 99%, or 100% identity to SEQ ID NOs: 59, 62, 63, 64, 71, 76, 81, or 83. In some embodiments, the hMPV F protein ectodomain shares at least 85%, at least 90%, at least 95%, at least 99%, or 100% identity to SEQ ID NOs: 72, 79, or 80. In some embodiments, the hMPV F protein ectodomain shares at least 85%, at least 90%, at least 95%, at least 99%, or 100% identity to SEQ ID NOs: 65, 66, 82, 84, 85, 90, or 91. In some embodiments, the hMPV F protein ectodomain shares at least 85%, at least 90%, at least 95%, at least 99%, or 100% identity to SEQ ID NOs: 65, 79, or 80. In some embodiments, the first component shares at least 85%, at least 90%, at least 95%, at least 99%, or 100% identity to SEQ ID NOs: 92-124. In some embodiments, the first component shares at least 85%, at least 90%, at least 95%, at least 99%, or 100% identity to SEQ ID NOs: 97-116, 119, or 122. In some embodiments, the first component shares at least 85%, at least 90%, at least 95%, at least 99%, or 100% identity to SEQ ID NOs: 92-94, 96, 117, 118, 120, 121, 123, or 124. In some embodiments, the first component shares at least 85%, at least 90%, at least 95%, at least 99%, or 100% identity to SEQ ID NOs: 99, 112, 117, or 118.

In some embodiments, the VLP binds one or more hMPV F protein antibodies selected from MF1, MF2, MF3, MF9, MF12, MF14, MF15, MF11, MF16, MF20, MF17, MF18, MF19, MF10, or MPE8. In some embodiments, the VLP binds two or more antibodies selected from MF1, MF2, MF3, MF9, MF12, MF14, MF15, MF11, MF16, MF20, MF17, MF18, MF19, MF10, MPE8. In some embodiments, the VLP binds three or more antibodies selected from MF1, MF2, MF3, MF9, MF12, MF14, MF15, MF11, MF16, MF20, MF17, MF18, MF19, MF10, MPE8.

In some embodiments, the hMPV F protein ectodomain binds an antibody that preferentially binds the prefusion form of the hMPV F protein ectodomain. In some embodiments, the first component shares at least 85%, at least 90%, at least 95%, at least 99%, or 100% identity to SEQ ID NOs: 42, 45, 58, 61, 63, or 64. In some embodiments, the hMPV F protein ectodomain has no or low binding to an antibody that preferentially binds the postfusion form of the hMPV F protein ectodomain. In some embodiments, the VLP sequence shares at least 85%, at least 90%, at least 95%, at least 99%, or 100% identity to SEQ ID NOs: 99, 115, 117, or 118.

In some embodiments, the first component shares at least 85%, at least 90%, at least 95%, at least 99%, or 100% identity with SEQ ID NO: 99.

In some embodiments, the first component is a single chain. In some embodiments, the single chain shares at least 85%, at least 90%, at least 95%, at least 99% or 100% identity with SEQ ID NO: 123.

In some embodiments, the first component shares at least 85%, at least 90%, at least 95%, at least 99%, or 100% identity with SEQ ID NO: 117.

In one aspect, the disclosure provides a polynucleotide encoding the VLP described herein.

In one aspect, the disclosure provides a host cell, comprising the polynucleotide described herein.

In one aspect, the disclosure provides a method of manufacturing a vaccine, comprising culturing the host cell described herein in a culture medium so that the host cell secretes the antigen into the culture media; optionally purifying the antigen from the culture media; mixing the antigen with a second component, wherein the second component multimerizes with the antigen to form a virus-like particle; and optionally purifying the virus-like particle.

In one aspect, the disclosure provides a vaccine, comprising the VLP described herein, wherein the vaccine optionally comprises one or more pharmaceutically acceptable diluents, adjuvants, or excipients. In some embodiments, the vaccine is a stable emulsion. In some embodiments, the vaccine comprises one or more adjuvants. In some embodiments, the one or more adjuvants is squalene, SLA, GLA, R848, IMQ, 3M-052, CpG, saponin (QS21), or combinations thereof. In some embodiments, the adjuvant is alum. In some embodiments, the adjuvant is a squalene-based emulsion. In some embodiments, the squalene-based emulsion is MF59.

In one aspect, the disclosure provides a method of immunizing a subject against infection by human metapneumovirus, the method comprising administering the vaccine described herein. In some embodiments, the subject is simultaneously immunized against infection by respiratory syncytial virus (RSV). In some embodiments, the vaccine is administered by subcutaneous injection. In some embodiments, wherein the vaccine is administered by intramuscular injection. In some embodiments, wherein the vaccine is administered by intradermal injection. In some embodiments, wherein the vaccine is administered intranasally. In one aspect, the disclosure provides a pre-filled syringe comprising the vaccine described herein. In one aspect, the disclosure provides a kit comprising the vaccine described herein or the pre-filled syringe described herein.

BRIEF DESCRIPTION OF THE DRAWINGS

FIGS. 3A-3C is a series of plots showing antibody binding profiles to illustrative VLPs of the disclosure. Antibodies are specific for various forms of the hMPV F protein. MF14 binds pre- and postfusion forms of hMPV F protein at the site II epitope (FIG. 3A). MF16 binds pre- and postfusion forms of hMPV F protein at the site IV epitope (FIG. 3B). MPE8 binds the pre-fusion form of hMPV F protein at the site III epitope (FIG. 3C).

FIG. 4 is a series of plots showing the time-course induction of neutralizing antibody titers in mice in response to dosing with hMPV F protein VLPs formulated with adjuvants.

FIGS. 7A and 7B show the immunogenicity of VLPs displaying an hMPV F protein mutant, hMPV008. Neutralizing antibody titers were determined for hMPV/A (FIG. 7A) and hMPV/B (FIG. 7B) in serum samples collected on day 35 after the first immunization.

DETAILED DESCRIPTION

Figure 1A:
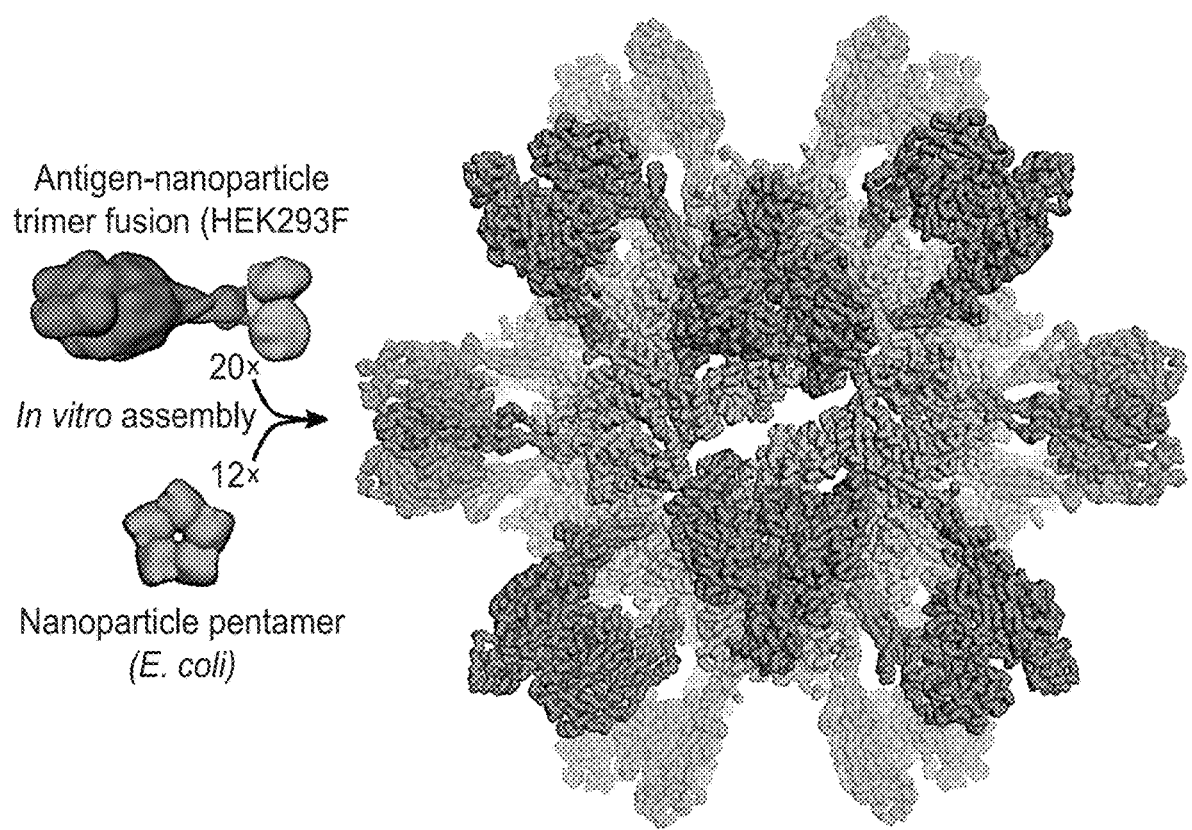
FIG. 1A shows an illustrative embodiment of a protein-based virus-like particle (VLP) according to the present disclosure.

Provided are protein-based virus-like particle (VLP) vaccines for human metapneumovirus (hMPV) in which the hMPV F protein ectodomain is linked to, and thereby displayed on, a protein-based VLP, e.g., a designed VLP, e.g., a symmetric VLP. For example, the vaccine antigen may be a N-terminal fusion of the ectodomain of hMPV F protein to a protein having a multimerization domain for a one- or two-component de novo designed VLP, such as a two-component icosahedral VLP. Further provided are vaccine compositions, methods of manufacturing, and methods of use, e.g., immunizing a subject to generate a protective immune response to hMPV virus.

Definitions

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

The term "virus-like particle" or "VLP" refers to a molecular assembly that resembles a virus but is non-infectious that displays an antigenic protein, or antigenic fragment thereof, of a viral protein or glycoprotein. A "protein-based VLP" refers to a VLP formed from proteins or glycoproteins and substantially free of other components (e.g., lipids). Protein-based VLPs may include post-translation modification and chemical modification, but are to be distinguished from micellar VLPs and VLPs formed by extraction of viral proteins from live or live inactivated virus preparations. The term "designed VLP" refers to a VLP comprising one or more polypeptides generated by computational protein design. Illustrative designed VLP are VLPs that comprise nanostructures depicted in FIG. 1B. The term "symmetric VLP" refers to a protein-based VLP with a symmetric core, such as shown in FIG. 1B. These include but are not limited to designed VLPs. For example, the protein ferritin has been used to generate a symmetric, protein-based VLP using naturally occurring ferritin sequences. Ferritin-based VLPs are distinguished from designed VLPs in that no protein engineering is necessary to form a symmetric VLP from ferritin, other than fusing the viral protein to the ferritin molecule. Protein design methods can be used to generate similar one- and two-component nanostructures based on template structures (e.g., structures deposited in the Protein Data Bank) or de novo (i.e., by computational design of new proteins having a desired structure but little or no homology to naturally occurring proteins). Such one- and two-component nanostructures can then be used as the core of a designed VLP.

The VLP of the present disclosure display antigens capable of eliciting immune responses to human metapneumovirus or other metapneumoviruses. The vaccines of the present disclosure are useful for preventing and/or decreasing the severity of infection with human metapneumovirus.

The term "icosahedral particle" refers to a designed VLP having a core with icosahedral symmetry (e.g., the particles labeled 153 and 152 in Table 1). 153 refers to an icosahedral particle constructed from pentamers and trimers. 152 refers to an icosahedral particle constructed from pentamers and dimers. T33 refers to a tetrahedral particle constructed from two sets of trimers. T32 refers to a tetrahedral particle constructed from trimers and dimers.

The antigens may be attached to the core of the protein-based VLP either non-covalently or covalently, including as a fusion protein or by other means disclosed herein. Multimeric antigens may optionally be displayed along a symmetry axis of the VLP. Also provided are proteins and nucleic acid molecules encoding such proteins, formulations, and methods of use.

The term "antigen" refers to a polypeptide or polypeptide complex including at least one component designed to elicit an immune response. The term antigen, as used herein, is not limited to the portion of the polypeptide or polypeptide complex that contains antigenic epitopes.

The term "polypeptide" refers to a series of amino acid residues joined by peptide bonds and optionally one or more post-translational modifications (e.g., glycosylation) and/or other modifications (including but not limited to conjugation of the polypeptide moiety used as a marker—such as a fluorescent tag—or an adjuvant).

The term "infection" refers to both symptomatic and asymptomatic infections.

The term "ectodomain" refers to the portion of a transmembrane protein or glycoprotein that, in the native state of the protein, is on the outside of the cellular or viral membrane.

The term "variant" refers to a polypeptide having one or more insertions, deletions, or amino acid substitutions relative to a reference polypeptide, but retains one or more properties of the reference protein.

The term "antigenic variant" refers to a variant that has one or more epitopes in common with a reference polypeptide and/or generates the same or similar immune response when administered to a subject as a reference polypeptide.

The term "functional variant" refers to a variant that exhibits the same or similar functional effect(s) as a reference polypeptide. For example, a functional variant of a multimerization domain is able to promote multimerization to the same extent, or to similar extent, as a reference multimerization domain and/or is able to multimerize with the same cognate multimerization domains as a reference multimerization domain.

The term "linker" refers to either chemical linkage (i.e., a covalent bond or series of covalent bonds with intervening chemical moieties) or to a polypeptide that is N-terminally and C-terminally joined by peptide bonds to product a fusion protein.

The term "domain" refers to refers to any portion of a polypeptide that adopts a tertiary structure.

The terms "multimerization domain" and "multimerize" refer to the ability of a polypeptide, or domain of a polypeptide, to form dimers, trimers, tetramers, pentamers, or hexamers and/or to form heteromers with other multimerization domains.

The term "trimerization domain" refers to a multimerization domain that forms trimers.

The term "VLP-forming domain" refers to a multimerization domain that, alone or with other multimerization domains, forms a symmetric protein complex.

The term "fragment" refers to a polypeptide having one or more N-terminal or C-terminal truncations compared to a reference polypeptide.

The term "functional fragment" refers to a functional variant of a fragment.

The term "amino acid substitution" refers to replacing a single amino acid in a sequence with another amino acid residue. The standard form of abbreviations for amino acid substitution are used. For example, V94R refers to substitution of valine (V) in a reference sequence with arginine (R). The abbreviation Arg94 refers to any sequence in which the $94^{th}$ residue, relative to a reference sequence, is arginine (Arg).

The terms "helix" or "helical" refer to an α-helical secondary structure in a polypeptide that is known to occur, or predicted to occur. For example, a sequence may be described as helical when computational modeling suggests the sequence is likely to adopt a helical conformation.

The term "component" refers to a protein, or protein complex, capable of assembly into a virus-like particle under appropriate conditions (e.g., an antigen or polypeptide comprising a multimerization domain).

The term "vaccine" refers to a pharmaceutical composition capable of use in producing an immune response in a subject.

The term "pharmaceutically acceptable excipients" means excipients biologically or pharmacologically compatible for in vivo use in animals or humans, and can mean excipients approved by a regulatory agency of the Federal or a state government or listed in the U.S. Pharmacopeia or other generally recognized pharmacopeia for use in animals, and more particularly in humans.

The term "adjuvants" refers to a pharmaceutically acceptable substance that enhances the immune response to an antigen when co-administered with the antigen or administered before, during, or after administration of the antigen to a subject.

The term "TLR4 immunostimulant" refers to an adjuvant that stimulates Toll-like Receptor 4 (TLR4) in the immune cells of a subject to modulate an immune response e.g., Monophosphoryl Lipid A (MPL), Glucopyranosyl Lipid A (GLA), and/or Soluble Leishmania Antigen (SLA).

The term "effective amount" refers to the amount of a formulation according to the invention that, when administered to a patient for treating a state, disorder or condition is sufficient to effect such treatment or when administered to a patient for generating an immune response is sufficient to generate such an immune response. The "effective amount" will vary depending on the active ingredient, the state, disorder, or condition to be treated and its severity, and the age, weight, physical condition and responsiveness of the subject to be treated.

The term "immune response" refers to elicitation of activity of one or more immune cell types in the subject. Immune responses include, for example, T cell and B cell responses.

The term "humoral immune response" refers to an immune response that generates plasma or serum antibodies (e.g., IgG).

The term "protective immune response" refers to an immune response that prevents and/or reduces the severity of infection with a pathogen when the subject is later challenged with the pathogen, or to an immune response that generates a level of immune response that correlates with protection. For example, vaccination may generate a protective immune response if it results in production, in the plasma or serum, of the subject (e.g., human, pet, or agricultural animal), of neutralizing antibodies that protect the subject against subsequent infection and/or are present in a quantity observed to confer protection upon test subjects (e.g., New Zealand White (NZW) rabbits).

The term "polyclonal antibody response" refers to an antibody response comprising antibodies having more than one specificities and/or variation in their antibody sequences.

The term "neutralizing" (e.g., "neutralizing antibody response") refers to antibodies that prevent infection and/or reduce the level of infection by a pathogen. A neutralizing antibody response can be measured either in in vitro assays (e.g., infection of cells in culture by a pathogen in the presence of the antibody) or in an in vivo assay (e.g., by determining a protective dose of an antibody through administering the antibody to a subject prior to challenge with an infective dose of a pathogen).

An antibody "binds to" or is "specific to" or "specifically binds" (used interchangeably herein) to a target (e.g., human metapneumovirus or an hMPV protein) are terms well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. For example, an immunoglobulin that specifically or preferentially binds to thymocyte is an immunoglobulin that binds thymocytes with greater affinity, avidity, more readily, and/or with greater duration than it binds to other cells. An immunoglobulin that specifically binds to a first cell or substance may or may not specifically or preferentially bind to a second cell or substance. As such, "specific binding" does not necessarily require (although it can include) exclusive binding. Generally, but not necessarily, reference to binding means specific binding.

The term "predetermined time" refers to an interval of time selected as appropriate for observing a particular effect. A predetermined time may be selected before, or during, an experiment or procedure.

The term "post-exposure prophylaxis" refers to administering an antigenic composition (e.g., a vaccine) to a subject previously exposed to and/or infected with a pathogen in order to elicit an immune response to protect against infection by the pathogen and/or decrease the severity of one or more symptoms of infection by the pathogen.

The term "administering" refers to providing a composition to a subject in a manner that permits the composition to have its intended effect. Administration for vaccination or post-exposure prophylaxis may be performed by intramuscular injection, intravenous injection, intraperitoneal injection, or any other suitable route.

The terms "immunization" and "immunizing" refer to administering a composition to a subject (e.g., a virus-like particle) in an amount sufficient to elicit, after one or more administering steps, a desired immune response (e.g., a humoral immune response to the VLP). Immunization may comprise between one and ten, or more administrations (e.g., injections) of the composition, such as 1, 2, 3, 4, 5, 6, 7, 8, 9, 10, or more administrations. The first administration may elicit no detectable immune response as generally each subsequent administration will boost the immune response generated by prior administrations. The term "immunizing" as used herein includes post-exposure prophylaxis.

The term "subject" refers to a human or non-human animal to which a composition may be administered for vaccination, treatment, or other purpose. In some embodiments, the non-human animal is a non-human primate, rabbit, hamster, gerbil, pig, cow, sheep, goat, guinea pig, rat, mouse, squirrel, wolf, fox, horse, zebra, giraffe, elephant, cat, dog, llama, or ferret.

The term "manufacturing" refers to production of a recombinant polypeptide or virus-like particle at any scale, including at least 25-mL, 50-mL, 1-L, 1,000-L, 50,000-L, or greater scale.

The terms "culturing" and "culture medium" refers to standard cell culture and recombinant protein expression techniques.

The term "host cell" refers to any cell capable of use in expression of a recombinant polypeptide.

The term "secretes" refers to the ability of host cells to secretes polypeptides into the media in which they are cultured.

The term "signal sequence" refers to a polypeptide sequence, typically at the N terminus of a polypeptide expressed in a host cell, that directs the polypeptide to a particular cellular compartment. A signal sequence may be a secretion signal to cause the host cell to secrete the polypeptide into the media in which with host cell is cultured. Various signal sequences are known and it is within the skill of an ordinary artisan to select an appropriate signal sequence.

The term "mixing" refers to placing two solutions into contact to permit the solutions to mix.

The term "purify" refers to separating a molecule from other substances present in a composition. Polypeptides may be purified by affinity (e.g., to an antibody or to a tag, e.g., using a His-tag capture resin), by charge (e.g., ion-exchange chromatography), by size (e.g., preparative ultracentrifugation, size exclusion chromatography), or otherwise.

The terms "polynucleotide" and "nucleic acid," used interchangeably herein, refer to a polymeric form of nucleotides of more than about 100 nucleotides, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

The terms "identity", "identical", and "sequence identity" refer to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared.

Methods of sequence alignment for comparison and determination of percent sequence identity is well known in the art. Optimal alignment of sequences for comparison can be conducted, e.g., by the homology alignment algorithm of Needleman and Wunsch, (1970) *J. Mol. Biol.* 48:443, by the search for similarity method of Pearson and Lipman, (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) *Nuc. Acids Res.* 25:3389-3402; and Altschul et al., (1990) *J Mol. Biol.* 215:403-410, respectively. Software for performing BLAST analyses is publicly available through the National Center for Biotechnology Information.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation. Alternatively, "about" can mean plus or minus a range of up to 20%, up to 10%, or up to 5%.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

The following description includes information that may be useful in understanding the present invention. It is not an admission that any of the information provided herein is prior art or relevant to the presently claimed inventions, or that any publication specifically or implicitly referenced is prior art.

Overview

Vaccination is a treatment modality used to prevent or decrease the severity of infection with various infectious agents, including bacteria, viruses, and parasites. Development of new vaccines has important commercial and public health implications. In particular, lyme disease, pertussis, herpes virus, orthomyxovirus, paramyxovirus, pneumovirus, filovirus, flavivirus, reovirus, retrovirus, coronavirus, and malaria are infectious agents for which vaccines already exist, are being developed, or would be desirable.

Subunit vaccines are vaccines made from isolated antigens, usually proteins expressed recombinantly in bacterial, insect, or mammalian cell hosts. Typically, the antigenic component of a subunit vaccine is selected from among the proteins of an infectious agent observed to elicit a natural immune response upon infection, although in some cases other components of the infectious agent can be used. Typical antigens for use in subunit vaccines include protein expressed on the surface of the target infectious agent, as such surface-expressed envelope glycoproteins of viruses. Preferably, the antigen is a target for neutralizing antibodies. More preferably, the antigen is a target for broadly neutralizing antibodies, such that the immune response to the antigen covers immunity against multiple strains of the infectious agent. In some cases, glycans that are N-linked or O-linked to the subunit vaccine may also be important in vaccination, either by contributing to the epitope of the antigen or by guiding the immune response to particular epitopes on the antigen by steric hindrance. The immune response that occurs in response to vaccination may be direct to the protein itself, to the glycan, or to both the protein and linked glycans. Subunit vaccines have various advantages including that they contain no live pathogen, which eliminates concerns about infection of the patient by the vaccine; they may be designed using standard genetic engineering techniques; they are more homogenous than other forms of vaccine; and they can be manufactured in standardized recombinant protein expression production systems using well-characterized expression systems. In some cases, the antigen may be genetically engineered to favor generation of desirable antibodies, such as neutralizing or broadly neutralizing antibodies. In particular, structural information about an antigen of interest, obtained by X-ray crystallography, electron microscopy, or nuclear magnetic resonance experiments, can be used to guide rational design of subunit vaccines.

A known limitation of subunit vaccines is that the immune response elicited may sometimes be weaker than the immune response to other types of vaccines, such as whole virus, live, or live-attenuated vaccines. The present inventors have recognized and herein disclose that designed and/or protein-based VLP vaccines have the potential to harness the advantages of subunit vaccines while increasing the potency and breadth of the vaccine-induced immune response through multivalent display of the antigen in symmetrically ordered arrays. In the present disclosure, protein-based VLPs are distinguished from nanoparticle vaccines, because the term nanoparticle vaccine has been used in the art to refer to protein-based or glycoprotein-based vaccines (see, e.g. U.S. Pat. No. 9,441,019), polymerized liposomes (see, e.g., U.S. Pat. No. 7,285,289), surfactant micelles (see, e.g., US Patent Pub. No. US 2004/0038406 A1), and synthetic biodegradable particles (see, e.g., U.S. Pat. No. 8,323,696).

The protein-based VLPs of the present disclosure are distinguishable from VLPs that display an antigen on the surface of a micelle particle containing a surfactant (e.g., NP-9); or alternatively, made by extracting antigenic proteins from live virus while retaining lipid constituents of the viral envelope. By contrast, the protein-based VLPs described herein are free of, or substantially free of, lipid and surfactants. Furthermore, the symmetric display of the hMPV F protein on some embodiments of the protein-based VLPs of this disclosure may generate superior immune response to the F protein compared to other VLPs.

EMBODIMENTS

The present disclosure relates to protein-based VLPs and protein-based VLP vaccines. The VLP of the present disclosure display an antigen capable of eliciting immune responses to hMPV. Some vaccines of the present disclosure are useful for preventing or decreasing the severity of infection with hMPV. In particular, the antigens of the disclosure display the ectodomain of the hMPV F protein. The ectodomain may be attached to the core of the VLP either non-covalently or covalently, including as a fusion protein or by other means disclosed herein. In some embodiments, a linker connects the ectodomain to a first polypeptide comprising a multimerization domain. The linker may be any chemical linkage including but not limited to a polypeptide used to form a N-terminal or C-terminal fusion of the ectodomain to the first polypeptide. The hMPV F protein may optionally be displayed along a symmetry axis of the VLP. In some embodiments, the F protein is C-terminally linked to the first polypeptide comprising a trimerization domain and optionally an additional trimerization tag (e.g., FoldOn tag). Also provided are proteins and nucleic acid molecules encoding such proteins, formulations, and methods of use.

Protein-Based Virus-Like Particles

The VLPs of the present invention may comprise multimeric protein assemblies adapted for display of the ectodomain of hMPV F protein, or an antigenic fragment thereof. The VLPs of the present invention comprise at least a first plurality of polypeptides. The first plurality of polypeptides (also referred to a "first component") may be derived from a naturally-occurring protein sequence by substitution of at least one amino acid residue or by additional at the N- or C-terminus of one or more residues. In some cases, the first component comprises a protein sequence determined by computational methods. This first component may form the entire core of the VLP; or the core of the VLP may comprise one or more additional polypeptides (also referred to a "second component" or third, fourth, fifth component and so on), such that the VLP comprises two, three, four, five, six, seven, or more pluralities of polypeptides. In some cases, the first plurality will form trimers related by 3-fold rotational symmetry and the second plurality will form pentamers related by 5-fold rotational symmetry. In such cases, the VLP forms an "icosahedral particle" having 153 symmetry. Together these one or more pluralities of polypeptides may be arranged such that the members of each plurality of polypeptides are related to one another by symmetry operators. A general computational method for designing self-assembling protein materials, involving symmetrical docking of protein building blocks in a target symmetric architecture, is disclosed in Patent Pub. No. US 2015/0356240 A1.

The "core" of the VLP is used herein to describe the central portion of the VLP that links together the several copies of the hMPV F protein ectodomain, or antigenic fragments thereof, displayed by the VLP. In an embodiment, the first component comprises a first polypeptide comprising a hMPV F protein ectodomain or antigenic variant thereof, a linker, and a first polypeptide comprising a multimerization domain. Thereby, the "antigen" is a single polypeptide, capable of self-assembly into a VLP either alone or this a second component (third, fourth, or fifth, etc., components). An advantage of designing the antigens themselves to self-assemble is that the entire VLP then acts as the antigenic component of the vaccine. In other embodiments, the ectodomain, or antigenic fragment thereof, is non-covalently or covalently linked to the first polypeptide comprising a multimerization domain. For example, an antibody or antigenic fragment thereof may be fused to the first polypeptide and configured to bind a portion of the first polypeptide, or a chemical tag on the first polypeptide. A streptavidin-biotin (or neuravidin-biotin) linker can be employed. Or various chemical linkers may be used. An advantage of designing a core to be a generic platform is that the one or more pluralities of polypeptides that comprise the core can be designed and optimized in advance and then applied to the ectodomain serially to identify VLP(s) having superior efficacy as vaccines. It will be understood that in some cases, the same polypeptide may form a portion of the "core" and then extend outward as either an adaptor for attachment of the hMPV F protein ectodomain and to include the ectodomain (i.e., a fusion protein). In embodiments of the present disclosure, the antigen comprises further polypeptide sequences in addition to the hMPV F protein ectodomain. In certain embodiments, the ectodomain is glycosylated either natively or using alternative oligosaccharides (e.g., oligosaccharides specific to the host cell used to express the antigen).

In some cases, self-assembly may be further promoted by multimerization of the ectodomain even though the core would, in absence of the ectodomain, be independently capable of self-assembly. The hMPV F protein is detected as a trimer in its native state (Cseke et al. *J. Virol.* 21(2):698-707 (2007)). Display of the ectodomain on a VLP, at least in some embodiments, decreases the thermodynamic barrier for assembly and/or the equilibrium ratio of assembled to non-assembled VLP components. In some cases, the trimeric ectodomain placed along a 3-fold axis of the VLP promotes proper folding and conformation stability of the ectodomain and makes self-assembly of the VLP a cooperative process, in that the ectodomain is trimerized properly in part due to its display on a 3-fold axis of the core of the VLP, and the VLP is stabilized in its assembled form, at least in part, by non-covalent or covalent interactions amongst the trimer units. In some cases, introduction of mutations to the antigen or to the VLP components may optionally further stabilize assembly, in particular if cysteine residues are positioned to create intramolecular disulfide bonds. In some examples, a dimeric, trimeric, tetrameric, pentameric, or hexameric antigen is displayed upon a core designed to have a matching 2-fold, 3-fold, 4-fold, 5-fold, or 6-fold symmetry axis such that the core accommodates the arrangement of the multimeric antigen with the native symmetry of the antigen.

Various Non-Limiting Examples of VLPs

Figure 1B:
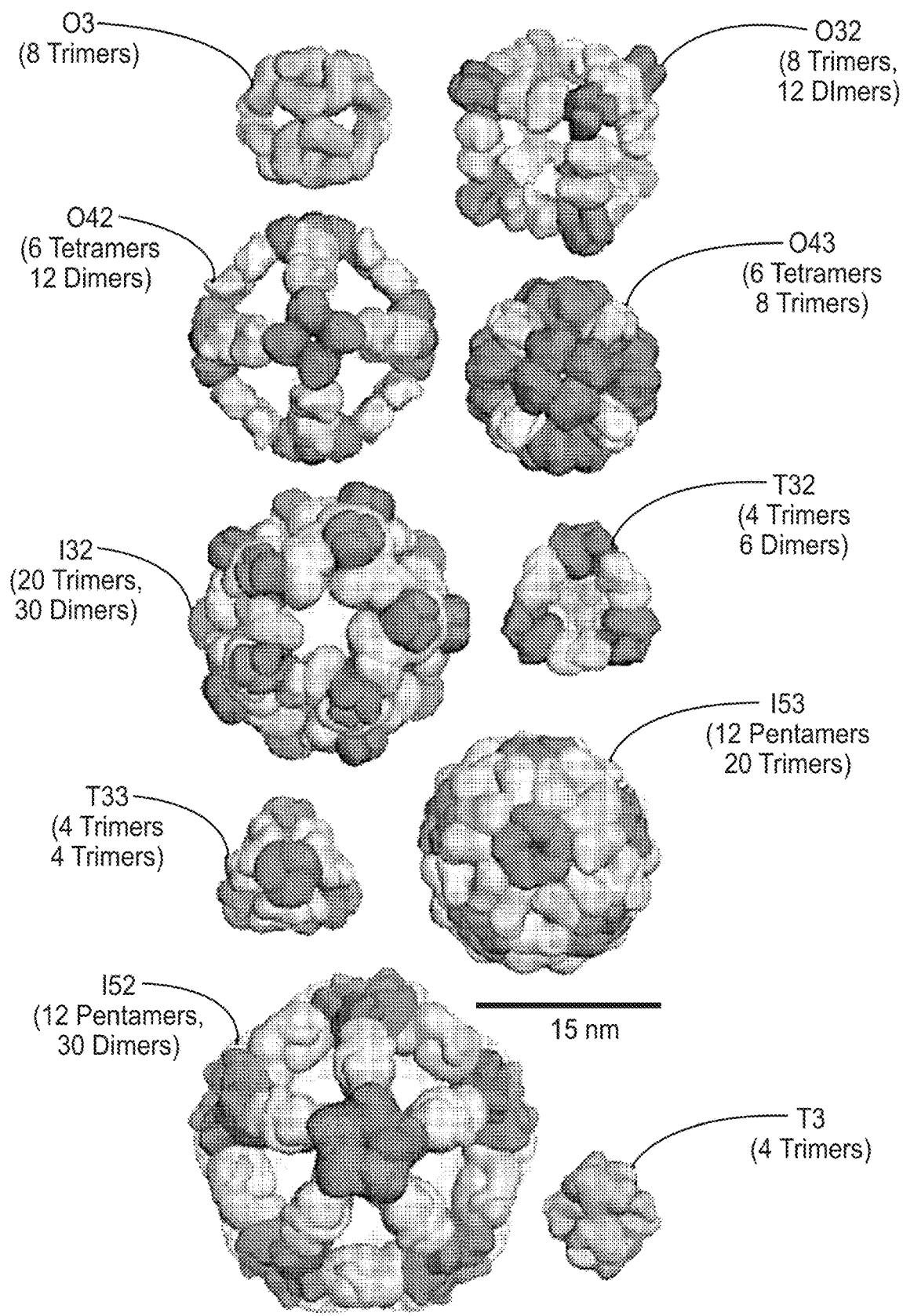
FIG. 1B shows further illustrative embodiments of VLPs and VLP components (with G protein not shown).

A non-limiting example of an embodiment is shown in FIG. 1A, which depicts an ectodomain antigen genetically fused to a component (a first plurality of polypeptides) of the VLP, which optionally is expressed recombinantly in a host cell (e.g., 293F cells); along with a pentameric protein assembly (a second plurality of polypeptides), which is optionally expressed recombinantly in the same or a different host cell (e.g., *E. coli* cells), these two pluralities of polypeptides self-assembling into a VLP displaying 20 antigen trimers around an icosahedral core. In this embodiment, the core has a generic design. As explained below, in other embodiments, an antigen of the disclosure is mixed with another antigen protein in the same VLP, such as an ectodomain of a protein from a second virus, or such as a trimeric glycoprotein from another virus. In some embodiments, the VLP comprises, in addition to a hMPV F protein ectodomain, the trimeric glycoproteins of HIV-1, HIV-2, EBV, CMV, RSV, influenza, Ebola, Marburg, Dengue, SARS, MERS, Hanta, or Zika virus. In some embodiments, the VLP comprises the trimeric glycoproteins of viruses that are related evolutionarily or in sequence identity to any of these illustrative virus, including without limitation, a herpes virus, orthomyxovirus, paramyxovirus, pneumovirus, filovirus, flavivirus, reovirus, or retrovirus. In an embodiment, the VLP comprises the extracellular domain or domains of a transmembrane protein or glycoprotein, or an antigenic fragment thereof. In some embodiments, the VLP is further linked to polypeptides or other agents capable of acting as an adjuvant. In some embodiments, the antigen (first component) and/or the second component comprises one or more T cell epitopes, optionally a T cell epitope of heterologous origin.

Trimeric antigens that may be used with VLPs of the disclose to form mixed VLPs are in some cases, without limitation, SARS-CoV-2, respiratory syncytial virus, HIV gp140, influenza HA, dengue E protein, or Ebola sGP. Mixed VLPs of the disclosure include those that comprise both a hMPV F protein ectodomain and antigenic protein(s) from one or more of Vesicular stomatitis virus, Herpes simplex virus, Baculovirus, Thogotovirus, and Bornaviridae. When other trimeric antigens are used, they may optionally be placed on the 3-fold symmetry axis of the VLP. In some cases, the antigen chosen is monomeric and nevertheless placed on a 3-fold axis. Thus, the VLP depicted in FIG. 1A is capable of displaying 20 trimeric antigens or 60 monomeric antigens. Additionally or alternatively the pentameric complexes of the VLP is used to display a 12 pentameric antigens or 70 monomeric antigens. In an embodiment, the VLP comprises 20 copies of a trimeric antigen and 12 copies of a pentameric antigen.

VLP Cores

Other potential arrangements of polypeptides of the present disclosure are shown in FIG. 1B. In some embodiments, the VLP is adapted for display of up to 8 trimers; 8 trimers and 12 dimers; 6 tetramers and 12 dimers; 6 tetramers and 8 trimers; 20 trimers and 30 dimers; 4 trimers and 6 dimers; 4 first trimers and 4 second trimers, or 8 trimers; 12 pentamers and 20 trimers; or 12 pentamers and 30 dimers; or 4 trimers. In some cases, one of the symmetric axes is not used for antigen display, thus, in some embodiments the VLP is adapted for display of up to 8 trimers; 12 dimers; 6 tetramers; 20 trimers; 30 dimers; 4 trimers; 6 dimers; 8 trimers; or 12 pentamers. In some cases, monomeric antigens are displayed and thus, the VLP is adapted for display of up to 12, 24, 60, or 70 monomeric antigens. In some cases, the VLP comprises mixed pluralities of polypeptides such that otherwise identical polypeptides of the core of the VLP display different antigens or no antigen. Thus, depending on the ratio of polypeptides, the VLP is in some cases adapted for display of between 1 and 130 antigens (e.g., on the 152 particle) where each of the antigens displayed may be the same or may be different members of mixed population in proportion to any ratio chosen. The antigens may be co-expressed in a recombinant expression system and self-assembled before purification. Alternatively, the antigens may be expressed separately and then mixed together, either before or after purification from expression host and associated contaminants. In various embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more antigens are displayed. Non-limiting illustrative VLPs are provided in Bale et al. *Science* 353:389-94 (2016); Heinze et al. *J. Phys. Chem B.* 120:5945-5952 (2016); King et al. *Nature* 510:103-108 (2014); and King et al. *Science* 336:1171-71 (2012).

Mixed VLPs

In some cases, the VLP is adapted to display the same antigen from two or more diverse strains of hMPV. In non-limiting examples, the same VLP displays mixed populations of homotrimeric protein antigens or mixed heterotrimers of protein antigens from different strains of hMPV. In an embodiment, the VLP displays the F proteins, or antigenic fragment thereof, disclosed in any sequence of GenBank found by searching the Protein database with the keyword "human metapneumovirus F," individually or in mixed VLPs.

When mixed VLPs are made, it may be advantageous to ensure formation of homomultimers in a strain-specific manner rather than permit heteromultimerization, such that, for example all strain 1 F proteins are displayed on one 3-fold axis of a T33 particle whereas all strain 2 F proteins are displayed on the other 3-fold axis of the T33 particle. This may be achieved by use a VLP comprising two or more pluralities of polypeptides as the core of the VLP with each plurality of polypeptides attached to a different antigen. Alternatively, a VLP may be engineered with one or more symmetry-breaking mutations, such as knob-in-hole mutations or intramolecular disulfide mutations, which have the effect of preventing trimer formation between the different antigens. In that case, the VLP displays multimeric antigens from different strains at symmetrically equivalent positions on the VLP, but each position on the VLP is occupied by homomultimers from the same strain, with only an insignificant proportion of inter-strain heteromeric antigens. In some cases, the antigen itself may be genetically engineered to prevent inter-strain heteromultimerization. In an embodiment, the VLP is engineered to prevent heteromultimerization of two antigenic proteins with conserved structure but divergent antigenicity, such as for example, a strain 1 F protein and strain 2 F protein, or a hMPV F protein and a non-hMPV antigenic protein. Furthermore, when mixed VLPs are made and the antigens are displayed as fusion proteins, the VLP will comprise three or more different proteins, as the fusion proteins will share identical (or equivalent) domains used to form the core of the VLP with different antigenic domains, one for each antigen displayed on the VLP.

Attachment Modalities (Linkers)

The VLPs of the present disclosure display antigenic proteins in various ways including as gene fusion or by other means disclosed herein. As used herein, "linked to" or "attached to" denotes any means known in the art for causing two polypeptides to associate. The association may be direct or indirect, reversible or irreversible, weak or strong, covalent or non-covalent, and selective or nonselective.

In some embodiments, attachment is achieved by genetic engineering to create an N- or C-terminus fusion of an antigen to one of the pluralities of polypeptides composing the VLP. Thus, the VLP may consist of, or consist essentially of, one, two, three, four, five, six, seven, eight, nine, or ten pluralities of polypeptides displaying one, two, three, four, five, six, seven, eight, nine, or ten pluralities of antigens, where at least one of the pluralities of antigen is genetically fused to at least one of the plurality of polypeptides. In some cases, the VLP consists essentially of one plurality of polypeptides capable of self-assembly and comprising the plurality of antigenic proteins genetically fused thereto. In some cases, the VLP consists essentially of a first plurality of polypeptides comprising a plurality of antigens; and a second plurality of polypeptides capable of co-assembling into two-component VLP, one plurality of polypeptides linking the antigenic protein to the VLP and the other plurality of polypeptides promoting self-assembly of the VLP.

In some embodiments, attachment is achieved by post-translational covalent attachment between one or more pluralities of polypeptides and one or more pluralities of antigenic protein. In some cases, chemical cross-linking is used to non-specifically attach the antigen to a VLP polypeptide. In some cases, chemical cross-linking is used to specifically attach the antigenic protein to a VLP polypeptide (e.g. to the first polypeptide or the second polypeptide). Various specific and non-specific cross-linking chemistries are known in the art, such as Click chemistry and other methods. In general, any cross-linking chemistry used to link two proteins may be adapted for use in the presently disclosed VLPs. In particular, chemistries used in creation of immunoconjugates or antibody drug conjugates may be used. In some cases, an VLP is created using a cleavable or non-cleavable linker. Processes and methods for conjugation of antigens to carriers are provided by, e.g., Patent Pub. No. US 2008/0145373 A1.

In an embodiment, attachment is achieved by non-covalent attachment between one or more pluralities of polypeptides and one or more pluralities of antigen. In some cases, the antigenic protein is engineered to be negatively charged on at least one surface and the core polypeptide is engineered to be positively charged on at least one surface, or positively and negatively charged, respectively. This promotes intermolecular association between the antigenic protein and the core polypeptide by electrostatic force. In some cases, shape complementarity is employed to cause linkage of antigen protein to core. Shape complementarity can be pre-existing or rationally designed. In some cases, computational designed of protein-protein interfaces is used to achieve attachment. In an embodiment, the antigen is biotin-labeled and the polypeptide comprises a streptavidin, or vice versa. In an embodiment, streptavidin is displayed by gene fusion or otherwise as a tetramer on a 4-fold axis of the core and the biotin-labeled antigen is monomeric, dimeric, or tetrameric, permitting association to the core in a configuration appropriate for native multimerization of the antigen. In some cases, a protein-based adaptor is used to capture the antigenic protein. In some cases, the polypeptide is fused to a protein capable of binding a complementary protein, which is fused to the antigenic protein.

The immune reaction to hMPV F may be controlled by altering the orientation of the ectodomain relative to the core. Depending on how the antigenic protein is attached to the core of the VLP, the antigenic protein may be displayed in various orientations. In some embodiments, the antigenic protein is displayed so that one or more known epitopes are oriented at or towards the distal end of the antigenic protein, such that these epitope(s) are preferentially accessible to the immune system. In some cases, the orientation will recapitulate the orientation of a viral protein with respect to the virus. The choice of orientation may direct the immune system to one or the other epitope.

In some embodiments, epitope preference is control by other means, such as positioning of glycans on the VLP by addition or subtraction of the N-linked glycan sequence motif N—X-[T/S] at predetermined positions in the amino acid sequence of any of the polypeptides of the VLP including in the amino acid sequence of the antigenic protein.

In some cases, the epitopes found at intermediate distances from the proximal to the distal end will be the preferred over epitopes more distally located depending on various considerations including but not limited to the overall geometry of the VLP, surface hydrophobicity, surface charge, and competitive binding of proteins endogenously present in the subject or proteins exogenously provided in the vaccine composition. The present disclosure encompasses all known methods of rational design of protein structure and the foregoing is not intended to be limiting.

VLP Polypeptide Sequences

The polypeptides of the present disclosure may have any of various amino acids sequences. Patent Pub No. US 2015/0356240 A1 describes various methods for designing protein assemblies. As described in US Patent Pub No. US 2016/0122392 A1 and in International Patent Pub. No. WO 2014/124301 A1, the isolated polypeptides of SEQ ID NOS:1-51 were designed for their ability to self-assemble in pairs to form VLPs, such as icosahedral particles. The design involved design of suitable interface residues for each member of the polypeptide pair that can be assembled to form the VLP. The VLPs so formed include symmetrically repeated, non-natural, non-covalent polypeptide-polypeptide interfaces that orient a first assembly and a second assembly into a VLP, such as one with an icosahedral symmetry. Thus, in one embodiment the first polypeptide and second polypeptides (that is, the two polypeptides of the core of the VLP) are selected from the group consisting of SEQ ID NOS:1-51. In each case, an N-terminal methionine residue present in the full length protein but may be removed to make a fusion is not included in the sequence. The identified residues in Table 1 are numbered beginning with an N-terminal methionine (not shown). In various embodiments, one or more additional residues are deleted from the N-terminus and/or additional residues are added to the N-terminus (e.g. to form a helical extension).

TABLE 1

| Name | Component Multimer | Amino Acid Sequence | Identified interface residues |
|---|---|---|---|
| I53-34A SEQ ID NO: 1 | trimer | EGMDPLAVLAESRLLPLLTVRGGEDLAGLATVLELMGVGALEITLRTEKGLE ALKALRKSGLLLGAGTVRSPKEAEAALEAGAAFLVSPGLLEEVAALAQARGV PYLPGVLTPTEVERALALGLSALKFFPAEPFQGVRVLRAYAEVFPEVRFLPT GGIKEEHLPHYAALPNLLAVGGSWLLQGDLAAVMKKVKAAKALLSPQAPG | I53-34A: 28, 32, 36, 37, 186, 188, 191, 192, 195 |
| I53-34B SEQ ID NO: 2 | pentamer | TKKVGIVDTTFARVDMAEAAIRTLKALSPNIKIIRKTVPGIKDLPVACKKLL EEEGCDIVMALGMPGKAEKDKVCAHEASLGLMLAQLMTNKHIIEVFVHEDEA KDDDELDILALVRAIEHAANVYYLLFKPEYLTRMAGKGLRQGREDAGPARE | I53-34B: 19, 20, 23, 24, 27, 109, 113, 116, 117, 120, 124, 148 |
| I53-40A SEQ ID NO: 3 | pentamer | TKKVGIVDTTFARVDMASAAILTLKMESPNIKIIRKTVPGIKDLPVACKKLL EEEGCDIVMALGMPGKAEKDKVCAHEASLGLMLAQLMTNKHIIEVFVHEDEA KDDAELKILAARRAIEHALNVYYLLFKPEYLTRMAGKGLRQGFEDAGPARE | I53-40A: 20, 23, 24, 27, 28, 109, 112, 113, 116, 120, 124 |
| I53-40B SEQ ID NO: 4 | trimer | STINNQLKALKVIPVIAIDNAEDIIPLGKVLAENGLPAAEITFRSSAAVKAI MLLRSAQPEMLIGAGTILNGVQALAAKEAGATFVVSPGFNPNTVRACQIIGI DIVPGVNNPSTVEAALEMGLTTLKFFPAEASGGISMVKSLVGPYGDIRLMPT GGITPSNIDNYLAIPQVLACGGTWMVDKKLVTNGEWDEIARLTREIVEQVNP | I53-40B: 47, 51, 54, 58, 74, 102 |
| I53-47A SEQ ID NO: 5 | trimer | PIFTLNTNIKATDVPSDFLSLTSRLVGLILSKPGSYVAVHINTDQQLSFGGS TNPAAFGTLMSIGGIEPSKNRDHSAVLFDHLNAMLGIPKNRMYIHFVNLNGD DVGWNGTTF | I53-47A: 22, 25, 29, 72, 79, 86, 87 |
| I53-47B SEQ ID NO: 6 | pentamer | NQHSHKDYETVRIAVVRARWHADIVDACVEAFEIAMAAIGGDRFAVDVFDVP GAYEIPLHARTLAETGRYGAVLGTAFVVNGGIYRHEFVASAVIDGMMNVQLS TGVPVLSAVLTPHRYRDSAEHHRFFAAHFAVKGVEAARACIEILAAREKIAA | I53-47B: 28, 31, 35, 36, 39, 131, 132, 135, 139, 146 |
| I53-50A SEQ ID NO: 7 | trimer | EELFKKHKIVAVLRANSVEEAIEKAVAVFAGGVHLIEITFTVPDADTVIKAL SVLKEKGAIIGAGTVTSVEQCRKAVESGAEFIVSPHLDEEISQFCKEKGVFY MPGVMTPTELVKAMKLGHTILKLFPGEVVGPQFVKAMKGPFPNVKFVPTGGV NLDNVCEWFKAGVLAVGVGSALVKGTPDEVREKAKAFVEKIRGCTE | I53-50A: 25, 29, 33, 54, 57 |
| I53-50B SEQ ID NO: 8 | pentamer | NQHSHKDYETVRIAVVRARWHAEIVDACVSAFEAAMADIGGDRFAVDVFDVP GAYEIPLHARTLAETGRYGAVLGTAFVVNGGIYRHEFVASAVIDGMMNVQLS TGVPVLSAVLTPHRYRDSDAHTLLFLALFAVKGMEAARACVEILAAREKIAA | I53-50B: 24, 28, 36, 124, 125, 127, 128, 129, 131, 132, 133, 135, 139 |
| I53-51A SEQ ID NO: 9 | trimer | FTKSGDDGNTNVINKRVGKDSPLVNFLGDLDELNSFIGFAISKIPWEDMKKD LERVQVELFEIGEDLSTQSSKKKIDESYVLWLLAATAIYRIESGPVKLFVTP GGSEEASVLHVTRSVARRVERNAVKYTKELPEINRMIIVYLNRLSSLLFAMA LVANKRRNQSEKIYEIGKSW | I53-51A: 80, 83, 86, 87, 88, 90, 91, 94, 166, 172, 176 |
| I53-51B SEQ ID NO: 10 | pentamer | NQHSHKDYETVRIAVVRARWHADIVDQCVRAFEEAMADAGGDRFAVDVFDVP GAYEIPLHARTLAETGRYGAVLGTAFVVNGGIYRHEFVASAVIDGMMNVQLS TGVPVLSAVLTPHRYRSSREHHEFFREHFMVKGVEAAAACITILAAREKIAA | I53-51B: 31, 35, 36, 40, 122, 124, 128, 131, 135, 139, 143, 146, 147 |
| I52-03A SEQ ID NO: 11 | pentamer | GHTKGPTPQQHDGSALRIGIVHARWNKTIIMPLLIGTIAKLLECGVKASNIV VQSVPGSWELPIAVQRLYSASQLQTPSSGPSLSAGDLLGSSTTDLTALPTTT ASSTGPPFDALIAIGVLIKGETMHFEYIADSVSHGLMRVQLDTGVPVIFGVLT VLTDDQAKARAGVIEGSHNHGEDWGLAAVEMGVRRRDWAAGKTE | I52-03A: 28, 32, 36, 39, 44, 49 |

TABLE 1-continued

| Name | Component Multimer | Amino Acid Sequence | Identified interface residues |
|---|---|---|---|
| I52-03B SEQ ID NO: 12 | dimer | YEVDHADVYDLFYLGRGKDYAAEASDIADLVRSRTPEASSLLDVACGTGTHL EHFTKEFGDTAGLELSEDMLTHARKRLPDATLHQGDMRDFQLGRKFSAVVSM FSSVGYLKTVAELGAAVASFAEHLEPGGVVVVEPWWFPETFADGWVSADVVR RDGRTVARVSHSVREGNATRMEVHFTVADPGKGVRHFSDVHLITLFHQREYE AAFMAAGLRVEYLEGGPSGRGLFVGVPA | I52-03B: 94, 115, 116, 206, 213 |
| I52-32A SEQ ID NO: 13 | dimer | GMKEKFVLIITHGDFGKGLLSGAEVIIGKQENVHTVGLNLGDNIEKVAKEVM RIIIAKLAEDKEIIIVVDLFGGSPFNIALEMMKTFDVKVITGINMPMLVELL TSINVYDTTELLENISKIGKDGIKVIEKSSLKM | I52-32A: 47, 49, 53, 54, 57, 58, 61, 83, 87, 88 |
| I52-32B SEQ ID NO: 14 | pentamer | KYDGSKLRIGILHARWNLEIIAALVAGAIKRLQEFGVKAENIIIETVPGSFE LPYGSKLFVEKQRLGKPLDAIIPIGVLIKGSTMHFEYICDSTTHQLMKLNF ELGIPVIFGVLTCLTDEQAEARAGLIEGKMHNHGEDWGAAAVEMATKFN | I52-32B: 19, 20, 23, 30, 40 |
| I52-33A SEQ ID NO: 15 | pentamer | AVKGLGEVDQKYDGSKLRIGILHARWNRKIILALVAGAVLRLLEFGVKAENI IIETVPGSFELPYGSKLFVEKQRLGKPLDAIIPIGVLIKGSTMHFEYICDS TTHQLMKLNFELGIPVIFGVLTCLTDEQAEARAGLIEGKMHNHGEDWGAAAV EMATKFN | I52-33A: 33, 41, 44, 50 |
| I52-33B SEQ ID NO: 16 | dimer | GANWYLDNESSRLSFTSTKNADIAEVHRFLVLHGKVDPKGLAEVEVETESIS TGIPLRDMLLRVLVFQVSKFPVAQINAQLDMRPINNLAPGAQLELRLPLTVS LRGKSHSYNAELLATRLDERRFQVVTLEPLVIHAQDFDMVRAFNALRLVAGL SAVSLSVPVGAVLIFTAR | I52-33B: 61, 63, 66, 67, 72, 147, 148, 154, 155 |
| I32-06A SEQ ID NO: 17 | dimer | TDYIRDGSAIKALSFAIILAEADLRHIPQDLQRLAVRVIHACGMVDVANDLA FSEGAGKAGRNALLAGAPILCDARMVAEGITRSRLPADNRVIYTLSDPSVPE LAKKIGNTRSAAALDLWLPHIEGSIVAIGNAPTALFRLFELLDAGAPKPALI IGMPVGFVGAAESKDELAANSRGVPYVIVRGRRGGSAMTAAAVNALASERE | I32-06A: 9, 12, 13, 14, 20, 30, 33, 34 |
| I32-06B SEQ ID NO: 18 | trimer | ITVFGLKSKLAPRREKLAEVIYSSLHLGLDIPKGKHAIRFLCLEKEDFYYPF DRSDDYTVTEINLMAGRSEETKMLLIFLLFLALERKLGIRAHDVEITIKEQP AHCWGFRGRTGDSARDLDYDIYV | I32-06B: 24, 71, 73, 76, 77, 80, 81, 84, 85, 88, 114, 118 |
| I32-19A SEQ ID NO: 19 | trimer | GSDLQKLQRFSTCDISDGLLNVYNIPTGGYFPNLTAISPPQNSSIVGTAYTV LFAPIDDPRPAVNYIDSVPPNSILVLALEPHLQSQFHPFIKITQAMYGGLMS TRAQYLKSNGTVVFGRIRDVDEHRTLNHPVFAYGVGSCAPKAVVKAVGTNVQ LKILTSDGVTQTICPGDYIAGDNNGIVRIPVQETDISKLVTYIEKSIEVDRL VSEAIKNGLPAKAAQTARRMVLKDYI | I32-19A: 208, 213, 218, 222, 225, 226, 229, 233 |
| I32-19B SEQ ID NO: 20 | dimer | SGMRVYLGADHAGYELKQAIIAFLKMTGHEPIDCGALRYDADDDYPAFCIAA ATRTVADPGSLGIVLGGSGNGEQIAANKVPGARCALAWSVQTAALAREHNNA QLIGIGGRMHTLEEALRIVKAFVTTPWSKAQRHQRRIDILAEYERTHEAPPV PGAPA | I32-19B: 20, 23, 24, 27, 117, 118, 122, 125 |
| I32-28A SEQ ID NO: 21 | trimer | GDDARIAAIGDVDELNSQIGVLLAEPLPDDVRAALSAIQHDLFDLGGELCIP GHAAITEDHLLRLALWLVHYNGQLPPLEEFILPGGARGAALAHVCRTVCRRA ERSIKALGASEPLNIAPAAYVNLLSDLLFVLARVLNRAAGGADVLWDRTRAH | I32-28A: 60, 61, 64, 67, 68, 71, 110, 120, 123, 124, 128 |
| I32-28B SEQ ID NO: 22 | dimer | ILSAEQSFTLRHPHGQAAALAFVREPAAALAGVQRLRGLDSDGEQVWGELLV RVPLLGEVDLPFRSEIVRTPQGAELRPLTLTGERAWVAVSGQATAAEGGEMA FAFQFQAHLATPEAEGEGGAAFEVMVQAAAGVTLLLVAMALPQGLAAGLPPA | I32-28B: 35, 36, 54, 122, 129, 137, 140, 141, 144, 148 |
| I53-40A.1 SEQ ID NO: 23 | pentamer | TKKVGIVDTTFARVDMASAAILTLKMESPNIKIIRKTVPGIKDLPVACKKLL EEEGCDIVMALGMPGKKEKDKVCAHEASLGLMLAQLMTNKHIIEVFVHEDEA KDDAELKILAARRAIEHALNVYYLLFKPEYLTRMAGKGLRQGFEDAGPARE | I53-40A: 20, 23, 24, 27, 28, 109, 112, 113, 116, 120, 124 |
| I53-40B.1 SEQ ID NO: 24 | trimer | DDINNQLKRLKVIPVIAIDNAEDIIPLGKVLAENGLPAAEITFRSSAAVKAI MLLRSAQPEMLIGAGTILNGVQALAAKEAGADFVVSPGFNPNTVRACQIIGT DIVPGVNNPSTVEQALEMGLTTLKFFPAEASGGISMVKSLVGPYGDIRLMPT GGITPDNIDNYLAIPQVLACGGTWMVDKKLVRNGEWDEIARLTREIVEQVNP | I53-40B: 47, 51, 54, 58, 74, 102 |
| I53-47A.1 SEQ ID NO: 25 | trimer | PIFTLNTNIKADDVPSDFLSLTSRLVGLILSKPGSYVAVHINTDQQLSFGGS TNPAAFGTLMSIGGIEPDKNRDHSAVLFDHLNAMLGIPKNRMYIHFVNLNGD DVGWNGTTF | I53-47A: 22, 25, 29, 72, 79, 86, 87 |

TABLE 1-continued

| Name | Component Multimer | Amino Acid Sequence | Identified interface residues |
|---|---|---|---|
| I53-47A.1NegT2 SEQ ID NO: 26 | trimer | PIFTLNTNIKADDVPSDFLSLTSRLVGLILSEPGSYVAVHINTDQQLSFGGS TNPAAFGTLMSIGGIEPDKNEDHSAVLFDHLNAMLGIPKNRMYIHFVDLDGD DVGWNGTTF | I53-47A: 22, 25, 29, 72, 79, 86, 87 |
| I53-47B.1 SEQ ID NO: 27 | pentamer | NQHSHKDHETVRIAVVRARWHADIVDACVEAFEIAMAAIGGDRFAVDVFDVP GAYEIPLHARTLAETGRYGAVLGTAFVVNGGIYRHEFVASAVIDGMMNVQLD TGVPVLSAVLTPHRYRDSDEHHRFFAAHFAVKGVEAARACIEILNAREKIAA | I53-47B: 28, 31, 35, 36, 39, 131, 132, 135, 139, 146 |
| I53-47B.1NegT2 SEQ ID NO: 28 | pentamer | NQHSHKDHETVRIAVVRARWHADIVDACVEAFEIAMAAIGGDRFAVDVFDVP GAYEIPLHARTLAETGRYGAVLGTAFVVDGGIYDHEFVASAVIDGMMNVQLD TGVPVLSAVLTPHEYEDSDEDHEFFAAHFAVKGVEAARACIEILNAREKIAA | I53-47B: 28, 31, 35, 36, 39, 131, 132, 135, 139, 146 |
| I53-50A.1 SEQ ID NO: 29 | trimer | EELFKKHKIVAVLRANSVEEAIEKAVAVFAGGVHLIEITFTVPDADTVIKAL SVLKEKGAIIGAGTVTSVEQCRKAVESGAEFIVSPHLDEEISQFCKEKGVFY MPGVMTPTELVKAMKLGHDILKLFPGEWGPQFVKAMKGPFPNVKFVPTGGV NLDNVCEWFKAGVLAVGVGDALVKGDPDEVREKAKKFVEKIRGCTE | I53-50A: 25, 29, 33, 54, 57 |
| I53-50A.1NegT2 SEQ ID NO: 30 | trimer | EELFKKHKIVAVLRANSVEEAIEKAVAVFAGGVHLIEITFTVPDADTVIKAL SVLKEKGAIIGAGTVTSVEQCRKAVESGAEFIVSPHLDEEISQFCKEKGVFY MPGVMTPTELVKAMKLGHDILKLFPGEWGPEFVEAMKGPFPNVKFVPTGGV DLDDVCEWFDAGVLAVGVGDALVEGDPDEVREDAKEFVEEIRGCTE | I53-50A: 25, 29, 33, 54, 57 |
| I53-50A.1PosT1 SEQ ID NO: 31 | trimer | EELFKKHKIVAVLRANSVEEAIEKAVAVFAGGVHLIEITFTVPDADTVIKAL SVLKEKGAIIGAGTVTSVEQCRKAVESGAEFIVSPHLDEEISQFCKEKGVFY MPGVMTPTELVKAMKLGHDILKLFPGEWGPQFVKAMKGPFPNVKFVPTGGV NLDNVCKWFKAGVLAVGVGKALVKGKPDEVREKAKKFVKKIRGCTE | I53-50A: 25, 29, 33, 54, 57 |
| I53-50B.1 SEQ ID NO: 32 | pentamer | NQHSHKDHETVRIAVVRARWHAEIVDACVSAFEAAMRDIGGDRFAVDVFDVP GAYEIPLHARTLAETGRYGAVLGTAFVVNGGIYRHEFVASAVIDGMMNVQLD TGVPVLSAVLTPHRYRDSDAHTLLFLALFAVKGMEAARACVEILAAREKIAA | I53-50B: 24, 28, 36, 124, 125, 127, 128, 129, 131, 132, 133, 135, 139 |
| I53-50B.1NegT2 SEQ ID NO: 33 | pentamer | NQHSHKDHETVRIAVVRARWHAEIVDACVSAFEAAMRDIGGDRFAVDVFDVP GAYEIPLHARTLAETGRYGAVLGTAFVVDGGIYDHEFVASAVIDGMMNVQLD TGVPVLSAVLTPHEYEDSDADTLLFLALFAVKGMEAARACVEILAAREKIAA | I53-50B: 24, 28, 36, 124, 125, 127, 128, 129, 131, 132, 133, 135, 139 |
| I53-50B.4PosT1 SEQ ID NO: 34 | trimer | NQHSHKDHETVRIAVVRARWHAEIVDACVSAFEAAMRDIGGDRFAVDVFDVP GAYEIPLHARTLAETGRYGAVLGTAFVVNGGIYRHEFVASAVINGMMNVQLN TGVPVLSAVLTPHNYDKSKAHTLLFLALFAVKGMEAARACVEILAAREKIAA | I53-50B: 24, 28, 36, 124, 125, 127, 128, 129, 131, 132, 133, 135, 139 |
| I53-40A genus SEQ ID NO: 35 | pentamer | TKKVGIVDTTFARVDMASAAILTLKMESPNIKIIRKTVPGIKDLPVACKKLL EEEGCDIVMALGMPGK(A/K)EKDKVCAHEASLGLMLAQLMTNKHIIEVFVH EDEAKDDAELKILAARRAIEHALNVYYLLFKPEYLTRMAGKGLRQGFEDAGP ARE | |
| I53-40B genus SEQ ID NO: 36 | trimer | (S/D)(T/D)INNQLK(A/R)LKVIPVIAIDNAEDIIPLGKVLAENGLPAAE ITFRSSAAVKAIMLLRSAQPEMLIGAGTILNGVQALAAKEAGA(T/D)FVVS PGFNPNTVRACQIIGIDIVPGVNNPSTVE(A/Q)ALEMGLTTLKFFPAEASG GISMVKSLVGPYGDIRLMPTGGITP(S/D)NIDNYIAIPQVLACGGTWMVDK KLV(T/R)NGEWDEIARLTREIVEQVNP | |
| I53-47A genus SEQ ID NO: 37 | trimer | PIFTLNTNIKA(T/D)DVPSDFLSLTSRLVGLILS(K/E)PGSYVAVHINTD QQLSFGGSTNPAAFGTLMSIGGIEP(S/D)KN(R/E)DHSAVLFDHLNAMLG IPKNRMYIHFV(N/D)L(N/D)GDDVGWNGTTF | |
| I53-47B genus SEQ ID NO: 38 | pentamer | NQHSHKD(Y/H)ETVRIAVVRARWHADIVDACVEAFEIAMAAIGGDRFAVDV FDVPGAYEIPLHARTLAETGRYGAVLGTAFVV(N/D)GGIY(R/D)HEFVAS AVIDGMMNVQL(S/D)TGVPVLSAVLTPH(R/E)Y(R/E)DS(A/D)E(H/D )H(R/E)FFAAHFAVKGVEAARACIEIL(A/N)AREKIAA | |
| I53-50A genus SEQ ID NO: 39 | trimer | EELFKKHKIVAVLRANSVEEAIEKAVAVFAGGVHLIEITFTVPDADTVIKAL SVLKEKGAIIGAGTVTSVEQCRKAVESGAEFIVSPHLDEEISQFCKEKGVFY MPGVMTPTELVKAMKLGH(T/D)ILKLFPGEVVGP(Q/E)FV(K/E)AMKGP FPNVKFVPTGGV(N/D)LD(N/D)VC(E/K)WF(K/D)AGVLAVGVG(S/K/ D)ALV(K/E)G(T/D/K)PDEVRE(K/D)AK(A/E/K)FV(E/K)(K/E)IR GCTE | |

TABLE 1-continued

| Name | Component Multimer | Amino Acid Sequence | Identified interface residues |
|---|---|---|---|
| I53-50B genus SEQ ID NO: 40 | pentamer | NQHSHKD(Y/H)ETVRIAVVRARWHAEIVDACVSAFEAAM(A/R)DIGGDRF AVDVFDVPGAYEIPLHARTIAETGRYGAVLGTAFVV(N/D)GGIY(R/D)HE FVASAVI(D/N)GMMNVQL(S/D/N)TGVPVLSAVLTPH(R/E/N)Y(R/D/ E)(D/K)3(D/K)A(H/D)TLLFLALFAVKGMEAARACVEILAAREKIAA | |
| T32-28A SEQ ID NO: 41 | dimer | GEVPIGDPKELNGMEIAAVYLQPIEMEPRGIDLAASLADIHLEADIHALKNN PNGFPEGFWMPYLTLAYALANADTGAIKTGTLMPMVADDGPHYGANIAMEKD KKGGFGVGTYALTFLISNPEKQGFGRHVDEETGVGKWFEPFVVTYFFKYTGT PK | |
| T32-28B SEQ ID NO: 42 | trimer | SQAIGILELTSIAKGMELGDAMLKSANVDLLVSKTISPGKFLLMLGGDIGAI QQAIETGTSQAGEMLVDSLVLANIHPSVLPAISGLNSVDKRQAVGIVETWSV AACISAADLAVKGSNVTLVRVHMAFGIGGKCYMVVAGDVLDVAAAVATASLA AGAKGLLVYAS11PRPHEAMWRQMVEG | |
| T33-09A SEQ ID NO: 43 | trimer | EEVVLITVPSALVAVKIAHALVEERLAACVNIVPGLTSIYRWQGSVVSDHEL LLLVKTTTHAFPKLKERVKALHPYTVPEIVALPIAEGNREYLDWLRENTG | |
| T33-09B SEQ ID NO: 44 | trimer | VRGIRGAITVEEDTPAAILAATIELLLKMLEANGIQSYEELAAVIFTVTEDL TSAFPAEAARLIGMHRVPLLSAREVPVPGSLPRVIRVLALWNTDTPQDRVRH VYLNEAVRLRPDLESAQ | |
| T33-15A SEQ ID NO: 45 | trimer | SKAKIGIVTVSDRASAGITADISGKAIILALNLYLTSEWEPIYQVIPDEQDV IETTLIKMADEQDCCLIVTTGGTGPAKRDVTPEATEAVCDRMMPGFGELMRA ESLKEVPTAILSRQTAGLRGDSLIVNLPGDPASISDCLLAVFPAIPYCIDLM EGPYLECNEAMIKPFRPKAK | |
| T33-15B SEQ ID NO: 46 | trimer | VRGIRGAITVNSDTPTSIIIATILLLEKMLEANGIQSYEELAAVIFTVTEDL TSAFPAEAARQIGMHRVPLLSAREVPVPGSLPRVIRVLALWNTDTPQDRVRH VYLSEAVRLRPDLESAQ | |
| T33-21A SEQ ID NO: 47 | trimer | RITTKVGDKGSTRLFGGEEVWKDSPIIEANGTLDELTSFIGEAKHYVDEEMK GILEEIQNDIYKIMGEIGSKGKIEGISEERIAWLLKLILRYMEMVNLKSFVL PGGTLESAKLDVCRTIARRALRKVLTVTREFGIGAEAAAYLLALSDLLFLLA RVIEIEKNKLKEVRS | |
| T33-21B SEQ ID NO: 48 | trimer | PHLVIEATANLRLETSPGELLEQANKALFASGQFGEADIKSRFVTLEAYRQG TAAVERAYLHACLSILDGRDIATRTLLGASLCAVLAEAVAGGGEEGVQVSVE VREMERLSYAKRVVARQR | |
| T33-28A SEQ ID NO: 49 | trimer | ESVNTSFLSPSLVTIRDFDNGQFAVLRIGRTGFPADKGDIDLCLDKMIGVRA AQIFLGDDTEDGFKGPHIRIRCVDIDDKHTYNAMVYVDLIVGTGASEVERET AEEEAKLALRVALQVDIADEHSCVTQFEMKLREELLSSDSFHPDKDEYYKDF L | |
| T33-28B SEQ ID NO: 50 | trimer | PVIQTFVSTPLDHHKRLLLAIIYRIVTRVVLGKPEDLVMMTFHDSTPMHFFG STDPVACVRVEALGGYGPSEPEKVTSIVTAAITAVCGIVADRIFVLYFSPLH CGWNGTNF | |
| T33-31A SEQ ID NO: 51 | trimer | EEWLITVPSALVAVKIAHALVEERLAACVNIVPGLTSIYREEGSWSDHEL LLLVKTTTDAFPKLKERVKELHPYEVPEIVALPIAEGNREYLDWLRENTG | |
| I53-50A ACys SEQ ID NO: 53 | trimer | EELFKKHKIVAVLRANSVEEAIEKAVAVFAGGVHLIEITFTVPDADTVIFAL SVLKEKGAIIGAGTVTSVEQARKAVESGAEFIVSPHLDEEISQFAKEKGVFY MPGVMTPTELVKAMKLGHTILKLFPGEWGPQFVKAMKGPFPNVKFVPTGGV NLDNVAEWFKAGVLAVGVGSALVKGTPDEVREKAKAFVEKIRGATE | |
| T33_dn2A SEQ ID NO: 135 | | NLAEKMYKAGNAMYRKGQYTIAIIAYTLALLKDPNNAEAWYNLGNAAYKKGE YDEAIEAYQKALELDPNNAEAWYNLGNAYYKQGDYDEAIEYYKKALRLDPRN VDAIENLIEAEEKQG | |
| T33_dn2B SEQ ID NO: 136 | | EEAELAYLLGELAYKLGEYRIAIRAYRIALKRDPNNAEAWYNLGNAYYKQGD YREAIRYYLRALKLDPENAEAWYNLGNALYKQGKYDLAIIAYQAALEEDPNN AEAKQNLGNAKQKG | |
| T33_dn5A SEQ ID NO: 137 | | NSAEAMYKMGNAAYKQGDYILAIIAYLLALEKDPNNAEAWYNLGNAAYKQGD YDEAIEYYQKALELDPNNAEAWYNLGNAYYKQGDYDEAIEYYEKALELDPNN AEALKNLLEAIAEQD | |

TABLE 1-continued

| Name | Component Multimer | Amino Acid Sequence | Identified interface residues |
|---|---|---|---|
| T33_dn5A SEQ ID NO: 138 | | TDPLAVILYIAILKAEKSIARAKAAEALGKIGDERAVEPLIKALKDEDALVR AAAADALGQIGDERAVEPLIKALKDEEGLVRASAALALGQIGDERAVQPLIK ALTDERDLVRVAAAVALGRIGDEKAVRPLIIVLKDEEGEVREAAALALGSIG GERVRAAMEKLAERGTGFARKVAVNYLETHK | |
| T33_dn10A SEQ ID NO: 139 | | EEAELAYLLGELAYKLGEYRIAIRAYRIALKRDPNNAEAWYNLGNAYYKQGD YDEAIEYYQKALELDPNNAEAWYNLGNAYYKQGDYDEAIEYYEKALELDPEN LEALQNLLNAMDKOG | |
| T33_dn10B SEQ ID NO: 140 | | IEEVVAEMIDILAESSKKSIEELARAADNKTTEKAVAEAIEEIARLATAAIQ LIEALAKNLASEEFMARAISAIAELAKKAIEAIYRLADNHTTDTFMARAIAA IANLAVTAILAIAALASNHTTEEFMARAISAIAELAKKAIEAIYRLADNHTT DKFMAAAIEAIALLATLAILAIALLASNHTTEKFMARAIMAIAILAAKAIEA IYRIADNHTSPTYIEKAIEAIEKIARKAIKAIEMLAKNITTEEYKEKAKKII DIIRKLAKMAIKKLEDNRT | |
| I53_dn5A SEQ ID NO: 141 | | KYDGSKLRIGILHARWNAEIILALVLGALKRLQEFGVKRENIIIETVPGSFE LPYGSKLFVEKQKRLGKPLDAIIPIGVLIKGSTMHFEYICDSTTHQLMKLNF ELGIPVIFGVLTCLTDEQAEARAGLIEGKMHNHGEDWGAAAVEMATKFN | |
| I53_dn5B SEQ ID NO: 142 | | EEAELAYLLGELAYKLGEYRIAIRAYRIALKRDPNNAEAWYNLGNAYYKQGR YREAIEYYQKALELDPNNAEAWYNLGNAYYERGEYEEAIEYYRKALRLDPNN ADAMQNLLNAKMREE | |

Table 1 provides the amino acid sequence of the first polypeptide and second polypeptides of embodiments of the present disclosure. In each case, the pairs of sequences together form an I53 multimer with icosahedral symmetry. The right hand column in Table 1 identifies the residue numbers in each illustrative polypeptide that were identified as present at the interface of resulting assembled virus-like particles (i.e.: "identified interface residues"). As can be seen, the number of interface residues for the illustrative polypeptides of SEQ ID NO:1-34 range from 4-13. In various embodiments, the first polypeptide and second polypeptides comprise an amino acid sequence that is at least 75%, 80%, 85%, 90%, 91%, 92%, 93%, 94%, 95%, 96%, 97%, 98%, or 99% identical over its length, and identical at least at 1, 2, 3, 4, 5, 6, 7, 8, 9, 10, 11, 12, or 13 identified interface positions (depending on the number of interface residues for a given polypeptide), to the amino acid sequence of a polypeptide selected from the group consisting of SEQ ID NOS: 1-34. SEQ ID NOs: 35-51 represent other amino acid sequences of the first polypeptide and second polypeptides from embodiments of the present disclosure. In other embodiments, the first polypeptide and/or second polypeptides comprise an amino acid sequence that is at least 75%, 80%, 85%, 90%, 91%, 92%, 93%, 94%, 95%, 96%, 97%, 98%, or 99% identical over its length, and identical at least at 20%, 25%, 33%, 40%, 50%, 60%, 70%, 75%, 80%, 90%, or 100% of the identified interface positions, to the amino acid sequence of a polypeptide selected from the group consisting of SEQ ID NOS:1-51.

As is the case with proteins in general, the polypeptides are expected to tolerate some variation in the designed sequences without disrupting subsequent assembly into virus-like particles: particularly when such variation comprises conservative amino acid substitutions. As used here, "conservative amino acid substitution" means that: hydrophobic amino acids (Ala, Cys, Gly, Pro, Met, Val, Ile, Leu) can only be substituted with other hydrophobic amino acids; hydrophobic amino acids with bulky side chains (Phe, Tyr, Trp) can only be substituted with other hydrophobic amino acids with bulky side chains; amino acids with positively charged side chains (Arg, His, Lys) can only be substituted with other amino acids with positively charged side chains; amino acids with negatively charged side chains (Asp, Glu) can only be substituted with other amino acids with negatively charged side chains; and amino acids with polar uncharged side chains (Ser, Thr, Asn, Gln) can only be substituted with other amino acids with polar uncharged side chains.

In various embodiments of the VLPs of the invention, the first polypeptide and second polypeptides, or the vice versa, comprise polypeptides with the amino acid sequence selected from the following pairs, or modified versions thereof (i.e., permissible modifications as disclosed for the polypeptides of the invention: isolated polypeptides comprising an amino acid sequence that is at least 75%, at least 80%, at least 85%, at least 90%, at least 95%, at least 99%, at least 100% over its length, and/or identical at least at one identified interface position, to the amino acid sequence indicated by the SEQ ID NO):

SEQ ID NO:1 and SEQ ID NO:2 (I53-34A and I53-34B);
SEQ ID NO:3 and SEQ ID NO:4 (I53-40A and I53-40B);
SEQ ID NO:3 and SEQ ID NO:24 (I53-40A and I53-40B.1);
SEQ ID NO:23 and SEQ ID NO:4 (I53-40A.1 and I53-40B);
SEQ ID NO:35 and SEQ ID NO:36 (I53-40A genus and I53-40B genus);
SEQ ID NO:5 and SEQ ID NO:6 (I53-47A and I53-47B);
SEQ ID NO:5 and SEQ ID NO:27 (I53-47A and I53-47B.1);
SEQ ID NO:5 and SEQ ID NO:28 (I53-47A and I53-47B.1NegT2);
SEQ ID NO:25 and SEQ ID NO:6 (I53-47A.1 and I53-47B);
SEQ ID NO:25 and SEQ ID NO:27 (I53-47A.1 and I53-47B.1);

SEQ ID NO:25 and SEQ ID NO:28 (I53-47A.1 and I53-47B.1NegT2);
SEQ ID NO:26 and SEQ ID NO:6 (I53-47A.1NegT2 and I53-47B);
SEQ ID NO:26 and SEQ ID NO:27 (I53-47A.1NegT2 and I53-47B.1);
SEQ ID NO:26 and SEQ ID NO:28 (I53-47A.1NegT2 and I53-47B.1NegT2);
SEQ ID NO:37 and SEQ ID NO:38 (I53-47A genus and I53-47B genus);
SEQ ID NO:7 and SEQ ID NO:8 (I53-50A and I53-50B);
SEQ ID NO:7 and SEQ ID NO:32 (I53-50A and I53-50B.1);
SEQ ID NO:7 and SEQ ID NO:33 (I53-50A and I53-50B.1NegT2);
SEQ ID NO:7 and SEQ ID NO:34 (I53-50A and I53-50B.4PosT1);
SEQ ID NO:29 and SEQ ID NO:8 (I53-50A.1 and I53-50B);
SEQ ID NO:29 and SEQ ID NO:32 (I53-50A.1 and I53-50B.1);
SEQ ID NO:29 and SEQ ID NO:33 (I53-50A.1 and I53-50B.1NegT2);
SEQ ID NO:29 and SEQ ID NO:34 (I53-50A.1 and I53-50B.4PosT1);
SEQ ID NO:30 and SEQ ID NO:8 (I53-50A.1NegT2 and I53-50B);
SEQ ID NO:30 and SEQ ID NO:32 (I53-50A.1NegT2 and I53-50B.1);
SEQ ID NO:30 and SEQ ID NO:33 (I53-50A.1NegT2 and I53-50B.1NegT2);
SEQ ID NO:30 and SEQ ID NO:34 (I53-50A.1NegT2 and I53-50B.4PosT1);
SEQ ID NO:31 and SEQ ID NO:8 (I53-50A.1PosT1 and I53-50B);
SEQ ID NO:31 and SEQ ID NO:32 (I53-50A.1PosT1 and I53-50B.1);
SEQ ID NO:31 and SEQ ID NO:33 (I53-50A.1PosT1 and I53-50B.1NegT2);
SEQ ID NO:31 and SEQ ID NO:34 (I53-50A.1PosT1 and I53-50B.4PosT1);
SEQ ID NO:39 and SEQ ID NO:40 (I53-50A genus and I53-50B genus);
SEQ ID NO:9 and SEQ ID NO:10 (I53-51A and I53-51B);
SEQ ID NO:11 and SEQ ID NO:12 (I52-03A and I52-03B);
SEQ ID NO:13 and SEQ ID NO:14 (I52-32A and I52-32B);
SEQ ID NO:15 and SEQ ID NO:16 (I52-33A and I52-33B)
SEQ ID NO:17 and SEQ ID NO:18 (I32-06A and I32-06B);
SEQ ID NO:19 and SEQ ID NO:20 (I32-19A and I32-19B);
SEQ ID NO:21 and SEQ ID NO:22 (I32-28A and I32-28B);
SEQ ID NO:23 and SEQ ID NO:24 (I53-40A.1 and I53-40B.1);
SEQ ID NO:41 and SEQ ID NO:42 (T32-28A and T32-28B);
SEQ ID NO:43 and SEQ ID NO:44 (T33-09A and T33-09B);
SEQ ID NO:45 and SEQ ID NO:46 (T33-15A and T33-15B);
SEQ ID NO:47 and SEQ ID NO:48 (T33-21A and T33-21B);
SEQ ID NO:49 and SEQ ID NO:50 (T33-28A and T32-28B); and
SEQ ID NO:51 and SEQ ID NO:44 (T33-31A and T33-09B (also referred to as T33-31B))

In some embodiments, the one or more hMPV F proteins, or antigenic fragments thereof, are expressed as a fusion protein with the first multimerization domain. In some embodiments, the first multimerization domain and the hMPV F protein ectodomain are joined by a linker sequence. In some embodiments, the linker sequence comprises a foldon, wherein the foldon sequence is EKAAKAEEAARK (SEQ ID NO: 125).

Non-limiting examples of designed protein complexes useful in protein-based VLPs of the present disclosure include those disclosed in U.S. Pat. No. 9,630,994; Int'l Pat. Pub No. WO2018187325A1; U.S. Pat. Pub. No. 2018/0137234 A1; U.S. Pat. Pub. No. 2019/0155988 A2, each of which is incorporated herein in its entirety.

In various embodiments of the VLPs of the disclosure, the multimerization domains are polypeptides with the amino acid sequence selected from the following pairs, or modified versions thereof (i.e., permissible modifications as disclosed for the polypeptides of the invention: isolated polypeptides comprising an amino acid sequence that is at least 75%, at least 80%, at least 85%, at least 90%, at least 95%, at least 99%, at least 100% over its length, and/or identical at least at one identified interface position, to the amino acid sequence indicated by the SEQ ID NO):

SEQ ID NO: 135 and SEQ ID NO: 136 (T33_dn2A and T33_dn2B);
SEQ ID NO: 137 and SEQ ID NO: 138 (T33_dn5A and T33_dn5B);
SEQ ID NO: 139 and SEQ ID NO: 140 (T33_dn10A and T33_dn10B); or
SEQ ID NO: 141 and SEQ ID NO: 142 (I53_dn5A and I53_dn5B).

Antigenic Proteins

The present disclosure provides protein-based VLP vaccines for hMPV in humans or animals (in particular pets, agricultural animals, and any animal linked to spread of the disease). The present disclosure relates to incorporation of any of antigenic fragment of hMPV F protein—e.g., the ectodomain or an antigenic fragment thereof-into VLP vaccines. Guidance is particularly available from studies of the immune response to infection or vaccination, such as isolation of binding or neutralizing antibodies, genetic analysis of F protein sequence, structural studies of antigenic proteins and antibodies, and most particularly clinical and veterinary experience with subunit vaccines. Subunit vaccine for hMPV can be adapted for use with the VLPs of the present disclosure by employing the display modalities provided above. The disclosure refers to the ectodomain of hMPV F but it will be understood that portions of the transmembrane domain may be included.

Figure 2:
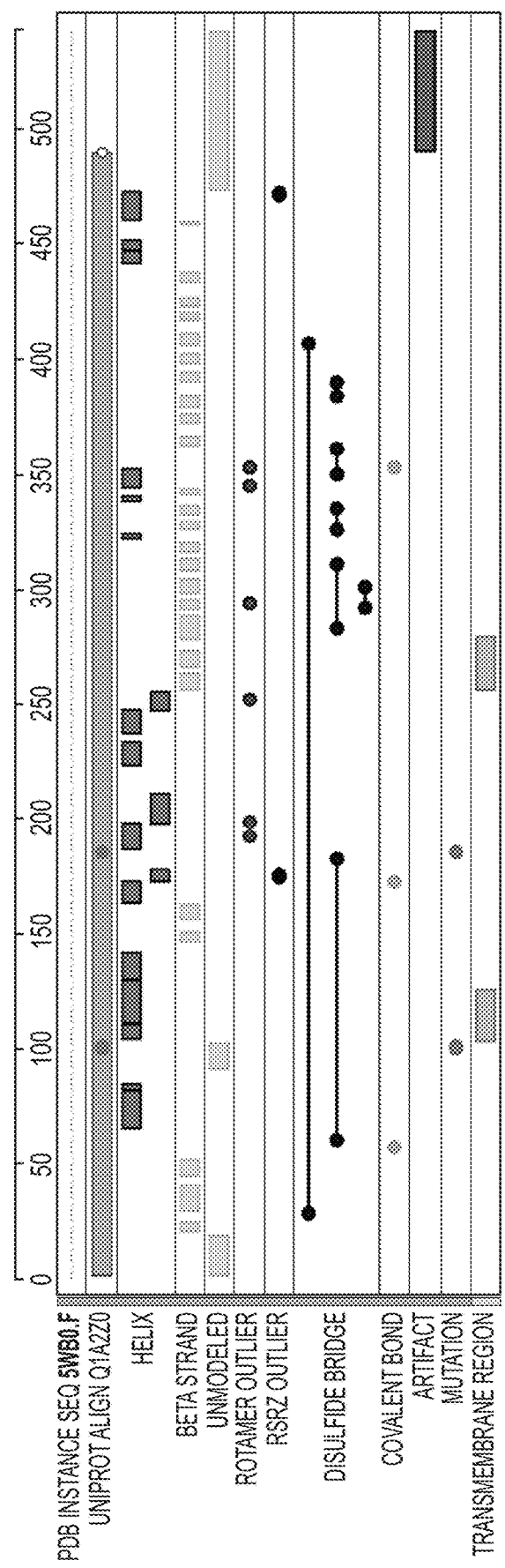
FIG. 2 shows a secondary structure map of hMPV F protein in the pre-fusion configuration (PDB ID: 5WB0; diagram generated at www.rcsb.org).

The term "antigenic fragment" refers to any fragment of a protein that generates an immune response (humoral or T cell response) to the protein in vivo. The antigenic fragment may be a linear epitope, discontinuous epitope, or a conformation epitope (e.g., a folded domain). The antigenic fragment may preserve the secondary, tertiary, and/or quaternary structure of the full-length protein. In some embodiments, the antigenic fragment comprises a neutralizing epitope. In such cases, the VLP may generate a neutralizing antibody response. Antigenic fragments may be designed computationally, such as by predicting the secondary structure and rationally removing N- or C-terminal unstructured regions or internally loops, or entire structural elements (alpha helices and/or beta sheets). FIG. 2 provides an illustrative secondary structure map. In some embodiments, the ectodomain comprises a truncation or deletion of some or all of the N-terminal signal peptide (e.g., MSWKVVIIFSLLITPQHGL (SEQ ID NO: 133) or MSWKVMIIISLLITPQHGL (SEQ ID NO: 134).

In some embodiments, the hMPV F protein ectodomain is a C-terminal truncation. In some embodiments, the hMPV F protein ectodomain sequence terminates at residue 470, 471, 472, 473, 474, 475, 476, 477, 478, 479, 480, 481, 482, 483, 484, 485, 486, 487, 488, 489, or 490 of the native sequence.

The native sequence of the A strain hMPV F protein (GenBank AY145297) is shown below with the signal sequence underlined and italicized and the transmembrane and intracellular portion underlined (SEQ ID NO: 56):

```
                                         (SEQ ID NO: 56)
  1 MSWKVVIIFS LLITPQHGLK ESYLEESCST ITEGYLSVLR

41 TGWYTNVFTL EVGDVENLTC SDGPSLIKTE LDLTKSALRE

81 LKTVSADQLA REEQIENPRQ SRFVLGAIAL GVATAAAVTA

121 GVAIAKTIRL ESEVTAIKNA LKTTNEAVST LGNGVRVLAT

161 AVRELKDFVS KNLTRAINKN KCDIDDLKMA VSFSQFNRRF

201 LNVVRQFSDN AGITPAISLD LMTDAELARA VSNMPTSAGQ

241 IKLMLENRAM VRRKGFGILI GVYGSSVIYM VQLPIFGVID

281 TPCWIVKAAP SCSGKKGNYA CLLREDQGWY CQNAGSTVYY

321 PNEKDCETRG DHVFCDTAAG INVAEQSKEC NINISTTNYP

361 CKVSTGRHPI SMVALSPLGA LVACYKGVSC SIGSNRVGII

401 KQLNKGCSYI TNQDADTVTI DNTVYQLSKV EGEQHVIKGR

441 PVSSSFDPIK FPEDQFNVAL DQVFENIENS QALVDQSNRI

481 LSSAEKGNTG FIIVIILIAV LGSSMILVSI FIIIKKTKKP

521 TGAPPELSGV TNNGFIPHS
```

The native signal sequence is post-translationally cleaved when the protein is expressed. The native signal sequence may be replaced with another signal sequence for expression of the ectodomain, or in some embodiments no signal sequence is used. Thus, in some embodiments the hMPV F protein ectodomain is SE ID NO: 57, or a variant thereof:

```
                                         (SEQ ID NO: 57)
  1                     K ESYLEESCST ITEGYLSVLR

41 TGWYTNVFTL EVGDVENLTC SDGPSLIKTE LDLTKSALRE

81 LKTVSADQLA REEQIENPRQ SRFVLGAIAL GVATAAAVTA

121 GVAIAKTIRL ESEVTAIKNA LKTTNEAVST LGNGVRVLAT

161 AVRELKDFVS KNLTRAINKN KCDIDDLKMA VSFSQFNRRF

201 LNVVRQFSDN AGITPAISLD LMTDAELARA VSNMPTSAGQ

241 IKLMLENRAM VRRKGFGILI GVYGSSVIYM VQLPIFGVID

281 TPCWIVKAAP SCSGKKGNYA CLLREDQGWY CQNAGSTVYY

321 PNEKDCETRG DHVFCDTAAG INVAEQSKEC NINISTTNYP

361 CKVSTGRHPI SMVALSPLGA LVACYKGVSC SIGSNRVGII

401 KQLNKGCSYI TNQDADTVTI DNTVYQLSKV EGEQHVIKGR

441 PVSSSFDPIK FPEDQFNVAL DQVFENIENS QALVDQSNRI

481 LSSAEKGNTG F

521
```

In some embodiments, the hMPV F protein ectodomain shares at least 90%, 95%, 96%, 97%, 98%, 99%, or 100% sequence identity to SEQ ID NO: 57, or an antigenic fragment thereof.

Further hMPV F protein sequences are provided in Table 2. In some embodiments, the hMPV F protein ectodomain shares at least 90%, 95%, 96%, 97%, 98%, 99%, or 100% sequence identity to an ectodomain in Table 2, or an antigenic fragment thereof.

Various signal sequences can be used, paired with the native ectodomain sequence or swapped between different hMPV sequences. Thus, in some embodiments, the antigen comprises a sequence that shares at least 90%, 95%, 96%, 97%, 98%, 99%, or 100% sequence identity to a signal sequence in Table 2.

The hMPV F protein may comprise one or more substitutions.

Illustrative substitutions include A185P, Q100R, S101R, T127C, N153C, V84C, A140C, A147C, A249C, N97G, P98G, R99G, Q100G, S101G, R102G, A63C, K188C, K450C, S470C, G106 deletion, A113C, A120C, A339C, Q426C, T160F, Q100K, S101A, I177L, K450A, S470A, G294E, T365C, V463C, L219K, H368N, and/or V231I relative to SEQ ID NO: 57. Thus, in various embodiments, the hMPV F protein ectodomain comprises one or more substitutions selected from this list.

Illustrative substitutions include V84C, A140C, A147C, N97G, P98G, Q100G, S101G, R102G, A63C, K188C, K450C, S470C, R99G, A113C, A120C, A339C, Q426C, T160F, Q100K, S101A, Q100R, S101R, G106 deletion, S101R, A185P, I177L, and G294E relative to SEQ ID NO: 57. Thus, in various embodiments, the hMPV F protein ectodomain comprises one or more substitutions selected from this list.

Illustrative substitutions include V84C, A140C, A147C, N97G, P98G, Q100G, S101G, R102G, A63C, K188C, K450C, S470C, R99G, A113C, A120C, A339C, Q426C, T160F, Q100K, S101A, Q100R, S101R, G106 deletion, S101R, A185P, I177L, and G294E. Thus, in various embodiments, the hMPV F protein ectodomain comprises two or more substitutions selected from this list.

Illustrative substitutions include A185P, Q100R, S101R, T127C, N153C, T365C, V463C, L219K, V231I, G294E, N153C, N97G, P98G, R99G, Q100G, S101G, and R102G. Thus, in various embodiments, the hMPV F protein ectodomain comprises one or more substitutions selected from this list.

Illustrative substitutions include A185P, Q100R, S101R, T127C, N153C, T365C, V463C, L219K, V231I, G294E, N153C, N97G, P98G, R99G, Q100G, S101G, and R102G. Thus, in various embodiments, the hMPV F protein ectodomain comprises two or more substitutions selected from this list.

In some embodiments, the hMPV F protein ectodomain comprises the substitutions Q100R and S101R. In some embodiments, the hMPV F protein ectodomain comprises the substitutions A185P, Q100R, and S101R. In some embodiments, the hMPV F protein ectodomain comprises the substitutions A185P, T127C, N153C, Q100R, and S101R. In some embodiments, the hMPV F protein ectodomain comprises the substitutions V84C, A140C, A147C, A249C, N97G, P98G, R99G, Q100G, S101G, and R102G. In some embodiments, the hMPV F protein ectodomain comprises the substitutions A63C, A140C, A147C, K188C, K450C, S470C, N97G, P98G, R99G, Q100G, S101G, and R102G. In some embodiments, the hMPV F protein ectodomain comprises the substitutions and deletion A63C, A140C, A147C, K188C, G106 deletion, N97G, P98G, R99G, Q100G, S101G, and R102G. In some embodiments, the hMPV F protein ectodomain comprises the substitutions A113C, A120C, A339C, Q426C, T160F, I177L, Q100K, and S101A. In some embodiments, the hMPV F protein ectodomain comprises the substitutions V84C, A140C, A147C, A249C, Q100R, and S101R. In some embodiments, the hMPV F protein ectodomain comprises the substitutions A63C, A140C, A147C, K188C, K450C, S470C, Q100R, and S101R. In some embodiments, the hMPV F protein ectodomain comprises the substitutions and deletion A63C, A140C, A147C, K188C, G106 deletion, Q100R, and S101R. In some embodiments, the hMPV F protein ectodomain comprises the substitutions A113C, A120C, A339C, Q426C, T160F, I177L, Q100R, and S101R. In some embodiments, the hMPV F protein ectodomain comprises the substitutions A185P, A113C, A339C, Q100R, and S101R. In some embodiments, the hMPV F protein ectodomain comprises the substitutions A185P, T160F, I177L, Q100R, and S101R. In some embodiments, the hMPV F protein ectodomain comprises the substitutions A185P, A113C, A339C, T160F, I177L, Q100R, and S101R. In some embodiments, the hMPV F protein ectodomain comprises the substitutions A63C, K188C, N97G, P98G, R99G, Q100G, S101G, and R102G. In some embodiments, the hMPV F protein ectodomain comprises the substitutions A63C, K188C, K450A, S470A, N97G, P98G, R99G, Q100G, S101G, and R102G. In some embodiments, the hMPV F protein ectodomain comprises the substitutions A63C, A140C, A147C, K188C, G294E, N97G, P98G, R99G, Q100G, S101G, and R102G. In some embodiments, the hMPV F protein ectodomain comprises the substitutions A63C, A140C, A147C, K188C, K450C, S470C, N97G, P98G, R99G, Q100G, S101G, R102G, and G294E. In some embodiments, the hMPV F protein ectodomain comprises the substitutions A63C, K188C, N97G, P98G, R99G, Q100G, S101G, R102G, and G294E. In some embodiments, the hMPV F protein ectodomain comprises the substitutions T127C, N153C, T365C, V463C, A185P, L219K, V231I, G294E, H368N, Q100R, and S101R. In some embodiments, the hMPV F protein ectodomain comprises the substitutions A63C, A140C, A147C, K188C, K450C, S470C, N97G, P98G, R99G, Q100G, S101G, and R102G. In some embodiments, the hMPV F protein ectodomain comprises the substitutions V84C, A140C, A147C, A249C, N97G, P98G, R99G, Q100G, S101G, and R102G. In some embodiments, the hMPV F protein ectodomain comprises the substitutions T127C, N153C, T365C, V463C, A185P, L219K, V231I, G294E, N97G, P98G, R99G, Q100G, S101G, H368N, and R102G.

Further illustrative amino acid substitutions are provided in Table 2 In various embodiments, the ectodomain comprises one or more substitutions selected from substitutions and alternative substitutions listed in Table 2 In some embodiments, the substitutions has the intended effect on the VLP, it being understood that the intended effect is not achieved in every embodiment of the VLP having that substitution. In some embodiments, the intended effect is increased expression in a production cell line (Mas et al. PLoS Pathog. 12: e1005859 (2016)). In some embodiments, the intended effect is to stabilize a post-fusion or pre-fusion form of the hMPV F protein ectodomain (Battles et al. Nat Commun. 8:1528 (2017)). In some embodiments, the intended effect is binding neutralizing antibodies against hMPV F protein. The antigen may further comprise a Leucine at the N-terminus.

TABLE 2

Illustrative hMPV Protein F Ectodomain Antigenic Variants

| SEQ ID NO: | Ectodomain | hMPV Antigen Mutations | C-term F protein Termination Residue |
|---|---|---|---|
| 58 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKTIRLESEVTAIKNALKKTNEAV STLGNGVRVLATAVRELKDFVSKNLTRAINKNKCDIPDLKMAV SFSQFNRRFLNVVRQFSDNAGITPAISLDLMTDAELARAVSNM PTSAGQIKLMLENRAMVRRKGFGFLIGVYGSSVIYMVQLPIFG VIDTPCWIVKAAPSCSGKKGNYACLLREDQGWYCQNAGSTVYY PNEKDCETRGDHVFCDTAAGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQALVDQSNRIL | A185P, Q100R, S101R | 481 |
| 59 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKTIRLESEVTAIKNALKKTNEAV STLGNGVRVLATAVRELKDFVSKNLTRAINKNKCDIPDLKMAV SFSQFNRRFLNVVRQFSDNAGITPAISLDLMTDAELARAVSNM PTSAGQIKLMLENRAMVRRKGFGFLIGVYGSSVIYMVQLPIFG VIDTPCWIVKAAPSCSGKKGNYACLLREDQGWYCQNAGSTVYY PNEKDCETRGDHVFCDTAAGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQA | A185P, Q100R, S101R | 472 |

TABLE 2-continued

Illustrative hMPV Protein F Ectodomain Antigenic Variants

| SEQ ID NO: | Ectodomain | hMPV Antigen Mutations | C-term F protein Termination Residue |
|---|---|---|---|
| 60 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKTIRLESEVTAIKNALKKTNEAV STLGNGVRVLATAVRELKDFVSKNLTRAINKNKCDIPDLKMAV SFSQFNRRFLNVVRQFSDNAGITPAISLDLMTDAELARAVSNM PTSAGQIKLMLENRAMVRRKGFGFLIGVYGSSVIYMVQLPIFG VIDTPCWIVKAAPSCSGKKGNYACLLREDQGWYCQNAGSTVYY PNEKDCETRGDHVFCDTAAGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQALVDQSNRILSSAEKGNT | A185P, Q100R, S101R | 489 |
| 61 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKTIRLESEVTAIKNALKKTNEAV STLGNGVRVLATAVRELKDFVSKNLTRAINKNKCDIADLKMAV SFSQFNRRFLNVVRQFSDNAGITPAISLDLMTDAELARAVSNM PTSAGQIKLMLENRAMVRRKGFGFLIGVYGSSVIYMVQLPIFG VIDTPCWIVKAAPSCSGKKGNYACLLREDQGWYCQNAGSTVYY PNEKDCETRGDHVFCDTAAGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQA | Q100R, S101R | 472 |
| 62 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKCIRLESEVTAIKNALKKTNEAV STLGCGVRVLATAVRELKDFVSKNLTRAINKNKCDIPDLKMAV SFSQFNRRFLNVVRQFSDNAGITPAISLDLMTDAELARAVSNM PTSAGQIKLMLENRAMVRRKGFGILIGVYGSSVIYMVQLPIFG VIDTPCWIVKAAPSCSGKKGNYACLLREDQGWYCQNAGSTVYY PNEKDCETRGDHVFCDTAAGINVAEQSKECNINISTTNYPCKV STGRNPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQA | A185P, T127C, N153C, Q100R, S101R | 472 |
| 63 | KESYLEESCSTITEGYLSVLRTGWYTNVFTLEVGDVENLTCTD GPSLIKTELDLTKSALRELKTCSADQLAREEQIEGGGGGGFVL GAIALGVATAAAVTAGIAIAKTIRLESEVNAIKGCLKTTNECV STLGNGVRVLATAVRELKEFVSKNLTSAINKNKCDIADLKMAV SFSQFNRRFLNVVRQFSDNAGITPAISLDLMTDAELARAVSYM PTSAGQIKLMLENRCMVRRKGFGILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI KFPEDQFNVALDQVFESIENSQA | V84C, A140C, A147C, A249C, N97G, P98G, R99G, Q100G, S101G, R102G | 472 |
| 64 | KESYLEESCSTITEGYLSVLRTGWYTNVFTLEVGDVENLTCTD GPSLIKTELDLTKSALRELKTCSADQLAREEQIEGGGGGGFVL GAIALGVATAAAVTAGIAIAKTIRLESEVNAIKGCLKTTNECV STLGNGVRVLATAVRELKEFVSKNLTSAINKNKCDIADLKMAV SFSQFNRRFLNVVRQFSDNAGITPAISLDLMTDAELARAVSYM PTSAGQIKLMLENRCMVRRKGFGILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI KFPEDQFNVALDQVFESIENSQALVDQSNKILNSAESAI | V84C, A140C, A147C, A249C, N97G, P98G, R99G, Q100G, S101G, R102G | 488 |
| 65 | KESYLEESCSTITEGYLSVLRTGWYTNVFTLEVGDVENLTCTD CPSLIKTELDLTKSALRELKTVSADQLAREEQIEGGGGGGFVL GAIALGVATAAAVTAGIAIAKTIRLESEVNAIKGCLKTTNECV STLGNGVRVLATAVRELKEFVSKNLTSAINKNKCDIADLCMAV SFSQFNRRFLNVVRQFSDNAGITPAISLDLMTDAELARAVSYM PTSAGQIKLMLENRAMVRRKGFGILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI CFPEDQFNVALDQVFESIENCQA | A63C, A140C, A147C, K188C, K450C, S470C, N97G, P98G, R99G, Q100G, S101G, R102G | 472 |

TABLE 2-continued

Illustrative hMPV Protein F Ectodomain Antigenic Variants

| SEQ ID NO: | Ectodomain | hMPV Antigen Mutations | C-term F protein Termination Residue |
|---|---|---|---|
| 66 | KESYLEESCSTITEGYLSVLRTGWYTNVFTLEVGDVENLTCTD CPSLIKTELDLTKSALRELKTVSADQLAREEQIEGGGGGGFVL GAIALGVATAAAVTAGIAIAKTIRLESEVNAIKGCLKTTNECV STLGNGVRVLATAVRELKEFVSKNLTSAINKNKCDIADLCMAV SFSQFNRRFLNVVRQFSDNAGITPAISLDLMTDAELARAVSYM PTSAGQIKLMLENRAMVRRKGFGILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI CFPEDQFNVALDQVFESIENCQALVDQSNKILNSAESAI | A63C, A140C, A147C, K188C, K450C, S470C, N97G, P98G, R99G, Q100G, S101G, R102G | 488 |
| 67 | KESYLEESCSTITEGYLSVLRTGWYTNVFTLEVGDVENLTCSD CPSLIKTELDLTKSALRELKTVSADQLAREEQIEGGGGGGFVL AIALGVATAAAVTAGVAIAKTIRLESEVTAIKNCLKTTNECVS TLGNGVRVLATAVRELKDFVSKNLTSAINKNKCDIDDLCMAVS FSQFNRRFLNVVRQFSDNAGITPAISLDLMTDAELARAVSNMP TSAGQIKLMLENRAMVRRKGFGILIGVYGSSVIYMVQLPIFGV IDTPCWIIKAAPSCSGKKGNYACLLREDQGWYCQNAGSTVYYP NEKDCETRGDHVFCDTAAGINVAEQSKECNINISTTNYPCKVS TGRHPISMVALSPLGALVACYKGVSCSIGSNRVGIIKQLNKGC SYITNQDADTVTIDNTVYQLSKVEGEQHVIKGRPVSSSFDPIK FPEDQFNVALDQVFENIENSQA | A63C, A140C, A147C, K188C, G106 deleted, N97G, P98G, R99G, Q100G, S101G, R102G | 472 |
| 68 | KESYLEESCSTITEGYLSVLRTGWYTNVFTLEVGDVENLTCSD CPSLIKTELDLTKSALRELKTVSADQLAREEQIEGGGGGGFVL AIALGVATAAAVTAGVAIAKTIRLESEVTAIKNCLKTTNECVS TLGNGVRVLATAVRELKDFVSKNLTSAINKNKCDIDDLCMAVS FSQFNRRFLNVVRQFSDNAGITPAISLDLMTDAELARAVSNMP TSAGQIKLMLENRAMVRRKGFGILIGVYGSSVIYMVQLPIFGV IDTPCWIIKAAPSCSGKKGNYACLLREDQGWYCQNAGSTVYYP NEKDCETRGDHVFCDTAAGINVAEQSKECNINISTTNYPCKVS TGRHPISMVALSPLGALVACYKGVSCSIGSNRVGIIKQLNKGC SYITNQDADTVTIDNTVYQLSKVEGEQHVIKGRPVSSSFDPIK FPEDQFNVALDQVFENIENSQALVDQSNRILSSAESAI | A63C, A140C, A147C, K188C, G106 deleted, N97G, P98G, R99G, Q100G, S101G, R102G | 488 |
| 69 | KESYLEESCSTITEGYLSVLRTGWYTNVFTLEVGDVENLTCTD GPSLIKTELDLTKSALRELKTVSADQLAREEQIENPRKARFVL GAIALGVCTAAAVTCGIAIAKTIRLESEVNAIKGALKTTNEAV STLGNGVRVLAFAVRELKEFVSKNLTSALNKNKCDIADLKMAV SFSQFNRRFLNVVRQFSDNAGITPAISLDLMTDAELARAVSYM PTSAGQIKLMLENRAMVRRKGFGILIGVYGSSVIYMVQLPIFG VIDTPCWIIKAAPSCSEKDGNYACLLREDQGWYCKNAGSTVYY PNDKDCETRGDHVFCDTACGINVAEQSRECNINISTTNYPCKV STGRHPISMVALSPLGALVACYKGVSCSIGSNRVGIIKQLPKG CSYITNQDADTVTIDNTVYCLSKVEGEQHVIKGRPVSSSFDPI KFPEDQFNVALDQVFESIENSQA | A113C, A120C, A339C, Q426C, T160F, I17L, Q100K, S101A | 472 |
| 70 | KESYLEESCSTITEGYLSVLRTGWYTNVFTLEVGDVENLTCTD GPSLIKTELDLTKSALRELKTVSADQLAREEQIENPRKARFVL GAIALGVCTAAAVTCGIAIAKTIRLESEVNAIKGALKTTNEAV STLGNGVRVLAFAVRELKEFVSKNLTSALNKNKCDIADLKMAV SFSQFNRRFLNVVRQFSDNAGITPAISLDLMTDAELARAVSYM PTSAGQIKLMLENRAMVRRKGFGILIGVYGSSVIYMVQLPIFG VIDTPCWIIKAAPSCSEKDGNYACLLREDQGWYCKNAGSTVYY PNDKDCETRGDHVFCDTACGINVAEQSRECNINISTTNYPCKV STGRHPISMVALSPLGALVACYKGVSCSIGSNRVGIIKQLPKG CSYITNQDADTVTIDNTVYCLSKVEGEQHVIKGRPVSSSFDPI KFPEDQFNVALDQVFESIENSQALVDQSNKILNSAESAI | A113C, A120C, A339C, Q426C, T160F, I177L, Q100K, S101A | 488 |
| 71 | MSWKVMIIISLLITPQHGLKESYLEESCSTITEGYLSVLRTGW YTNVFTLEVGDVENLTCTDGPSLIKTELDLTKSALRELKTCSA DQLAREEQIENPRRRFVLGAIALGVATAAAVTAGIAIAKTIR LESEVNAIKGCLKTTNECVSTLGNGVRVLATAVRELKEFVSKN LTSAINKNKCDIADLKMAVSFSQFNRRFLNVVRQFSDNAGITP AISLDLMTDAELARAVSYMPTSAGQIKLMLENRCMVRRKGFGI LIGVYGSSVIYMVQLPIFGVIDTPCWIIKAAPSCSEKDGNYAC LLREDQGWYCKNAGSTVYYPNDKDCETRGDHVFCDTAAGINVA EQSRECNINISTTNYPCKVSTGRHPISMVALSPLGALVACYKG VSCSIGSNRVGIIKQLPKGCSYITNQDADTVTIDNTVYQLSKV EGEQHVIKGRPVSSSFDPIKFPEDQFNVALDQVFESIENSQA | V84C, A140C, A147C, A249C, Q100R, S101R | 472 |

TABLE 2-continued

Illustrative hMPV Protein F Ectodomain Antigenic Variants

| SEQ ID NO: | Ectodomain | hMPV Antigen Mutations | C-term F protein Termination Residue |
|---|---|---|---|
| 72 | KESYLEESCSTITEGYLSVLRTGWYTNVFTLEVGDVENLTCTD CPSLIKTELDLTKSALRELKTVSADQLAREEQIENPRRRRFVL GAIALGVATAAAVTAGIAIAKTIRLESEVNAIKGCLKTTNECV STLGNGVRVLATAVRELKEFVSKNLTSAINKNKCDIADLCMAV SFSQFNRRFLNVVRQFSDNAGITPAISLDLMTDAELARAVSYM PTSAGQIKLMLENRAMVRRKGFGILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI CFPEDQFNVALDQVFESIENCQA | A63C, A140C, A147C, K188C, K450C, S470C, Q100R, S101R | 472 |
| 73 | KESYLEESCSTITEGYLSVLRTGWYTNVFTLEVGDVENLTCSD CPSLIKTELDLTKSALRELKTVSADQLAREEQIENPRRRRFVL AIALGVATAAAVTAGVAIAKTIRLESEVTAIKNCLKTTNECVS TLGNGVRVLATAVRELKDFVSKNLTSAINKNKCDIDDLCMAVS FSQFNRRFLNVVRQFSDNAGITPAISLDLMTDAELARAVSNMP TSAGQIKLMLENRAMVRRKGFGILIGVYGSSVIYMVQLPIFGV IDTPCWIIKAAPSCSGKKGNYACLLREDQGWYCQNAGSTVYYP NEKDCETRGDHVFCDTAAGINVAEQSKECNINISTTNYPCKVS TGRHPISMVALSPLGALVACYKGVSCSIGSNRVGIIKQLNKGC SYITNQDADTVTIDNTVYQLSKVEGEQHVIKGRPVSSSFDPIK FPEDQFNVALDQVFENIENSQA | A63C, A140C, A147C, K188C, G106 deleted, Q100R, S101R | 472 |
| 74 | KESYLEESCSTITEGYLSVLRTGWYTNVFTLEVGDVENLTCTD GPSLIKTELDLTKSALRELKTVSADQLAREEQIENPRRRRFVL GAIALGVCTAAAVTCGIAIAKTIRLESEVNAIKGALKTTNEAV STLGNGVRVLAFAVRELKEFVSKNLTSALNKNKCDIADLKMAV SFSQFNRRFLNVVRQFSDNAGITPAISLDLMTDAELARAVSYM PTSAGQIKLMLENRAMVRRKGFGILIGVYGSSVIYMVQLPIFG VIDTPCWIIKAAPSCSEKDGNYACLLREDQGWYCKNAGSTVYY PNDKDCETRGDHVFCDTACGINVAEQSRECNINISTTNYPCKV STGRHPISMVALSPLGALVACYKGVSCSIGSNRVGIIKQLPKG CSYITNQDADTVTIDNTVYCLSKVEGEQHVIKGRPVSSSFDPI KFPEDQFNVALDQVFESIENSQA | A113C, A120C, A339C, Q426C, T160F, I177L, Q100R, S101R | 472 |
| 75 | KESYLEESCSTITEGYLSVLRTGWYTNVFTLEVGDVENLTCAD GPSLIKTELDLTKSALRELRTVSADQLAREEQIENPRRRRFVL GAIALGVCTAAAVTAGVAIAKTIRLESEVTAIKNALKKTNEAV STLGNGVRVLATAVRELKDFVSKNLTRAINKNKCDIPDLKMAV SFSQFNRRFLNVVRQFSDNAGITPAISLDLMTDAELARAVSNM PTSAGQIKLMLENRAMVRRKGFGFLIGVYGSSVIYMVQLPIFG VIDTPCWIVKAAPSCSGKKGNYACLLREDQGWYCQNAGSTVYY PNEKDCETRGDHVFCDTACGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQA | A185P, A113C, A339C, Q100R, S101R | 472 |
| 76 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKTIRLESEVTAIKNALKKTNEAV STLGNGVRVLAFAVRELKDFVSKNLTRALNKNKCDIPDLKMAV SFSQFNRRFLNVVRQFSDNAGITPAISLDLMTDAELARAVSNM PTSAGQIKLMLENRAMVRRKGFGFLIGVYGSSVIYMVQLPIFG VIDTPCWIVKAAPSCSGKKGNYACLLREDQGWYCQNAGSTVYY PNEKDCETRGDHVFCDTAAGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQA | A185P, T160F, I177L, Q100R, S101R | 472 |
| 77 | KESYLEESCSTITEGYLSVLRTGWYTNVFTLEVGDVENLTCAD GPSLIKTELDLTKSALRELRTVSADQLAREEQIENPRRRRFVL GAIALGVCTAAAVTAGVAIAKTIRLESEVTAIKNALKKTNEAV STLGNGVRVLAFAVRELKDFVSKNLTRALNKNKCDIPDLKMAV SFSQFNRRFLNVVRQFSDNAGITPAISLDLMTDAELARAVSNM PTSAGQIKLMLENRAMVRRKGFGFLIGVYGSSVIYMVQLPIFG VIDTPCWIVKAAPSCSGKKGNYACLLREDQGWYCQNAGSTVYY PNEKDCETRGDHVFCDTACGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQA | A185P, A113C, A339C, T160F, I177L, Q100R, S101R | 472 |

TABLE 2-continued

Illustrative hMPV Protein F Ectodomain Antigenic Variants

| SEQ ID NO: | Ectodomain | hMPV Antigen Mutations | C-term F protein Termination Residue |
|---|---|---|---|
| 78 | KESYLEESCSTITEGYLSVLRTGWYTNVFTLEVGDVENLTCTD CPSLIKTELDLTKSALRELKTVSADQLAREEQIEGGGGGFVL GAIALGVATAAAVTAGIAIAKTIRLESEVNAIKGALKTTNEAV STLGNGVRVLATAVRELKEFVSKNLTSAINKNKCDIADLCMAV SFSQFNRRFLNVVRQFSDNAGITPAISLDLMTDAELARAVSYM PTSAGQIKLMLENRAMVRRKGFGILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI KFPEDQFNVALDQVFESIENSQA | A63C, K188C, N97G, P98G, R99G, Q100G, S101G, R102G | 472 |
| 79 | KESYLEESCSTITEGYLSVLRTGWYTNVFTLEVGDVENLTCTD CPSLIKTELDLTKSALRELKTVSADQLAREEQIEGGGGGFVL GAIALGVATAAAVTAGIAIAKTIRLESEVNAIKGALKTTNEAV STLGNGVRVLATAVRELKEFVSKNLTSAINKNKCDIADLCMAV SFSQFNRRFLNVVRQFSDNAGITPAISLDLMTDAELARAVSYM PTSAGQIKLMLENRAMVRRKGFGILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI AFPEDQFNVALDQVFESIENAQA | A63C, K188C, K450A, S470A, N97G, P98G, R99G, Q100G, S101G, R102G | 472 |
| 80 | KESYLEESCSTITEGYLSVLRTGWYTNVFTLEVGDVENLTCSD CPSLIKTELDLTKSALRELKTVSADQLAREEQIEGGGGGFVL GAIALGVATAAAVTAGVAIAKTIRLESEVTAIKNCLKTTNECV STLGNGVRVLATAVRELKDFVSKNLTSAINKNKCDIDDLCMAV SFSQFNRRFLNVVRQFSDNAGITPAISLDLMTDAELARAVSNM PTSAGQIKLMLENRAMVRRKGFGILIGVYGSSVIYMVQLPIFG VIDTPCWIIKAAPSCSEKKGNYACLLREDQGWYCQNAGSTVYY PNEKDCETRGDHVFCDTAAGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPI KFPEDQFNVALDQVFENIENSQA | A63C, A140C, A147C, K188C, G294E, N97G, P98G, R99G, Q100G, S101G, R102G | 472 |
| 81 | KESYLEESCSTITEGYLSVLRTGWYTNVFTLEVGDVENLTCAD CPSLIKTELDLTKSALRELRTVSADQLAREEQIEGGGGGFVL GAIALGVATAAAVTAGVAIAKTIRLESEVTAIKNCLKKTNECV STLGNGVRVLATAVRELKDFVSKNLTRAINKNKCDIADLCMAV SFSQFNRRFLNVVRQFSDNAGITPAISLDLMTDAELARAVSNM PTSAGQIKLMLENRAMVRRKGFGILIGVYGSSVIYMVQLPIFG VIDTPCWIVKAAPSCSEKKGNYACLLREDQGWYCQNAGSTVYY PNEKDCETRGDHVFCDTAAGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV CFPEDQFNVALDQVFESIENCQA | A63C, A140C, A147C, K188C, K450C, S470C, N97G, P98G, R99G, Q100G, S101G, R102G, G294E | 472 |
| 82 | KESYLEESCSTITEGYLSVLRTGWYTNVFTLEVGDVENLTCAD CPSLIKTELDLTKSALRELRTVSADQLAREEQIEGGGGGFVL GAIALGVATAAAVTAGVAIAKTIRLESEVTAIKNALKKTNEAV STLGNGVRVLATAVRELKDFVSKNLTRAINKNKCDIADLCMAV SFSQFNRRFLNVVRQFSDNAGITPAISLDLMTDAELARAVSNM PTSAGQIKLMLENRAMVRRKGFGLIGVYGSSVIYMVQLPIFG VIDTPCWIVKAAPSCSEKKGNYACLLREDQGWYCQNAGSTVYY PNEKDCETRGDHVFCDTAAGINVAEQSKECNINISTTNYPCKV STGRHPISMVALSPLGALVACYKGVSCSIGSNRVGIIKQLNKG CSYITNQDADTVTIDNTVYQLSKVEGEQHVIKGRPVSSSFDPV KFPEDQFNVALDQVFESIENSQA | A63C, K188C, N97G, P98G, R99G, Q100G, S101G, R102G, G294E | 472 |
| 83 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKCIRLESEVTAIKNALKKTNEAV STLGCGVRVLATAVRELKDFVSKNLTRAINKNKCDIPDLKMAV SFSQFNRRFLNVVRQFSDNAGITPAISKDLMTDAELARAISNM PTSAGQIKLMLENRAMVRRKGFGILIGVYGSSVIYMVQLPIFG VIDTPCWIVKAAPSCSEKKGNYACLLREDQGWYCQNAGSTVYY PNEKDCETRGDHVFCDTAAGINVAEQSKECNINISTTNYPCKV SCGRNPISMVALSPLGALVACYKGVSCSIGSNRVGIIKQLNKG CSYITNQDADTVTIDNTVYQLSKVEGEQHVIKGRPVSSSFDPV KFPEDQFNVALDQCFESIENSQA | T127C, N153C, T365C, V463C, A185P, L219K, V231I, G294E, H368N, Q100R, S101R | 472 |

TABLE 2-continued

Illustrative hMPV Protein F Ectodomain Antigenic Variants

| SEQ ID NO: | Ectodomain | hMPV Antigen Mutations | C-term F protein Termination Residue |
|---|---|---|---|
| 84 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKCIRLESEVTAIKNALKKTNEAV STLGCGVRVLATAVRELKDFVSKNLTRAINKNKCDIPDLKMAV SFSQFNRRFLNVVRQFSDNAGITPAISKDLMTDAELARAISNM PTSAGQIKLMLENRAMVRRKGFILIGVYGSSVIYMVQLPIFG VIDTPCWIVKAAPSCSEKKGNYACLLREDQGWYCQNAGSTVYY PNEKDCETRGDHVFCDTAAGINVAEQSKECNINISTTNYPCKV SCGRNPISMVALSPLGALVACYKGVSCSIGSNRVGIIKQLNKG CSYITNQDADTVTIDNTVYQLSKVEGEQHVIKGRPVSSSFDPV KFPEDQFNVALDQCFESIENSQALVDQSNRILSSAEKGNTG | T127C, N153C, T365C, V463C, A185P, L219K, V231I, G294E, H368N, Q100R, S101R | 490 |
| 85 | KESYLEESCSTITEGYLSVLRTGWYTNVFTLEVGDVENLTCTD CPSLIKTELDLTKSALRELKTVSADQLAREEQIEGGGGGGFVL GAIALGVATAAAVTAGIAIAKTIRLESEVNAIKGCLKTTNECV STLGNGVRVLATAVRELKEFVSKNLTSAINKNKCDIADLCMAV SFSQFNRRFLNVVRQFSDNAGITPAISLDLMTDAELARAVSYM PTSAGQIKLMLENRAMVRRKGFILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI CFPEDQFNVALDQVFESIENCQA | A63C, A140C, A147C, K188C, K450C, S470C, N97G, P98G, R99G, Q100G, S101G, R102G | 472 |
| 86 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKCIRLESEVTAIKNALKKTNEAV STLGCGVRVLATAVRELKDFVSKNLTRAINKNKCDIPDLKMAV SFSQFNRRFLNVVRQFSDNAGITPAISKDLMTDAELARAISNM PTSAGQIKLMLENRAMVRRKGFILIGVYGSSVIYMVQLPIFG VIDTPCWIVKAAPSCSEKKGNYACLLREDQGWYCQNAGSTVYY PNEKDCETRGDHVFCDTAAGINVAEQSKECNINISTTNYPCKV SCGRNPISMVALSPLGALVACYKGVSCSIGSNRVGIIKQLNKG CSYITNQDADTVTIDNTVYQLSKVEGEQHVIKGRPVSSSFDPV KFPEDQFNVALDQCFESIENSQA | T127C, N153C, T365C, V463C, A185P, L219K, V231I, G294E, Q100R, S101R | 472 |
| 87 | KESYLEESCSTITEGYLSVLRTGWYTNVFTLEVGDVENLTCAD GPSLIKTELDLTKSALRELRTVSADQLAREEQIENPRRRRFVL GAIALGVATAAAVTAGVAIAKCIRLESEVTAIKNALKKTNEAV STLGCGVRVLATAVRELKDFVSKNLTRAINKNKCDIPDLKMAV SFSQFNRRFLNVVRQFSDNAGITPAISKDLMTDAELARAISNM PTSAGQIKLMLENRAMVRRKGFILIGVYGSSVIYMVQLPIFG VIDTPCWIVKAAPSCSEKKGNYACLLREDQGWYCQNAGSTVYY PNEKDCETRGDHVFCDTAAGINVAEQSKECNINISTTNYPCKV SCGRNPISMVALSPLGALVACYKGVSCSIGSNRVGIIKQLNKG CSYITNQDADTVTIDNTVYQLSKVEGEQHVIKGRPVSSSFDPV KFPEDQFNVALDQCFESIENSQALVDQSNRILSSAEKGNTG | T127C, N153C, T365C, V463C, A185P, L219K, V231I, G294E, Q100R, S101R | 490 |
| 88 | KESYLEESCSTITEGYLSVLRTGWYTNVFTLEVGDVENLTCTD GPSLIKTELDLTKSALRELKTCSADQLAREEQIEGGGGGGFVL GAIALGVATAAAVTAGIAIAKTIRLESEVNAIKGCLKTTNECV STLGNGVRVLATAVRELKEFVSKNLTSAINKNKCDIADLKMAV SFSQFNRRFLNVVRQFSDNAGITPAISLDLMTDAELARAVSYM PTSAGQIKLMLENRCMVRRKGFILIGVYGSSVIYMVQLPIFG VIDTPCWIIKAAPSCSEKDGNYACLLREDQGWYCKNAGSTVYY PNDKDCETRGDHVFCDTAAGINVAEQSRECNINISTTNYPCKV STGRHPISMVALSPLGALVACYKGVSCSIGSNRVGIIKQLPKG CSYITNQDADTVTIDNTVYQLSKVEGEQHVIKGRPVSSSFDPI KFPEDQFNVALDQVFESIENSQA | V84C, A140C, A147C, A249C, N97G, P98G, R99G, Q100G, S101G, R102G | 472 |
| 89 | KESYLEESCSTITEGYLSVLRTGWYTNVFTLEVGDVENLTCAD GPSLIKTELDLTKSALRELRTVSADQLAREEQIEGGGGGGFVL GAIALGVATAAAVTAGVAIAKTIRLESEVTAIKNALKKTNEAV STLGCGVRVLATAVRELKDFVSKNLTRAINKNKCDIPDLKMAV SFSQFNRRFLNVVRQFSDNAGITPAISKDLMTDAELARAISNM PTSAGQIKLMLENRAMVRRKGFILIGVYGSSVIYMVQLPIFG | T127C, N153C, T365C, V463C, A185P, L219K, | 472 |

TABLE 2-continued

Illustrative hMPV Protein F Ectodomain Antigenic Variants

| SEQ ID NO: | Ectodomain | hMPV Antigen Mutations | C-term F protein Termination Residue |
|---|---|---|---|
|  | VIDTPCWIVKAAPSCSEKKGNYACLLREDQGWYCQNAGSTVYY PNEKDCETRGDHVFCDTAAGINVAEQSKECNINISTTNYPCKV SCGRNPISMVALSPLGALVACYKGVSCSIGSNRVGIIKQLNKG CSYITNQDADTVTIDNTVYQLSKVEGEQHVIKGRPVSSSFDPV KFPEDQFNVALDQCFESIENSQA | V231I, G294E, N97G, P98G, R99G, Q100G, S101G, H368N, R102G |  |
| 90 | KESYLEESCSTITEGYLSVLRTGWYTNVFTLEVGDVENLTCAD GPSLIKTELDLTKSALRELRTVSADQLAREEQIEGGGGGGFVL GAIALGVATAAAVTAGVAIAKCIRLESEVTAIKNALKKTNEAV STLGCGVRVLATAVRELKDFVSKNLTRAINKNKCDIPDLKMAV SFSQFNRRFLNVVRQFSDNAGITPAISKDLMTDAELARAISNM PTSAGQIKLMLENRAMVRRKGFGILIGVYGSSVIYMVQLPIFG VIDTPCWIVKAAPSCSEKKGNYACLLREDQGWYCQNAGSTVYY PNEKDCETRGDHVFCDTAAGINVAEQSKECNINISTTNYPCKV SCGRNPISMVALSPLGALVACYKGVSCSIGSNRVGIIKQLNKG CSYITNQDADTVTIDNTVYQLSKVEGEQHVIKGRPVSSSFDPV KFPEDQFNVALDQCFESIENSQALVDQSNRILSSAEKGNTG | T127C, N153C, T365C, V463C, A185P, L219K, V231I, G294E, N97G, P98G, R99G, Q100G, S101G, H368N, R102G | 490 |

Thus, in some embodiments, the hMPV F protein ectodomain shares at least 90%, 95%, 96%, 97%, 98%, 99%, or 10000 sequence identity to SEQ ID NOs: 58-90, or an antigenic fragment thereof.

In some embodiments, the hMPV F protein comprises one or more furin cleavage sites, optionally one or more copies of an Arg-X—X-Arg motif (SEQ ID NO: 52), such as the native sequence RQSR (SEQ ID NO: 54). Where a furin cleavage site is present in the hMPV ectodomain, expression yields may, in some cases, be increased by co-expression of furin, or functional variant thereof, from a transfected plasmid or from a stably integrated polynucleotide sequence in the host cell. In some embodiments, the furin cleavage site of hMPV F protein is modified by mutating the RQSR (SEQ ID NO: 54) motif to RRRR (SEQ ID NO: 55), or removed by substituting a Gly linker, or by making other amino acid substitutions.

hMPV neutralizing activity is mediated by antibodies recognizing both pre-fusion and post-fusion F protein conformations and antibodies generated in an in vivo immunological response can either selectively recognize pre-fusion specific or post-fusion specific sites, or can recognize both the pre-fusion and post-fusion forms of F protein. Battles et al. *Nat Commun.* 8:1528 (2017). The DS7, MPV196, MPV201, and MPV314 neutralizing antibodies bind an antigenic site accessible in both the pre-fusion and post-fusion forms of F protein, and is located on the DI and DII head domains of the F protein. Wen et al. *Nat Struct Mol Biol.* 19(4):461-463 (2012); Bar-Peled et al. *J Virol.* 93:e00342-19 (2019)). The MPE8 neutralizing antibody binds an epitope on F protein spanning the DI, DII, and DIII subunits, forming contacts dependent on the prefusion F conformation. Wen et al. *Nat Microbiol.* 2:16272 (2017). Several antigenic epitopes are shared with the respiratory syncytial virus (RSV) F protein, such as for example, the site III and site IV epitopes Huang et al. *Front Immunol.* 10:2778 (2019). These are examples and not an exhaustive list of epitopes described for neutralization antibodies against hMPV F protein.

The neutralizing epitopes are generally conformation epitopes so peptides corresponding to the epitopes do not bind the antibodies and thus do not induce neutralizing titers. Neutralizing antibodies can be isolated from healthy donors that are seropositive for hMPV, Battles et al., or can be generated by immunization in animal models, Gabriella et al. *J Virol.* 81(2):698-707 (2007).

In some embodiments, the VLPs of the disclosure comprising an hMPV F protein ectodomain can bind a neutralizing antibody against the hMPV F protein, also referred to as anti-hMPV F protein antibodies. In some embodiments, the VLPs described herein can bind anti-hMPV F protein antibodies known to selectively bind the prefusion form of hMPV F protein. Examples of antibodies that selectively bind the prefusion form of hMPV F protein include, without limitation, the MF10 and MPE8 antibodies. In some embodiments, the VLPs described herein bind anti-hMPV F protein antibodies known to selectively bind the postfusion form of hMPV F protein. Examples of antibodies that selectively bind the postfusion form of hMPV F protein include, without limitation, the MF1, MF2, MF3, MF11, MF17, MF18, and MF19 antibodies. In some embodiments, the VLPs described herein can bind antibodies that bind both the prefusion and postfusion forms of hMPV F protein. Examples of antibodies that bind the prefusion and postfusion forms of hMPV F protein include, without limitation, the MF9, MF12, MF14, MF15, MF16, and MF20 antibodies. In some embodiments, the VLPs described herein bind one or more anti-hMPV F protein antibodies. In some embodiments, the VLPs described herein bind two or more anti-hMPV F protein antibodies.

Multimerization Domains and Linkers

In some embodiments, the VLP comprises a trimeric assembly of antigens comprising a first polypeptide comprising a first multimerization domain and a first polypeptide comprising a second multimerization domain. The first multimerization domain comprises a protein-protein interface that induces three copies of the first polypeptides to self-associate to form trimeric building blocks. In VLPs that have two or more components, each copy of the first multimerization domain further comprises a surface-exposed interface that interacts with a complementary surface-exposed interface on the second multimerization domain. Similarly stated, the second multimerization domain is adapted to multimerize with first multimerization domain (of the first polypeptide of the first component). As described in King et al. (Nature 510, 103-108, 2014), Bale et al. (Science 353, 389-394, 2016), and patent publications WO2014124301 A1 and US20160122392 A1, the complementary protein-protein interface between the first multimerization domains and second multimerization domains drives the assembly of multiple copies of the trimeric assembly domain and second assembly domain into a target VLP. In some embodiments, each copy of the trimeric assembly domains of the VLP bears an antigenic protein, or antigenic fragment thereof, linked thereto (e.g., as a genetic fusion); these VLPs display the proteins at full valency. In other embodiments, the VLPs of the disclosure comprise one or more copies of first multimerization domains bearing antigens proteins, or antigenic fragments thereof (e.g., as genetic fusions) as well as one or more first multimerization domains that do not bear antigenic proteins; these VLPs display the G proteins at partial valency. The first multimerization domains can be any polypeptide sequence that forms a trimer and interacts with a second multimerization domains to drive assembly to a target VLP. In some embodiments, the VLP comprises first polypeptide and a second polypeptide selected from those disclosed in US 20130274441 A1, US 2015/0356240 A1, US 2016/0122392 A1, WO 2018/187325 A1, each of which is incorporated by reference herein in its entirety.

In some embodiments of the VLPs of the present disclosure, the antigenic protein and the core of the VLP may be genetically fused such that they are both present in a single polypeptide, also called a single chain polypeptide. The linkage between the protein and the core allows the antigenic protein, or antigenic fragment thereof, to be displayed on the exterior of the VLP. As such, the point of connection to the core should be on the exterior of the core of the virus-like particle formed. A wide variety of polypeptide sequences can be used to link the proteins, or antigenic fragments thereof and the core of the virus-like particle. In some cases the linker comprises that polypeptide sequence. Any suitable linker polypeptide can be used. In some embodiments, the linker imposes a rigid relative orientation of the antigenic protein (e.g. ectodomain) or antigenic fragment thereof to the core. In some embodiments, the linker flexibly links the antigenic protein (e.g. ectodomain) or antigenic fragment thereof to the core. In some embodiments, the linker includes additional trimerization domains (e.g., the foldon domain of T4 fibritin) to assist in stabilizing the trimeric form of the F protein—e.g., GYIPEAPRDGQAYVRKDGEWVLLSTFL (SEQ ID NO: 91) or a functional variant thereof.

In some embodiments, the linker may comprise a Gly-Ser linker (i.e. a linker consisting of glycine and serine residues) of any suitable length. In some embodiments, the Gly-Ser linker may be 3, 4, 5, 6, 7, 8, 9, 10, 11, 12, 13, 14, 15, 16, 17, 18, 19, 20, or more amino acids in length. In some embodiments, the Gly-Ser linker may comprise or consist of the amino acid sequence of GSGGSGSGSGGSGSG (SEQ ID NO: 127), GGSGGSGS (SEQ ID NO: 128) or GSGGSGSG (SEQ ID NO: 129). In some embodiments, the linker comprises the sequence GSGSGSG (SEQ ID NO: 130). In some embodiments, the linker comprises the sequence GSGSGSGSGSGSGSG (SEQ ID NO: 131). In some embodiments, the linker comprises the sequence GSGGSGSGSGGS (SEQ ID NO: 126).

In some embodiments of the VLPs of the present disclosure, the first component may optionally contain a poly-His tag, HHHHHH (SEQ ID NO: 143).

Table 3 shows illustrative examples of the VLP sequences described herein. The sequences comprise a multimerization domain, an hMPV F protein ectodomain, a linker, a poly-His tag, and a signal sequence. The signal and poly-His tag sequences are underlined and optionally included in the sequence.

TABLE 3

Illustrative Amino Acid Sequences of VLPs of the Disclosure

| Construct name | SEQ ID NO: | Amino Acid Sequence |
|---|---|---|
| hMPV001 | 92 | MSWKVVIIFSLLITPQHGLKESYLEESCSTITEGYLSVLRTGWYTNVFTLEVGDV<br>ENLTCADGPSLIKTELDLTKSALRELRTVSADQLAREEQIENPRRRRFVLGAIAL<br>GVATAAAVTAGVAIAKTIRLESEVTAIKNALKKTNEAVSTLGNGVRVLATAVREL<br>KDFVSKNLTRAINKNKCDIPDLKMAVSFSQFNRRFLNVVRQFSDNAGITPAISLD<br>LMTDAELARAVSNMPTSAGQIKLMLENRAMVRRKGFGFLIGVYGSSVIYMVQLPI<br>FGVIDTPCWIVKAAPSCSGKKGNYACLLREDQGWYCQNAGSTVYYPNEKDCETRG<br>DHVFCDTAAGINVAEQSKECNINISTTNYPCKVSTGRHPISMVALSPLGALVACY<br>KGVSCSIGSNRVGIIKQLNKGCSYITNQDADTVTIDNTVYQLSKVEGEQHVIKGR<br>PVSSSFDPVKFPEDQFNVALDQVFESIENSQALVDQSNRILGSGGSGSGSGGSEK<br>AAKAEEAARKMEELFKKHKIVAVLRANSVEEAIEKAVAVFAGGVHLIEITFTVPD<br>ADTVIKALSVLEKGAIIGAGTVTSVEQARKAVESGAEFIVSPHLDEEISQFAKE<br>KGVFYMPGVMTPTELVKAMKLGHTILKLFPGEVVGPQFVKAMKGPFPNVKFVPTG<br>GVNLDNVAEWFKAGVLAVGVGSALVKGTPDEVREKAKAFVEKIRGATELE<br>HHHHHH |
| hMPV002 | 93 | MSWKVVIIFSLLITPQHGLKESYLEESCSTITEGYLSVLRTGWYTNVFTLEVGDV<br>ENLTCADGPSLIKTELDLTKSALRELRTVSADQLAREEQIENPRRRRFVLGAIAL<br>GVATAAAVTAGVAIAKTIRLESEVTAIKNALKKTNEAVSTLGNGVRVLATAVREL<br>KDFVSKNLTRAINKNKCDIPDLKMAVSFSQFNRRFLNVVRQFSDNAGITPAISLD<br>LMTDAELARAVSNMPTSAGQIKLMLENRAMVRRKGFGFLIGVYGSSVIYMVQLPI<br>FGVIDTPCWIVKAAPSCSGKKGNYACLLREDQGWYCQNAGSTVYYPNEKDCETRG<br>DHVFCDTAAGINVAEQSKECNINISTTNYPCKVSTGRHPISMVALSPLGALVACY<br>KGVSCSIGSNRVGIIKQLNKGCSYITNQDADTVTIDNTVYQLSKVEGEQHVIKGR<br>PVSSSFDPVKFPEDQFNVALDQVFESIENSQAGSGGSGSGSGGSEKAAKAEEAAR |

TABLE 3-continued

Illustrative Amino Acid Sequences of VLPs of the Disclosure

| Construct name | SEQ ID NO: | Amino Acid Sequence |
|---|---|---|
| | | KMEELFKKHKIVAVLRANSVEEAIEKAVAVFAGGVHLIEITFTVPDADTVIKALS VLKEKGAIIGAGTVTSVEQARKAVESGAEFIVSPHLDEEISQFAKEKGVFYMPGV MTPTELVKAMKLGHTILKLFPGEVVGPQFVKAMKGPFPNVKFVPTGGVNLDNVAE WFKAGVLAVGVGSALVKGTPDEVREKAKAFVEKIRGATELE<u>HHHHHH</u> |
| hMPV003 | 94 | <u>MSWKVVIIFSLLITPQHG</u>LKESYLEESCSTITEGYLSVLRTGWYTNVFTLEVGDV ENLTCADGPSLIKTELDLTKSALRELRTVSADQLAREEQIENPRRRRFVLGAIAL GVATAAAVTAGVAIAKTIRLESEVTAIKNALKKTNEAVSTLGNGVRVLATAVREL KDFVSKNLTRAINKNKCDIPDLKMAVSFSQFNRRFLNVVRQFSDNAGITPAISLD LMTDAELARAVSNMPTSAGQIKLMLENRAMVRRKGFGFLIGVYGSSVIYMVQLPI FGVIDTPCWIVKAAPSCSGKKGNYACLLREDQGWYCQNAGSTVYYPNEKDCETRG DHVFCDTAAGINVAEQSKECNINISTTNYPCKVSTGRHPISMVALSPLGALVACY KGVSCSIGSNRVGIIKQLNKGCSYITNQDADTVTIDNTVYQLSKVEGEQHVIKGR PVSSSFDPVKFPEDQFNVALDQVFESIENSQALVDQSNRILSSAEKGNTGGSGGS GSGSGGSEKAAKAEEEAARKMEELFKKHKIVAVLRANSVEEAIEKAVAVFAGGVHL IEITFTVPDADTVIKALSVLKEKGAIIGAGTVTSVEQARKAVESGAEFIVSPHLD EEISQFAKEKGVFYMPGVMTPTELVKAMKLGHTILKLFPGEVVGPQFVKAMKGPF PNVKFVPTGGVNLDNVAEWFKAGVLAVGVGSALVKGTPDEVREKAKAFVEKIRGA TELE<u>HHHHHH</u> |
| hMPV004 | 95 | <u>MSWKVVIIFSLLITPQHG</u>LKESYLEESCSTITEGYLSVLRTGWYTNVFTLEVGDV ENLTCADGPSLIKTELDLTKSALRELRTVSADQLAREEQIENPRRRRFVLGAIAL GVATAAAVTAGVAIAKTIRLESEVTAIKNALKKTNEAVSTLGNGVRVLATAVREL KDFVSKNLTRAINKNKCDIADLKMAVSFSQFNRRFLNVVRQFSDNAGITPAISLD LMTDAELARAVSNMPTSAGQIKLMLENRAMVRRKGFGFLIGVYGSSVIYMVQLPI FGVIDTPCWIVKAAPSCSGKKGNYACLLREDQGWYCQNAGSTVYYPNEKDCETRG DHVFCDTAAGINVAEQSKECNINISTTNYPCKVSTGRHPISMVALSPLGALVACY KGVSCSIGSNRVGIIKQLNKGCSYITNQDADTVTIDNTVYQLSKVEGEQHVIKGR PVSSSFDPVKFPEDQFNVALDQVFESIENSQAGSGGSGSGGSEKAAKAEEEAAR KMEELFKKHKIVAVLRANSVEEAIEKAVAVFAGGVHLIEITFTVPDADTVIKALS VLKEKGAIIGAGTVTSVEQARKAVESGAEFIVSPHLDEEISQFAKEKGVFYMPGV MTPTELVKAMKLGHTILKLFPGEVVGPQFVKAMKGPFPNVKFVPTGGVNLDNVAE WFKAGVLAVGVGSALVKGTPDEVREKAKAFVEKIRGATELE<u>HHHHHH</u> |
| hMPV005 | 96 | <u>MSWKVVIIFSLLITPQHG</u>LKESYLEESCSTITEGYLSVLRTGWYTNVFTLEVGDV ENLTCADGPSLIKTELDLTKSALRELRTVSADQLAREEQIENPRRRRFVLGAIAL GVATAAAVTAGVAIAKCIRLESEVTAIKNALKKTNEAVSTLGCGVRVLATAVREL KDFVSKNLTRAINKNKCDIPDLKMAVSFSQFNRRFLNVVRQFSDNAGITPAISLD LMTDAELARAVSNMPTSAGQIKLMLENRAMVRRKGFGILIGVYGSSVIYMVQLPI FGVIDTPCWIVKAAPSCSGKKGNYACLLREDQGWYCQNAGSTVYYPNEKDCETRG DHVFCDTAAGINVAEQSKECNINISTTNYPCKVSTGRNPISMVALSPLGALVACY KGVSCSIGSNRVGIIKQLNKGCSYITNQDADTVTIDNTVYQLSKVEGEQHVIKGR PVSSSFDPVKFPEDQFNVALDQVFESIENSQAGSGGSGSGGSEKAAKAEEEAAR KMEELFKKHKIVAVLRANSVEEAIEKAVAVFAGGVHLIEITFTVPDADTVIKALS VLKEKGAIIGAGTVTSVEQARKAVESGAEFIVSPHLDEEISQFAKEKGVFYMPGV MTPTELVKAMKLGHTILKLFPGEVVGPQFVKAMKGPFPNVKFVPTGGVNLDNVAE WFKAGVLAVGVGSALVKGTPDEVREKAKAFVEKIRGATELE<u>HHHHHH</u> |
| hMPV006 | 97 | <u>MSWKVMIISLLITPQHG</u>LKESYLEESCSTITEGYLSVLRTGWYTNVFTLEVGDV ENLTCTDGPSLIKTELDLTKSALRELKTCSADQLAREEQIEGGGGGGFVLGAIAL GVATAAAVTAGIAIAKTIRLESEVNAIKGCLKTTNECVSTLGNGVRVLATAVREL KEFVSKNLTSAINKNKCDIADLKMAVSFSQFNRRFLNVVRQFSDNAGITPAISLD LMTDAELARAVSYMPTSAGQIKLMLENRCMVRRKGFGILIGVYGSSVIYMVQLPI FGVIDTPCWIIKAAPSCSEKDGNYACLLREDQGWYCKNAGSTVYYPNDKDCETRG DHVFCDTAAGINVAEQSRECNINISTTNYPCKVSTGRHPISMVALSPLGALVACY KGVSCSIGSNRVGIIKQLPKGCSYITNQDADTVTIDNTVYQLSKVEGEQHVIKGR PVSSSFDPIKFPEDQFNVALDQVFESIENSQAGSGGSGSGGSEKAAKAEEEAAR KMEELFKKHKIVAVLRANSVEEAIEKAVAVFAGGVHLIEITFTVPDADTVIKALS VLKEKGAIIGAGTVTSVEQARKAVESGAEFIVSPHLDEEISQFAKEKGVFYMPGV MTPTELVKAMKLGHTILKLFPGEVVGPQFVKAMKGPFPNVKFVPTGGVNLDNVAE WFKAGVLAVGVGSALVKGTPDEVREKAKAFVEKIRGATELE<u>HHHHHH</u> |
| hMPV007 | 98 | <u>MSWKVMIISLLITPQHG</u>LKESYLEESCSTITEGYLSVLRTGWYTNVFTLEVGDV ENLTCTDGPSLIKTELDLTKSALRELKTCSADQLAREEQIEGGGGGGFVLGAIAL GVATAAAVTAGIAIAKTIRLESEVNAIKGCLKTTNECVSTLGNGVRVLATAVREL KEFVSKNLTSAINKNKCDIADLKMAVSFSQFNRRFLNVVRQFSDNAGITPAISLD LMTDAELARAVSYMPTSAGQIKLMLENRCMVRRKGFGILIGVYGSSVIYMVQLPI FGVIDTPCWIIKAAPSCSEKDGNYACLLREDQGWYCKNAGSTVYYPNDKDCETRG DHVFCDTAAGINVAEQSRECNINISTTNYPCKVSTGRHPISMVALSPLGALVACY KGVSCSIGSNRVGIIKQLPKGCSYITNQDADTVTIDNTVYQLSKVEGEQHVIKGR PVSSSFDPIKFPEDQFNVALDQVFESIENSQALVDQSNKILNSAESAIGSGGSGS GGSEKAAKAEEEAARKMEELFKKHKIVAVLRANSVEEAIEKAVAVFAGGVHLIE |

TABLE 3-continued

Illustrative Amino Acid Sequences of VLPs of the Disclosure

| Construct name | SEQ ID NO: | Amino Acid Sequence |
|---|---|---|
| | | itftvpdadtvikalsvlkekgaiigagtvtsveqarkavesgaefivsphldee<br>ISQFAKEKGVFYMPGVMTPTELVKAMKLGHTILKLFPGEVVGPQFVKAMKGPFPN<br>VKFVPTGGVNLDNVAEWFKAGVLAVGVGSALVKGTPDEVREKAKAFVEKIRGATE<br>LEHHHHHH |
| hMPV008 | 99 | MSWKVMIISLLITPQHGLKESYLEESCSTITEGYLSVLRTGWYTNVFTLEVGDV<br>ENLTCTDCPSLIKTELDLTKSALRELKTVSADQLAREEQIEGGGGGGFVLGAIAL<br>GVATAAAVTAGIAIAKTIRLESEVNAIKGCLKTTNECVSTLGNGVRVLATAVREL<br>KEFVSKNLTSAINKNKCDIADLCMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTAAGINVAEQSRECNINISTTNYPCKVSTGRHPISMVALSPLGALVACY<br>KGVSCSIGSNRVGIIKQLPKGCSYITNQDADTVTIDNTVYQLSKVEGEQHVIKGR<br>PVSSSFDPICFPEDQFNVALDQVFESIENCQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELEHHHHHH |
| hMPV009 | 100 | MSWKVMIISLLITPQHGLKESYLEESCSTITEGYLSVLRTGWYTNVFTLEVGDV<br>ENLTCTDCPSLIKTELDLTKSALRELKTVSADQLAREEQIEGGGGGGFVLGAIAL<br>GVATAAAVTAGIAIAKTIRLESEVNAIKGCLKTTNECVSTLGNGVRVLATAVREL<br>KEFVSKNLTSAINKNKCDIADLCMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTAAGINVAEQSRECNINISTTNYPCKVSTGRHPISMVALSPLGALVACY<br>KGVSCSIGSNRVGIIKQLPKGCSYITNQDADTVTIDNTVYQLSKVEGEQHVIKGR<br>PVSSSFDPICFPEDQFNVALDQVFESIENCQALVDQSNKILNSAESAIGSGGSGS<br>GSGGSEKAAKAEEAARKMEELFKKHKIVAVLRANSVEEAIEKAVAVFAGGVHLIE<br>ITFTVPDADTVIKALSVLKEKGAIIGAGTVTSVEQARKAVESGAEFIVSPHLDEE<br>ISQFAKEKGVFYMPGVMTPTELVKAMKLGHTILKLFPGEVVGPQFVKAMKGPFPN<br>VKFVPTGGVNLDNVAEWFKAGVLAVGVGSALVKGTPDEVREKAKAFVEKIRGATE<br>LEHHHHHH |
| hMPV010 | 101 | MSWKVVIIFSLLITPQHGLKESYLEESCSTITEGYLSVLRTGWYTNVFTLEVGDV<br>ENLTCSDCPSLIKTELDLTKSALRELKTVSADQLAREEQIEGGGGGGFVLAIALG<br>VATAAAVTAGVAIAKTIRLESEVTAIKNCLKTTNECVSTLGNGVRVLATAVRELK<br>DFVSKNLTSAINKNKCDIDDLCMAVSFSQFNRRFLNVVRQFSDNAGITPAISLDL<br>MTDAELARAVSNMPTSAGQIKLMLENRAMVRRKGFGILIGVYGSSVIYMVQLPIF<br>GVIDTPCWIIKAAPSCSGKKGNYACLLREDQGWYCQNAGSTVYYPNEKDCETRGD<br>HVFCDTAAGINVAEQSKECNINISTTNYPCKVSTGRHPISMVALSPLGALVACYK<br>GVSCSIGSNRVGIIKQLNKGCSYITNQDADTVTIDNTVYQLSKVEGEQHVIKGRP<br>VSSSFDPIKFPEDQFNVALDQVFENIENSQAGSGGSGSGSGGSEKAAKAEEEARK<br>MEELFKKHKIVAVLRANSVEEAIEKAVAVFAGGVHLIEITFTVPDADTVIKALSV<br>LKEKGAIIGAGTVTSVEQARKAVESGAEFIVSPHLDEEISQFAKEKGVFYMPGVM<br>TPTELVKAMKLGHTILKLFPGEVVGPQFVKAMKGPFPNVKFVPTGGVNLDNVAEW<br>FKAGVLAVGVGSALVKGTPDEVREKAKAFVEKIRGATELEHHHHHH |
| hMPV011 | 102 | MSWKVVIIFSLLITPQHGLKESYLEESCSTITEGYLSVLRTGWYTNVFTLEVGDV<br>ENLTCSDCPSLIKTELDLTKSALRELKTVSADQLAREEQIEGGGGGGFVLAIALG<br>VATAAAVTAGVAIAKTIRLESEVTAIKNCLKTTNECVSTLGNGVRVLATAVRELK<br>DFVSKNLTSAINKNKCDIDDLCMAVSFSQFNRRFLNVVRQFSDNAGITPAISLDL<br>MTDAELARAVSNMPTSAGQIKLMLENRAMVRRKGFGILIGVYGSSVIYMVQLPIF<br>GVIDTPCWIIKAAPSCSGKKGNYACLLREDQGWYCQNAGSTVYYPNEKDCETRGD<br>HVFCDTAAGINVAEQSKECNINISTTNYPCKVSTGRHPISMVALSPLGALVACYK<br>GVSCSIGSNRVGIIKQLNKGCSYITNQDADTVTIDNTVYQLSKVEGEQHVIKGRP<br>VSSSFDPIKFPEDQFNVALDQVFENIENSQALVDQSNRILSSAESAIGSGGSGSG<br>SGGSEKAAKAEEAARKMEELFKKHKIVAVLRANSVEEAIEKAVAVFAGGVHLIEI<br>TFTVPDADTVIKALSVLKEKGAIIGAGTVTSVEQARKAVESGAEFIVSPHLDEEI<br>SQFAKEKGVFYMPGVMTPTELVKAMKLGHTILKLFPGEVVGPQFVKAMKGPFPNV<br>KFVPTGGVNLDNVAEWFKAGVLAVGVGSALVKGTPDEVREKAKAFVEKIRGATEL<br>EHHHHHH |
| hMPV012 | 103 | MSWKVMIISLLITPQHGLKESYLEESCSTITEGYLSVLRTGWYTNVFTLEVGDV<br>ENLTCTDGPSLIKTELDLTKSALRELKTVSADQLAREEQIENPRKARFVLGAIAL<br>GVCTAAAVTCGIAIAKTIRLESEVNAIKGALKTTNEAVSTLGNGVRVLAFAVREL<br>KEFVSKNLTSALNKNKCDIADLKMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTACGINVAEQSRECNINISTTNYPCKVSTGRHPISMVALSPLGALVACY<br>KGVSCSIGSNRVGIIKQLPKGCSYITNQDADTVTIDNTVYCLSKVEGEQHVIKGR<br>PVSSSFDPIKFPEDQFNVALDQVFESIENSQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV |

TABLE 3-continued

Illustrative Amino Acid Sequences of VLPs of the Disclosure

| Construct name | SEQ ID NO: | Amino Acid Sequence |
|---|---|---|
| | | MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELE<u>HHHHHH</u> |
| hMPV013 | 104 | <u>MSWKVMIIISLLITPQHG</u>LKESYLEESCSTITEGYLSVLRTGWYTNVFTLEVGDV<br>ENLTCTDGPSLIKTELDLTKSALRELKTVSADQLAREEQIENPRKARFVLGAIAL<br>GVCTAAAVTCGIAIAKTIRLESEVNAIKGALKTTNEAVSTLGNGVRVLAFAVREL<br>KEFVSKNLTSALNKNKCDIADLKMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTACGINVAEQSRECNINISTTNYPCKVSTGRHPISMVALSPLGALVACY<br>KGVSCSIGSNRVGIIKQLPKGCSYITNQDADTVTIDNTVYCLSKVEGEQHVIKGR<br>PVSSSFDPIKFPEDQFNVALDQVFESIENSQALVDQSNKILNSAESAIGSGGSGS<br>GSGGSEKAAKAEEEAARKMEELFKKHKIVAVLRANSVEEAIEKAVAVFAGGVHLIE<br>ITFTVPDADTVIKALSVLKEKGAIIGAGTVTSVEQARKAVESGAEFIVSPHLDEE<br>ISQFAKEKGVFYMPGVMTPTELVKAMKLGHTILKLFPGEVVGPQFVKAMKGPFPN<br>VKFVPTGGVNLDNVAEWFKAGVLAVGVGSALVKGTPDEVREKAKAFVEKIRGATE<br>LE<u>HHHHHH</u> |
| hMPV014 | 105 | <u>MSWKVMIIISLLITPQHG</u>LKESYLEESCSTITEGYLSVLRTGWYTNVFTLEVGDV<br>ENLTCTDGPSLIKTELDLTKSALRELKTCSADQLAREEQIENPRRRFVLGAIAL<br>GVATAAAVTAGIAIAKTIRLESEVNAIKGCLKTTNECVSTLGNGVRVLATAVREL<br>KEFVSKNLTSAINKNKCDIADLKMAVSFSQFNRRFLNVVRQFSDNAGITPAISLD<br>LMTDAELARAVSYMPTSAGQIKLMLENRCMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTAAGINVAEQSRECNINISTTNYPCKVSTGRHPISMVALSPLGALVACY<br>KGVSCSIGSNRVGIIKQLPKGCSYITNQDADTVTIDNTVYQLSKVEGEQHVIKGR<br>PVSSSFDPIKFPEDQFNVALDQVFESIENSQAGSGGSGSGSGGSEKAAKAEEEAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELE<u>HHHHHH</u> |
| hMPV015 | 106 | <u>MSWKVMIIISLLITPQHG</u>LKESYLEESCSTITEGYLSVLRTGWYTNVFTLEVGDV<br>ENLTCTDCPSLIKTELDLTKSALRELKTVSADQLAREEQIENPRRRFVLGAIAL<br>GVATAAAVTAGIAIAKTIRLESEVNAIKGCLKTTNECVSTLGNGVRVLATAVREL<br>KEFVSKNLTSAINKNKCDIADLCMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTAAGINVAEQSRECNINISTTNYPCKVSTGRHPISMVALSPLGALVACY<br>KGVSCSIGSNRVGIIKQLPKGCSYITNQDADTVTIDNTVYQLSKVEGEQHVIKGR<br>PVSSSFDPICFPEDQFNVALDQVFESIENCQAGSGGSGSGSGGSEKAAKAEEEAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELE<u>HHHHHH</u> |
| hMPV016 | 107 | <u>MSWKVVIIFSLLITPQHG</u>LKESYLEESCSTITEGYLSVLRTGWYTNVFTLEVGDV<br>ENLTCSDCPSLIKTELDLTKSALRELKTVSADQLAREEQIENPRRRFVLAIALG<br>VATAAAVTAGVAIAKTIRLESEVTAIKNCLKTTNECVSTLGNGVRVLATAVRELK<br>DFVSKNLTSAINKNKCDIDDLCMAVSFSQFNRRFLNVVRQFSDNAGITPAISLDL<br>MTDAELARAVSNMPTSAGQIKLMLENRAMVRRKGFGILIGVYGSSVIYMVQLPIF<br>GVIDTPCWIIKAAPSCSGKKGNYACLLREDQGWYCQNAGSTVYYPNEKDCETRGD<br>HVFCDTAAGINVAEQSKECNINISTTNYPCKVSTGRHPISMVALSPLGALVACYK<br>GVSCSIGSNRVGIIKQLNKGCSYITNQDADTVTIDNTVYQLSKVEGEQHVIKGRP<br>VSSSFDPIKFPEDQFNVALDQVFENIENSQAGSGGSGSGSGGSEKAAKAEEEAARK<br>MEELFKKHKIVAVLRANSVEEAIEKAVAVFAGGVHLIEITFTVPDADTVIKALSV<br>LKEKGAIIGAGTVTSVEQARKAVESGAEFIVSPHLDEEISQFAKEKGVFYMPGVM<br>TPTELVKAMKLGHTILKLFPGEVVGPQFVKAMKGPFPNVKFVPTGGVNLDNVAEW<br>FKAGVLAVGVGSALVKGTPDEVREKAKAFVEKIRGATELE<u>HHHHHH</u> |
| hMPV017 | 108 | <u>MSWKVMIIISLLITPQHG</u>LKESYLEESCSTITEGYLSVLRTGWYTNVFTLEVGDV<br>ENLTCTDGPSLIKTELDLTKSALRELKTVSADQLAREEQIENPRRRFVLGAIAL<br>GVCTAAAVTCGIAIAKTIRLESEVNAIKGALKTTNEAVSTLGNGVRVLAFAVREL<br>KEFVSKNLTSALNKNKCDIADLKMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTACGINVAEQSRECNINISTTNYPCKVSTGRHPISMVALSPLGALVACY<br>KGVSCSIGSNRVGIIKQLPKGCSYITNQDADTVTIDNTVYCLSKVEGEQHVIKGR<br>PVSSSFDPIKFPEDQFNVALDQVFESIENSQAGSGGSGSGSGGSEKAAKAEEEAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELE<u>HHHHHH</u> |

TABLE 3-continued

Illustrative Amino Acid Sequences of VLPs of the Disclosure

| Construct name | SEQ ID NO: | Amino Acid Sequence |
|---|---|---|
| hMPV018 | 109 | MSWKVVIIFSLLITPQHGLKESYLEESCSTITEGYLSVLRTGWYTNVFTLEVGDV<br>ENLTCADGPSLIKTELDLTKSALRELRTVSADQLAREEQIENPRRRRFVLGAIAL<br>GVCTAAAVTAGVAIAKTIRLESEVTAIKNALKKTNEAVSTLGNGVRVLATAVREL<br>KDFVSKNLTRAINKNKCDIPDLKMAVSFSQFNRRFLNVVRQFSDNAGITPAISLD<br>LMTDAELARAVSNMPTSAGQIKLMLENRAMVRRKGFGFLIGVYGSSVIYMVQLPI<br>FGVIDTPCWIVKAAPSCSGKKGNYACLLREDQGWYCQNAGSTVYYPNEKDCETRG<br>DHVFCDTACGINVAEQSKECNINISTTNYPCKVSTGRHPISMVALSPLGALVACY<br>KGVSCSIGSNRVGIIKQLNKGCSYITNQDADTVTIDNTVYQLSKVEGEQHVIKGR<br>PVSSSFDPVKFPEDQFNVALDQVFESIENSQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELEHHHHHH |
| hMPV019 | 110 | MSWKVVIIFSLLITPQHGLKESYLEESCSTITEGYLSVLRTGWYTNVFTLEVGDV<br>ENLTCADGPSLIKTELDLTKSALRELRTVSADQLAREEQIENPRRRRFVLGAIAL<br>GVATAAAVTAGVAIAKTIRLESEVTAIKNALKKTNEAVSTLGNGVRVLAFAVREL<br>KDFVSKNLTRALNKNKCDIPDLKMAVSFSQFNRRFLNVVRQFSDNAGITPAISLD<br>LMTDAELARAVSNMPTSAGQIKLMLENRAMVRRKGFGFLIGVYGSSVIYMVQLPI<br>FGVIDTPCWIVKAAPSCSGKKGNYACLLREDQGWYCQNAGSTVYYPNEKDCETRG<br>DHVFCDTAAGINVAEQSKECNINISTTNYPCKVSTGRHPISMVALSPLGALVACY<br>KGVSCSIGSNRVGIIKQLNKGCSYITNQDADTVTIDNTVYQLSKVEGEQHVIKGR<br>PVSSSFDPVKFPEDQFNVALDQVFESIENSQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELEHHHHHH |
| hMPV020 | 111 | MSWKVVIIFSLLITPQHGLKESYLEESCSTITEGYLSVLRTGWYTNVFTLEVGDV<br>ENLTCADGPSLIKTELDLTKSALRELRTVSADQLAREEQIENPRRRRFVLGAIAL<br>GVCTAAAVTAGVAIAKTIRLESEVTAIKNALKKTNEAVSTLGNGVRVLAFAVREL<br>KDFVSKNLTRALNKNKCDIPDLKMAVSFSQFNRRFLNVVRQFSDNAGITPAISLD<br>LMTDAELARAVSNMPTSAGQIKLMLENRAMVRRKGFGFLIGVYGSSVIYMVQLPI<br>FGVIDTPCWIVKAAPSCSGKKGNYACLLREDQGWYCQNAGSTVYYPNEKDCETRG<br>DHVFCDTACGINVAEQSKECNINISTTNYPCKVSTGRHPISMVALSPLGALVACY<br>KGVSCSIGSNRVGIIKQLNKGCSYITNQDADTVTIDNTVYQLSKVEGEQHVIKGR<br>PVSSSFDPVKFPEDQFNVALDQVFESIENSQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELEHHHHHH |
| hMPV021 | 112 | MSWKVMIISLLITPQHGLKESYLEESCSTITEGYLSVLRTGWYTNVFTLEVGDV<br>ENLTCTDCPSLIKTELDLTKSALRELKTVSADQLAREEQIEGGGGGGFVLGAIAL<br>GVATAAAVTAGIAIAKTIRLESEVNAIKGALKTTNEAVSTLGNGVRVLATAVREL<br>KEFVSKNLTSAINKNKCDIADLCMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTAAGINVAEQSRECNINISTTNYPCKVSTGRHPISMVALSPLGALVACY<br>KGVSCSIGSNRVGIIKQLPKGCSYITNQDADTVTIDNTVYQLSKVEGEQHVIKGR<br>PVSSSFDPIKFPEDQFNVALDQVFESIENSQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELEHHHHHH |
| hMPV022 | 113 | MSWKVMIISLLITPQHGLKESYLEESCSTITEGYLSVLRTGWYTNVFTLEVGDV<br>ENLTCTDCPSLIKTELDLTKSALRELKTVSADQLAREEQIEGGGGGGFVLGAIAL<br>GVATAAAVTAGIAIAKTIRLESEVNAIKGALKTTNEAVSTLGNGVRVLATAVREL<br>KEFVSKNLTSAINKNKCDIADLCMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTAAGINVAEQSRECNINISTTNYPCKVSTGRHPISMVALSPLGALVACY<br>KGVSCSIGSNRVGIIKQLPKGCSYITNQDADTVTIDNTVYQLSKVEGEQHVIKGR<br>PVSSSFDPIAFPEDQFNVALDQVFESIENAQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELEHHHHHH |
| hMPV023 | 114 | MSWKVVIIFSLLITPQHGLKESYLEESCSTITEGYLSVLRTGWYTNVFTLEVGDV<br>ENLTCSDCPSLIKTELDLTKSALRELKTVSADQLAREEQIEGGGGGGFVLGAIAL<br>GVATAAAVTAGVAIAKTIRLESEVTAIKNCLKTTNECVSTLGNGVRVLATAVREL<br>KDFVSKNLTSAINKNKCDIDDLCMAVSFSQFNRRFLNVVRQFSDNAGITPAISLD |

TABLE 3-continued

Illustrative Amino Acid Sequences of VLPs of the Disclosure

| Construct name | SEQ ID NO: | Amino Acid Sequence |
|---|---|---|
| | | LMTDAELARAVSNMPTSAGQIKLMLENRAMVRRKGFGILIGVYGSSVIYMVQLPI<br>FGVIDTPCWIIKAAPSCSEKKGNYACLLREDQGWYCQNAGSTVYYPNEKDCETRG<br>DHVFCDTAAGINVAEQSKECNINISTTNYPCKVSTGRHPISMVALSPLGALVACY<br>KGVSCSIGSNRVGIIKQLNKGCSYITNQDADTVTIDNTVYQLSKVEGEQHVIKGR<br>PVSSSFDPIKFPEDQFNVALDQVFENIENSQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELE<u>HHHHHH</u> |
| hMPV024 | 115 | <u>MSWKVVIIFSLLITPQHG</u>LKESYLEESCSTITEGYLSVLRTGWYTNVFTLEVGDV<br>ENLTCADCPSLIKTELDLTKSALRELRTVSADQLAREEQIEGGGGGGGFVLGAIAL<br>GVATAAAVTAGVAIAKTIRLESEVTAIKNCLKKTNECVSTLGNGVRVLATAVREL<br>KDFVSKNLTRAINKNKCDIADLCMAVSFSQFNRRFLNVVRQFSDNAGITPAISLD<br>LMTDAELARAVSNMPTSAGQIKLMLENRAMVRRKGFGLIGVYGSSVIYMVQLPI<br>FGVIDTPCWIVKAAPSCSEKKGNYACLLREDQGWYCQNAGSTVYYPNEKDCETRG<br>DHVFCDTAAGINVAEQSKECNINISTTNYPCKVSTGRHPISMVALSPLGALVACY<br>KGVSCSIGSNRVGIIKQLNKGCSYITNQDADTVTIDNTVYQLSKVEGEQHVIKGR<br>PVSSSFDPVCFPEDQFNVALDQVFESIENCQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELE<u>HHHHHH</u> |
| hMPV025 | 116 | <u>MSWKVVIIFSLLITPQHG</u>LKESYLEESCSTITEGYLSVLRTGWYTNVFTLEVGDV<br>ENLTCADCPSLIKTELDLTKSALRELRTVSADQLAREEQIEGGGGGGGFVLGAIAL<br>GVATAAAVTAGVAIAKTIRLESEVTAIKNALKKTNEAVSTLGNGVRVLATAVREL<br>KDFVSKNLTRAINKNKCDIADLCMAVSFSQFNRRFLNVVRQFSDNAGITPAISLD<br>LMTDAELARAVSNMPTSAGQIKLMLENRAMVRRKGFGLIGVYGSSVIYMVQLPI<br>FGVIDTPCWIVKAAPSCSEKKGNYACLLREDQGWYCQNAGSTVYYPNEKDCETRG<br>DHVFCDTAAGINVAEQSKECNINISTTNYPCKVSTGRHPISMVALSPLGALVACY<br>KGVSCSIGSNRVGIIKQLNKGCSYITNQDADTVTIDNTVYQLSKVEGEQHVIKGR<br>PVSSSFDPVKFPEDQFNVALDQVFESIENSQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELE<u>HHHHHH</u> |
| hMPV026 | 117 | <u>MSWKVVIIFSLLITPQHG</u>LKESYLEESCSTITEGYLSVLRTGWYTNVFTLEVGDV<br>ENLTCADGPSLIKTELDLTKSALRELRTVSADQLAREEQIENPRRRFVLGAIAL<br>GVATAAAVTAGVAIAKCIRLESEVTAIKNALKKTNEAVSTLGCGVRVLATAVREL<br>KDFVSKNLTRAINKNKCDIPDLKMAVSFSQFNRRFLNVVRQFSDNAGITPAISKD<br>LMTDAELARAISNMPTSAGQIKLMLENRAMVRRKGFGILIGVYGSSVIYMVQLPI<br>FGVIDTPCWIVKAAPSCSEKKGNYACLLREDQGWYCQNAGSTVYYPNEKDCETRG<br>DHVFCDTAAGINVAEQSKECNINISTTNYPCKVSCGRNPISMVALSPLGALVACY<br>KGVSCSIGSNRVGIIKQLNKGCSYITNQDADTVTIDNTVYQLSKVEGEQHVIKGR<br>PVSSSFDPVKFPEDQFNVALDQCFESIENSQAGSGGSGSGSGGSEKAAKAEEAAR<br>KMEELFKKHKIVAVLRANSVEEAIEKAVAVFAGGVHLIEITFTVPDADTVIKALS<br>VLKEKGAIIGAGTVTSVEQARKAVESGAEFIVSPHLDEEISQFAKEKGVFYMPGV<br>MTPTELVKAMKLGHTILKLFPGEVVGPQFVKAMKGPFPNVKFVPTGGVNLDNVAE<br>WFKAGVLAVGVGSALVKGTPDEVREKAKAFVEKIRGATELE<u>HHHHHH</u> |
| hMPV027 | 118 | <u>MSWKVVIIFSLLITPQHG</u>LKESYLEESCSTITEGYLSVLRTGWYTNVFTLEVGDV<br>ENLTCADGPSLIKTELDLTKSALRELRTVSADQLAREEQIENPRRRFVLGAIAL<br>GVATAAAVTAGVAIAKCIRLESEVTAIKNALKKTNEAVSTLGCGVRVLATAVREL<br>KDFVSKNLTRAINKNKCDIPDLKMAVSFSQFNRRFLNVVRQFSDNAGITPAISKD<br>LMTDAELARAISNMPTSAGQIKLMLENRAMVRRKGFGILIGVYGSSVIYMVQLPI<br>FGVIDTPCWIVKAAPSCSEKKGNYACLLREDQGWYCQNAGSTVYYPNEKDCETRG<br>DHVFCDTAAGINVAEQSKECNINISTTNYPCKVSCGRNPISMVALSPLGALVACY<br>KGVSCSIGSNRVGIIKQLNKGCSYITNQDADTVTIDNTVYQLSKVEGEQHVIKGR<br>PVSSSFDPVKFPEDQFNVALDQCFESIENSQALVDQSNRILSSAEKGNTGGSGGS<br>GSGSGGSEKAAKAEEAARKMEELFKKHKIVAVLRANSVEEAIEKAVAVFAGGVHL<br>IEITFTVPDADTVIKALSVLKEKGAIIGAGTVTSVEQARKAVESGAEFIVSPHLD<br>EEISQFAKEKGVFYMPGVMTPTELVKAMKLGHTILKLFPGEVVGPQFVKAMKGPF<br>PNVKFVPTGGVNLDNVAEWFKAGVLAVGVGSALVKGTPDEVREKAKAFVEKIRGA<br>TELE<u>HHHHHH</u> |
| hMPV028 | 119 | <u>MSWKVMIISLLITPQHG</u>LKESYLEESCSTITEGYLSVLRTGWYTNVFTLEVGDV<br>ENLTCTDCPSLIKTELDLTKSALRELKTVSADQLAREEQIEGGGGGGGFVLGAIAL<br>GVATAAAVTAGIAIAKTIRLESEVNAIKGCLKTTNECVSTLGNGVRVLATAVREL<br>KEFVSKNLTSAINKNKCDIADLCMAVSFSQFNRRFLNVVRQFSDNAGITPAISLD<br>LMTDAELARAVSYMPTSAGQIKLMLENRAMVRRKGFGILIGVYGSSVIYMVQLPI<br>FGVIDTPCWIIKAAPSCSEKDGNYACLLREDQGWYCKNAGSTVYYPNDKDCETRG<br>DHVFCDTAAGINVAEQSRECNINISTTNYPCKVSTGRHPISMVALSPLGALVACY |

TABLE 3-continued

Illustrative Amino Acid Sequences of VLPs of the Disclosure

| Construct name | SEQ ID NO: | Amino Acid Sequence |
|---|---|---|
| | | KGVSCSIGSNRVGIIKQLPKGCSYITNQDADTVTIDNTVYQLSKVEGEQHVIKGR PVSSSFDPICFPEDQFNVALDQVFESIENCQAGSGGSGSGSGGSEKAAKAEEAAR KMEELFKKHKIVAVLRANSVEEAIEKAVAVFAGGVHLIEITFTVPDADTVIKALS VLKEKGAIIGAGTVTSVEQCRKAVESGAEFIVSPHLDEEISQFCKEKGVFYMPGV MTPTELVKAMKLGHTILKLFPGEVVGPQFVKAMKGPFPNVKFVPTGGVNLDNVCE WFKAGVLAVGVGSALVKGTPDEVREKAKAFVEKIRGCTELE<u>HHHHHH</u> |
| hMPV029 | 120 | <u>MSWKVVIIFSLLITPQHG</u>LKESYLEESCSTITEGYLSVLRTGWYTNVFTLEVGDV ENLTCADGPSLIKTELDLTKSALRELRTVSADQLAREEQIENPRRRRFVLGAIAL GVATAAAVTAGVAIAKCIRLESEVTAIKNALKKTNEAVSTLGCGVRVLATAVREL KDFVSKNLTRAINKNKCDIPDLKMAVSFSQFNRRFLNVVRQFSDNAGITPAISKD LMTDAELARAISNMPTSAGQIKLMLENRAMVRRKGFGILIGVYGSSVIYMVQLPI FGVIDTPCWIVKAAPSCSEKKGNYACLLREDQGWYCQNAGSTVYYPNEKDCETRG DHVFCDTAAGINVAEQSKECNINISTTNYPCKVSCGRNPISMVALSPLGALVACY KGVSCSIGSNRVGIIKQLNKGCSYITNQDADTVTIDNTVYQLSKVEGEQHVIKGR PVSSSFDPVKFPEDQFNVALDQCFESIENSQAGSGGSGSGSGGSEKAAKAEEAAR KMEELFKKHKIVAVLRANSVEEAIEKAVAVFAGGVHLIEITFTVPDADTVIKALS VLKEKGAIIGAGTVTSVEQCRKAVESGAEFIVSPHLDEEISQFCKEKGVFYMPGV MTPTELVKAMKLGHTILKLFPGEVVGPQFVKAMKGPFPNVKFVPTGGVNLDNVCE WFKAGVLAVGVGSALVKGTPDEVREKAKAFVEKIRGCTELE<u>HHHHHH</u> |
| hMPV030 | 121 | <u>MSWKVVIIFSLLITPQHG</u>LKESYLEESCSTITEGYLSVLRTGWYTNVFTLEVGDV ENLTCADGPSLIKTELDLTKSALRELRTVSADQLAREEQIENPRRRRFVLGAIAL GVATAAAVTAGVAIAKCIRLESEVTAIKNALKKTNEAVSTLGCGVRVLATAVREL KDFVSKNLTRAINKNKCDIPDLKMAVSFSQFNRRFLNVVRQFSDNAGITPAISKD LMTDAELARAISNMPTSAGQIKLMLENRAMVRRKGFGILIGVYGSSVIYMVQLPI FGVIDTPCWIVKAAPSCSEKKGNYACLLREDQGWYCQNAGSTVYYPNEKDCETRG DHVFCDTAAGINVAEQSKECNINISTTNYPCKVSCGRNPISMVALSPLGALVACY KGVSCSIGSNRVGIIKQLNKGCSYITNQDADTVTIDNTVYQLSKVEGEQHVIKGR PVSSSFDPVKFPEDQFNVALDQCFESIENSQALVDQSNRILSSAEKGNTGGSGGS GSGSGGSEKAAKAEEAARKMEELFKKHKIVAVLRANSVEEAIEKAVAVFAGGVHL IEITFTVPDADTVIKALSVLKEKGAIIGAGTVTSVEQCRKAVESGAEFIVSPHLD EEISQFCKEKGVFYMPGVMTPTELVKAMKLGHTILKLFPGEVVGPQFVKAMKGPF PNVKFVPTGGVNLDNVCEWFKAGVLAVGVGSALVKGTPDEVREKAKAFVEKIRGC TELE<u>HHHHHH</u> |
| hMPV031 | 122 | <u>MSWKVMIIISLLITPQHG</u>LKESYLEESCSTITEGYLSVLRTGWYTNVFTLEVGDV ENLTCTDGPSLIKTELDLTKSALRELKTCSADQLAREEQIEGGGGGGFVLGAIAL GVATAAAVTAGIAIAKTIRLESEVNAIKGCLKTTNECVSTLGNGVRVLATAVREL KEFVSKNLTSAINKNKCDIADLKMAVSFSQFNRRFLNVVRQFSDNAGITPAISLD LMTDAELARAVSYMPTSAGQIKLMLENRCMVRRKGFGILIGVYGSSVIYMVQLPI FGVIDTPCWIIKAAPSCSEKDGNYACLLREDQGWYCKNAGSTVYYPNDKDCETRG DHVFCDTAAGINVAEQSRECNINISTTNYPCKVSTGRHPISMVALSPLGALVACY KGVSCSIGSNRVGIIKQLPKGCSYITNQDADTVTIDNTVYQLSKVEGEQHVIKGR PVSSSFDPIKFPEDQFNVALDQVFESIENSQAGSGGSGSGSGGSEKAAKAEEAAR KMEELFKKHKIVAVLRANSVEEAIEKAVAVFAGGVHLIEITFTVPDADTVIKALS VLKEKGAIIGAGTVTSVEQCRKAVESGAEFIVSPHLDEEISQFCKEKGVFYMPGV MTPTELVKAMKLGHTILKLFPGEVVGPQFVKAMKGPFPNVKFVPTGGVNLDNVCE WFKAGVLAVGVGSALVKGTPDEVREKAKAFVEKIRGCTELE<u>HHHHHH</u> |
| hMPV033 | 123 | <u>MSWKVVIIFSLLITPQHG</u>LKESYLEESCSTITEGYLSVLRTGWYTNVFTLEVGDV ENLTCADGPSLIKTELDLTKSALRELRTVSADQLAREEQIEGGGGGGFVLGAIAL GVATAAAVTAGVAIAKCIRLESEVTAIKNALKKTNEAVSTLGCGVRVLATAVREL KDFVSKNLTRAINKNKCDIPDLKMAVSFSQFNRRFLNVVRQFSDNAGITPAISKD LMTDAELARAISNMPTSAGQIKLMLENRAMVRRKGFGILIGVYGSSVIYMVQLPI FGVIDTPCWIVKAAPSCSEKKGNYACLLREDQGWYCQNAGSTVYYPNEKDCETRG DHVFCDTAAGINVAEQSKECNINISTTNYPCKVSCGRNPISMVALSPLGALVACY KGVSCSIGSNRVGIIKQLNKGCSYITNQDADTVTIDNTVYQLSKVEGEQHVIKGR PVSSSFDPVKFPEDQFNVALDQCFESIENSQAGSGGSGSGSGGSEKAAKAEEAAR KMEELFKKHKIVAVLRANSVEEAIEKAVAVFAGGVHLIEITFTVPDADTVIKALS VLKEKGAIIGAGTVTSVEQARKAVESGAEFIVSPHLDEEISQFAKEKGVFYMPGV MTPTELVKAMKLGHTILKLFPGEVVGPQFVKAMKGPFPNVKFVPTGGVNLDNVAE WFKAGVLAVGVGSALVKGTPDEVREKAKAFVEKIRGATELE<u>HHHHHH</u> |
| hMPV034 | 124 | <u>MSWKVVIIFSLLITPQHG</u>LKESYLEESCSTITEGYLSVLRTGWYTNVFTLEVGDV ENLTCADGPSLIKTELDLTKSALRELRTVSADQLAREEQIEGGGGGGFVLGAIAL GVATAAAVTAGVAIAKCIRLESEVTAIKNALKKTNEAVSTLGCGVRVLATAVREL KDFVSKNLTRAINKNKCDIPDLKMAVSFSQFNRRFLNVVRQFSDNAGITPAISKD LMTDAELARAISNMPTSAGQIKLMLENRAMVRRKGFGILIGVYGSSVIYMVQLPI FGVIDTPCWIVKAAPSCSEKKGNYACLLREDQGWYCQNAGSTVYYPNEKDCETRG DHVFCDTAAGINVAEQSKECNINISTTNYPCKVSCGRNPISMVALSPLGALVACY KGVSCSIGSNRVGIIKQLNKGCSYITNQDADTVTIDNTVYQLSKVEGEQHVIKGR PVSSSFDPVKFPEDQFNVALDQCFESIENSQALVDQSNRILSSAEKGNTGGSGGS GSGSGGSEKAAKAEEAARKMEELFKKHKIVAVLRANSVEEAIEKAVAVFAGGVHL |

TABLE 3-continued

Illustrative Amino Acid Sequences of VLPs of the Disclosure

| Construct name | SEQ ID NO: | Amino Acid Sequence |
|---|---|---|
| | | IEITFTVPDADTVIKALSVLKEKGAIIGAGTVTSVEQARKAVESGAEFIVSPHLD EEISQFAKEKGVFYMPGVMTPTELVKAMKLGHTILKLFPGEVVGPQFVKAMKGPF PNVKFVPTGGVNLDNVAEWFKAGVLAVGVGSALVKGTPDEVREKAKAFVEKIRGA TELEHHHHHH |

Assembly of VLPs

In some embodiments, a single component self-assembles into the VLP. In some embodiments, one or more purified samples of first and second components for use in forming a VLP are mixed in an approximately equimolar molar ratio in aqueous conditions (e.g., an I53-50A/B icosahedral VLP). The first and second components (through the multimerization domains and optionally through the ectodomains) interact with one another to drive assembly of the target VLP. Successful assembly of the target VLP can be confirmed by analyzing the in vitro assembly reaction by common biochemical or biophysical methods used to assess the physical size of proteins or protein assemblies, including but not limited to size exclusion chromatography, native (non-denaturing) gel electrophoresis, dynamic light scattering, multi-angle light scattering, analytical ultracentrifugation, negative stain electron microscopy, cryo-electron microscopy, or X-ray crystallography. If necessary, the assembled VLP can be purified from other species or molecules present in the in vitro assembly reaction using preparative techniques commonly used to isolate proteins by their physical size, including but not limited to size exclusion chromatography, preparative ultracentrifugation, tangential flow filtration, or preparative gel electrophoresis. The presence of the antigenic protein in the VLP can be assessed by techniques commonly used to determine the identity of protein molecules in aqueous solutions, including but not limited to SDS-PAGE, mass spectrometry, protein sequencing, ELISA, surface plasmon resonance, biolayer interferometry, or amino acid analysis. The accessibility of the protein on the exterior of the particle, as well as its conformation or antigenicity, can be assessed by techniques commonly used to detect the presence and conformation of an antigen, including but not limited to binding by monoclonal antibodies, conformation-specific monoclonal antibodies, surface plasmon resonance, biolayer interferometry, or antisera specific to the antigen.

In various embodiments, the VLPs of the disclosure comprise two or more distinct first polypeptides bearing different antigenic proteins as genetic fusions; these VLPs co-display multiple different proteins on the same VLP. These multi-antigen VLPs are produced by performing in vitro assembly with mixtures of two or more antigens each comprising a multimerization domain. The fraction of each antigen in the mixture determines the average valency of each antigenic protein in the resulting VLPs. The presence and average valency of each antigen in a given sample can be assessed by quantitative analysis using the techniques described above for evaluating the presence of antigenic proteins in full-valency VLPs.

In various embodiments, the VLPs are between about 20 nanometers (nm) to about 40 nm in diameter, with interior lumens between about 15 nm to about 32 nm across and pore sizes in the protein shells between about 1 nm to about 14 nm in their longest dimensions.

In some embodiments, the VLPs has icosahedral symmetry. In such embodiment, the VLP may comprise 60 copies of a first component and 60 copies of a second component. In one such embodiment, the number of identical first polypeptides in each first assembly is different than the number of identical first polypeptides in each second assembly. For example, in some embodiments, the VLP comprises twelve first assemblies and twenty second assemblies; in such embodiments, each first assembly may, for example, comprise five copies of the identical first component, and each second assembly may, for example, comprise three copies of the identical second component. In other embodiments, the VLP comprises twelve first assemblies and thirty second assemblies; in such an embodiment, each first assembly may, for example, comprise five copies of the identical first component, and each second assembly may, for example, comprise two copies of the identical second component. In further embodiments, the VLP comprises twenty first assemblies and thirty second assemblies; in this embodiment, each first assembly may, for example, comprise three copies of the identical first component, and each second assembly may, for example, comprise two copies of the identical second component. All of these embodiments are capable of forming protein-based VLPs with regular icosahedral symmetry.

In various further embodiments, oligomeric states of the first and second multimerization domains are as follows:

I53-34A: trimer+I53-34B: pentamer;
I53-40A: pentamer+I53-40B: trimer;
I53-47A: trimer+I53-47B: pentamer;
I53-50A: trimer+I53-50B: pentamer;
I53-51A: trimer+I53-51B: pentamer;
I32-06A: dimer+I32-06B: trimer;
I32-19A: trimer+I32-19B: dimer;
I32-28A: trimer+I32-28B: dimer;
I52-03A: pentamer+I52-03B: dimer;
I52-32A: dimer+I52-32B: pentamer; and
I52-33A: pentamer+I52-33B: dimer In some embodiments, the second multimerization domain of the second polypeptide comprises a sequence that shares at least 95% identity to I53-50A or a variant thereof:

I53-50A
(SEQ ID NO: 144)
 1 MEELFKKHKI VAVLRANSVE EAIEKAVAVF AGGVHLIEIT

41 FTVPDADTVI KALSVLKEKG AIIGAGTVTS VEQCRKAVES

81 GAEFIVSPHL DEEISQFCKE KGVFYMPGVM TPTELVKAMK

```
121 LGHTILKLFP GEVVGPQFVK AMKGPFPNVK FVPTGGVNLD

161 NVCEWFKAGV LAVGVGSALV KGTPDEVREK AKAFVEKIRG

201 CTE
```

In some embodiments, the second multimerization domain shares at least 90%, 95%, 96%, 97%, 98%, 99%, or 100% sequence identity to SEQ ID NO: 7 or SEQ ID NO: 144, or an antigenic fragment thereof.

The I53-50A protein sequence has two intra-monomer disulfide bonds. In some embodiments, the cysteine residues are mutated to residues that do not contain a thiol group (e.g. alanine or serine). Removal of the thiol group may promote correct protein folding while not impairing multimerization. In some embodiments, the multimerization domain of the first polypeptide comprises an amino acid substitution at one or more of positions 74, 98, 163, and 201 relative to SEQ ID NO: 144, as shown here:

```
I53-50A
                                        (SEQ ID NO: 144)
  1 MEELFKKHKI VAVLRANSVE EAIEKAVAVF AGGVHLIEIT

41 FTVPDADTVI KALSVLKEKG AIIGAGTVTS VEQCRKAVES

81 GAEFIVSPHL DEEISQFCKE KGVFYMPGVM TPTELVKAMK

121 LGHTILKLFP GEVVGPQFVK AMKGPFPNVK FVPTGGVNLD

161 NVCEWFKAGV LAVGVGSALV KGTPDEVREK AKAFVEKIRG

201 CTE
```

In some embodiments, the multimerization domain of the first polypeptide comprises an amino acid substitution of one or more of C74A, C98A, C163A, and C201A relative to SEQ ID NO: 132. In some embodiments, the multimerization domain of the first polypeptide comprises SEQ ID NO: 132 or a variant thereof.

```
I53-50A-Δcys (disulfide-free form)
                                        (SEQ ID NO: 132)
  1 MEELFKKHKI VAVLRANSVE EAIEKAVAVF AGGVHLIEIT

41 FTVPDADTVI KALSVLKEKG AIIGAGTVTS VEQARKAVES

81 GAEFIVSPHL DEEISQFAKE KGVFYMPGVM TPTELVKAMK

121 LGHTILKLFP GEWGPQFVK AMKGPFPNVK FVPTGGVNLD

161 NVAEWFKAGV LAVGVGSALV KGTPDEVREK AKAFVEKIRG

201 ATE
```

In some embodiments, the multimerization domain shares at least 90%, 95%, 96%, 97%, 98%, 99%, or 100% sequence identity to SEQ ID NO: 144 or SEQ ID NO: 132, or an antigenic fragment thereof, and comprises one, two, three or four amino acid substitutions selected from C74A, C98A, C163A, and C201A. Alternatively, the substitution may be of C to A, T, S, L, I, or any amino acid other than C.

Nucleic Acids

In another aspect, the present disclosure provides isolated nucleic acids encoding an antigen, a first component, and/or a second component, of the present disclosure. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the proteins of the disclosure.

In a further aspect, the present disclosure provides recombinant expression vectors comprising the isolated nucleic acid of any embodiment or combination of embodiments of the disclosure operatively linked a suitable control sequence. "Recombinant expression vector" includes vectors that operatively link a nucleic acid coding region or gene to any control sequences capable of effecting expression of the gene product. "Control sequences" operably linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, TX). The expression vector must be replicable in the host organisms either as an episome or by integration into host chromosomal DNA. In a preferred embodiment, the expression vector comprises a plasmid. However, the disclosure is intended to include other expression vectors that serve equivalent functions, such as viral vectors.

In another aspect, the present disclosure provides host cells that have been transfected or transduced with the recombinant expression vectors disclosed herein, wherein the host cells can be either prokaryotic or eukaryotic. The cells can be transiently or stably transfected or transduced. Such transfection or transduction of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2nd Ed. (R. I. Freshney. 1987. Liss, Inc. New York, NY).

In another aspect, the disclosure provides a method of producing an antigen, component, or VLP according to the disclosure. In some embodiments, the method comprises the steps of (a) culturing a host according to this aspect of the disclosure under conditions conducive to the expression of the polypeptide, and (b) optionally, recovering the expressed polypeptide.

In some embodiments, the disclosure provides a method of manufacturing a vaccine, comprising culturing a host cell comprising a polynucleotide comprising a sequence encoding the antigen of the disclosure in a culture medium so that the host cell secretes the antigen into the culture media; optionally purifying the antigen from the culture media; mixing the antigen with a second component, wherein the second component multimerizes with the antigen to form a VLP; and optionally purifying the VLP.

In some embodiments, the disclosure provides method of manufacturing a vaccine, comprising culturing a host cell comprising one or more polynucleotides comprising sequences encoding both components of the VLP of any one of disclosure so that the host cell secretes the first component and the second component into the culture media; and optionally purifying the VLP from the culture media.

Illustrative host cells in include *E. coli* cells, 293 and 293F cells, HEK293 cells, Sf9 cells, Chinese hamster ovary (CHO) cells and any other cell line used in the production of recombinant proteins.

In various embodiments, the first component expresses at about 0.5 mg/mL, about 1.0 mg/mL, about 1.5 mg/mL, about 2.5 mg/mL, about 5 mg/mL, about 10 mg/mL, about 25 mg/mL, about 50 mg/mL, about 75 mg/mL, about 100 mg/mL, or greater in a method of manufacturing according to the disclosure (e.g. 293F cells grown in suspension). In various embodiments, the first component expresses at least 50%, at least 60%, at least 70%, at least 80%, at least 90%, or at least 95% of the expression level of a hMPV F protein (optionally the same ectodomain as in the VLP) in the same or similar expression system. In various embodiments, the first component expresses at least 105%, at least 110%, at least 115%, at least 120%, at least 125%, at least 150%, at least 175%, or at least 200% of the expression level of a hMPV F protein (optionally the same ectodomain as in the VLP) in the same or similar expression system.

In some embodiments, the hMPV F protein ectodomain of the first component is in the prefusion conformation, or a substantial fraction of the hMPV F protein ectodomain is in the prefusion conformation. In various embodiments, at least 50%, at least 60%, at least 70%, at least 80%, at least 90%, or at least 95% of the hMPV F protein ectodomain of the first component is in the prefusion conformation. In some embodiments, the hMPV F protein ectodomain of the VLP is in the prefusion conformation, or a substantial fraction of the hMPV F protein ectodomain is in the prefusion conformation. In various embodiments, at least 50%, at least 60%, at least 70%, at least 80%, at least 90%, or at least 95% of the hMPV F protein ectodomain of the VLP is in the prefusion conformation.

In some embodiments, the fraction of hMPV F protein ectodomain in the prefusion state is determined by binding to a conformation-specific antibody (e.g., D1-25 and 1112-1). In some embodiments, the fraction of hMPV F protein ectodomain in the first component in the prefusion conformation is at least 105%, at least 110%, at least 115%, at least 120%, at least 125%, at least 150%, at least 175%, or at least 200% greater than the fraction in a reference component, or than the fraction in a reference protein not linked to a multimerization domain. In some embodiments, the fraction of hMPV F protein ectodomain in the first component in the prefusion conformation is at least 105%, at least 110%, at least 115%, at least 120%, at least 125%, at least 150%, at least 175%, or at least 200% greater than the fraction in a VLP (e.g., micelle VLP)

Vaccines and Administration

The disclosure also provides vaccines comprising the VLPs described herein. Such compositions can be used to raise antibodies in a mammal (e.g. a human). The vaccines compositions of the disclosure typically include a pharmaceutically acceptable carrier, and a thorough discussion of such carriers is available in Remington: The Science and Practice of Pharmacy.

The pH of the composition is usually between about 4.5 to about 11, such as between about 5 to about 11, between about 5.5 to about 11, between about 6 to about 11, between about 5 to about 10.5, between about 5.5 to about 10.5, between about 6 to about 10.5, between about 5 to about 10, between about 5.5 to about 10, between about 6 to about 10, between about 5 to about 9.5, between about 5.5 to about 9.5, between about 6 to about 9.5, between about 5 to about 9, between about 5.5 to about 9, between about 6 to about 9, between about 5 to about 8.5, between about 5.5 to about 8.5, between about 6 to about 8.5, between about 5 to about 8, between about 5.5 to about 8, between about 6 to about 8, about 4.5, about 5, about 6.5, about 6, about 6.5, about 7, about 7.5, about 8, about 8.5, about 9, about 9.5, about 10, about 10.5, about 11, etc. Stable pH may be maintained by the use of a buffer e.g. a Tris buffer, a citrate buffer, phosphate buffer, or a histidine buffer. Thus a composition will generally include a buffer.

A composition may be sterile and/or pyrogen free. Compositions may be isotonic with respect to humans.

A vaccine composition comprises an immunologically effective amount of its antigen(s). An "immunologically effective amount" or "effective amount" is an amount which, when administered to a subject, is effective for eliciting an antibody response against the antigen. This amount can vary depending upon the health and physical condition of the individual to be treated, their age, the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the disclosure will generally be expressed in terms of the mass of protein per dose. A dose of 10-500 μg (e.g. 50 μg) per antigen can be useful.

Vaccine compositions may include an immunological adjuvant. Illustrative adjuvants include the following: 1. mineral-containing compositions; 2. oil emulsions; 3. saponin formulations; 4. virosomes and virus-like particles; 5. bacterial or microbial derivatives; 6. bioadhesives and mucoadhesives; 7. liposomes; 8. polyoxyethylene ether and polyoxyethylene ester formulations; 9. polyphosphazene (pcpp); 10. muramyl peptides; 11. imidazoquinolone compounds; 12. thiosemicarbazone compounds; 13. tryptanthrin compounds; 14. human immunomodulators; 15. lipopeptides; 16. benzonaphthyridines; 17. microparticles; 18. immunostimulatory polynucleotide (such as rna or dna; e.g., cpg-containing oligonucleotides).

For example, the composition may include an aluminum salt adjuvant, an oil in water emulsion (e.g. an oil-in-water emulsion comprising squalene, such as MF59 or AS03), a TLR7 agonist (such as imidazoquinoline or imiquimod), or a combination thereof. Suitable aluminum salts include hydroxides (e.g. oxyhydroxides), phosphates (e.g. hydroxyphosphates, orthophosphates), (e.g. see chapters 8 & 9 of Vaccine Design. (1995) eds. Powell & Newman. ISBN: 030644867X. Plenum), or mixtures thereof. The salts can take any suitable form (e.g. gel, crystalline, amorphous, etc.), with adsorption of antigen to the salt being an example. The concentration of $Al^{+++}$ in a composition for administration to a patient may be less than 5 mg/ml e.g. <4 mg/ml, <3 mg/ml, <2 mg/ml, <1 mg/ml, etc. A preferred range is between 0.3 and 1 mg/ml. A maximum of 0.85 mg/dose is preferred. Aluminum hydroxide and aluminium phosphate adjuvants are suitable for use with the disclosure.

Exemplary adjuvants that may be used in a pharmaceutical composition provided herein include, but are not limited to, 3M-052, Adju-Phos™, Alhydrogel™, Adjumer™, albumin-heparin microparticles, Algal Glucan, Algammulin, Alum, Antigen Formulation, AS-2 adjuvant, AS01, AS03, autologous dendritic cells, autologous PBMC, Avridine™, B7-2, BAK, BAY R1005, BECC TLR-4 agonists, Bupivacaine, Bupivacaine-HCl, BWZL, Calcitriol, Calcium Phosphate Gel, CCR5 peptides, CFA, Cholera holotoxin (CT) and Cholera toxin B subunit (CTB), Cholera toxin A1-subunit-Protein A D-fragment fusion protein, CpG, CPG-1018, CRL1005, Cytokine-containing Liposomes, D-Murapalmitine, DDA, DHEA, Diphtheria toxoid, DL-PGL, DMPC, DMPG, DOC/Alum Complex, Fowlpox, Freund's Complete Adjuvant, Gamma Inulin, Gerbu Adjuvant, GM-CSF, GMDP, hGM-CSF, hIL-12 (N222L), hTNF-alpha, IFA, IFN-gamma in pcDNA3, IL-12 DNA, IL-12 plasmid, IL-12/GMCSF plasmid (Sykes), IL-2 in pcDNA3, IL-2/Ig plasmid, IL-2/Ig protein, IL-4, IL-4 in pcDNA3, Imiquimod™, ImmTher™, Immunoliposomes Containing Antibodies to Costimulatory Molecules, Interferon-gamma, Interleukin-1 beta, Interleukin-12, Interleukin-2, Interleukin-7, ISCOM(s)™, Iscoprep 7.0.3™, Keyhole Limpet Hemocyanin, Lipid-based Adjuvant, Liposomes, Loxoribine, LT(R192G), LT-OA or LT Oral Adjuvant, LT-R192G, LTK63, LTK72, Matrix-M™ adjuvant, MF59, MONTANIDE ISA 51, MONTANIDE ISA 720, MPL™, MPL-SE, MTP-PE, MTP-PE Liposomes, Murametide, Murapalmitine, NAGO, nCT native Cholera Toxin, Non-Ionic Surfactant Vesicles, non-toxic mutant E112K of Cholera Toxin mCT-E112K, p-Hydroxybenzoique acid methyl ester, pCIL-10, pCIL12, pCMVmCAT1, pCMVN, Peptomer-NP, Pleuran, PLG, PLGA, PGA, and PLA, Pluronic L121, PMMA, PODDSM, Poly rA: Poly rU, Polysorbate 80, Protein Cochleates, QS-21, Quadri A saponin, Quil-A, Rehydragel HPA, Rehydragel LV, RIBI, Ribi like adjuvant system (MPL, TMD, CWS), S-28463, SAF-1, Sclavo peptide, Sendai Proteoliposomes, Sendai-containing Lipid Matrices, Span 85, Specol, Squalane 1, Squalene 2, Stearyl Tyrosine, SWE, Tetanus toxoid (TT), Theramide™, Threonyl muramyl dipeptide (TMDP), Ty Particles, and Walter Reed Liposomes.

In preferred embodiments, the adjuvant is an aluminium hydroxide gel (e.g., Alhydrogel™). In preferred embodiments, the adjuvant is SWE. In preferred embodiments, the adjuvant is MF59.

MF59 is an oil-in-water emulsion containing squalene (4.3%) in citric acid buffer with stabilizing nonionic surfactants Tween 80 (0.5%) and Span 85 (0.5%). MF59 has been shown to be well-tolerated in humans and is used in vaccines against seasonal influenza (see Ko and Kang, Hum Vaccin Immunother. 2018; 14(12): 3041-3045; U.S. Pat. No. 6,299,884).

For example, the composition may include an aluminum salt adjuvant, an oil in water emulsion (e.g. an oil-in-water emulsion comprising squalene, such as MF59, SWE, or AS03), a TLR9 agonist (such as CpG oligodeoxynucleotides), a TLR7 agonist (such as imidazoquinoline or imiquimod), or a combination thereof. In some embodiments, the adjuvant is a combination of an aluminum salt and CPG1018. Suitable aluminum salts include hydroxides (e.g. oxyhydroxides), phosphates (e.g. hydroxyphosphates, orthophosphates), (e.g. see chapters 8 & 9 of Vaccine Design. (1995) eds. Powell & Newman. ISBN: 030644867X. Plenum), or mixtures thereof. The salts can take any suitable form (e.g. gel, crystalline, amorphous, etc.), with adsorption of antigen to the salt being an example. The concentration of Al+++ in a composition for administration to a patient may be less than 5 mg/ml e.g. <4 mg/ml, <3 mg/ml, <2 mg/ml, <1 mg/ml, etc. A preferred range is between 0.3 and 1 mg/ml. A maximum of 0.85 mg/dose is preferred. Aluminum hydroxide and aluminium phosphate adjuvants are suitable for use with the disclosure. In a preferred embodiment, a pharmaceutical composition provided herein comprises aluminum hydroxide as an adjuvant. In some embodiment, a pharmaceutical composition provided herein comprises 500 µg aluminium hydroxide.

Selection of an adjuvant depends on the subject to be treated. Preferably, a pharmaceutically acceptable adjuvant is used.

In some embodiments, the adjuvant is a squalene emulsion.

In some embodiments, the adjuvant is a TLR4 immunostimulant (e.g., SLA, GLA), e.g., as described in Van Hoeven at al. PLoS One. 11(2):e0149610 (2016).

In some embodiments, the adjuvant is a TLR7/8 immunostimulant (e.g., R848, IMQ, 3M-052), e.g., as described in Dowling D. *ImmunoHorizons* (6):185-197 (2018).

In some embodiments, the adjuvant is a TLR9 immunostimulant (CpG), e.g., as described in Bode et al. *Expert Rev Vaccines*. 10(4):499-511 (2011).

In some embodiments, the adjuvant is saponin (QS21), e.g., as described in Zhu et al. *Nat Prod Chem Res*. 3(4):e113 (2016).

In some embodiments, the vaccine comprises a combination of two or more adjuvants (e.g. squalene emulsion and alum or a TLR4 immunostimulant).

One suitable immunological adjuvant comprises a compound of Formula (I) as defined in WO2011/027222, or a pharmaceutically acceptable salt thereof, adsorbed to an aluminum salt. Many further adjuvants can be used, including any of those disclosed in Powell & Newman (1995).

Compositions may include an antimicrobial, particularly when packaged in multiple dose format. Antimicrobials such as thiomersal and 2-phenoxyethanol are commonly found in vaccines, but sometimes it may be desirable to use either a mercury-free preservative or no preservative at all.

Compositions may comprise detergent e.g. a polysorbate, such as polysorbate 80. Detergents are generally present at low levels e.g. <0.01%.

Compositions may include sodium salts (e.g. sodium chloride) to give tonicity. A concentration of 10±2 mg/ml NaCl is typical e.g. about 9 mg/ml.

In some embodiments, the buffer in the vaccine composition is a Tris buffer, a histidine buffer, a phosphate buffer, a citrate buffer or an acetate buffer. The composition may also include a lyoprotectant, e.g. sucrose, sorbitol or trehalose. In certain embodiments, the composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the composition includes a bulking agent, like glycine. In yet other embodiments, the composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The composition may also include a tonicity adjusting agent, e.g., a compound that renders the formulation substantially isotonic or isoosmotic with human blood. Illustrative tonicity adjusting agents include sucrose, sorbitol, glycine, methionine, mannitol, dextrose, inositol, sodium chloride, arginine and arginine hydrochloride. In other embodiments, the composition additionally includes a stabilizer, e.g., a molecule which substantially prevents or reduces chemical and/or physical instability of the VLP, in lyophilized or liquid form. Illustrative stabilizers include sucrose, sorbitol, glycine, inositol, sodium chloride, methionine, arginine, and arginine hydrochloride.

In some embodiments, the disclosure provides a vaccine (immunogenic composition) comprising one or more pharmaceutically acceptable excipients.

In some embodiments, the vaccine (immunogenic composition) is a stable emulsion.

In some embodiments, the disclosure provides a vaccine (immunogenic composition) comprises one or more adjuvants. In some embodiments, the one or more adjuvants comprises a TLR4 immunostimulant, e.g., Monophosphoryl Lipid A (MPL), Glucopyranosyl Lipid A (GLA), and/or Soluble Leishmania Antigen (SLA).

In another aspect, the disclosure provides a method of inducing an immune response against hMPV, comprising administering to a subject in need thereof an immunologically effective amount of the immunogenic composition described herein, which comprises the VLP as described herein.

In certain embodiments, the immune response comprises the production of neutralizing antibodies against an infectious agent. In certain embodiments, the neutralizing antibodies are complement-independent.

The immune response can comprise a humoral immune response, a cell-mediated immune response, or both. In some embodiments an immune response is induced against each delivered antigenic protein. A cell-mediated immune response can comprise a Helper T-cell (Th) response, a CD8+ cytotoxic T-cell (CTL) response, or both. In some embodiments the immune response comprises a humoral immune response, and the antibodies are neutralizing antibodies. Neutralizing antibodies block viral infection of cells. Viruses infect epithelial cells and also fibroblast cells. In some embodiments the immune response reduces or prevents infection of both cell types. Neutralizing antibody responses can be complement-dependent or complement-independent. In some embodiments the neutralizing antibody response is complement-independent. In some embodiments the neutralizing antibody response is cross-neutralizing; i.e., an antibody generated against an administered composition neutralizes a virus of a strain other than the strain used in the composition.

A useful measure of antibody potency in the art is "50% neutralization titer." To determine 50% neutralizing titer, serum from immunized animals is diluted to assess how dilute serum can be yet retain the ability to block entry of 50% of viruses into cells. For example, a titer of 700 means that serum retained the ability to neutralize 50% of virus after being diluted 700-fold. Thus, higher titers indicate more potent neutralizing antibody responses. In some embodiments, this titer is in a range having a lower limit of about 200, about 400, about 600, about 800, about 1000, about 1500, about 2000, about 2500, about 3000, about 3500, about 4000, about 4500, about 5000, about 5500, about 6000, about 6500, or about 7000. The 50% neutralization titer range can have an upper limit of about 400, about 600, about 800, about 1000, about 1500, about 2000, about 2500, about 3000, about 3500, about 4000, about 4500, about 5000, about 5500, about 6000, about 6500, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, or about 30000. For example, the 50% neutralization titer can be about 3000 to about 25000. "About" means plus or minus 10% of the recited value.

In some embodiments, the virus-like particles of the disclosure generate an immune response of 0.5 IU/mL, 1.0 IU/mL, 1.5 IU/mL, 2.0 IU/mL, 10 IU/mL, 25 IU/mL, 50 IU/mL, 100 IU/mL or greater. In some embodiments, the virus-like particles of the disclosure generate an immune response of 0.5 IU/mL or greater.

Compositions of the disclosure will generally be administered directly to a subject. Direct delivery may be accomplished by parenteral injection (e.g. subcutaneously, intraperitoneally, intravenously, intramuscularly, or to the interstitial space of a tissue), orally, intranasal, or by any other suitable route. For example, intramuscular administration may be used e.g. to the thigh or the upper arm. Injection may be via a needle (e.g. a hypodermic needle), but needle-free injection may alternatively be used. A typical intramuscular dosage volume is 0.5 ml.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.). Multiple doses may be administered at least 1 month apart (e.g., about 2 months, about 3 months, about 4 months, about 6 months, about 8 months, about 10 months, about 12 months, about 16 months, etc.). A second or subsequent does may be administered over longer intervals, e.g., about 1 year or about 2 years after the previous dose.

Where the vaccine is for prophylactic use, the human is preferably a child (e.g., a toddler or infant), a teenager, or an adult; where the vaccine is for therapeutic use, the human is preferably a teenager or an adult. A vaccine intended for children may also be administered to adults, e.g., to assess safety, dosage, immunogenicity, etc.

Vaccines of the disclosure may be prophylactic (i.e. to prevent disease) or therapeutic (i.e. to reduce or eliminate the symptoms of a disease). The term prophylactic may be considered as reducing the severity of or preventing the onset of a particular condition. For the avoidance of doubt, the term prophylactic vaccine may also refer to vaccines that ameliorate the effects of a future infection, for example by reducing the severity or duration of such an infection.

Isolated and/or purified VLPs described herein can be administered alone or as either prime or boost in mixed-modality regimes, such as a RNA prime or DNA primer followed by a protein boost. Benefits of the RNA-prime/ protein-boost strategy, as compared to a protein-prime/ protein-boost strategy, include, for example, increased antibody titers, a more balanced IgG1:IgG2a subtype profile, induction of TH1-type CD4+ T cell-mediated immune response that was similar to that of viral particles, and reduced production of non-neutralizing antibodies. The RNA prime can increase the immunogenicity of compositions regardless of whether they contain or do not contain an adjuvant.

In the RNA-prime/protein boost-strategy, the RNA and the protein are directed to the same target antigen. Examples of suitable modes of delivering RNAs include virus-like replicon particles (VRPs), alphavirus RNA, replicons encapsulated in lipid nanoparticles (LNPs) or formulated RNAs, such as replicons formulated with cationic nanoemulsions (CNEs). Suitable cationic oil-in-water nanoemulsions are disclosed in WO2012/006380 e.g. comprising an oil core (e.g. comprising squalene) and a cationic lipid (e.g. DOTAP, DMTAP, DSTAP, DC-cholesterol, etc.).

Alternatively, two doses of the VLP may be administered at a predetermined interval to achieve a prime-boost effect. The predetermined interval may be 1, 2, 3, 4, 6, 7, 10, or 14 days; or 3-5 days, 7-10 days, or 10-14 days or the like. The predetermined interval may be 1, 2, 3, 4, or 6 weeks; or 2-3 weeks, 3-4 weeks, or 5-6 weeks or the like. The predetermined interval may be 1, 2, 3, or 4 months.

In some embodiments, the RNA molecule is encapsulated in, bound to or adsorbed on a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, a cationic nanoemulsion, or combinations thereof.

The disclosure further provides combination vaccines. The vaccines of the disclosure include vaccines comprising both a hMPV VLP and vaccines for one or more of SARS-CoV-2, respiratory syncytial virus, Rabies, Typhoid fever, Hepatitis A, Polio, Influenza, Hepatitis B, Yellow Fever, Japanese encephalitis, Parvovirus, Distemper, Adenovirus, Parainfluenza, Influenza, Measles, Lyme disease, Coronavirus, Vesicular stomatitis virus, Herpes simplex virus, Baculovirus, Thogotovirus, and Bornaviridae.

Also provided herein are kits for administration of nucleic acid (e.g., RNA), purified proteins, and purified VLPs described herein, and instructions for use. The disclosure also provides a delivery device pre-filled with a composition or a vaccine disclosed herein.

The pharmaceutical compositions described herein can be administered in combination with one or more additional therapeutic agents. The additional therapeutic agents may include, but are not limited to antibiotics or antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferon, ribavirin, hormones, and other toll-like receptor modulators, immunoglobulins (Igs), and antibodies modulating Ig function (such as anti-IgE (omalizumab)).

In certain embodiments, the compositions disclosed herein may be used as a medicament, e.g., for use in inducing or enhancing an immune response in a subject in need thereof, such as a mammal.

In certain embodiments, the compositions disclosed herein may be used in the manufacture of a medicament for inducing or enhancing an immune response in a subject in need thereof, such as a mammal.

One way of checking efficacy of therapeutic treatment involves monitoring infection by an infectious agent after administration of the compositions or vaccines disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

EXAMPLES

Example 1

This example illustrates production of a two-component, icosahedral VLP intended for use as a vaccine for hMPV virus. As first component A, the vaccine uses a polypeptide antigen composed of the ectodomain of hMPV F protein, C-terminally fused to the I53-50A protein (SEQ ID NO: 144). As component B, the VLP uses the I53-50B protein. It is known that I53-50A and I53-50B spontaneously assemble in 3:5 ratio to form a VLP having icosahedral (I53) symmetry, as shown in FIGS. 1A and B.

The expression level of hMPV F proteins fused to CompA were determined. Human codon-optimized polynucleotide sequences were made by gene synthesis and cloned into expression vectors. Each expression vector was individually expressed by transient transfection in Expi293 cells. Supernatants were collected four days after transfection.

To determine if the recombinant expressed fusion proteins were secreted into the supernatant, a Western blot using an anti-His6 monoclonal antibody was performed. Conditioned media were diluted a minimum of 10-fold in 2× Laemmli loading buffer (Bio-Rad) with 5% (v/v) β-mercaptoethanol and heated to 95° C. for 10 minutes and 10 μl run on a gel. Reference samples of recombinant His-tagged human serum albumin (HSA) were prepared by an initial dilution to 0.01 mg/mL, followed by a 2-fold dilution series to obtain a standard curve from 6.25 to 100 ng in a 10 μL loading volume in 2× Laemmli loading buffer. Samples were loaded onto a NUPAGE 4-12% Bis-Tris protein gel and run for 45 minutes at 150V. Proteins were transferred onto an Immuno-Blot PDVF membrane (Bio-Rad). Following transfer, the blot was blocked with 3% BSA (w/v) in TBST for 1 hour at room temperature with shaking. An anti-His, HRP-conjugated antibody (R&D Systems MAB050H) was diluted 1:8,000 in 3% BSA (w/v) in TBST and incubated with the membrane for 1 hour at room temperature. The membrane was then washed three times for five minutes using TBST, then His-tagged protein was detected using a luminol chemiluminescent substrate (VisiGlo, VWR) and captured using a 10-20 second exposure time on a UVP Chemstudio (Analytik Jena).

Table 4 shows the expression levels of hMPV F protein fused to CompA. Expression levels were assessed by visual inspection of Western blots and designated as no expression (X) or low expression (*) to high expression (****). The hMPV008, hMPV009, hMPV024, hMPV026, hMPV027, hMPV033, and hMPV034 CompA fusion proteins showed the highest expression levels in this system.

TABLE 4 hMPV F-CompA Fusion Proteins Tested for Expression in Expi293 cells.

| Construct Name | Mutations | hMPV strain (A or B) | CompA: Ala or Cys | C-term Truncation | Expression Level |
|---|---|---|---|---|---|
| hMPV001 | A185P, Q100R, S101R | A | Ala | 481 | * |
| hMPV002 | A185P, Q100R, S101R | A | Ala | 472 | ** |
| hMPV003 | A185P, Q100R, S101R | A | Ala | 489 | * |
| hMPV004 | Q100R, S101R | A | Ala | 472 | * |
| hMPV005 | A185P, T127C, N153C, Q100R, S101R | A | Ala | 472 | ** |
| hMPV006 | V84C, A140C, A147C, A249C, N97G, P98G, R99G, Q100G, S101G, R102G | B | Ala | 472 | ** |
| hMPV007 | V84C, A140C, A147C, A249C, N97G, P98G, R99G, Q100G, S101G, R102G | B | Ala | 488 | ** |
| hMPV008 | A63C, A140C, A147C, K188C, K450C, S470C, N97G, P98G, R99G, Q100G, S101G, R102G | B | Ala | 472 | **** |
| hMPV009 | A63C, A140C, A147C, K188C, K450C, S470C, N97G, P98G, R99G, Q100G, S101G, R102G | B | Ala | 488 | **** |
| hMPV010 | A63C, A140C, A147C, K188C, G106 deleted, N97G, P98G, R99G, Q100G, S101G, R102G | A | Ala | 472 | X |
| hMPV011 | A63C, A140C, A147C, K188C, G106 deleted, N97G, P98G, R99G, Q100G, S101G, R102G | A | Ala | 488 | X |
| hMPV012 | A113C, A120C, A339C, Q426C, T160F, I177L, Q100K, S101A | B | Ala | 472 | X |
| hMPV013 | A113C, A120C, A339C, Q426C, T160F, I177L, Q100K, S101A | B | Ala | 488 | X |
| hMPV014 | V84C, A140C, A147C, A249C, Q100R, S101R | B | Ala | 472 | ** |
| hMPV015 | A63C, A140C, A147C, K188C, K450C, S470C, Q100R, S101R | B | Ala | 472 | *** |
| hMPV016 | A63C, A140C, A147C, K188C, G106 deleted, Q100R, S101R | A | Ala | 472 | X |
| hMPV017 | A113C, A120C, A339C, Q426C, T160F, I177L, Q100R, S101R | B | Ala | 472 | X |
| hMPV018 | A185P, A113C, A339C, Q100R, S101R | A | Ala | 472 | ** |
| hMPV019 | A185P, T160F, I177L, Q100R, S101R | A | Ala | 472 | * |
| hMPV020 | A185P, A113C, A339C, T160F, I177L, Q100R, S101R | A | Ala | 472 | * |
| hMPV021 | A63C, K188C, N97G, P98G, R99G, Q100G, S101G, R102G | B | Ala | 472 | *** |
| hMPV022 | A63C, K188C, K450A, S470A, N97G, P98G, R99G, Q100G, S101G, R102G | B | Ala | 472 | *** |
| hMPV023 | A63C, A140C, A147C, K188C, G294E, N97G, P98G, R99G, Q100G, S101G, R102G | B | Ala | 472 | ** |
| hMPV024 | A63C, A140C, A147C, K188C, K450C, S470C, N97G, P98G, R99G, Q100G, S101G, R102G, G294E | A | Ala | 472 | **** |
| hMPV025 | A63C, K188C, N97G, P98G, R99G, Q100G, S101G, R102G, G294E | A | Ala | 472 | ** |
| hMPV026 | T127C, N153C, T365C, V463C, A185P, L219K, V231I, G294E, H368N, Q100R, S101R | A | Ala | 472 | **** |
| hMPV027 | T127C, N153C, T365C, V463C, A185P, L219K, V231I, G294E, H368N, Q100R, S101R | A | Ala | 490 | **** |
| hMPV028 | A63C, A140C, A147C, K188C, K450C, S470C, N97G, P98G, R99G, Q100G, S101G, R102G | B | Cys | 472 | * |
| hMPV029 | T127C, N153C, T365C, V463C, A185P, L219K, V231I, G294E, H368N, Q100R, S101R | A | Cys | 472 | * |
| hMPV030 | T127C, N153C, T365C, V463C, A185P, L219K, V231I, G294E, H368N, Q100R, S101R | A | Cys | 490 | * |
| hMPV031 | V84C, A140C, A147C, A249C, N97G, P98G, R99G, Q100G, S101G, R102G | B | Cys | 472 | * |
| hMPV033 | T127C, N153C, T365C, V463C, A185P, L219K, V231I, G294E, N97G, P98G, R99G, Q100G, H368N, S101G, R102G | A | Ala | 472 | **** |
| hMPV034 | T127C, N153C, T365C, V463C, A185P, L219K, V231I, G294E, N97G, P98G, R99G, H368N, Q100G, S101G, R102G | A | Ala | 490 | **** |

Example 2

In this example, conditioned media containing the hMPV F-CompA fusion protein were characterized using antibody binding activity to determine the conformation of the hMPV F protein. The fusion proteins hMPV005, hMPV008, hMPV021, hMPV024, hMPV026, hMPV027, hMPV027C, and hMPV033 were evaluated (Table 5). Constructs hMPV026 and hMPV027 contain a furin cleavage site that was not cleaved in the Expi293 transient transfections. Upon co-transfection of human furin, the expressed protein was properly cleaved and termed hMPV026C or hMPV027C to represent the cleaved form.

To characterize the conformation of the recombinant expressed hMPV F protein fused to CompA, an ELISA was performed using 15 monoclonal antibodies that bind to specific forms of the hMPV F protein ectodomain.

Wells of a 96 well plate were coated with 200 ng of each antibody, or 50 ng for MPE8, in 100 μL 50 mM sodium carbonate-bicarbonate buffer, pH 9.6, at 4° C. overnight. Plates were washed 3× with 300 μl PBS with 0.05% Tween 20. After blocking with 150 μl PBS with 1% BSA for 1 hour at room temperature, the plates were emptied by tapping onto an absorbent pad. Conditioned media supernatants from the Expi293 transfections of each construct were diluted based on semi-quantitative Western blots such that antigen concentrations would bracket the expected $EC_{50}$ of the antigen (from Mas data). Three dilutions for each construct were plated at 100 μL per well for each antibody and the plates were incubated for 1 hour at room temperature. Plates were washed 6× with 300 μl PBS with 0.05%

Tween 20. An anti-His monoclonal antibody (R&D Systems MAB050H) was diluted 1:15,000 and 100 µL was added to each well and the plate incubated for 1 hour at room temperature. After washing the plates 6× with 300 µl PBS with 0.05% Tween 20, 100 µl TMB substrate was added and the plate was developed in the dark for 10 minutes. The reaction was stopped by addition of 100 µl 0.6 N $H_2SO_4$ and absorbance was measured at 450 nm on a plate reader.

The postfusion specific antibodies bound hMPV021 suggesting this construct has a postfusion conformation. The other constructs did not bind the postfusion specific Abs and did bind MPE8 along with multiple Abs that recognize both prefusion and postfusion conformation. This data suggest the fusion proteins have prefusion conformation characteristics.

Example 3

Binding activity seen with purified hMPV F-CompA fusion proteins. FIGS. 3A-3C show binding with known concentrations of purified component A (CompA) fusions—that is, hMPV F protein ectodomains N-terminally fused to I53-50A (SEQ ID NO: 144) or I53-50A ΔCys (SEQ ID NO: 145). MF14, MPE8, and MF16 recognize antigenic sites II, III, and IV respectively and these antigenic sites are the primary sites recognized by neutralizing antibodies. In addition, MPE8 recognizes preferentially the prefusion form of hMPV F protein. Wells of a 96 well plate were coated with 50 ng of MPE8 and 100 ng of MF14 and MF16 in 100 µL 50 mM sodium carbonate-bicarbonate buffer, pH 9.6, at 4° C. overnight. Plates were washed 3× with 300 µl PBS with 0.05% Tween 20. After blocking with 150 µl PBS with 1% BSA for 1 hour at room temperature, the plates were emptied by tapping onto an absorbent pad. Purified samples of each construct were diluted to 40 µg/mL (hMPV008, 021, 026, and 027) or 4 µg/mL (hMPV026C and 033), followed by a 3-fold or 4-fold dilution series respectively in PBS with 1% BSA and plated at 100 µL per well and the plates were incubated for 1 hour at room temperature. Plates were washed 6× with 300 µl PBS with 0.05% Tween 20. An anti-His monoclonal antibody (R&D Systems MAB050H) was diluted 1:15,000 and 100 µL was added to each well and the plate incubated for 1 hour at room temperature. After washing the plates 6× with 300 µl PBS with 0.05% Tween 20, 100 µl TMB substrate was added and the plate was developed in the dark for 10 minutes. The reaction was stopped by addition of 100 µl 0.6 N $H_2SO_4$ and absorbance was measured at 450 nm on a plate reader. Binding to MF14 (site II, FIG. 3A) and MF16 (site IV, FIG. 3B) are similar but binding with MPE8 (site III, FIG. 3C) has a higher $EC_{50}$ than with hMPV008 and hMPV021 (Table 6). This suggests that site III, a neutralizing antibody recognition site, is more conserved in hMPV026, hMPV027, and hMPV033 and these constructs more preferentially adopt the prefusion conformation than hMPV008 and hMPV021.

TABLE 6

Neutralizing Antibody Binding $EC_{50}$ Values

| Construct: | $EC_{50}$ | | |
| --- | --- | --- | --- |
| | MPE8 | MF14 | MF16 |
| hMPV008 | 8.19E+00 | 1.78E−01 | 1.99E−01 |
| hMPV021 | 1.28E+01 | 1.66E−01 | 1.86E−01 |
| hMPV026 | 7.70E−02 | 9.57E−02 | 1.01E−01 |
| hMPV026C | 1.24E−01 | 1.36E−01 | 1.40E−01 |
| hMPV027 | 7.96E−02 | 9.37E−02 | 9.65E−02 |
| hMPV033 | 9.68E−02 | 1.08E−01 | 1.17E−01 |

Example 4

In this example, assembled hMPV008 VLPs or hMPV008 CompA alone were injected intramuscular in both hind legs of female Balb/c mice on day 0 and day 21. The quantity and formulation of each group is listed in Table 7. Blood draws were collected on days 0, 24 and 35 and processed into serum. Day 0 serum samples were pooled by group. All serum samples were evaluated in a hMPV neutralization antibody titer assay (FIG. 4). hMPV008 formulations with adjuvants Alhydrogel (Alum) or Addavax (squalene oil-in-water emulsion) induced measurable neutralizing titers at all doses at day 24 and 35, and were comparable to titers of healthy adult serum (FIG. 4). These results show that hMPV008 VLPs induce robust neutralizing titers comparable to healthy human control sera.

TABLE 7

Quantity and Formulations of Injected VLPs

| Antigen | Dose | Formulation |
| --- | --- | --- |
| hMPV008 VLP | 5 µg | Addavax |
| hMPV008 VLP | 5 µg | Alhydrogel |
| hMPV008 VLP | 0.25 µg | Alhydrogel |
| hMPV008 CompA | 4.08 µg | Alhydrogel |
| hMPV008 CompA | 0.2 µg | Alhydrogel |

TABLE 5

Antibody Binding to Illustrative CompA Fusion Proteins

| Ab | Ag site | Pre/Post Preference | Neut A/B | hMPV005 | hMPV008 | hMPV021 | hMPV024 | hMPV026‡ | hMPV027‡ | hMPV027C | hMPV033 |
| --- | --- | --- | --- | --- | --- | --- | --- | --- | --- | --- | --- |
| MF1 | 6HB | post | No | low | NB | very high | low | NB | NB | NB | NB |
| MF2 | 6HB | post | No | low | NB | very high | low | NB | NB | NB | NB |
| MF3 | 6HB | post | No | low | NB | medium | NB | NB | NB | NB | NB |
| MF9 | Site II | pre/post (B preferential) | A/B | very high | very high | very high | very high | very high | very high | very high | very high |
| MF12 | Site II | pre/post | A/B | very high | very high | very high | very high | very high | very high | very high | very high |
| MF14 | Site II | pre/post | A/B | very high | very high | very high | very high | very high | very high | very high | very high |
| MF15 | Site II | pre/post | A/B | very high | very high | very high | very high | very high | very high | very high | very high |

TABLE 5-continued

Antibody Binding to Illustrative CompA Fusion Proteins

| Ab | Ag site | Pre/Post Preference | Neut A/B | hMPV005 | hMPV008 | hMPV021 | hMPV024 | hMPV026‡ | hMPV027‡ | hMPV027C | hMPV033 |
|---|---|---|---|---|---|---|---|---|---|---|---|
| MF11 | Site IV | post preferential | No | medium | low | very high | high | NB | NB | NB | NB |
| MF16 | Site IV | pre/post | A/B | very high | very high | very high | high | very high | very high | very high | very high |
| MF20 | Site IV | pre/post (B preferential) | A/B | very high | medium | very high | medium | low | low | low | low |
| MF17 | Site I | post preferential | B | high | NB | high | low | low | low | low | low |
| MF18 | Site I | post preferential | B | very high | low | very high | medium | low | low | low | low |
| MF19 | Site I | post preferential | B | very high | medium | very high | medium | low | low | low | medium |
| MF10 | Site Ø | Pre (A preferential) | A | very high | NB | NB | low | very high | very high | very high | very high |
| MPE8 | Site III | pre | A/B | high | high | high | high | high | high | high | high |

*A very high response indicates OD450 > 2.0, a high response indicates an OD450 > 1.0 but less than 2.0, medium response indicates OD450 > 0.5 but < 1.0 and low response indicates OD450 > 0.1 but < 0.5 and NB (no binding) is < 0.1.
‡Construct retains native furin cleavage site.

Example 5

Figures 5A, 5B:
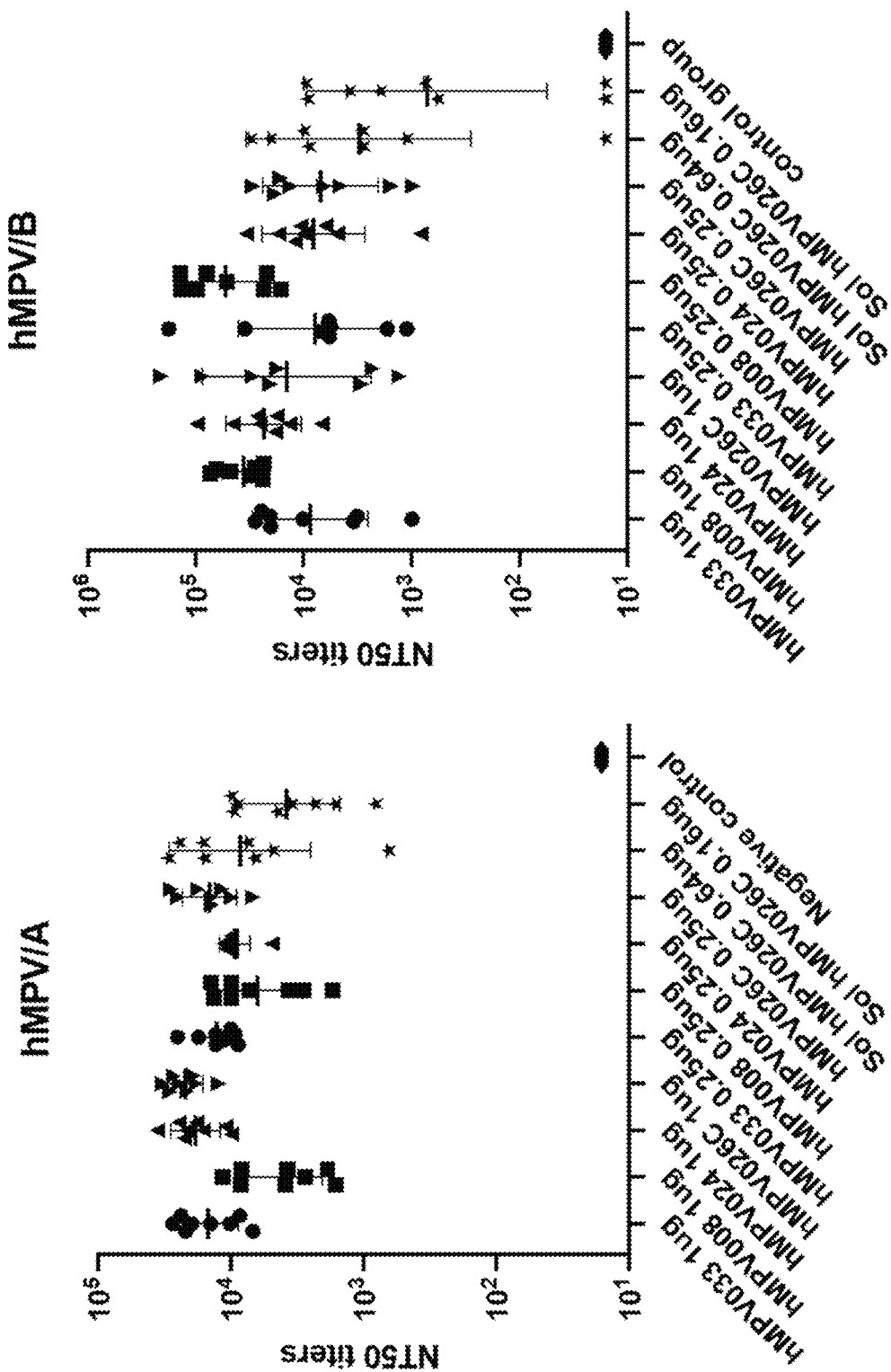
FIGS. 5A and 5B show the immunogenicity of hMPV F protein mutants on a 2-component virus-like particle (VLP). Graphs show neutralizing antibody titers against hMPV/A (FIG. 5A) and hMPV/B (FIG. 5B) in serum samples collected on day 35 after the first immunization.

A study was undertaken in naïve mice to explore the immunogenicity hMPV F protein mutants displayed on a 2-component virus-like particle (VLP). VLPs containing one of four different hMPV F protein mutants, hMPV008, hMPV024, hMPV026C, and hMPV033 or a soluble protein corresponding to hMPV026C were tested. Each group consisted of 8 female Balb/c mice. Mice were immunized on day 0 and day 21. All test articles were formulated with Addavax, an oil in water adjuvant. Two dose levels (1 µg and 0.25 µg) or an equivalent antigen content of soluble protein were administered (Table 8). Neutralizing antibody titers against hMPV/A and hMPV/B were determined from day 35 serum (FIGS. 5A and 5B, respectively). The results demonstrated robust neutralizing titers were induced by all VLPs against both strains of hMPV. The soluble protein also induced titers against both hMPV strains at a lower level than the VLPs.

TABLE 8

Quantity and Formulations of Injected VLPs

| Antigen | Dose | Formulation |
|---|---|---|
| hMPV033 VLP | 1 µg | Addavax |
| hMPV008 VLP | 1 µg | Addavax |
| hMPV024 VLP | 1 µg | Addavax |
| hMPV026C VLP | 1 µg | Addavax |
| hMPV033 VLP | 0.25 µg | Addavax |
| hMPV008 VLP | 0.25 µg | Addavax |
| hMPV024 VLP | 0.25 µg | Addavax |
| hMPV026C VLP | 0.25 µg | Addavax |
| Soluble hMPV026C | 0.64 µg | Addavax |
| Soluble hMPV026C | 0.16 µg | Addavax |
| No treatment | N/A | N/A |

Example 6

Figure 6A:
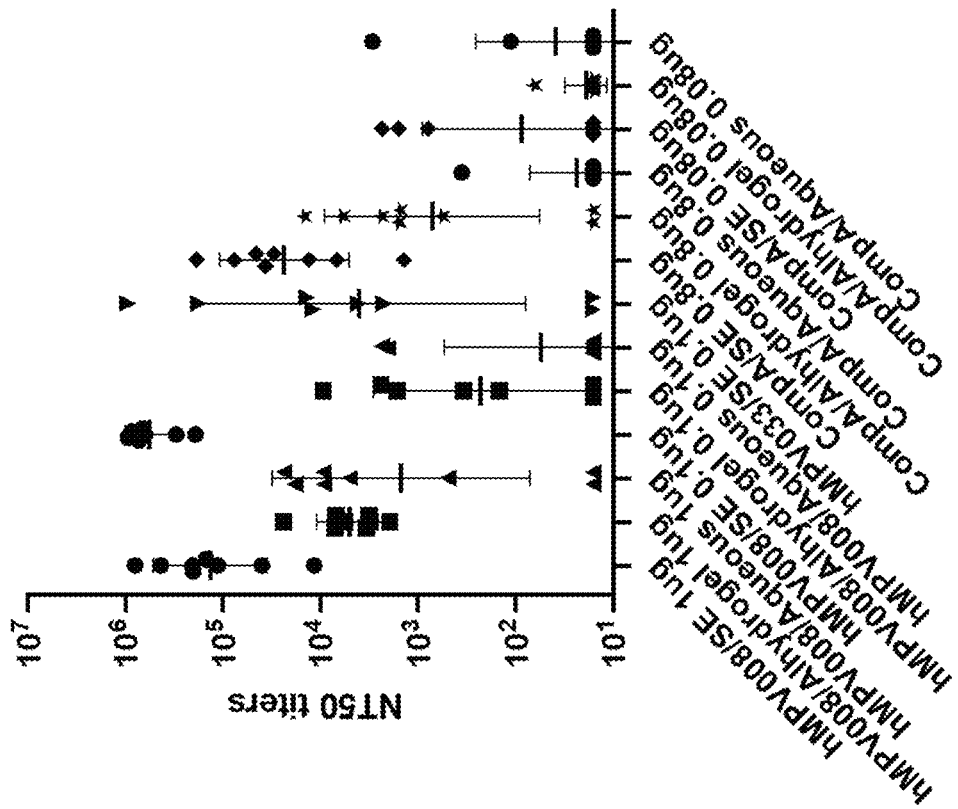
FIGS. 6A and 6B show the immunogenicity of hMPV008 VLPs and the corresponding soluble protein, CompA-hMPV008. Graphs show neutralizing antibody titers against hMPV/A (FIG. 6A) and hMPV/B (FIG. 6B) in serum samples collected on day 35 after the first immunization.
Figure 6B:
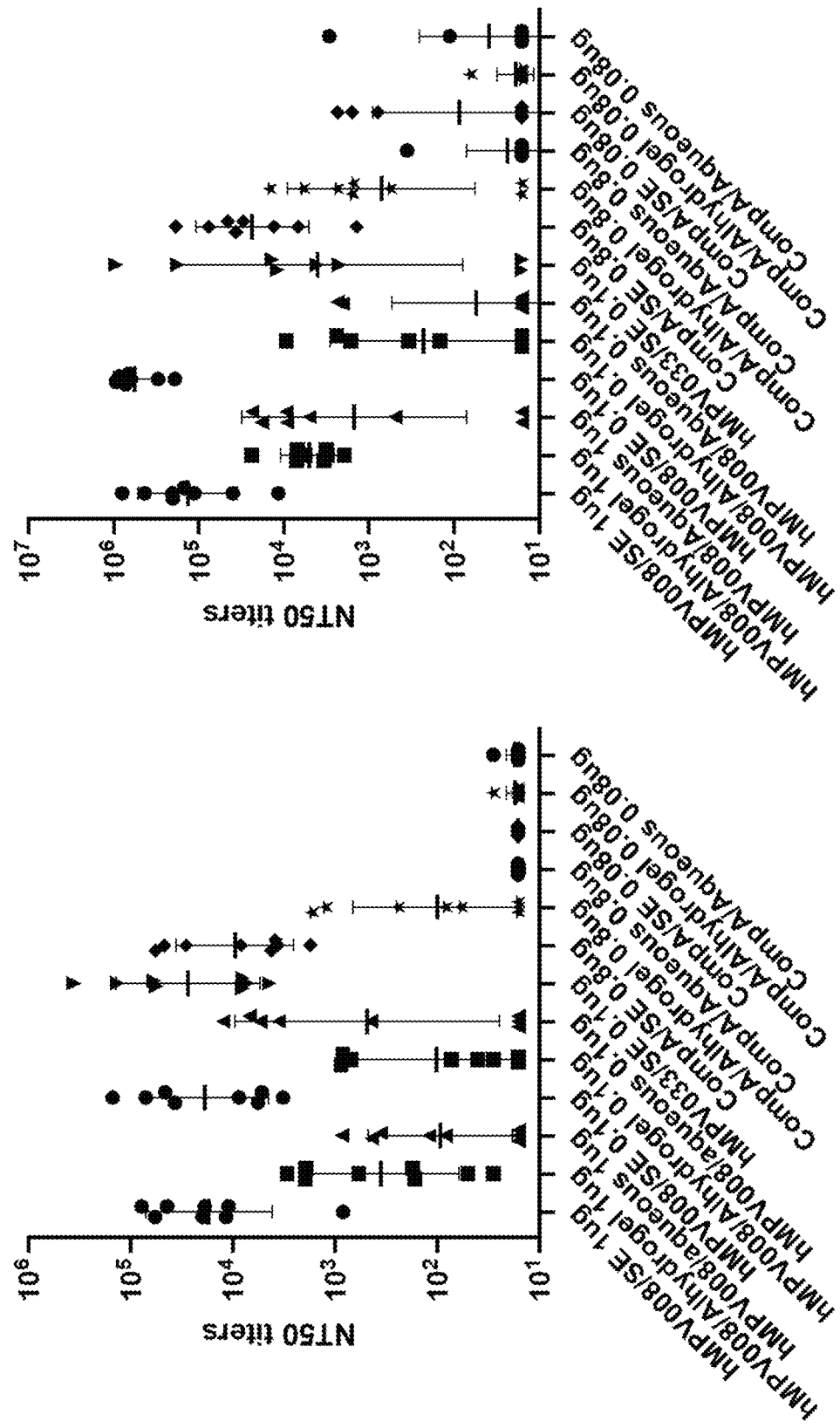

A study was undertaken in naïve mice to explore the immunogenicity of hMPV008 VLPs and the corresponding soluble protein, CompA-hMPV008. hMPV008 VLPs and CompA-hMPV008 were formulated in aqueous buffer, a squalene-based adjuvant (SE), or Alhydrogel at two dose levels (1 µg and 0.1 µg VLP and the equivalent antigen dose for CompA-hMPV008). In addition, one group with hMPV033 VLP (0.1 µg) formulated with SE was included (Table 9). Each group consisted of 8 female Balb/c mice. Mice were immunized on day 0 and day 21. Neutralizing antibody titers against hMPV/A and hMPV/B were determined from day 35 serum. Results demonstrated that hMPV008 VLPs formulated with SE resulted in higher titers than Alhydrogel or aqueous formulations (FIGS. 6A and 6B). VLPs induced higher neutralizing titers than the soluble protein CompA-hMPV008 with all formulations (FIGS. 6A and 6B).

TABLE 9

Quantity and Formulations of Injected VLPs

| Antigen | Dose | Formulation |
|---|---|---|
| hMPV008 VLP | 1 µg | SE |
| hMPV008 VLP | 1 µg | Alhydrogel |
| hMPV08 VLP | 1 µg | Aqueous |
| hMPV008 VLP | 0.1 µg | SE |
| hMPV008 VLP | 0.1 µg | Alhydrogel |
| hMPV008 VLP | 0.1 µg | Aqueous |
| CompA-hMPV008 | 0.81 µg | SE |
| CompA-hMPV008 | 0.81 µg | Alhydrogel |
| CompA-hMPV008 | 0.81 µg | Aqueous |
| CompA-hMPV008 | 0.081 µg | SE |
| CompA-hMPV008 | 0.081 µg | Alhydrogel |
| CompA-hMPV008 | 0.081 µg | Aqueous |
| hMPV033 | 0.1 µg | SE |

Example 7

A study was undertaken in naïve mice to explore the immunogenicity VLPs displaying an hMPV F protein mutant, hMPV008. Each group consisted of 8 female Balb/c mice. Mice were immunized on day 0 and day 21 with hMPV008 formulated with Addavax, an oil in water adjuvant. Two dose levels (1 ug and 0.2 ug) of VLP were administered as indicated in Table 10. Neutralizing antibody titers were determined for hMPV/A and hMPV/B from serum samples collected on day 35. Results demonstrated that robust hMPV/A and hMPV/B neutralizing titers were induced by hMPV008 with both dose levels (FIGS. 7A and 7B).

TABLE 10

| Quantity and Formulations of Injected VLPs | | |
|---|---|---|
| Antigen | Dose | Formulation |
| hMPV008 | 1 µg | Addavax |
| hMPV008 | 0.2 µg | Addavax |

Example 8

Figure 8A:
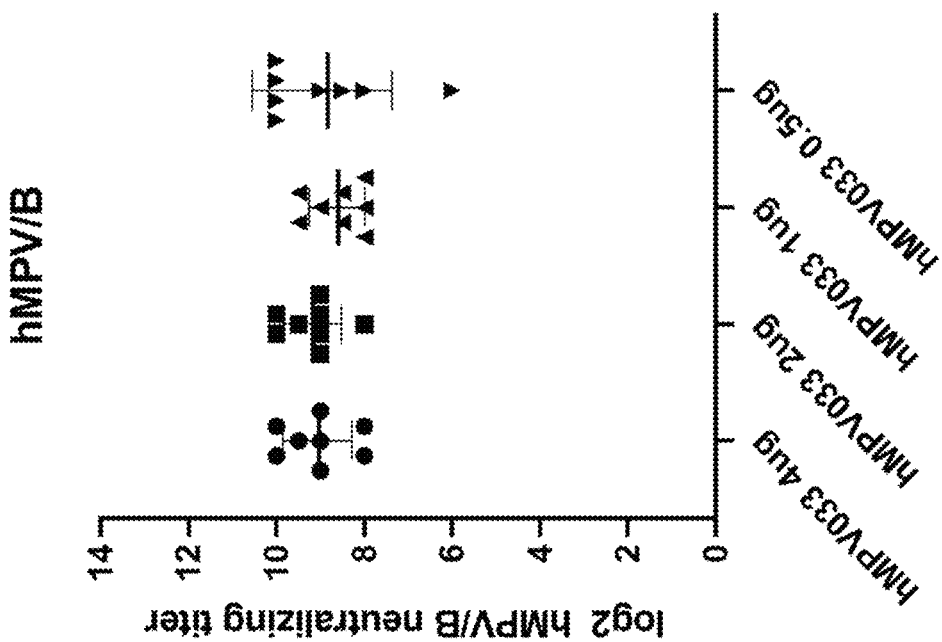
FIGS. 8A and 8B show the immunogenicity of hMPV033. Neutralizing antibody titers were determined for hMPV/A (FIG. 8A) and hMPV/B (FIG. 8B) in serum samples collected on day 35 after the first immunization.
Figure 8B:
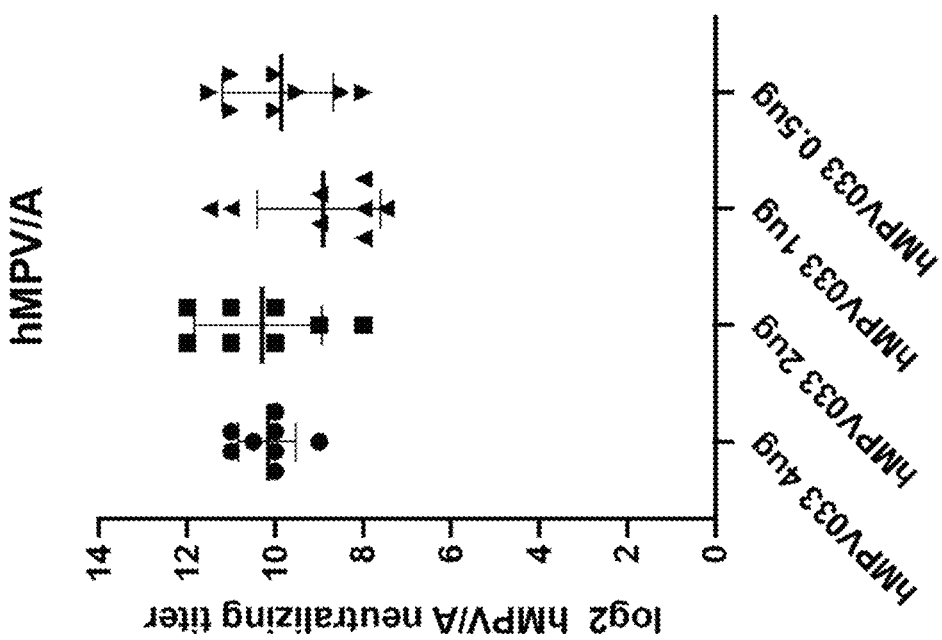

A study was undertaken in naïve mice to explore the immunogenicity of hMPV033. Each group consisted of 8 female Balb/c mice. Mice were immunized on day 0 and 21 with hMPV033 formulated with Addavax, an oil in water adjuvant, at 4 dose levels (4, 2, 1, and 0.5 µg) (Table 11). Neutralizing antibody titers were determined for hMPV/A and hMPV/B from serum samples collected on day 35. Results demonstrated that robust hMPV/A and hMPV/B neutralizing titers were induced by hMPV033 with all dose levels (FIGS. 8A and 8B, respectively).

TABLE 11

| Quantity and Formulations of Injected VLPs | | |
|---|---|---|
| Antigen | Dose | Formulation |
| hMPV033 | 4 µg | Addavax |
| hMPV033 | 2 µg | Addavax |
| hMPV033 | 1 µg | Addavax |
| hMPV033 | 0.5 µg | Addavax |

Example 9

Figures 9A, 9B, 9C:
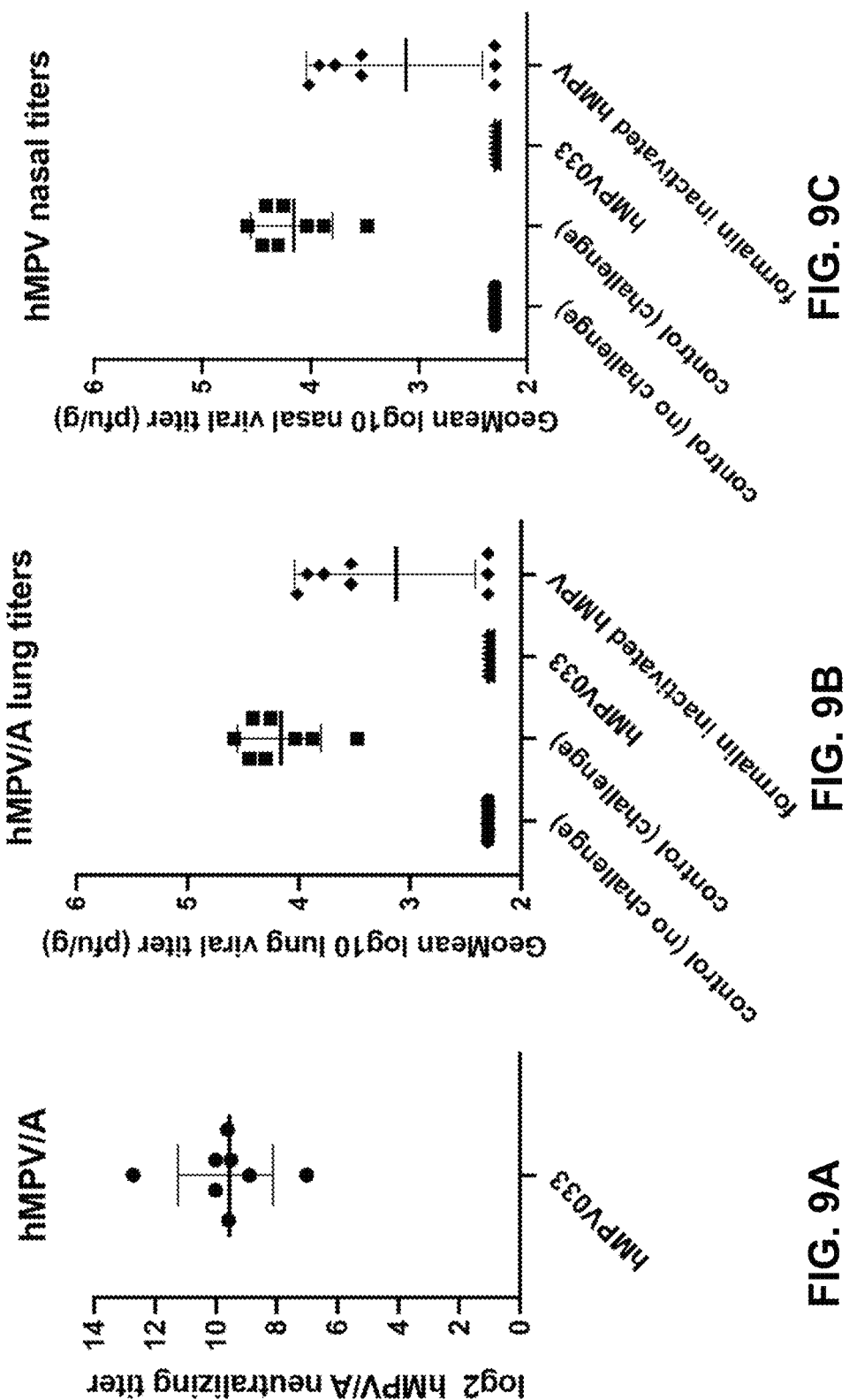
FIGS. 9A-9C show the protective effect of hMPV033 against hMPV infection in cotton rats. Neutralizing titers against hMPV/A were determined in serum (FIG. 9C), lung (FIG. 9B), and nasal (FIG. 9C) samples collected on day 35 after the first immunization.

A study was undertaken in naïve cotton rats to assess and evaluate the ability of hMPV033 to protect against hMPV infection in cotton rats. hMPV033 was administered on day 0 and 21 with a dose level of 1 µg formulated with Addavax (Table 12). Each group consisted of 8 female cotton rats. Neutralizing titers against hMPV/A were determined from day 35 serum samples (FIG. 9A). Groups were challenged with $10^5$ pfu hMPV on day 35 (Table 12) and sacrificed on day 40. Viral titers were determined from lung or nasal turbinates in a plaque assay. Results demonstrated that hMPV033 induced robust neutralizing titers (FIG. 9A). Plaque assays on lung and nasal turbinate tissue homogenates demonstrated that high viral titers were detected in lung and nasal turbinates following challenge of control animals. In contrast, viral titers in vaccinated cotton rats were below the lower limit of detection for lung and nasal turbinate samples. (FIGS. 9B and 9C). Formalin inactivated hMPV vaccination did not protect against subsequent challenge (FIGS. 9B-9C).

TABLE 12

| Quantity and Formulations of Injected VLPs | | | |
|---|---|---|---|
| Antigen | Dose | Formulation | hMPV challenge |
| PBS | N/A | N/A | No |
| PBS | N/A | N/A | Yes |
| hMPV033 | 1 µg | Addavax | Yes |
| Formalin inactivated hMPV | | N/A | Yes |

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

```
SEQUENCE LISTING

Sequence total quantity: 143
SEQ ID NO: 1           moltype = AA  length = 206
FEATURE                Location/Qualifiers
REGION                 1..206
                       note = synthetic construct
source                 1..206
                       mol_type = protein
                       organism = synthetic construct
SEQUENCE: 1
EGMDPLAVLA ESRLLPLLTV RGGEDLAGLA TVLELMGVGA LEITLRTEKG LEALKALRKS   60
GLLLGAGTVR SPKEAEAALE AGAAFLVSPG LLEEVAALAQ ARGVPYLPGV LTPTEVERAL  120
ALGLSALKFF PAEPFQGVRV LRAYAEVFPE VRFLPTGGIK EEHLPHYAAL PNLLAVGGSW  180
LLQGDLAAVM KKVKAAKALL SPQAPG                                      206

SEQ ID NO: 2           moltype = AA  length = 155
FEATURE                Location/Qualifiers
REGION                 1..155
                       note = synthetic construct
source                 1..155
                       mol_type = protein
                       organism = synthetic construct
SEQUENCE: 2
TKKVGIVDTT FARVDMAEAA IRTLKALSPN IKIIRKTVPG IKDLPVACKK LLEEEGCDIV   60
MALGMPGKAE KDKVCAHEAS LGLMLAQLMT NKHIIEVFVH EDEAKDDDEL DILALVRAIE  120
HAANVYYLLF KPEYLTRMAG KGLRQGREDA GPARE                            155
```

```
SEQ ID NO: 3              moltype = AA   length = 155
FEATURE                   Location/Qualifiers
REGION                    1..155
                          note = synthetic construct
source                    1..155
                          mol_type = protein
                          organism = synthetic construct
SEQUENCE: 3
TKKVGIVDTT FARVDMASAA ILTLKMESPN IKIIRKTVPG IKDLPVACKK LLEEEGCDIV    60
MALGMPGKAE KDKVCAHEAS LGLMLAQLMT NKHIIEVFVH EDEAKDDAEL KILAARRAIE   120
HALNVYYLLF KPEYLTRMAG KGLRQGFEDA GPARE                              155

SEQ ID NO: 4              moltype = AA   length = 208
FEATURE                   Location/Qualifiers
REGION                    1..208
                          note = synthetic construct
source                    1..208
                          mol_type = protein
                          organism = synthetic construct
SEQUENCE: 4
STINNQLKAL KVIPVIAIDN AEDIIPLGKV LAENGLPAAE ITFRSSAAVK AIMLLRSAQP    60
EMLIGAGTIL NGVQALAAKE AGATFVVSPG FNPNTVRACQ IIGIDIVPGV NNPSTVEAAL   120
EMGLTTLKFF PAEASGGISM VKSLVGPYGD IRLMPTGGIT PSNIDNYLAI PQVLACGGTW   180
MVDKKLVTNG EWDEIARLTR EIVEQVNP                                     208

SEQ ID NO: 5              moltype = AA   length = 113
FEATURE                   Location/Qualifiers
REGION                    1..113
                          note = synthetic construct
source                    1..113
                          mol_type = protein
                          organism = synthetic construct
SEQUENCE: 5
PIFTLNTNIK ATDVPSDFLS LTSRLVGLIL SKPGSYVAVH INTDQQLSFG GSTNPAAFGT    60
LMSIGGIEPS KNRDHSAVLF DHLNAMLGIP KNRMYIHFVN LNGDDVGWNG TTF          113

SEQ ID NO: 6              moltype = AA   length = 156
FEATURE                   Location/Qualifiers
REGION                    1..156
                          note = synthetic construct
source                    1..156
                          mol_type = protein
                          organism = synthetic construct
SEQUENCE: 6
NQHSHKDYET VRIAVVRARW HADIVDACVE AFEIAMAAIG GDRFAVDVFD VPGAYEIPLH    60
ARTLAETGRY GAVLGTAFVV NGGIYRHEFV ASAVIDGMMN VQLSTGVPVL SAVLTPHRYR   120
DSAEHHRFFA AHFAVKGVEA ARACIEILAA REKIAA                            156

SEQ ID NO: 7              moltype = AA   length = 203
FEATURE                   Location/Qualifiers
REGION                    1..203
                          note = synthetic construct
source                    1..203
                          mol_type = protein
                          organism = synthetic construct
SEQUENCE: 7
MEELFKKHKI VAVLRANSVE EAIEKAVAVF AGGVHLIEIT FTVPDADTVI KALSVLKEKG    60
AIIGAGTVTS VEQCRKAVES GAEFIVSPHL DEEISQFCKE KGVFYMPGVM TPTELVKAMK   120
LGHTILKLFP GEVVGPQFVK AMKGPFPNVK FVPTGGVNLD NVCEWFKAGV LAVGVGSALV   180
KGTPDEVREK AKAFVEKIRG CTE                                          203

SEQ ID NO: 8              moltype = AA   length = 156
FEATURE                   Location/Qualifiers
REGION                    1..156
                          note = synthetic construct
source                    1..156
                          mol_type = protein
                          organism = synthetic construct
SEQUENCE: 8
NQHSHKDYET VRIAVVRARW HAEIVDACVS AFEAAMADIG GDRFAVDVFD VPGAYEIPLH    60
ARTLAETGRY GAVLGTAFVV NGGIYRHEFV ASAVIDGMMN VQLSTGVPVL SAVLTPHRYR   120
DSDAHTLLFL ALFAVKGMEA ARACVEILAA REKIAA                            156
```

```
SEQ ID NO: 9              moltype = AA   length = 176
FEATURE                   Location/Qualifiers
REGION                    1..176
                          note = synthetic construct
source                    1..176
                          mol_type = protein
                          organism = synthetic construct
SEQUENCE: 9
FTKSGDDGNT NVINKRVGKD SPLVNFLGDL DELNSFIGFA ISKIPWEDMK KDLERVQVEL    60
FEIGEDLSTQ SSKKKIDESY VLWLLAATAI YRIESGPVKL FVIPGGSEEA SVLHVTRSVA   120
RRVERNAVKY TKELPEINRM IIVYLNRLSS LLFAMALVAN KRRNQSEKIY EIGKSW       176

SEQ ID NO: 10             moltype = AA   length = 156
FEATURE                   Location/Qualifiers
REGION                    1..156
                          note = synthetic construct
source                    1..156
                          mol_type = protein
                          organism = synthetic construct
SEQUENCE: 10
NQHSHKDYET VRIAVVRARW HADIVDQCVR AFEEAMADAG GDRFAVDVFD VPGAYEIPLH    60
ARTLAETGRY GAVLGTAFVV NGGIYRHEFV ASAVIDGMMN VQLSTGVPVL SAVLTPHRYR   120
SSREHHEFFR EHFMVKGVEA AAACITILAA REKIAA                             156

SEQ ID NO: 11             moltype = AA   length = 200
FEATURE                   Location/Qualifiers
REGION                    1..200
                          note = synthetic construct
source                    1..200
                          mol_type = protein
                          organism = synthetic construct
SEQUENCE: 11
GHTKGPTPQQ HDGSALRIGI VHARWNKTII MPLLIGTIAK LLECGVKASN IVVQSVPGSW    60
ELPIAVQRLY SASQLQTPSS GPSLSAGDLL GSSTTDLTAL PTTTASSTGP FDALIAIGVL   120
IKGETMHFEY IADSVSHGLM RVQLDTGVPV IFGVLTVLTD DQAKARAGVI EGSHNHGEDW   180
GLAAVEMGVR RRDWAAGKTE                                               200

SEQ ID NO: 12             moltype = AA   length = 236
FEATURE                   Location/Qualifiers
REGION                    1..236
                          note = synthetic construct
source                    1..236
                          mol_type = protein
                          organism = synthetic construct
SEQUENCE: 12
YEVDHADVYD LFYLGRGKDY AAEASDIADL VRSRTPEASS LLDVACGTGT HLEHFTKEFG    60
DTAGLELSED MLTHARKRLP DATLHQGDMR DFQLGRKFSA VVSMFSSVGY LKTVAELGAA   120
VASFAEHLEP GGVVVVEPWW FPETFADGWV SADVVRRDGR TVARVSHSVR EGNATRMEVH   180
FTVADPGKGV RHFSDVHLIT LFHQREYEAA FMAAGLRVEY LEGGPSGRGL FVGVPA       236

SEQ ID NO: 13             moltype = AA   length = 137
FEATURE                   Location/Qualifiers
REGION                    1..137
                          note = synthetic construct
source                    1..137
                          mol_type = protein
                          organism = synthetic construct
SEQUENCE: 13
GMKEKFVLII THGDFGKGLL SGAEVIIGKQ ENVHTVGLNL GDNIEKVAKE VMRIIIAKLA    60
EDKEIIIVVD LFGGSPFNIA LEMMKTFDVK VITGINMPML VELLTSINVY DTTELLENIS   120
KIGKDGIKVI EKSSLKM                                                  137

SEQ ID NO: 14             moltype = AA   length = 153
FEATURE                   Location/Qualifiers
REGION                    1..153
                          note = synthetic construct
source                    1..153
                          mol_type = protein
                          organism = synthetic construct
SEQUENCE: 14
KYDGSKLRIG ILHARWNLEI IAALVAGAIK RLQEFGVKAE NIIIETVPGS FELPYGSKLF    60
VEKQKRLGKP LDAIIPIGVL IKGSTMHFEY ICDSTTHQLM KLNFELGIPV IFGVLTCLTD   120
EQAEARAGLI EGKMHNHGED WGAAAVEMAT KFN                                153
```

```
SEQ ID NO: 15            moltype = AA  length = 163
FEATURE                  Location/Qualifiers
REGION                   1..163
                         note = synthetic construct
source                   1..163
                         mol_type = protein
                         organism = synthetic construct
SEQUENCE: 15
AVKGLGEVDQ KYDGSKLRIG ILHARWNRKI ILALVAGAVL RLLEFGVKAE NIIIETVPGS   60
FELPYGSKLF VEKQKRLGKP LDAIIPIGVL IKGSTMHFEY ICDSTTHQLM KLNFELGIPV  120
IFGVLTCLTD EQAEARAGLI EGKMHNHGED WGAAAVEMAT KFN                   163

SEQ ID NO: 16            moltype = AA  length = 174
FEATURE                  Location/Qualifiers
REGION                   1..174
                         note = synthetic construct
source                   1..174
                         mol_type = protein
                         organism = synthetic construct
SEQUENCE: 16
GANWYLDNES SRLSFTSTKN ADIAEVHRFL VLHGKVDPKG LAEVEVETES ISTGIPLRDM   60
LLRVLVFQVS KFPVAQINAQ LDMRPINNLA PGAQLELRLP LTVSLRGKSH SYNAELLATR  120
LDERRFQVVT LEPLVIHAQD FDMVRAFNAL RLVAGLSAVS LSVPVGAVLI FTAR        174

SEQ ID NO: 17            moltype = AA  length = 207
FEATURE                  Location/Qualifiers
REGION                   1..207
                         note = synthetic construct
source                   1..207
                         mol_type = protein
                         organism = synthetic construct
SEQUENCE: 17
TDYIRDGSAI KALSFAIILA EADLRHIPQD LQRLAVRVIH ACGMVDVAND LAFSEGAGKA   60
GRNALLAGAP ILCDARMVAE GITRSRLPAD NRVIYTLSDP SVPELAKKIG NTRSAAALDL  120
WLPHIEGSIV AIGNAPTALF RLFELLDAGA PKPALIIGMP VGFVGAAESK DELAANSRGV  180
PYVIVRGRRG GSAMTAAAVN ALASERE                                     207

SEQ ID NO: 18            moltype = AA  length = 127
FEATURE                  Location/Qualifiers
REGION                   1..127
                         note = synthetic construct
source                   1..127
                         mol_type = protein
                         organism = synthetic construct
SEQUENCE: 18
ITVFGLKSKL APRREKLAEV IYSSLHLGLD IPKGKHAIRF LCLEKEDFYY PFDRSDDYTV   60
IEINLMAGRS EETKMLLIFL LFIALERKLG IRAHDVEITI KEQPAHCWGF RGRTGDSARD  120
LDYDIYV                                                           127

SEQ ID NO: 19            moltype = AA  length = 234
FEATURE                  Location/Qualifiers
REGION                   1..234
                         note = synthetic construct
source                   1..234
                         mol_type = protein
                         organism = synthetic construct
SEQUENCE: 19
GSDLQKLQRF STCDISDGLL NVYNIPTGGY FPNLTAISPP QNSSIVGTAY TVLFAPIDDP   60
RPAVNYIDSV PPNSILVLAL EPHLQSQFHP FIKITQAMYG GLMSTRAQYL KSNGTVVFGR  120
IRDVDEHRTL NHPVFAYGVG SCAPKAVVKA VGTNVQLKIL TSDGVTQTIC PGDYIAGDNN  180
GIVRIPVQET DISKLVTYIE KSIEVDRLVS EAIKNGLPAK AAQTARRMVL KDYI        234

SEQ ID NO: 20            moltype = AA  length = 161
FEATURE                  Location/Qualifiers
REGION                   1..161
                         note = synthetic construct
source                   1..161
                         mol_type = protein
                         organism = synthetic construct
SEQUENCE: 20
SGMRVYLGAD HAGYELKQAI IAFLKMTGHE PIDCGALRYD ADDDYPAFCI AAATRTVADP   60
GSLGIVGGS GNGEQIAANK VPGARCALAW SVQTAALARE HNNAQLIGIG GRMHTLEEAL  120
RIVKAFVTTP WSKAQRHQRR IDILAEYERT HEAPPVPGAP A                    161
```

```
SEQ ID NO: 21            moltype = AA  length = 156
FEATURE                  Location/Qualifiers
REGION                   1..156
                         note = synthetic construct
source                   1..156
                         mol_type = protein
                         organism = synthetic construct
SEQUENCE: 21
GDDARIAAIG DVDELNSQIG VLLAEPLPDD VRAALSAIQH DLFDLGGELC IPGHAAITED    60
HLLRLALWLV HYNGQLPPLE EFILPGGARG AALAHVCRTV CRRAERSIKA LGASEPLNIA   120
PAAYVNLLSD LLFVLARVLN RAAGGADVLW DRTRAH                             156

SEQ ID NO: 22            moltype = AA  length = 156
FEATURE                  Location/Qualifiers
REGION                   1..156
                         note = synthetic construct
source                   1..156
                         mol_type = protein
                         organism = synthetic construct
SEQUENCE: 22
ILSAEQSFTL RHPHGQAAAL AFVREPAAAL AGVQRLRGLD SDGEQVWGEL LVRVPLLGEV    60
DLPFRSEIVR TPQGAELRPL TLTGERAWVA VSGQATAAEG GEMAFAFQFQ AHLATPEAEG   120
EGGAAFEVMV QAAAGVTLLL VAMALPQGLA AGLPPA                             156

SEQ ID NO: 23            moltype = AA  length = 155
FEATURE                  Location/Qualifiers
REGION                   1..155
                         note = synthetic construct
source                   1..155
                         mol_type = protein
                         organism = synthetic construct
SEQUENCE: 23
TKKVGIVDTT FARVDMASAA ILTLKMESPN IKIIRKTVPG IKDLPVACKK LLEEEGCDIV    60
MALGMPGKKE KDKVCAHEAS LGLMLAQLMT NKHIIEVFVH EDEAKDDAEL KILAARRAIE   120
HALNVYYLLF KPEYLTRMAG KGLRQGFEDA GPARE                              155

SEQ ID NO: 24            moltype = AA  length = 208
FEATURE                  Location/Qualifiers
REGION                   1..208
                         note = synthetic construct
source                   1..208
                         mol_type = protein
                         organism = synthetic construct
SEQUENCE: 24
DDINNQLKRL KVIPVIAIDN AEDIIPLGKV LAENGLPAAE ITFRSSAAVK AIMLLRSAQP    60
EMLIGAGTIL NGVQALAAKE AGADFVVSPG FNPNTVRACQ IIGIDIVPGV NNPSTVEQAL   120
EMGLTTLKFF PAEASGGISM VKSLVGPYGD IRLMPTGGIT PDNIDNYLAI PQVLACGGTW   180
MVDKKLVRNG EWDEIARLTR EIVEQVNP                                      208

SEQ ID NO: 25            moltype = AA  length = 113
FEATURE                  Location/Qualifiers
REGION                   1..113
                         note = synthetic construct
source                   1..113
                         mol_type = protein
                         organism = synthetic construct
SEQUENCE: 25
PIFTLNTNIK ADDVPSDFLS LTSRLVGLIL SKPGSYVAVH INTDQQLSFG GSTNPAAFGT    60
LMSIGGIEPD KNRDHSAVLF DHLNAMLGIP KNRMYIHFVN LNGDDVGWNG TTF          113

SEQ ID NO: 26            moltype = AA  length = 113
FEATURE                  Location/Qualifiers
REGION                   1..113
                         note = synthetic construct
source                   1..113
                         mol_type = protein
                         organism = synthetic construct
SEQUENCE: 26
PIFTLNTNIK ADDVPSDFLS LTSRLVGLIL SEPGSYVAVH INTDQQLSFG GSTNPAAFGT    60
LMSIGGIEPD KNEDHSAVLF DHLNAMLGIP KNRMYIHFVD LDGDDVGWNG TTF          113

SEQ ID NO: 27            moltype = AA  length = 156
FEATURE                  Location/Qualifiers
REGION                   1..156
                         note = synthetic construct
source                   1..156
                         mol_type = protein
                         organism = synthetic construct
```

```
SEQUENCE: 27
NQHSKDHET  VRIAVVRARW  HADIVDACVE  AFEIAMAAIG  GDRFAVDVFD  VPGAYEIPLH    60
ARTLAETGRY  GAVLGTAFVV  NGGIYRHEFV  ASAVIDGMMN  VQLDTGVPVL  SAVLTPHRYR   120
DSDEHHRFFA  AHFAVKGVEA  ARACIEILNA  REKIAA                              156

SEQ ID NO: 28           moltype = AA   length = 156
FEATURE                 Location/Qualifiers
REGION                  1..156
                        note = synthetic construct
source                  1..156
                        mol_type = protein
                        organism = synthetic construct
SEQUENCE: 28
NQHSKDHET  VRIAVVRARW  HADIVDACVE  AFEIAMAAIG  GDRFAVDVFD  VPGAYEIPLH    60
ARTLAETGRY  GAVLGTAFVV  DGGIYDHEFV  ASAVIDGMMN  VQLDTGVPVL  SAVLTPHEYE   120
DSDEDHEFFA  AHFAVKGVEA  ARACIEILNA  REKIAA                              156

SEQ ID NO: 29           moltype = AA   length = 202
FEATURE                 Location/Qualifiers
REGION                  1..202
                        note = synthetic construct
source                  1..202
                        mol_type = protein
                        organism = synthetic construct
SEQUENCE: 29
EELFKKHKIV  AVLRANSVEE  AIEKAVAVFA  GGVHLIEITF  TVPDADTVIK  ALSVLKEKGA    60
IIGAGTVTSV  EQCRKAVESG  AEFIVSPHLD  EEISQFCKEK  GVFYMPGVMT  PTELVKAMKL   120
GHDILKLFPG  EVVGPQFVKA  MKGPFPNVKF  VPTGGVNLDN  VCEWFKAGVL  AVGVGDALVK   180
GDPDEVREKA  KKFVEKIRGC  TE                                              202

SEQ ID NO: 30           moltype = AA   length = 202
FEATURE                 Location/Qualifiers
REGION                  1..202
                        note = synthetic construct
source                  1..202
                        mol_type = protein
                        organism = synthetic construct
SEQUENCE: 30
EELFKKHKIV  AVLRANSVEE  AIEKAVAVFA  GGVHLIEITF  TVPDADTVIK  ALSVLKEKGA    60
IIGAGTVTSV  EQCRKAVESG  AEFIVSPHLD  EEISQFCKEK  GVFYMPGVMT  PTELVKAMKL   120
GHDILKLFPG  EVVGPEFVEA  MKGPFPNVKF  VPTGGVDLDD  VCEWFDAGVL  AVGVGDALVE   180
GDPDEVREDA  KEFVEEIRGC  TE                                              202

SEQ ID NO: 31           moltype = AA   length = 202
FEATURE                 Location/Qualifiers
REGION                  1..202
                        note = synthetic construct
source                  1..202
                        mol_type = protein
                        organism = synthetic construct
SEQUENCE: 31
EELFKKHKIV  AVLRANSVEE  AIEKAVAVFA  GGVHLIEITF  TVPDADTVIK  ALSVLKEKGA    60
IIGAGTVTSV  EQCRKAVESG  AEFIVSPHLD  EEISQFCKEK  GVFYMPGVMT  PTELVKAMKL   120
GHDILKLFPG  EVVGPQFVKA  MKGPFPNVKF  VPTGGVNLDN  VCKWFKAGVL  AVGVGKALVK   180
GKPDEVREKA  KKFVKKIRGC  TE                                              202

SEQ ID NO: 32           moltype = AA   length = 156
FEATURE                 Location/Qualifiers
REGION                  1..156
                        note = synthetic construct
source                  1..156
                        mol_type = protein
                        organism = synthetic construct
SEQUENCE: 32
NQHSKDHET  VRIAVVRARW  HAEIVDACVS  AFEAAMRDIG  GDRFAVDVFD  VPGAYEIPLH    60
ARTLAETGRY  GAVLGTAFVV  NGGIYRHEFV  ASAVIDGMMN  VQLDTGVPVL  SAVLTPHRYR   120
DSDAHTLLFL  ALFAVKGMEA  ARACVEILAA  REKIAA                              156

SEQ ID NO: 33           moltype = AA   length = 156
FEATURE                 Location/Qualifiers
REGION                  1..156
                        note = synthetic construct
source                  1..156
                        mol_type = protein
                        organism = synthetic construct
SEQUENCE: 33
NQHSKDHET  VRIAVVRARW  HAEIVDACVS  AFEAAMRDIG  GDRFAVDVFD  VPGAYEIPLH    60
ARTLAETGRY  GAVLGTAFVV  DGGIYDHEFV  ASAVIDGMMN  VQLDTGVPVL  SAVLTPHEYE   120
DSDADTLLFL  ALFAVKGMEA  ARACVEILAA  REKIAA                              156
```

```
SEQ ID NO: 34              moltype = AA  length = 156
FEATURE                    Location/Qualifiers
REGION                     1..156
                           note = synthetic construct
source                     1..156
                           mol_type = protein
                           organism = synthetic construct
SEQUENCE: 34
NQHSHKDHET VRIAVVRARW HAEIVDACVS AFEAAMRDIG GDRFAVDVFD VPGAYEIPLH    60
ARTLAETGRY GAVLGTAFVV NGGIYRHEFV ASAVINGMMN VQLNTGVPVL SAVLTPHNYD   120
KSKAHTLLFL ALFAVKGMEA ARACVEILAA REKIAA                            156

SEQ ID NO: 35              moltype = AA  length = 155
FEATURE                    Location/Qualifiers
REGION                     1..155
                           note = synthetic construct
SITE                       69
                           note = Xaa is Ala or Lys
source                     1..155
                           mol_type = protein
                           organism = synthetic construct
SEQUENCE: 35
TKKVGIVDTT FARVDMASAA ILTLKMESPN IKIIRKTVPG IKDLPVACKK LLEEEGCDIV    60
MALGMPGKXE KDKVCAHEAS LGLMLAQLMT NKHIIEVFVH EDEAKDDAEL KILAARRAIE   120
HALNVYYLLF KPEYLTRMAG KGLRQGFEDA GPARE                             155

SEQ ID NO: 36              moltype = AA  length = 208
FEATURE                    Location/Qualifiers
REGION                     1..208
                           note = synthetic construct
SITE                       1
                           note = Xaa is Ser or Asp
SITE                       2
                           note = Xaa is Thr or Asp
SITE                       9
                           note = Xaa is Ala or Arg
SITE                       84
                           note = Xaa is Thr or Asp
SITE                       118
                           note = Xaa is Ala or Gln
SITE                       162
                           note = Xaa is Ser or Asp
SITE                       188
                           note = Xaa is Thr or Arg
source                     1..208
                           mol_type = protein
                           organism = synthetic construct
SEQUENCE: 36
XXINNQLKXL KVIPVIAIDN AEDIIPLGKV LAENGLPAAE ITFRSSAAVK AIMLLRSAQP    60
EMLIGAGTIL NGVQALAAKE AGAXFVVSPG FNPNTVRACQ IIGIDIVPGV NNPSTVEXAL   120
EMGLTTLKFF PAEASGGISM VKSLVGPYGD IRLMPTGGIT PXNIDNYLAI PQVLACGGTW   180
MVDKKLVXNG EWDEIARLTR EIVEQVNP                                     208

SEQ ID NO: 37              moltype = AA  length = 113
FEATURE                    Location/Qualifiers
REGION                     1..113
                           note = synthetic construct
SITE                       12
                           note = Xaa is Thr or Asp
SITE                       32
                           note = Xaa is Lys or Glu
SITE                       70
                           note = Xaa is Ser or Asp
SITE                       73
                           note = Xaa is Arg or Glu
SITE                       100
                           note = Xaa is Asn or Asp
SITE                       102
                           note = Xaa is Asn or Asp
source                     1..113
                           mol_type = protein
                           organism = synthetic construct
```

```
SEQUENCE: 37
PIFTLNTNIK AXDVPSDFLS LTSRLVGLIL SXPGSYVAVH INTDQQLSFG GSTNPAAFGT    60
LMSIGGIEPX KNXDHSAVLF DHLNAMLGIP KNRMYIHFVX LXGDDVGWNG TTF         113

SEQ ID NO: 38           moltype = AA  length = 156
FEATURE                 Location/Qualifiers
REGION                  1..156
                        note = synthetic construct
SITE                    8
                        note = Xaa is Tyr or His
SITE                    81
                        note = Xaa is Asn or Asp
SITE                    86
                        note = Xaa is Arg or Asp
SITE                    104
                        note = Xaa is Ser or Asp
SITE                    118
                        note = Xaa is Arg or Glu
SITE                    120
                        note = Xaa is Arg or Glu
SITE                    123
                        note = Xaa is Ala or Asp
SITE                    125
                        note = Xaa is His or Asp
SITE                    127
                        note = Xaa is Arg or Glu
SITE                    149
                        note = Xaa is Ala or Asn
source                  1..156
                        mol_type = protein
                        organism = synthetic construct
SEQUENCE: 38
NQHSHKDXET VRIAVVRARW HADIVDACVE AFEIAMAAIG GDRFAVDVFD VPGAYEIPLH    60
ARTLAETGRY GAVLGTAFVV XGGIYXHEFV ASAVIDGMMN VQLXTGVPVL SAVLTPHXYX   120
DSXEXHXFFA AHFAVKGVEA ARACIEILXA REKIAA                            156

SEQ ID NO: 39           moltype = AA  length = 202
FEATURE                 Location/Qualifiers
REGION                  1..202
                        note = synthetic construct
SITE                    123
                        note = Xaa is Thr or Asp
SITE                    136
                        note = Xaa is Gln or Glu
SITE                    139
                        note = Xaa is Lys or Glu
SITE                    157
                        note = Xaa is Asn or Asp
SITE                    160
                        note = Xaa is Asn or Asp
SITE                    163
                        note = Xaa is Glu or Lys
SITE                    166
                        note = Xaa is Lys or Asp
SITE                    176
                        note = Xaa is Ser, Lys or Asp
SITE                    180
                        note = Xaa is Lys or Glu
SITE                    182
                        note = Xaa is Thr, Asp or Lys
SITE                    189
                        note = Xaa is Lys or Asp
SITE                    192
                        note = Xaa is Ala, Glu or Lys
SITE                    195
                        note = Xaa is Glu or Lys
SITE                    196
                        note = Xaa is Lys or Glu
source                  1..202
                        mol_type = protein
                        organism = synthetic construct
SEQUENCE: 39
EELFKKHKIV AVLRANSVEE AIEKAVAVFA GGVHLIEITF TVPDADTVIK ALSVLKEKGA    60
IIGAGTVTSV EQCRKAVESG AEFIVSPHLD EEISQFCKEK GVFYMPGVMT PTELVKAMKL   120
GHXILKLFPG EVVGPXFVXA MKGPFPNVKF VPTGGVXLDX VCXWFXAGVL AVGVGXALVX   180
GXPDEVREXA KXFVXXIRGC TE                                           202
```

```
SEQ ID NO: 40            moltype = AA  length = 156
FEATURE                  Location/Qualifiers
REGION                   1..156
                         note = synthetic construct
SITE                     8
                         note = Xaa is Tyr or His
SITE                     37
                         note = Xaa is Ala or Arg
SITE                     81
                         note = Xaa is Asn or Asp
SITE                     86
                         note = Xaa is Arg or Asp
SITE                     96
                         note = Xaa is Asp or Asn
SITE                     104
                         note = Xaa is Ser, Asp or Asn
SITE                     118
                         note = Xaa is Arg, Glu or Asn
SITE                     120..121
                         note = Xaa is Arg, Asp or Glu
SITE                     120..121
                         note = Xaa is Asp or Lys
SITE                     123
                         note = Xaa is Asp or Lys
SITE                     125
                         note = Xaa is His or Asp
source                   1..156
                         mol_type = protein
                         organism = synthetic construct
SEQUENCE: 40
NQHSHKDXET VRIAVVRARW HAEIVDACVS AFEAAMXDIG GDRFAVDVFD VPGAYEIPLH   60
ARTLAETGRY GAVLGTAFVV XGGIYXHEFV ASAVIXGMMN VQLXTGVPVL SAVLTPHXYX  120
XSXAXTLLFL ALFAVKGMEA ARACVEILAA REKIAA                            156

SEQ ID NO: 41            moltype = AA  length = 158
FEATURE                  Location/Qualifiers
REGION                   1..158
                         note = synthetic construct
source                   1..158
                         mol_type = protein
                         organism = synthetic construct
SEQUENCE: 41
GEVPIGDPKE LNGMEIAAVY LQPIEMEPRG IDLAASLADI HLEADIHALK NNPNGFPEGF   60
WMPYLTIAYA LANADTGAIK TGTLMPMVAD DGPHYGANIA MEKDKKGGFG VGTYALTFLI  120
SNPEKQGFGR HVDEETGVGK WFEPFVVTYF FKYTGTPK                          158

SEQ ID NO: 42            moltype = AA  length = 183
FEATURE                  Location/Qualifiers
REGION                   1..183
                         note = synthetic construct
source                   1..183
                         mol_type = protein
                         organism = synthetic construct
SEQUENCE: 42
SQAIGILELT SIAKGMELGD AMLKSANVDL LVSKTISPGK FLLMLGGDIG AIQQAIETGT   60
SQAGEMLVDS LVLANIHPSV LPAISGLNSV DKRQAVGIVE TWSVAACISA ADLAVKGSNV  120
TLVRVHMAFG IGGKCYMVVA GDVLDVAAAV ATASLAAGAK GLLVYASIIP RPHEAMWRQM  180
VEG                                                                183

SEQ ID NO: 43            moltype = AA  length = 102
FEATURE                  Location/Qualifiers
REGION                   1..102
                         note = synthetic construct
source                   1..102
                         mol_type = protein
                         organism = synthetic construct
SEQUENCE: 43
EEVVLITVPS ALVAVKIAHA LVEERLAACV NIVPGLTSIY RWQGSVVSDH ELLLLVKTTT   60
HAFPKLKERV KALHPYTVPE IVALPIAEGN REYLDWLREN TG                     102

SEQ ID NO: 44            moltype = AA  length = 121
FEATURE                  Location/Qualifiers
REGION                   1..121
                         note = synthetic construct
source                   1..121
                         mol_type = protein
                         organism = synthetic construct
```

```
SEQUENCE: 44
VRGIRGAITV EEDTPAAILA ATIELLLKML EANGIQSYEE LAAVIFTVTE DLTSAFPAEA    60
ARLIGMHRVP LLSAREVPVP GSLPRVIRVL ALWNTDTPQD RVRHVYLNEA VRLRPDLESA   120
Q                                                                  121

SEQ ID NO: 45           moltype = AA  length = 176
FEATURE                 Location/Qualifiers
REGION                  1..176
                        note = synthetic construct
source                  1..176
                        mol_type = protein
                        organism = synthetic construct
SEQUENCE: 45
SKAKIGIVTV SDRASAGITA DISGKAIILA LNLYLTSEWE PIYQVIPDEQ DVIETTLIKM    60
ADEQDCCLIV TTGGTGPAKR DVTPEATEAV CDRMMPGFGE LMRAESLKEV PTAILSRQTA   120
GLRGDSLIVN LPGDPASISD CLLAVFPAIP YCIDLMEGPY LECNEAMIKP FRPKAK       176

SEQ ID NO: 46           moltype = AA  length = 121
FEATURE                 Location/Qualifiers
REGION                  1..121
                        note = synthetic construct
source                  1..121
                        mol_type = protein
                        organism = synthetic construct
SEQUENCE: 46
VRGIRGAITV NSDTPTSIII ATILLLEKML EANGIQSYEE LAAVIFTVTE DLTSAFPAEA    60
ARQIGMHRVP LLSAREVPVP GSLPRVIRVL ALWNTDTPQD RVRHVYLSEA VRLRPDLESA   120
Q                                                                  121

SEQ ID NO: 47           moltype = AA  length = 171
FEATURE                 Location/Qualifiers
REGION                  1..171
                        note = synthetic construct
source                  1..171
                        mol_type = protein
                        organism = synthetic construct
SEQUENCE: 47
RITTKVGDKG STRLFGGEEV WKDSPIIEAN GTLDELTSFI GEAKHYVDEE MKGILEEIQN    60
DIYKIMGEIG SKGKIEGISE ERIAWLLKLI LRYMEMVNLK SFVLPGGTLE SAKLDVCRTI   120
ARRALRKVLT VTREFGIGAE AAAYLLALSD LLFLLARVIE IEKNKLKEVR S            171

SEQ ID NO: 48           moltype = AA  length = 122
FEATURE                 Location/Qualifiers
REGION                  1..122
                        note = synthetic construct
source                  1..122
                        mol_type = protein
                        organism = synthetic construct
SEQUENCE: 48
PHLVIEATAN LRLETSPGEL LEQANKALFA SGQFGEADIK SRFVTLEAYR QGTAAVERAY    60
LHACLSILDG RDIATRTLLG ASLCAVLAEA VAGGGEEGVQ VSVEVREMER LSYAKRVVAR   120
QR                                                                 122

SEQ ID NO: 49           moltype = AA  length = 157
FEATURE                 Location/Qualifiers
REGION                  1..157
                        note = synthetic construct
source                  1..157
                        mol_type = protein
                        organism = synthetic construct
SEQUENCE: 49
ESVNTSFLSP SLVTIRDFDN GQFAVLRIGR TGFPADKGDI DLCLDKMIGV RAAQIFLGDD    60
TEDGFKGPHI RIRCVDIDDK HTYNAMVYVD LIVGTGASEV ERETAEEEAK LALRVALQVD   120
IADEHSCVTQ FEMKLREELL SSDSFHPDKD EYYKDFL                            157

SEQ ID NO: 50           moltype = AA  length = 112
FEATURE                 Location/Qualifiers
REGION                  1..112
                        note = synthetic construct
source                  1..112
                        mol_type = protein
                        organism = synthetic construct
SEQUENCE: 50
PVIQTFVSTP LDHHKRLLLA IIYRIVTRVV LGKPEDLVMM TFHDSTPMHF FGSTDPVACV    60
RVEALGGYGP SEPEKVTSIV TAAITAVCGI VADRIFVLYF SPLHCGWNGT NF           112
```

```
SEQ ID NO: 51              moltype = AA  length = 102
FEATURE                    Location/Qualifiers
REGION                     1..102
                           note = synthetic construct
source                     1..102
                           mol_type = protein
                           organism = synthetic construct
SEQUENCE: 51
EEVVLITVPS ALVAVKIAHA LVEERLAACV NIVPGLTSIY REEGSVVSDH ELLLLVKTTT    60
DAFPKLKERV KELHPYEVPE IVALPIAEGN REYLDWLREN TG                      102

SEQ ID NO: 52              moltype =    length =
SEQUENCE: 52
000

SEQ ID NO: 53              moltype = AA  length = 203
FEATURE                    Location/Qualifiers
REGION                     1..203
                           note = synthetic construct
source                     1..203
                           mol_type = protein
                           organism = synthetic construct
SEQUENCE: 53
MEELFKKHKI VAVLRANSVE EAIEKAVAVF AGGVHLIEIT FTVPDADTVI KALSVLKEKG    60
AIIGAGTVTS VEQARKAVES GAEFIVSPHL DEEISQFAKE KGVFYMPGVM TPTELVKAMK   120
LGHTILKLFP GEVVGPQFVK AMKGPFPNVK FVPTGGVNLD NVAEWFKAGV LAVGVGSALV   180
KGTPDEVREK AKAFVEKIRG ATE                                           203

SEQ ID NO: 54              moltype = AA  length = 4
FEATURE                    Location/Qualifiers
REGION                     1..4
                           note = furin cleavage sites
source                     1..4
                           mol_type = protein
                           organism = synthetic construct
SEQUENCE: 54
RQSR                                                                  4

SEQ ID NO: 55              moltype = AA  length = 4
FEATURE                    Location/Qualifiers
REGION                     1..4
                           note = furin cleavage sites
source                     1..4
                           mol_type = protein
                           organism = synthetic construct
SEQUENCE: 55
RRRR                                                                  4

SEQ ID NO: 56              moltype = AA  length = 539
FEATURE                    Location/Qualifiers
source                     1..539
                           mol_type = protein
                           organism = Human metapneumovirus
SEQUENCE: 56
MSWKVVIIFS LLITPQHGLK ESYLEESCST ITEGYLSVLR TGWYTNVFTL EVGDVENLTC    60
SDGPSLIKTE LDLTKSALRE LKTVSADQLA REEQIENPRQ SRFVLGAIAL GVATAAAVTA   120
GVAIAKTIRL ESEVTAIKNA LKTTNEAVST LGNGVRVLAT AVRELKDFVS KNLTRAINKN   180
KCDIDDLKMA VSFSQFNRRF LNVVRQFSDN AGITPAISLD LMTDAELARA VSNMPTSAGQ   240
IKLMLENRAM VRRKGFGILI GVYGSSVIYM VQLPIFGVID TPCWIVKAAP SCSGKKGNYA   300
CLLREDQGWY CQNAGSTVYY PNEKDCETRG DHVFCDTAAG INVAEQSKEC NINISTTNYP   360
CKVSTGRHPI SMVALSPLGA LVACYKGVSC SIGSNRVGII KQLNKGCSYI TNQDADTVTI   420
DNTVYQLSKV EGEQHVIKGR PVSSSFDPIK FPEDQFNVAL DQVFENIENS QALVDQSNRI   480
LSSAEKGNTG FIIVIILIAV LGSSMILVSI FIIIKKTKKP TGAPPELSGV TNNGFIPHS    539

SEQ ID NO: 57              moltype = AA  length = 472
FEATURE                    Location/Qualifiers
source                     1..472
                           mol_type = protein
                           organism = Human metapneumovirus
SEQUENCE: 57
KESYLEESCS TITEGYLSVL RTGWYTNVFT LEVGDVENLT CSDGPSLIKT ELDLTKSALR    60
ELKTVSADQL AREEQIENPR QSRFVLGAIA LGVATAAAVT AGVAIAKTIR LESEVTAIKN   120
ALKTTNEAVS TLGNGVRVLA TAVRELKDFV SKNLTRAINK NKCDIDDLKM AVSFSQFNRR   180
FLNVVRQFSD NAGITPAISL DLMTDAELAR AVSNMPTSAG QIKLMLENRA MVRRKGFGIL   240
IGVYGSSVIY MVQLPIFGVI DTPCWIVKAA PSCSGKKGNY ACLLREDQGW YCQNAGSTVY   300
YPNEKDCETR GDHVFCDTAA GINVAEQSKE CNINISTTNY PCKVSTGRHP ISMVALSPLG   360
ALVACYKGVS CSIGSNRVGI IKQLNKGCSY ITNQDADTVT IDNTVYQLSK VEGEQHVIKG   420
RPVSSSFDPI KFPEDQFNVA LDQVFENIEN SQALVDQSNR ILSSAEKGNT GF           472
```

```
SEQ ID NO: 58              moltype = AA    length = 462
FEATURE                    Location/Qualifiers
REGION                     1..462
                           note = synthetic construct
source                     1..462
                           mol_type = protein
                           organism = synthetic construct
SEQUENCE: 58
KESYLEESCS TITEGYLSVL RTGWYTNVFT LEVGDVENLT CADGPSLIKT ELDLTKSALR    60
ELRTVSADQL AREEQIENPR RRRFVLGAIA LGVATAAAVT AGVAIAKTIR LESEVTAIKN   120
ALKKTNEAVS TLGNGVRVLA TAVRELKDFV SKNLTRAINK NKCDIPDLKM AVSFSQFNRR   180
FLNVVRQFSD NAGITPAISL DLMTDAELAR AVSNMPTSAG QIKLMLENRA MVRRKGFGFL   240
IGVYGSSVIY MVQLPIFGVI DTPCWIVKAA PSCSGKKGNY ACLLREDQGW YCQNAGSTVY   300
YPNEKDCETR GDHVFCDTAA GINVAEQSKE CNINISTTNY PCKVSTGRHP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQVFESIEN SQALVDQSNR IL                     462

SEQ ID NO: 59              moltype = AA    length = 453
FEATURE                    Location/Qualifiers
REGION                     1..453
                           note = synthetic construct
source                     1..453
                           mol_type = protein
                           organism = synthetic construct
SEQUENCE: 59
KESYLEESCS TITEGYLSVL RTGWYTNVFT LEVGDVENLT CADGPSLIKT ELDLTKSALR    60
ELRTVSADQL AREEQIENPR RRRFVLGAIA LGVATAAAVT AGVAIAKTIR LESEVTAIKN   120
ALKKTNEAVS TLGNGVRVLA TAVRELKDFV SKNLTRAINK NKCDIPDLKM AVSFSQFNRR   180
FLNVVRQFSD NAGITPAISL DLMTDAELAR AVSNMPTSAG QIKLMLENRA MVRRKGFGFL   240
IGVYGSSVIY MVQLPIFGVI DTPCWIVKAA PSCSGKKGNY ACLLREDQGW YCQNAGSTVY   300
YPNEKDCETR GDHVFCDTAA GINVAEQSKE CNINISTTNY PCKVSTGRHP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQVFESIEN SQA                               453

SEQ ID NO: 60              moltype = AA    length = 470
FEATURE                    Location/Qualifiers
REGION                     1..470
                           note = synthetic construct
source                     1..470
                           mol_type = protein
                           organism = synthetic construct
SEQUENCE: 60
KESYLEESCS TITEGYLSVL RTGWYTNVFT LEVGDVENLT CADGPSLIKT ELDLTKSALR    60
ELRTVSADQL AREEQIENPR RRRFVLGAIA LGVATAAAVT AGVAIAKTIR LESEVTAIKN   120
ALKKTNEAVS TLGNGVRVLA TAVRELKDFV SKNLTRAINK NKCDIPDLKM AVSFSQFNRR   180
FLNVVRQFSD NAGITPAISL DLMTDAELAR AVSNMPTSAG QIKLMLENRA MVRRKGFGFL   240
IGVYGSSVIY MVQLPIFGVI DTPCWIVKAA PSCSGKKGNY ACLLREDQGW YCQNAGSTVY   300
YPNEKDCETR GDHVFCDTAA GINVAEQSKE CNINISTTNY PCKVSTGRHP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQVFESIEN SQALVDQSNR ILSSAEKGNT             470

SEQ ID NO: 61              moltype = AA    length = 453
FEATURE                    Location/Qualifiers
REGION                     1..453
                           note = synthetic construct
source                     1..453
                           mol_type = protein
                           organism = synthetic construct
SEQUENCE: 61
KESYLEESCS TITEGYLSVL RTGWYTNVFT LEVGDVENLT CADGPSLIKT ELDLTKSALR    60
ELRTVSADQL AREEQIENPR RRRFVLGAIA LGVATAAAVT AGVAIAKTIR LESEVTAIKN   120
ALKKTNEAVS TLGNGVRVLA TAVRELKDFV SKNLTRAINK NKCDIADLKM AVSFSQFNRR   180
FLNVVRQFSD NAGITPAISL DLMTDAELAR AVSNMPTSAG QIKLMLENRA MVRRKGFGFL   240
IGVYGSSVIY MVQLPIFGVI DTPCWIVKAA PSCSGKKGNY ACLLREDQGW YCQNAGSTVY   300
YPNEKDCETR GDHVFCDTAA GINVAEQSKE CNINISTTNY PCKVSTGRHP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQVFESIEN SQA                               453

SEQ ID NO: 62              moltype = AA    length = 453
FEATURE                    Location/Qualifiers
REGION                     1..453
                           note = synthetic construct
source                     1..453
                           mol_type = protein
                           organism = synthetic construct
SEQUENCE: 62
KESYLEESCS TITEGYLSVL RTGWYTNVFT LEVGDVENLT CADGPSLIKT ELDLTKSALR    60
ELRTVSADQL AREEQIENPR RRRFVLGAIA LGVATAAAVT AGVAIAKCIR LESEVTAIKN   120
```

```
ALKKTNEAVS TLGCGVRVLA TAVRELKDFV SKNLTRAINK NKCDIPDLKM AVSFSQFNRR    180
FLNVVRQFSD NAGITPAISL DLMTDAELAR AVSNMPTSAG QIKLMLENRA MVRRKGFGIL    240
IGVYGSSVIY MVQLPIFGVI DTPCWIVKAA PSCSGKKGNY ACLLREDQGW YCQNAGSTVY    300
YPNEKDCETR GDHVFCDTAA GINVAEQSKE CNINISTTNY PCKVSTGRNP ISMVALSPLG    360
ALVACYKGVS CSIGSNRVGI IKQLNKGCSY ITNQDADTVT IDNTVYQLSK VEGEQHVIKG    420
RPVSSSFDPV KFPEDQFNVA LDQVFESIEN SQA                                 453

SEQ ID NO: 63          moltype = AA   length = 453
FEATURE                Location/Qualifiers
REGION                 1..453
                       note = synthetic construct
source                 1..453
                       mol_type = protein
                       organism = synthetic construct
SEQUENCE: 63
KESYLEESCS TITEGYLSVL RTGWYTNVFT LEVGDVENLT CTDGPSLIKT ELDLTKSALR     60
ELKTCSADQL AREEQIEGGG GGGFVLGAIA LGVATAAAVT AGIAIAKTIR LESEVNAIKG    120
CLKTTNECVS TLGNGVRVLA TAVRELKEFV SKNLTSAINK NKCDIADLKM AVSFSQFNRR    180
FLNVVRQFSD NAGITPAISL DLMTDAELAR AVSYMPTSAG QIKLMLENRC MVRRKGFGIL    240
IGVYGSSVIY MVQLPIFGVI DTPCWIIKAA PSCSEKDGNY ACLLREDQGW YCKNAGSTVY    300
YPNDKDCETR GDHVFCDTAA GINVAEQSRE CNINISTTNY PCKVSTGRHP ISMVALSPLG    360
ALVACYKGVS CSIGSNRVGI IKQLPKGCSY ITNQDADTVT IDNTVYQLSK VEGEQHVIKG    420
RPVSSSFDPI KFPEDQFNVA LDQVFESIEN SQA                                 453

SEQ ID NO: 64          moltype = AA   length = 469
FEATURE                Location/Qualifiers
REGION                 1..469
                       note = synthetic construct
source                 1..469
                       mol_type = protein
                       organism = synthetic construct
SEQUENCE: 64
KESYLEESCS TITEGYLSVL RTGWYTNVFT LEVGDVENLT CTDGPSLIKT ELDLTKSALR     60
ELKTCSADQL AREEQIEGGG GGGFVLGAIA LGVATAAAVT AGIAIAKTIR LESEVNAIKG    120
CLKTTNECVS TLGNGVRVLA TAVRELKEFV SKNLTSAINK NKCDIADLKM AVSFSQFNRR    180
FLNVVRQFSD NAGITPAISL DLMTDAELAR AVSYMPTSAG QIKLMLENRC MVRRKGFGIL    240
IGVYGSSVIY MVQLPIFGVI DTPCWIIKAA PSCSEKDGNY ACLLREDQGW YCKNAGSTVY    300
YPNDKDCETR GDHVFCDTAA GINVAEQSRE CNINISTTNY PCKVSTGRHP ISMVALSPLG    360
ALVACYKGVS CSIGSNRVGI IKQLPKGCSY ITNQDADTVT IDNTVYQLSK VEGEQHVIKG    420
RPVSSSFDPI KFPEDQFNVA LDQVFESIEN SQALVDQSNK ILNSAESAI                469

SEQ ID NO: 65          moltype = AA   length = 453
FEATURE                Location/Qualifiers
REGION                 1..453
                       note = synthetic construct
source                 1..453
                       mol_type = protein
                       organism = synthetic construct
SEQUENCE: 65
KESYLEESCS TITEGYLSVL RTGWYTNVFT LEVGDVENLT CTDCPSLIKT ELDLTKSALR     60
ELKTVSADQL AREEQIEGGG GGGFVLGAIA LGVATAAAVT AGIAIAKTIR LESEVNAIKG    120
CLKTTNECVS TLGNGVRVLA TAVRELKEFV SKNLTSAINK NKCDIADLCM AVSFSQFNRR    180
FLNVVRQFSD NAGITPAISL DLMTDAELAR AVSYMPTSAG QIKLMLENRA MVRRKGFGIL    240
IGVYGSSVIY MVQLPIFGVI DTPCWIIKAA PSCSEKDGNY ACLLREDQGW YCKNAGSTVY    300
YPNDKDCETR GDHVFCDTAA GINVAEQSRE CNINISTTNY PCKVSTGRHP ISMVALSPLG    360
ALVACYKGVS CSIGSNRVGI IKQLPKGCSY ITNQDADTVT IDNTVYQLSK VEGEQHVIKG    420
RPVSSSFDPI CFPEDQFNVA LDQVFESIEN CQA                                 453

SEQ ID NO: 66          moltype = AA   length = 469
FEATURE                Location/Qualifiers
REGION                 1..469
                       note = synthetic construct
source                 1..469
                       mol_type = protein
                       organism = synthetic construct
SEQUENCE: 66
KESYLEESCS TITEGYLSVL RTGWYTNVFT LEVGDVENLT CTDCPSLIKT ELDLTKSALR     60
ELKTVSADQL AREEQIEGGG GGGFVLGAIA LGVATAAAVT AGIAIAKTIR LESEVNAIKG    120
CLKTTNECVS TLGNGVRVLA TAVRELKEFV SKNLTSAINK NKCDIADLCM AVSFSQFNRR    180
FLNVVRQFSD NAGITPAISL DLMTDAELAR AVSYMPTSAG QIKLMLENRA MVRRKGFGIL    240
IGVYGSSVIY MVQLPIFGVI DTPCWIIKAA PSCSEKDGNY ACLLREDQGW YCKNAGSTVY    300
YPNDKDCETR GDHVFCDTAA GINVAEQSRE CNINISTTNY PCKVSTGRHP ISMVALSPLG    360
ALVACYKGVS CSIGSNRVGI IKQLPKGCSY ITNQDADTVT IDNTVYQLSK VEGEQHVIKG    420
RPVSSSFDPI CFPEDQFNVA LDQVFESIEN CQALVDQSNK ILNSAESAI                469
```

```
SEQ ID NO: 67            moltype = AA   length = 452
FEATURE                  Location/Qualifiers
REGION                   1..452
                         note = synthetic construct
source                   1..452
                         mol_type = protein
                         organism = synthetic construct
SEQUENCE: 67
KESYLEESCS TITEGYLSVL RTGWYTNVFT LEVGDVENLT CSDCPSLIKT ELDLTKSALR    60
ELKTVSADQL AREEQIEGGG GGGFVLAIAL GVATAAAVTA GVAIAKTIRL ESEVTAIKNC   120
LKTTNECVST LGNGVRVLAT AVRELKDFVS KNLTSAINKN KCDIDDLCMA VSFSQFNRRF   180
LNVVRQFSDN AGITPAISLD LMTDAELARA VSNMPTSAGQ IKLMLENRAM VRRKGFGILI   240
GVYGSSVIYM VQLPIFGVID TPCWIIKAAP SCSGKKGNYA CLLREDQGWY CQNAGSTVYY   300
PNEKDCETRG DHVFCDTAAG INVAEQSKEC NINISTTNYP CKVSTGRHPI SMVALSPLGA   360
LVACYKGVSC SIGSNRVGII KQLNKGCSYI TNQDADTVTI DNTVYQLSKV EGEQHVIKGR   420
PVSSSFDPIK FPEDQFNVAL DQVFENIENS QA                                452

SEQ ID NO: 68            moltype = AA   length = 468
FEATURE                  Location/Qualifiers
REGION                   1..468
                         note = synthetic construct
source                   1..468
                         mol_type = protein
                         organism = synthetic construct
SEQUENCE: 68
KESYLEESCS TITEGYLSVL RTGWYTNVFT LEVGDVENLT CSDCPSLIKT ELDLTKSALR    60
ELKTVSADQL AREEQIEGGG GGGFVLAIAL GVATAAAVTA GVAIAKTIRL ESEVTAIKNC   120
LKTTNECVST LGNGVRVLAT AVRELKDFVS KNLTSAINKN KCDIDDLCMA VSFSQFNRRF   180
LNVVRQFSDN AGITPAISLD LMTDAELARA VSNMPTSAGQ IKLMLENRAM VRRKGFGILI   240
GVYGSSVIYM VQLPIFGVID TPCWIIKAAP SCSGKKGNYA CLLREDQGWY CQNAGSTVYY   300
PNEKDCETRG DHVFCDTAAG INVAEQSKEC NINISTTNYP CKVSTGRHPI SMVALSPLGA   360
LVACYKGVSC SIGSNRVGII KQLNKGCSYI TNQDADTVTI DNTVYQLSKV EGEQHVIKGR   420
PVSSSFDPIK FPEDQFNVAL DQVFENIENS QALVDQSNRI LSSAESAI               468

SEQ ID NO: 69            moltype = AA   length = 453
FEATURE                  Location/Qualifiers
REGION                   1..453
                         note = synthetic construct
source                   1..453
                         mol_type = protein
                         organism = synthetic construct
SEQUENCE: 69
KESYLEESCS TITEGYLSVL RTGWYTNVFT LEVGDVENLT CTDGPSLIKT ELDLTKSALR    60
ELKTVSADQL AREEQIENPR KARFVLGAIA LGVCTAAAVT CGIAIAKTIR LESEVNAIKG   120
ALKTTNEAVS TLGNGVRVLA FAVRELKEFV SKNLTSALNK NKCDIADLKM AVSFSQFNRR   180
FLNVVRQFSD NAGITPAISL DLMTDAELAR AVSYMPTSAG QIKLMLENRA MVRRKGFGIL   240
IGVYGSSVIY MVQLPIFGVI DTPCWIIKAA PSCSEKDGNY ACLLREDQGW YCKNAGSTVY   300
YPNDKDCETR GDHVFCDTAC GINVAEQSRE CNINISTTNY PCKVSTGRHP ISMVALSPLG   360
ALVACYKGVS CSIGSNRVGI IKQLPKGCSY ITNQDADTVT IDNTVYCLSK VEGEQHVIKG   420
RPVSSSFDPI KFPEDQFNVA LDQVFESIEN SQA                                453

SEQ ID NO: 70            moltype = AA   length = 469
FEATURE                  Location/Qualifiers
REGION                   1..469
                         note = synthetic construct
source                   1..469
                         mol_type = protein
                         organism = synthetic construct
SEQUENCE: 70
KESYLEESCS TITEGYLSVL RTGWYTNVFT LEVGDVENLT CTDGPSLIKT ELDLTKSALR    60
ELKTVSADQL AREEQIENPR KARFVLGAIA LGVCTAAAVT CGIAIAKTIR LESEVNAIKG   120
ALKTTNEAVS TLGNGVRVLA FAVRELKEFV SKNLTSALNK NKCDIADLKM AVSFSQFNRR   180
FLNVVRQFSD NAGITPAISL DLMTDAELAR AVSYMPTSAG QIKLMLENRA MVRRKGFGIL   240
IGVYGSSVIY MVQLPIFGVI DTPCWIIKAA PSCSEKDGNY ACLLREDQGW YCKNAGSTVY   300
YPNDKDCETR GDHVFCDTAC GINVAEQSRE CNINISTTNY PCKVSTGRHP ISMVALSPLG   360
ALVACYKGVS CSIGSNRVGI IKQLPKGCSY ITNQDADTVT IDNTVYCLSK VEGEQHVIKG   420
RPVSSSFDPI KFPEDQFNVA LDQVFESIEN SQALVDQSNK ILNSAESAI              469

SEQ ID NO: 71            moltype = AA   length = 472
FEATURE                  Location/Qualifiers
REGION                   1..472
                         note = synthetic construct
source                   1..472
                         mol_type = protein
                         organism = synthetic construct
SEQUENCE: 71
MSWKVMIIIS LLITPQHGLK ESYLEESCST ITEGYLSVLR TGWYTNVFTL EVGDVENLTC    60
TDGPSLIKTE LDLTKSALRE LKTCSADQLA REEQIENPRR RRFVLGAIAL GVATAAAVTA   120
```

```
GIAIAKTIRL ESEVNAIKGC LKTTNECVST LGNGVRVLAT AVRELKEFVS KNLTSAINKN   180
KCDIADLKMA VSFSQFNRRF LNVVRQFSDN AGITPAISLD LMTDAELARA VSYMPTSAGQ   240
IKLMLENRCM VRRKGFGILI GVYGSSVIYM VQLPIFGVID TPCWIIKAAP SCSEKDGNYA   300
CLLREDQGWY CKNAGSTVYY PNDKDCETRG DHVFCDTAAG INVAEQSREC NINISTTNYP   360
CKVSTGRHPI SMVALSPLGA LVACYKGVSC SIGSNRVGII KQLPKGCSYI TNQDADTVTI   420
DNTVYQLSKV EGEQHVIKGR PVSSSFDPIK FPEDQFNVAL DQVFESIENS QA           472

SEQ ID NO: 72           moltype = AA   length = 453
FEATURE                 Location/Qualifiers
REGION                  1..453
                        note = synthetic construct
source                  1..453
                        mol_type = protein
                        organism = synthetic construct
SEQUENCE: 72
KESYLEESCS TITEGYLSVL RTGWYTNVFT LEVGDVENLT CTDCPSLIKT ELDLTKSALR    60
ELKTVSADQL AREEQIENPR RRRFVLGAIA LGVATAAAVT AGIAIAKTIR LESEVNAIKG   120
CLKTTNECVS TLGNGVRVLA TAVRELKEFV SKNLTSAINK NKCDIADLCM AVSFSQFNRR   180
FLNVVRQFSD NAGITPAISL DLMTDAELAR AVSYMPTSAG QIKLMLENRA MVRRKGFGIL   240
IGVYGSSVIY MVQLPIFGVI DTPCWIIKAA PSCSEKDGNY ACLLREDQGW YCKNAGSTVY   300
YPNDKDCETR GDHVFCDTAA GINVAEQSRE CNINISTTNY PCKVSTGRHP ISMVALSPLG   360
ALVACYKGVS CSIGSNRVGI IKQLPKGCSY ITNQDADTVT IDNTVYQLSK VEGEQHVIKG   420
RPVSSSFDPI CFPEDQFNVA LDQVFESIEN CQA                                453

SEQ ID NO: 73           moltype = AA   length = 452
FEATURE                 Location/Qualifiers
REGION                  1..452
                        note = synthetic construct
source                  1..452
                        mol_type = protein
                        organism = synthetic construct
SEQUENCE: 73
KESYLEESCS TITEGYLSVL RTGWYTNVFT LEVGDVENLT CSDCPSLIKT ELDLTKSALR    60
ELKTVSADQL AREEQIENPR RRRFVLAIAL GVATAAAVTA GVAIAKTIRL ESEVTAIKNC   120
LKTTNECVST LGNGVRVLAT AVRELKDFVS KNLTSAINKN KCDIDDLCMA VSFSQFNRRF   180
LNVVRQFSDN AGITPAISLD LMTDAELARA VSNMPTSAGQ IKLMLENRAM VRRKGFGILI   240
GVYGSSVIYM VQLPIFGVID TPCWIIKAAP SCSGKKGNYA CLLREDQGWY CQNAGSTVYY   300
PNEKDCETRG DHVFCDTAAG INVAEQSKEC NINISTTNYP CKVSTGRHPI SMVALSPLGA   360
LVACYKGVSC SIGSNRVGII KQLNKGCSYI TNQDADTVTI DNTVYQLSKV EGEQHVIKGR   420
PVSSSFDPIK FPEDQFNVAL DQVFENIENS QA                                 452

SEQ ID NO: 74           moltype = AA   length = 453
FEATURE                 Location/Qualifiers
REGION                  1..453
                        note = synthetic construct
source                  1..453
                        mol_type = protein
                        organism = synthetic construct
SEQUENCE: 74
KESYLEESCS TITEGYLSVL RTGWYTNVFT LEVGDVENLT CTDGPSLIKT ELDLTKSALR    60
ELKTVSADQL AREEQIENPR RRRFVLGAIA LGVCTAAAVT CGIAIAKTIR LESEVNAIKG   120
ALKTTNEAVS TLGNGVRVLA FAVRELKEFV SKNLTSALNK NKCDIADLKM AVSFSQFNRR   180
FLNVVRQFSD NAGITPAISL DLMTDAELAR AVSYMPTSAG MVRRKGFGIL               240
IGVYGSSVIY MVQLPIFGVI DTPCWIIKAA PSCSEKDGNY ACLLREDQGW YCKNAGSTVY   300
YPNDKDCETR GDHVFCDTAC GINVAEQSRE CNINISTTNY PCKVSTGRHP ISMVALSPLG   360
ALVACYKGVS CSIGSNRVGI IKQLPKGCSY ITNQDADTVT IDNTVYCLSK VEGEQHVIKG   420
RPVSSSFDPI KFPEDQFNVA LDQVFESIEN SQA                                453

SEQ ID NO: 75           moltype = AA   length = 453
FEATURE                 Location/Qualifiers
REGION                  1..453
                        note = synthetic construct
source                  1..453
                        mol_type = protein
                        organism = synthetic construct
SEQUENCE: 75
KESYLEESCS TITEGYLSVL RTGWYTNVFT LEVGDVENLT CADGPSLIKT ELDLTKSALR    60
ELRTVSADQL AREEQIENPR RRRFVLGAIA LGVCTAAAVT AGVAIAKTIR LESEVTAIKN   120
ALKKTNEAVS TLGNGVRVLA TAVRELKDFV SKNLTRAINK NKCDIPDLKM AVSFSQFNRR   180
FLNVVRQFSD NAGITPAISL DLMTDAELAR AVSNMPTSAG QIKLMLENRA MVRRKGFGFL   240
IGVYGSSVIY MVQLPIFGVI DTPCWIVKAA PSCSGKKGNY ACLLREDQGW YCQNAGSTVY   300
YPNEKDCETR GDHVFCDTAC GINVAEQSKE CNINISTTNY PCKVSTGRHP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQVFESIEN SQA                                453
```

```
SEQ ID NO: 76          moltype = AA  length = 453
FEATURE                Location/Qualifiers
REGION                 1..453
                       note = synthetic construct
source                 1..453
                       mol_type = protein
                       organism = synthetic construct
SEQUENCE: 76
KESYLEESCS TITEGYLSVL RTGWYTNVFT LEVGDVENLT CADGPSLIKT ELDLTKSALR    60
ELRTVSADQL AREEQIENPR RRRFVLGAIA LGVATAAAVT AGVAIAKTIR LESEVTAIKN   120
ALKKTNEAVS TLGNGVRVLA FAVRELKDFV SKNLTRALNK NKCDIPDLKM AVSFSQFNRR   180
FLNVVRQFSD NAGITPAISL DLMTDAELAR AVSNMPTSAG QIKLMLENRA MVRRKGFGFL   240
IGVYGSSVIY MVQLPIFGVI DTPCWIVKAA PSCSGKKGNY ACLLREDQGW YCQNAGSTVY   300
YPNEKDCETR GDHVFCDTAA GINVAEQSKE CNINISTTNY PCKVSTGRHP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQVFESIEN SQA                                453

SEQ ID NO: 77          moltype = AA  length = 453
FEATURE                Location/Qualifiers
REGION                 1..453
                       note = synthetic construct
source                 1..453
                       mol_type = protein
                       organism = synthetic construct
SEQUENCE: 77
KESYLEESCS TITEGYLSVL RTGWYTNVFT LEVGDVENLT CADGPSLIKT ELDLTKSALR    60
ELRTVSADQL AREEQIENPR RRRFVLGAIA LGVCTAAAVT AGVAIAKTIR LESEVTAIKN   120
ALKKTNEAVS TLGNGVRVLA FAVRELKDFV SKNLTRALNK NKCDIPDLKM AVSFSQFNRR   180
FLNVVRQFSD NAGITPAISL DLMTDAELAR AVSNMPTSAG QIKLMLENRA MVRRKGFGFL   240
IGVYGSSVIY MVQLPIFGVI DTPCWIVKAA PSCSGKKGNY ACLLREDQGW YCQNAGSTVY   300
YPNEKDCETR GDHVFCDTAC GINVAEQSKE CNINISTTNY PCKVSTGRHP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQVFESIEN SQA                                453

SEQ ID NO: 78          moltype = AA  length = 453
FEATURE                Location/Qualifiers
REGION                 1..453
                       note = synthetic construct
source                 1..453
                       mol_type = protein
                       organism = synthetic construct
SEQUENCE: 78
KESYLEESCS TITEGYLSVL RTGWYTNVFT LEVGDVENLT CTDCPSLIKT ELDLTKSALR    60
ELKTVSADQL AREEQIEGGG GGGFVLGAIA LGVATAAAVT AGIAIAKTIR LESEVNAIKG   120
ALKTTNEAVS TLGNGVRVLA TAVRELKEFV SKNLTSAINK NKCDIADLCM AVSFSQFNRR   180
FLNVVRQFSD NAGITPAISL DLMTDAELAR AVSYMPTSAG QIKLMLENRA MVRRKGFGIL   240
IGVYGSSVIY MVQLPIFGVI DTPCWIIKAA PSCSEKDGNY ACLLREDQGW YCKNAGSTVY   300
YPNDKDCETR GDHVFCDTAA GINVAEQSRE CNINISTTNY PCKVSTGRHP ISMVALSPLG   360
ALVACYKGVS CSIGSNRVGI IKQLPKGCSY ITNQDADTVT IDNTVYQLSK VEGEQHVIKG   420
RPVSSSFDPI KFPEDQFNVA LDQVFESIEN SQA                                453

SEQ ID NO: 79          moltype = AA  length = 453
FEATURE                Location/Qualifiers
REGION                 1..453
                       note = synthetic construct
source                 1..453
                       mol_type = protein
                       organism = synthetic construct
SEQUENCE: 79
KESYLEESCS TITEGYLSVL RTGWYTNVFT LEVGDVENLT CTDCPSLIKT ELDLTKSALR    60
ELKTVSADQL AREEQIEGGG GGGFVLGAIA LGVATAAAVT AGIAIAKTIR LESEVNAIKG   120
ALKTTNEAVS TLGNGVRVLA TAVRELKEFV SKNLTSAINK NKCDIADLCM AVSFSQFNRR   180
FLNVVRQFSD NAGITPAISL DLMTDAELAR AVSYMPTSAG QIKLMLENRA MVRRKGFGIL   240
IGVYGSSVIY MVQLPIFGVI DTPCWIIKAA PSCSEKDGNY ACLLREDQGW YCKNAGSTVY   300
YPNDKDCETR GDHVFCDTAA GINVAEQSRE CNINISTTNY PCKVSTGRHP ISMVALSPLG   360
ALVACYKGVS CSIGSNRVGI IKQLPKGCSY ITNQDADTVT IDNTVYQLSK VEGEQHVIKG   420
RPVSSSFDPI AFPEDQFNVA LDQVFESIEN AQA                                453

SEQ ID NO: 80          moltype = AA  length = 453
FEATURE                Location/Qualifiers
REGION                 1..453
                       note = synthetic construct
source                 1..453
                       mol_type = protein
                       organism = synthetic construct
SEQUENCE: 80
KESYLEESCS TITEGYLSVL RTGWYTNVFT LEVGDVENLT CSDCPSLIKT ELDLTKSALR    60
ELKTVSADQL AREEQIEGGG GGGFVLGAIA LGVATAAAVT AGVAIAKTIR LESEVTAIKN   120
```

```
CLKTTNECVS TLGNGVRVLA TAVRELKDFV SKNLTSAINK NKCDIDDLCM AVSFSQFNRR    180
FLNVVRQFSD NAGITPAISL DLMTDAELAR AVSNMPTSAG QIKLMLENRA MVRRKGFGIL    240
IGVYGSSVIY MVQLPIFGVI DTPCWIIKAA PSCSEKKGNY ACLLREDQGW YCQNAGSTVY    300
YPNEKDCETR GDHVFCDTAA GINVAEQSKE CNINISTTNY PCKVSTGRHP ISMVALSPLG    360
ALVACYKGVS CSIGSNRVGI IKQLNKGCSY ITNQDADTVT IDNTVYQLSK VEGEQHVIKG    420
RPVSSSFDPI KFPEDQFNVA LDQVFENIEN SQA                                453

SEQ ID NO: 81            moltype = AA  length = 453
FEATURE                  Location/Qualifiers
REGION                   1..453
                         note = synthetic construct
source                   1..453
                         mol_type = protein
                         organism = synthetic construct
SEQUENCE: 81
KESYLEESCS TITEGYLSVL RTGWYTNVFT LEVGDVENLT CADCPSLIKT ELDLTKSALR     60
ELRTVSADQL AREEQIEGGG GGGFVLGAIA LGVATAAAVT AGVAIAKTIR LESEVTAIKN    120
CLKKTNECVS TLGNGVRVLA TAVRELKDFV SKNLTRAINK NKCDIADLCM AVSFSQFNRR    180
FLNVVRQFSD NAGITPAISL DLMTDAELAR AVSNMPTSAG QIKLMLENRA MVRRKGFGFL    240
IGVYGSSVIY MVQLPIFGVI DTPCWIVKAA PSCSEKKGNY ACLLREDQGW YCQNAGSTVY    300
YPNEKDCETR GDHVFCDTAA GINVAEQSKE CNINISTTNY PCKVSTGRHP ISMVALSPLG    360
ALVACYKGVS CSIGSNRVGI IKQLNKGCSY ITNQDADTVT IDNTVYQLSK VEGEQHVIKG    420
RPVSSSFDPV CFPEDQFNVA LDQVFESIEN CQA                                453

SEQ ID NO: 82            moltype = AA  length = 453
FEATURE                  Location/Qualifiers
REGION                   1..453
                         note = synthetic construct
source                   1..453
                         mol_type = protein
                         organism = synthetic construct
SEQUENCE: 82
KESYLEESCS TITEGYLSVL RTGWYTNVFT LEVGDVENLT CADCPSLIKT ELDLTKSALR     60
ELRTVSADQL AREEQIEGGG GGGFVLGAIA LGVATAAAVT AGVAIAKTIR LESEVTAIKN    120
ALKKTNEAVS TLGNGVRVLA TAVRELKDFV SKNLTRAINK NKCDIADLCM AVSFSQFNRR    180
FLNVVRQFSD NAGITPAISL DLMTDAELAR AVSNMPTSAG QIKLMLENRA MVRRKGFGFL    240
IGVYGSSVIY MVQLPIFGVI DTPCWIVKAA PSCSEKKGNY ACLLREDQGW YCQNAGSTVY    300
YPNEKDCETR GDHVFCDTAA GINVAEQSKE CNINISTTNY PCKVSTGRHP ISMVALSPLG    360
ALVACYKGVS CSIGSNRVGI IKQLNKGCSY ITNQDADTVT IDNTVYQLSK VEGEQHVIKG    420
RPVSSSFDPV KFPEDQFNVA LDQVFESIEN SQA                                453

SEQ ID NO: 83            moltype = AA  length = 453
FEATURE                  Location/Qualifiers
REGION                   1..453
                         note = synthetic construct
source                   1..453
                         mol_type = protein
                         organism = synthetic construct
SEQUENCE: 83
KESYLEESCS TITEGYLSVL RTGWYTNVFT LEVGDVENLT CADGPSLIKT ELDLTKSALR     60
ELRTVSADQL AREEQIENPR RRRFVLGAIA LGVATAAAVT AGVAIAKCIR LESEVTAIKN    120
ALKKTNEAVS TLGCGVRVLA TAVRELKDFV SKNLTRAINK NKCDIPDLKM AVSFSQFNRR    180
FLNVVRQFSD NAGITPAISK DLMTDAELAR AISNMPTSAG QIKLMLENRA MVRRKGFGIL    240
IGVYGSSVIY MVQLPIFGVI DTPCWIVKAA PSCSEKKGNY ACLLREDQGW YCQNAGSTVY    300
YPNEKDCETR GDHVFCDTAA GINVAEQSKE CNINISTTNY PCKVSCGRNP ISMVALSPLG    360
ALVACYKGVS CSIGSNRVGI IKQLNKGCSY ITNQDADTVT IDNTVYQLSK VEGEQHVIKG    420
RPVSSSFDPV KFPEDQFNVA LDQCFESIEN SQA                                453

SEQ ID NO: 84            moltype = AA  length = 471
FEATURE                  Location/Qualifiers
REGION                   1..471
                         note = synthetic construct
source                   1..471
                         mol_type = protein
                         organism = synthetic construct
SEQUENCE: 84
KESYLEESCS TITEGYLSVL RTGWYTNVFT LEVGDVENLT CADGPSLIKT ELDLTKSALR     60
ELRTVSADQL AREEQIENPR RRRFVLGAIA LGVATAAAVT AGVAIAKCIR LESEVTAIKN    120
ALKKTNEAVS TLGCGVRVLA TAVRELKDFV SKNLTRAINK NKCDIPDLKM AVSFSQFNRR    180
FLNVVRQFSD NAGITPAISK DLMTDAELAR AISNMPTSAG QIKLMLENRA MVRRKGFGIL    240
IGVYGSSVIY MVQLPIFGVI DTPCWIVKAA PSCSEKKGNY ACLLREDQGW YCQNAGSTVY    300
YPNEKDCETR GDHVFCDTAA GINVAEQSKE CNINISTTNY PCKVSCGRNP ISMVALSPLG    360
ALVACYKGVS CSIGSNRVGI IKQLNKGCSY ITNQDADTVT IDNTVYQLSK VEGEQHVIKG    420
RPVSSSFDPV KFPEDQFNVA LDQCFESIEN SQALVDQSNR ILSSAEKGNT G             471
```

```
SEQ ID NO: 85              moltype = AA  length = 453
FEATURE                    Location/Qualifiers
REGION                     1..453
                           note = synthetic construct
source                     1..453
                           mol_type = protein
                           organism = synthetic construct
SEQUENCE: 85
KESYLEESCS TITEGYLSVL RTGWYTNVFT LEVGDVENLT CTDCPSLIKT ELDLTKSALR    60
ELKTVSADQL AREEQIEGGG GGGFVLGAIA LGVATAAAVT AGIAIAKTIR LESEVNAIKG   120
CLKTTNECVS TLGNGVRVLA TAVRELKEFV SKNLTSAINK NKCDIADLCM AVSFSQFNRR   180
FLNVVRQFSD NAGITPAISL DLMTDAELAR AVSYMPTSAG QIKLMLENRA MVRRKGFGIL   240
IGVYGSSVIY MVQLPIFGVI DTPCWIIKAA PSCSEKDGNY ACLLREDQGW YCKNAGSTVY   300
YPNDKDCETR GDHVFCDTAA GINVAEQSRE CNINISTTNY PCKVSTGRHP ISMVALSPLG   360
ALVACYKGVS CSIGSNRVGI IKQLPKGCSY ITNQDADTVT IDNTVYQLSK VEGEQHVIKG   420
RPVSSSFDPI CFPEDQFNVA LDQVFESIEN CQA                                453

SEQ ID NO: 86              moltype = AA  length = 453
FEATURE                    Location/Qualifiers
REGION                     1..453
                           note = synthetic construct
source                     1..453
                           mol_type = protein
                           organism = synthetic construct
SEQUENCE: 86
KESYLEESCS TITEGYLSVL RTGWYTNVFT LEVGDVENLT CADGPSLIKT ELDLTKSALR    60
ELRTVSADQL AREEQIENPR RRRFVLGAIA LGVATAAAVT AGVAIAKCIR LESEVTAIKN   120
ALKKTNEAVS TLGCGVRVLA TAVRELKDFV SKNLTRAINK NKCDIPDLKM AVSFSQFNRR   180
FLNVVRQFSD NAGITPAISK DLMTDAELAR AISNMPTSAG QIKLMLENRA MVRRKGFGIL   240
IGVYGSSVIY MVQLPIFGVI DTPCWIVKAA PSCSEKKGNY ACLLREDQGW YCQNAGSTVY   300
YPNEKDCETR GDHVFCDTAA GINVAEQSKE CNINISTTNY PCKVSCGRNP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQCFESIEN SQA                                453

SEQ ID NO: 87              moltype = AA  length = 471
FEATURE                    Location/Qualifiers
REGION                     1..471
                           note = synthetic construct
source                     1..471
                           mol_type = protein
                           organism = synthetic construct
SEQUENCE: 87
KESYLEESCS TITEGYLSVL RTGWYTNVFT LEVGDVENLT CADGPSLIKT ELDLTKSALR    60
ELRTVSADQL AREEQIENPR RRRFVLGAIA LGVATAAAVT AGVAIAKCIR LESEVTAIKN   120
ALKKTNEAVS TLGCGVRVLA TAVRELKDFV SKNLTRAINK NKCDIPDLKM AVSFSQFNRR   180
FLNVVRQFSD NAGITPAISK DLMTDAELAR AISNMPTSAG QIKLMLENRA MVRRKGFGIL   240
IGVYGSSVIY MVQLPIFGVI DTPCWIVKAA PSCSEKKGNY ACLLREDQGW YCQNAGSTVY   300
YPNEKDCETR GDHVFCDTAA GINVAEQSKE CNINISTTNY PCKVSCGRNP ISMVALSPLG   360
ALVACYKGVS CSIGSNRVGI IKQLNKGCSY ITNQDADTVT IDNTVYQLSK VEGEQHVIKG   420
RPVSSSFDPV KFPEDQFNVA LDQCFESIEN SQALVDQSNR ILSSAEKGNT G            471

SEQ ID NO: 88              moltype = AA  length = 453
FEATURE                    Location/Qualifiers
REGION                     1..453
                           note = synthetic construct
source                     1..453
                           mol_type = protein
                           organism = synthetic construct
SEQUENCE: 88
KESYLEESCS TITEGYLSVL RTGWYTNVFT LEVGDVENLT CTDGPSLIKT ELDLTKSALR    60
ELKTCSADQL AREEQIEGGG GGGFVLGAIA LGVATAAAVT AGIAIAKTIR LESEVNAIKG   120
CLKTTNECVS TLGNGVRVLA TAVRELKEFV SKNLTSAINK NKCDIADLKM AVSFSQFNRR   180
FLNVVRQFSD NAGITPAISL DLMTDAELAR AVSYMPTSAG QIKLMLENRC MVRRKGFGIL   240
IGVYGSSVIY MVQLPIFGVI DTPCWIIKAA PSCSEKDGNY ACLLREDQGW YCKNAGSTVY   300
YPNDKDCETR GDHVFCDTAA GINVAEQSRE CNINISTTNY PCKVSTGRHP ISMVALSPLG   360
ALVACYKGVS CSIGSNRVGI IKQLPKGCSY ITNQDADTVT IDNTVYQLSK VEGEQHVIKG   420
RPVSSSFDPI KFPEDQFNVA LDQVFESIEN SQA                                453

SEQ ID NO: 89              moltype = AA  length = 453
FEATURE                    Location/Qualifiers
REGION                     1..453
                           note = synthetic construct
source                     1..453
                           mol_type = protein
                           organism = synthetic construct
SEQUENCE: 89
KESYLEESCS TITEGYLSVL RTGWYTNVFT LEVGDVENLT CADGPSLIKT ELDLTKSALR    60
ELRTVSADQL AREEQIEGGG GGGFVLGAIA LGVATAAAVT AGVAIAKCIR LESEVTAIKN   120
```

```
ALKKTNEAVS TLGCGVRVLA TAVRELKDFV SKNLTRAINK NKCDIPDLKM AVSFSQFNRR    180
FLNVVRQFSD NAGITPAISK DLMTDAELAR AISNMPTSAG QIKLMLENRA MVRRKGFGIL    240
IGVYGSSVIY MVQLPIFGVI DTPCWIVKAA PSCSEKKGNY ACLLREDQGW YCQNAGSTVY    300
YPNEKDCETR GDHVFCDTAA GINVAEQSKE CNINISTTNY PCKVSCGRNP ISMVALSPLG    360
ALVACYKGVS CSIGSNRVGI IKQLNKGCSY ITNQDADTVT IDNTVYQLSK VEGEQHVIKG    420
RPVSSSFDPV KFPEDQFNVA LDQCFESIEN SQA                                453

SEQ ID NO: 90           moltype = AA   length = 471
FEATURE                 Location/Qualifiers
REGION                  1..471
                        note = synthetic construct
source                  1..471
                        mol_type = protein
                        organism = synthetic construct
SEQUENCE: 90
KESYLEESCS TITEGYLSVL RTGWYTNVFT LEVGDVENLT CADGPSLIKT ELDLTKSALR     60
ELRTVSADQL AREEQIEGGG GGGFVLGAIA LGVATAAAVT AGVAIAKCIR LESEVTAIKN    120
ALKKTNEAVS TLGCGVRVLA TAVRELKDFV SKNLTRAINK NKCDIPDLKM AVSFSQFNRR    180
FLNVVRQFSD NAGITPAISK DLMTDAELAR AISNMPTSAG QIKLMLENRA MVRRKGFGIL    240
IGVYGSSVIY MVQLPIFGVI DTPCWIVKAA PSCSEKKGNY ACLLREDQGW YCQNAGSTVY    300
YPNEKDCETR GDHVFCDTAA GINVAEQSKE CNINISTTNY PCKVSCGRNP ISMVALSPLG    360
ALVACYKGVS CSIGSNRVGI IKQLNKGCSY ITNQDADTVT IDNTVYQLSK VEGEQHVIKG    420
RPVSSSFDPV KFPEDQFNVA LDQCFESIEN SQALVDQSNR ILSSAEKGNT G             471

SEQ ID NO: 91           moltype = AA   length = 27
FEATURE                 Location/Qualifiers
source                  1..27
                        mol_type = protein
                        organism = unidentified
SEQUENCE: 91
GYIPEAPRDG QAYVRKDGEW VLLSTFL                                         27

SEQ ID NO: 92           moltype = AA   length = 716
FEATURE                 Location/Qualifiers
REGION                  1..716
                        note = synthetic construct
source                  1..716
                        mol_type = protein
                        organism = synthetic construct
SEQUENCE: 92
MSWKVVIIFS LLITPQHGLK ESYLEESCST ITEGYLSVLR TGWYTNVFTL EVGDVENLTC     60
ADGPSLIKTE LDLTKSALRE LRTVSADQLA REEQIENPRR RRFVLGAIAL GVATAAAVTA    120
GVAIAKTIRL ESEVTAIKNA LKKTNEAVST LGNGVRVLAT AVRELKDFVS KNLTRAINKN    180
KCDIPDLKMA VSFSQFNRRF LNVVRQFSDN AGITPAISLD LMTDAELARA VSNMPTSAGQ    240
IKLMLENRAM VRRKGFGFLI GVYGSSVIYM VQLPIFGVID TPCWIVKAAP SCSGKKGNYA    300
CLLREDQGWY CQNAGSTVYY PNEKDCETRG DHVFCDTAAG INVAEQSKEC NINISTTNYP    360
CKVSTGRHPI SMVALSPLGA LVACYKGVSC SIGSNRVGII KQLNKGCSYI TNQDADTVTI    420
DNTVYQLSKV EGEQHVIKGR PVSSSFDPVK FPEDQFNVAL DQVFESIENS QALVDQSNRI    480
LGSGGSGSGS GGSEKAAKAE EAARKMEELF KKHKIVAVLR ANSVEEAIEK AVAVFAGGVH    540
LIEITFTVPD ADTVIKALSV LKEKGAIIGA GTVTSVEQAR KAVESGAEFI VSPHLDEEIS    600
QFAKEKGVFY MPGVMTPTEL VKAMKLGHTI LKLFPGEVVG PQFVKAMKGP FPNVKFVPTG    660
GVNLDNVAEW FKAGVLAVGV GSALVKGTPD EVREKAKAFV EKIRGATELE HHHHHH        716

SEQ ID NO: 93           moltype = AA   length = 707
FEATURE                 Location/Qualifiers
REGION                  1..707
                        note = synthetic construct
source                  1..707
                        mol_type = protein
                        organism = synthetic construct
SEQUENCE: 93
MSWKVVIIFS LLITPQHGLK ESYLEESCST ITEGYLSVLR TGWYTNVFTL EVGDVENLTC     60
ADGPSLIKTE LDLTKSALRE LRTVSADQLA REEQIENPRR RRFVLGAIAL GVATAAAVTA    120
GVAIAKTIRL ESEVTAIKNA LKKTNEAVST LGNGVRVLAT AVRELKDFVS KNLTRAINKN    180
KCDIPDLKMA VSFSQFNRRF LNVVRQFSDN AGITPAISLD LMTDAELARA VSNMPTSAGQ    240
IKLMLENRAM VRRKGFGFLI GVYGSSVIYM VQLPIFGVID TPCWIVKAAP SCSGKKGNYA    300
CLLREDQGWY CQNAGSTVYY PNEKDCETRG DHVFCDTAAG INVAEQSKEC NINISTTNYP    360
CKVSTGRHPI SMVALSPLGA LVACYKGVSC SIGSNRVGII KQLNKGCSYI TNQDADTVTI    420
DNTVYQLSKV EGEQHVIKGR PVSSSFDPVK FPEDQFNVAL DQVFESIENS QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                  707
```

```
SEQ ID NO: 94           moltype = AA  length = 725
FEATURE                 Location/Qualifiers
REGION                  1..725
                        note = synthetic construct
source                  1..725
                        mol_type = protein
                        organism = synthetic construct
SEQUENCE: 94
MSWKVVIIFS LLITPQHGLK ESYLEESCST ITEGYLSVLR TGWYTNVFTL EVGDVENLTC     60
ADGPSLIKTE LDLTKSALRE LRTVSADQLA REEQIENPRR RRFVLGAIAL GVATAAAVTA    120
GVAIAKTIRL ESEVTAIKNA LKKTNEAVST LGNGVRVLAT AVRELKDFVS KNLTRAINKN    180
KCDIPDLKMA VSFSQFNRRF LNVVRQFSDN AGITPAISLD LMTDAELARA VSNMPTSAGQ    240
IKLMLENRAM VRRKGFGFLI GVYGSSVIYM VQLPIFGVID TPCWIVKAAP SCSGKKGNYA    300
CLLREDQGWY CQNAGSTVYY PNEKDCETRG DHVFCDTAAG INVAEQSKEC NINISTTNYP    360
CKVSTGRHPI SMVALSPLGA LVACYKGVSC SIGSNRVGII KQLNKGCSYI TNQDADTVTI    420
DNTVYQLSKV EGEQHVIKGR PVSSSFDPVK FPEDQFNVAL DQVFESIENS QALVDQSNRI    480
LSSAEKGNTG GSGGSGSGSG GSEKAAKAEE AARKMEELFK KHKIVAVLRA NSVEEAIEKA    540
VAVFAGGVHL IEITFTVPDA DTVIKALSVL KEKGAIIGAG TVTSVEQARK AVESGAEFIV    600
SPHLDEEISQ FAKEKGVFYM PGVMTPTELV KAMKLGHTIL KLFPGEVVGP QFVKAMKGPF    660
PNVKFVPTGG VNLDNVAEWF KAGVLAVGVG SALVKGTPDE VREKAKAFVE KIRGATELEH    720
HHHHH                                                                725

SEQ ID NO: 95           moltype = AA  length = 707
FEATURE                 Location/Qualifiers
REGION                  1..707
                        note = synthetic construct
source                  1..707
                        mol_type = protein
                        organism = synthetic construct
SEQUENCE: 95
MSWKVVIIFS LLITPQHGLK ESYLEESCST ITEGYLSVLR TGWYTNVFTL EVGDVENLTC     60
ADGPSLIKTE LDLTKSALRE LRTVSADQLA REEQIENPRR RRFVLGAIAL GVATAAAVTA    120
GVAIAKTIRL ESEVTAIKNA LKKTNEAVST LGNGVRVLAT AVRELKDFVS KNLTRAINKN    180
KCDIADLKMA VSFSQFNRRF LNVVRQFSDN AGITPAISLD LMTDAELARA VSNMPTSAGQ    240
IKLMLENRAM VRRKGFGFLI GVYGSSVIYM VQLPIFGVID TPCWIVKAAP SCSGKKGNYA    300
CLLREDQGWY CQNAGSTVYY PNEKDCETRG DHVFCDTAAG INVAEQSKEC NINISTTNYP    360
CKVSTGRHPI SMVALSPLGA LVACYKGVSC SIGSNRVGII KQLNKGCSYI TNQDADTVTI    420
DNTVYQLSKV EGEQHVIKGR PVSSSFDPVK FPEDQFNVAL DQVFESIENS QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                  707

SEQ ID NO: 96           moltype = AA  length = 707
FEATURE                 Location/Qualifiers
REGION                  1..707
                        note = synthetic construct
source                  1..707
                        mol_type = protein
                        organism = synthetic construct
SEQUENCE: 96
MSWKVVIIFS LLITPQHGLK ESYLEESCST ITEGYLSVLR TGWYTNVFTL EVGDVENLTC     60
ADGPSLIKTE LDLTKSALRE LRTVSADQLA REEQIENPRR RRFVLGAIAL GVATAAAVTA    120
GVAIAKCIRL ESEVTAIKNA LKKTNEAVST LGCGVRVLAT AVRELKDFVS KNLTRAINKN    180
KCDIPDLKMA VSFSQFNRRF LNVVRQFSDN AGITPAISLD LMTDAELARA VSNMPTSAGQ    240
IKLMLENRAM VRRKGFGILI GVYGSSVIYM VQLPIFGVID TPCWIVKAAP SCSGKKGNYA    300
CLLREDQGWY CQNAGSTVYY PNEKDCETRG DHVFCDTAAG INVAEQSKEC NINISTTNYP    360
CKVSTGRNPI SMVALSPLGA LVACYKGVSC SIGSNRVGII KQLNKGCSYI TNQDADTVTI    420
DNTVYQLSKV EGEQHVIKGR PVSSSFDPVK FPEDQFNVAL DQVFESIENS QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                  707

SEQ ID NO: 97           moltype = AA  length = 707
FEATURE                 Location/Qualifiers
REGION                  1..707
                        note = synthetic construct
source                  1..707
                        mol_type = protein
                        organism = synthetic construct
SEQUENCE: 97
MSWKVMIIIS LLITPQHGLK ESYLEESCST ITEGYLSVLR TGWYTNVFTL EVGDVENLTC     60
TDGPSLIKTE LDLTKSALRE LKTCSADQLA REEQIEGGGG GGFVLGAIAL GVATAAAVTA    120
GIAIAKTIRL ESEVNAIKGC LKTTNECVST LGNGVRVLAT AVRELKEFVS KNLTSAINKN    180
KCDIADLKMA VSFSQFNRRF LNVVRQFSDN AGITPAISLD LMTDAELARA VSYMPTSAGQ    240
IKLMLENRCM VRRKGFGILI GVYGSSVIYM VQLPIFGVID TPCWIIKAAP SCSEKDGNYA    300
CLLREDQGWY CKNAGSTVYY PNDKDCETRG DHVFCDTAAG INVAEQSREC NINISTTNYP    360
```

```
CKVSTGRHPI SMVALSPLGA LVACYKGVSC SIGSNRVGII KQLPKGCSYI TNQDADTVTI    420
DNTVYQLSKV EGEQHVIKGR PVSSSFDPIK FPEDQFNVAL DQVFESIENS QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                 707

SEQ ID NO: 98             moltype = AA  length = 723
FEATURE                   Location/Qualifiers
REGION                    1..723
                          note = synthetic construct
source                    1..723
                          mol_type = protein
                          organism = synthetic construct
SEQUENCE: 98
MSWKVMIIIS LLITPQHGLK ESYLEESCST ITEGYLSVLR TGWYTNVFTL EVGDVENLTC    60
TDGPSLIKTE LDLTKSALRE LKTCSADQLA REEQIEGGGG GGFVLGAIAL GVATAAAVTA    120
GIAIAKTIRL ESEVNAIKGC LKTTNECVST LGNGVRVLAT AVRELKEFVS KNLTSAINKN    180
KCDIADLKMA VSFSQFNRRF LNVVRQFSDN AGITPAISLD LMTDAELARA VSYMPTSAGQ    240
IKLMLENRCM VRRKGFGILI GVYGSSVIYM VQLPIFGVID TPCWIIKAAP SCSEKDGNYA    300
CLLREDQGWY CKNAGSTVYY PNDKDCETRG DHVFCDTAAG INVAEQSREC NINISTTNYP    360
CKVSTGRHPI SMVALSPLGA LVACYKGVSC SIGSNRVGII KQLPKGCSYI TNQDADTVTI    420
DNTVYQLSKV EGEQHVIKGR PVSSSFDPIK FPEDQFNVAL DQVFESIENS QALVDQSNKI    480
LNSAESAIGS GGSGSGSGGS EKAAKAEEEA RKMEELFKKH KIVAVLRANS VEEAIEKAVA    540
VFAGGVHLIE ITFTVPDADT VIKALSVLKE KGAIIGAGTV TSVEQARKAV ESGAEFIVSP    600
HLDEEISQFA KEKGVFYMPG VMTPTELVKA MKLGHTILKL FPGEVVGPQF VKAMKGPFPN    660
VKFVPTGGVN LDNVAEWFKA GVLAVGVGSA LVKGTPDEVR EKAKAFVEKI RGATELEHHH    720
HHH                                                                 723

SEQ ID NO: 99             moltype = AA  length = 707
FEATURE                   Location/Qualifiers
REGION                    1..707
                          note = synthetic construct
source                    1..707
                          mol_type = protein
                          organism = synthetic construct
SEQUENCE: 99
MSWKVMIIIS LLITPQHGLK ESYLEESCST ITEGYLSVLR TGWYTNVFTL EVGDVENLTC    60
TDCPSLIKTE LDLTKSALRE LKTVSADQLA REEQIEGGGG GGFVLGAIAL GVATAAAVTA    120
GIAIAKTIRL ESEVNAIKGC LKTTNECVST LGNGVRVLAT AVRELKEFVS KNLTSAINKN    180
KCDIADLCMA VSFSQFNRRF LNVVRQFSDN AGITPAISLD LMTDAELARA VSYMPTSAGQ    240
IKLMLENRAM VRRKGFGILI GVYGSSVIYM VQLPIFGVID TPCWIIKAAP SCSEKDGNYA    300
CLLREDQGWY CKNAGSTVYY PNDKDCETRG DHVFCDTAAG INVAEQSREC NINISTTNYP    360
CKVSTGRHPI SMVALSPLGA LVACYKGVSC SIGSNRVGII KQLPKGCSYI TNQDADTVTI    420
DNTVYQLSKV EGEQHVIKGR PVSSSFDPIC FPEDQFNVAL DQVFESIENC QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                 707

SEQ ID NO: 100            moltype = AA  length = 723
FEATURE                   Location/Qualifiers
REGION                    1..723
                          note = synthetic construct
source                    1..723
                          mol_type = protein
                          organism = synthetic construct
SEQUENCE: 100
MSWKVMIIIS LLITPQHGLK ESYLEESCST ITEGYLSVLR TGWYTNVFTL EVGDVENLTC    60
TDCPSLIKTE LDLTKSALRE LKTVSADQLA REEQIEGGGG GGFVLGAIAL GVATAAAVTA    120
GIAIAKTIRL ESEVNAIKGC LKTTNECVST LGNGVRVLAT AVRELKEFVS KNLTSAINKN    180
KCDIADLCMA VSFSQFNRRF LNVVRQFSDN AGITPAISLD LMTDAELARA VSYMPTSAGQ    240
IKLMLENRAM VRRKGFGILI GVYGSSVIYM VQLPIFGVID TPCWIIKAAP SCSEKDGNYA    300
CLLREDQGWY CKNAGSTVYY PNDKDCETRG DHVFCDTAAG INVAEQSREC NINISTTNYP    360
CKVSTGRHPI SMVALSPLGA LVACYKGVSC SIGSNRVGII KQLPKGCSYI TNQDADTVTI    420
DNTVYQLSKV EGEQHVIKGR PVSSSFDPIC FPEDQFNVAL DQVFESIENC QALVDQSNKI    480
LNSAESAIGS GGSGSGSGGS EKAAKAEEAA RKMEELFKKH KIVAVLRANS VEEAIEKAVA    540
VFAGGVHLIE ITFTVPDADT VIKALSVLKE KGAIIGAGTV TSVEQARKAV ESGAEFIVSP    600
HLDEEISQFA KEKGVFYMPG VMTPTELVKA MKLGHTILKL FPGEVVGPQF VKAMKGPFPN    660
VKFVPTGGVN LDNVAEWFKA GVLAVGVGSA LVKGTPDEVR EKAKAFVEKI RGATELEHHH    720
HHH                                                                 723

SEQ ID NO: 101            moltype = AA  length = 706
FEATURE                   Location/Qualifiers
REGION                    1..706
                          note = synthetic construct
source                    1..706
                          mol_type = protein
                          organism = synthetic construct
```

```
SEQUENCE: 101
MSWKVVIIFS LLITPQHGLK ESYLEESCST ITEGYLSVLR TGWYTNVFTL EVGDVENLTC    60
SDCPSLIKTE LDLTKSALRE LKTVSADQLA REEQIEGGGG GGFVLAIALG VATAAAVTAG   120
VAIAKTIRLE SEVTAIKNCL KTTNECVSTL GNGVRVLATA VRELKDFVSK NLTSAINKNK   180
CDIDDLCMAV SFSQFNRRFL NVVRQFSDNA GITPAISLDL MTDAELARAV SNMPTSAGQI   240
KLMLENRAMV RRKGFGILIG VYGSSVIYMQ QLPIFGVIDT PCWIIKAAPS CSGKKGNYAC   300
LLREDQGWYC QNAGSTVYYP NEKDCETRGD HVFCDTAAGI NVAEQSKECN INISTTNYPC   360
KVSTGRHPIS MVALSPLGAL VACYKGVSCS IGSNRVGIIK QLNKGCSYIT NQDADTVTID   420
NTVYQLSKVE GEQHVIKGRP VSSSFDPIKF PEDQFNVALD QVFENIENSQ AGSGGSGSGS   480
GGSEKAAKAE EAARKMEELF KKHKIVAVLR ANSVEEAIEK AVAVFAGGVH LIEITFTVPD   540
ADTVIKALSV LKEKGAIIGA GTVTSVEQAR KAVESGAEFI VSPHLDEEIS QFAKEKGVFY   600
MPGVMTPTEL VKAMKLGHTI LKLFPGEVVG PQFVKAMKGP FPNVKFVPTG GVNLDNVAEW   660
FKAGVLAVGV GSALVKGTPD EVREKAKAFV EKIRGATELE HHHHHH              706

SEQ ID NO: 102        moltype = AA  length = 722
FEATURE               Location/Qualifiers
REGION                1..722
                      note = synthetic construct
source                1..722
                      mol_type = protein
                      organism = synthetic construct
SEQUENCE: 102
MSWKVVIIFS LLITPQHGLK ESYLEESCST ITEGYLSVLR TGWYTNVFTL EVGDVENLTC    60
SDCPSLIKTE LDLTKSALRE LKTVSADQLA REEQIEGGGG GGFVLAIALG VATAAAVTAG   120
VAIAKTIRLE SEVTAIKNCL KTTNECVSTL GNGVRVLATA VRELKDFVSK NLTSAINKNK   180
CDIDDLCMAV SFSQFNRRFL NVVRQFSDNA GITPAISLDL MTDAELARAV SNMPTSAGQI   240
KLMLENRAMV RRKGFGILIG VYGSSVIYMQ QLPIFGVIDT PCWIIKAAPS CSGKKGNYAC   300
LLREDQGWYC QNAGSTVYYP NEKDCETRGD HVFCDTAAGI NVAEQSKECN INISTTNYPC   360
KVSTGRHPIS MVALSPLGAL VACYKGVSCS IGSNRVGIIK QLNKGCSYIT NQDADTVTID   420
NTVYQLSKVE GEQHVIKGRP VSSSFDPIKF PEDQFNVALD QVFENIENSQ ALVDQSNRIL   480
SSAESAIGSG GSGSGSGGSE KAAKAEEEAAR KMEELFKKHK IVAVLRANSV EEAIEKAVAV   540
FAGGVHLIEI TFTVPDADTV IKALSVLKEK GAIIGAGTVT SVEQARKAVE SGAEFIVSPH   600
LDEEISQFAK EKGVFYMPGV MTPTELVKAM KLGHTILKLF PGEVVGPQFV KAMKGPFPNV   660
KFVPTGGVNL DNVAEWFKAG VLAVGVGSAL VKGTPDEVRE KAKAFVEKIR GATELEHHHH   720
HH                                                                722

SEQ ID NO: 103        moltype = AA  length = 707
FEATURE               Location/Qualifiers
REGION                1..707
                      note = synthetic construct
source                1..707
                      mol_type = protein
                      organism = synthetic construct
SEQUENCE: 103
MSWKVMIIIS LLITPQHGLK ESYLEESCST ITEGYLSVLR TGWYTNVFTL EVGDVENLTC    60
TDGPSLIKTE LDLTKSALRE LKTVSADQLA REEQIENPRK ARFVLGAIAL GVCTAAAVTC   120
GIAIAKTIRL ESEVNAIKGA LKTTNEAVST LGNGVRVLAF AVRELKEFVS KNLTSALNKN   180
KCDIADLKMA VSFSQFNRRF LNVVRQFSDN AGITPAISLD LMTDAELARA VSYMPTSAGQ   240
IKLMLENRAM VRRKGFGILI GVYGSSVIYM VQLPIFGVID TPCWIIKAAP SCSEKDGNYA   300
CLLREDQGWY CKNAGSTVYY PNDKDCETRG DHVFCDTACG INVAEQSREC NINISTTNYP   360
CKVSTGRHPI SMVALSPLGA LVACYKGVSC SIGSNRVGII KQLPKGCSYI TNQDADTVTI   420
DNTVYCLSKV EGEQHVIKGR PVSSSFDPIK FPEDQFNVAL DQVFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH              707

SEQ ID NO: 104        moltype = AA  length = 723
FEATURE               Location/Qualifiers
REGION                1..723
                      note = synthetic construct
source                1..723
                      mol_type = protein
                      organism = synthetic construct
SEQUENCE: 104
MSWKVMIIIS LLITPQHGLK ESYLEESCST ITEGYLSVLR TGWYTNVFTL EVGDVENLTC    60
TDGPSLIKTE LDLTKSALRE LKTVSADQLA REEQIENPRK ARFVLGAIAL GVCTAAAVTC   120
GIAIAKTIRL ESEVNAIKGA LKTTNEAVST LGNGVRVLAF AVRELKEFVS KNLTSALNKN   180
KCDIADLKMA VSFSQFNRRF LNVVRQFSDN AGITPAISLD LMTDAELARA VSYMPTSAGQ   240
IKLMLENRAM VRRKGFGILI GVYGSSVIYM VQLPIFGVID TPCWIIKAAP SCSEKDGNYA   300
CLLREDQGWY CKNAGSTVYY PNDKDCETRG DHVFCDTACG INVAEQSREC NINISTTNYP   360
CKVSTGRHPI SMVALSPLGA LVACYKGVSC SIGSNRVGII KQLPKGCSYI TNQDADTVTI   420
DNTVYCLSKV EGEQHVIKGR PVSSSFDPIK FPEDQFNVAL DQVFESIENS QALVDQSNKI   480
LNSAESAIGS GGSGSGSGGS EKAAKAEEAA RKMEELFKKH KIVAVLRANS VEEAIEKAVA   540
VFAGGVHLIE ITFTVPDADT VIKALSVLKE KGAIIGAGTV TSVEQARKAV ESGAEFIVSP   600
HLDEEISQFA KEKGVFYMPG VMTPTELVKA MKLGHTILKL FPGEVVGPQF VKAMKGPFPN   660
VKFVPTGGVN LDNVAEWFKA GVLAVGVGSA LVKGTPDEVR EKAKAFVEKI RGATELEHHH   720
HHH                                                               723
```

```
SEQ ID NO: 105           moltype = AA   length = 707
FEATURE                  Location/Qualifiers
REGION                   1..707
                         note = synthetic construct
source                   1..707
                         mol_type = protein
                         organism = synthetic construct
SEQUENCE: 105
MSWKVMIIIS LLITPQHGLK ESYLEESCST ITEGYLSVLR TGWYTNVFTL EVGDVENLTC    60
TDGPSLIKTE LDLTKSALRE LKTCSADQLA REEQIENPRR RRFVLGAIAL GVATAAAVTA   120
GIAIAKTIRL ESEVNAIKGC LKTTNECVST LGNGVRVLAT AVRELKEFVS KNLTSAINKN   180
KCDIADLKMA VSFSQFNRRF LNVVRQFSDN AGITPAISLD LMTDAELARA VSYMPTSAGQ   240
IKLMLENRCM VRRKGFGILI GVYGSSVIYM VQLPIFGVID TPCWIIKAAP SCSEKDGNYA   300
CLLREDQGWY CKNAGSTVYY PNDKDCETRG DHVFCDTAAG INVAEQSREC NINISTTNYP   360
CKVSTGRHPI SMVALSPLGA LVACYKGVSC SIGSNRVGII KQLPKGCSYI TNQDADTVTI   420
DNTVYQLSKV EGEQHVIKGR PVSSSFDPIK FPEDQFNVAL DQVFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH              707

SEQ ID NO: 106           moltype = AA   length = 707
FEATURE                  Location/Qualifiers
REGION                   1..707
                         note = synthetic construct
source                   1..707
                         mol_type = protein
                         organism = synthetic construct
SEQUENCE: 106
MSWKVMIIIS LLITPQHGLK ESYLEESCST ITEGYLSVLR TGWYTNVFTL EVGDVENLTC    60
TDCPSLIKTE LDLTKSALRE LKTVSADQLA REEQIENPRR RRFVLGAIAL GVATAAAVTA   120
GIAIAKTIRL ESEVNAIKGC LKTTNECVST LGNGVRVLAT AVRELKEFVS KNLTSAINKN   180
KCDIADLCMA VSFSQFNRRF LNVVRQFSDN AGITPAISLD LMTDAELARA VSYMPTSAGQ   240
IKLMLENRAM VRRKGFGILI GVYGSSVIYM VQLPIFGVID TPCWIIKAAP SCSEKDGNYA   300
CLLREDQGWY CKNAGSTVYY PNDKDCETRG DHVFCDTAAG INVAEQSREC NINISTTNYP   360
CKVSTGRHPI SMVALSPLGA LVACYKGVSC SIGSNRVGII KQLPKGCSYI TNQDADTVTI   420
DNTVYQLSKV EGEQHVIKGR PVSSSFDPIC FPEDQFNVAL DQVFESIENC QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH              707

SEQ ID NO: 107           moltype = AA   length = 706
FEATURE                  Location/Qualifiers
REGION                   1..706
                         note = synthetic construct
source                   1..706
                         mol_type = protein
                         organism = synthetic construct
SEQUENCE: 107
MSWKVVIIFS LLITPQHGLK ESYLEESCST ITEGYLSVLR TGWYTNVFTL EVGDVENLTC    60
SDCPSLIKTE LDLTKSALRE LKTVSADQLA REEQIENPRR RRFVLAIALG VATAAAVTAG   120
VAIAKTIRLE SEVTAIKNCL KTTNECVSTL GNGVRVLATA VRELKDFVSK NLTSAINKNK   180
CDIDDLCMAV SFSQFNRRFL NVVRQFSDNA GITPAISLDL MTDAELARAV SNMPTSAGQI   240
KLMLENRAMV RRKGFGILIG VYGSSVIYMV QLPIFGVIDT PCWIIKAAPS CSGKKGNYAC   300
LLREDQGWYC QNAGSTVYYP NEKDCETRGD HVFCDTAAGI NVAEQSKECN INISTTNYPC   360
KVSTGRHPIS MVALSPLGAL VACYKGVSCS IGSNRVGIIK QLNKGCSYIT NQDADTVTID   420
NTVYQLSKVE GEQHVIKGRP VSSSFDPIKF PEDQFNVALD QVFENIENSQ AGSGGSGSGS   480
GGSEKAAKAE EAARKMEELF KKHKIVAVLR ANSVEEAIEK AVAVFAGGVH LIEITFTVPD   540
ADTVIKALSV LKEKGAIIGA GTVTSVEQAR KAVESGAEFI VSPHLDEEIS QFAKEKGVFY   600
MPGVMTPTEL VKAMKLGHTI LKLFPGEVVG PQFVKAMKGP FPNVKFVPTG GVNLDNVAEW   660
FKAGVLAVGV GSALVKGTPD EVREKAKAFV EKIRGATELE HHHHHH               706

SEQ ID NO: 108           moltype = AA   length = 707
FEATURE                  Location/Qualifiers
REGION                   1..707
                         note = synthetic construct
source                   1..707
                         mol_type = protein
                         organism = synthetic construct
SEQUENCE: 108
MSWKVMIIIS LLITPQHGLK ESYLEESCST ITEGYLSVLR TGWYTNVFTL EVGDVENLTC    60
TDGPSLIKTE LDLTKSALRE LKTVSADQLA REEQIENPRR RRFVLGAIAL GVCTAAAVTA   120
GIAIAKTIRL ESEVNAIKGA LKTTNEAVST LGNGVRVLAF AVRELKEFVS KNLTSALNKN   180
KCDIADLKMA VSFSQFNRRF LNVVRQFSDN AGITPAISLD LMTDAELARA VSYMPTSAGQ   240
IKLMLENRAM VRRKGFGILI GVYGSSVIYM VQLPIFGVID TPCWIIKAAP SCSEKDGNYA   300
CLLREDQGWY CKNAGSTVYY PNDKDCETRG DHVFCDTACG INVAEQSREC NINISTTNYP   360
CKVSTGRHPI SMVALSPLGA LVACYKGVSC SIGSNRVGII KQLPKGCSYI TNQDADTVTI   420
DNTVYCLSKV EGEQHVIKGR PVSSSFDPIK FPEDQFNVAL DQVFESIENS QAGSGGSGSG   480
```

```
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH                707

SEQ ID NO: 109         moltype = AA  length = 707
FEATURE                Location/Qualifiers
REGION                 1..707
                       note = synthetic construct
source                 1..707
                       mol_type = protein
                       organism = synthetic construct
SEQUENCE: 109
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIENPRR RRFVLGAIAL GVCTAAAVTA   120
GVAIAKTIRL ESEVTAIKNA LKKTNEAVST LGNGVRVLAT AVRELKDFVS KNLTRAINKN   180
KCDIPDLKMA VSFSQFNRRF LNVVRQFSDN AGITPAISLD LMTDAELARA VSNMPTSAGQ   240
IKLMLENRAM VRRKGFGFLI GVYGSSVIYM VQLPIFGVID TPCWIVKAAP SCSGKKGNYA   300
CLLREDQGWY CQNAGSTVYY PNEKDCETRG DHVFCDTACG INVAEQSKEC NINISTTNYP   360
CKVSTGRHPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQVFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH                707

SEQ ID NO: 110         moltype = AA  length = 707
FEATURE                Location/Qualifiers
REGION                 1..707
                       note = synthetic construct
source                 1..707
                       mol_type = protein
                       organism = synthetic construct
SEQUENCE: 110
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIENPRR RRFVLGAIAL GVATAAAVTA   120
GVAIAKTIRL ESEVTAIKNA LKKTNEAVST LGNGVRVLAF AVRELKDFVS KNLTRALNKN   180
KCDIPDLKMA VSFSQFNRRF LNVVRQFSDN AGITPAISLD LMTDAELARA VSNMPTSAGQ   240
IKLMLENRAM VRRKGFGFLI GVYGSSVIYM VQLPIFGVID TPCWIVKAAP SCSGKKGNYA   300
CLLREDQGWY CQNAGSTVYY PNEKDCETRG DHVFCDTAAG INVAEQSKEC NINISTTNYP   360
CKVSTGRHPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQVFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH                707

SEQ ID NO: 111         moltype = AA  length = 707
FEATURE                Location/Qualifiers
REGION                 1..707
                       note = synthetic construct
source                 1..707
                       mol_type = protein
                       organism = synthetic construct
SEQUENCE: 111
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIENPRR RRFVLGAIAL GVCTAAAVTA   120
GVAIAKTIRL ESEVTAIKNA LKKTNEAVST LGNGVRVLAF AVRELKDFVS KNLTRALNKN   180
KCDIPDLKMA VSFSQFNRRF LNVVRQFSDN AGITPAISLD LMTDAELARA VSNMPTSAGQ   240
IKLMLENRAM VRRKGFGFLI GVYGSSVIYM VQLPIFGVID TPCWIVKAAP SCSGKKGNYA   300
CLLREDQGWY CQNAGSTVYY PNEKDCETRG DHVFCDTACG INVAEQSKEC NINISTTNYP   360
CKVSTGRHPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQVFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH                707

SEQ ID NO: 112         moltype = AA  length = 707
FEATURE                Location/Qualifiers
REGION                 1..707
                       note = synthetic construct
source                 1..707
                       mol_type = protein
                       organism = synthetic construct
SEQUENCE: 112
MSWKVMIIIS LLITPQHGLK ESYLEESCST ITEGYLSVLR TGWYTNVFTL EVGDVENLTC    60
TDCPSLIKTE LDLTKSALRE LKTVSADQLA REEQIEGGGG GGFVLGAIAL GVATAAAVTA   120
GIAIAKTIRL ESEVNAIKGA LKTTNEAVST LGNGVRVLAT AVRELKEFVS KNLTSAINKN   180
```

```
KCDIADLCMA VSFSQFNRRF LNVVRQFSDN AGITPAISLD LMTDAELARA VSYMPTSAGQ    240
IKLMLENRAM VRRKGFGILI GVYGSSVIYM VQLPIFGVID TPCWIIKAAP SCSEKDGNYA    300
CLLREDQGWY CKNAGSTVYY PNDKDCETRG DHVFCDTAAG INVAEQSREC NINISTTNYP    360
CKVSTGRHPI SMVALSPLGA LVACYKGVSC SIGSNRVGII KQLPKGCSYI TNQDADTVTI    420
DNTVYQLSKV EGEQHVIKGR PVSSSFDPIK FPEDQFNVAL DQVFESIENS QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                 707

SEQ ID NO: 113           moltype = AA   length = 707
FEATURE                  Location/Qualifiers
REGION                   1..707
                         note = synthetic construct
source                   1..707
                         mol_type = protein
                         organism = synthetic construct
SEQUENCE: 113
MSWKVMIIIS LLITPQHGLK ESYLEESCST ITEGYLSVLR TGWYTNVFTL EVGDVENLTC     60
TDCPSLIKTE LDLTKSALRE LKTVSADQLA REEQIEGGGG GGFVLGAIAL GVATAAAVTA    120
GIAIAKTIRL ESEVNAIKGA LKTTNEAVST LGNGVRVLAT AVRELKEFVS KNLTSAINKN    180
KCDIADLCMA VSFSQFNRRF LNVVRQFSDN AGITPAISLD LMTDAELARA VSYMPTSAGQ    240
IKLMLENRAM VRRKGFGILI GVYGSSVIYM VQLPIFGVID TPCWIIKAAP SCSEKDGNYA    300
CLLREDQGWY CKNAGSTVYY PNDKDCETRG DHVFCDTAAG INVAEQSREC NINISTTNYP    360
CKVSTGRHPI SMVALSPLGA LVACYKGVSC SIGSNRVGII KQLPKGCSYI TNQDADTVTI    420
DNTVYQLSKV EGEQHVIKGR PVSSSFDPIA FPEDQFNVAL DQVFESIENA QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                 707

SEQ ID NO: 114           moltype = AA   length = 707
FEATURE                  Location/Qualifiers
REGION                   1..707
                         note = synthetic construct
source                   1..707
                         mol_type = protein
                         organism = synthetic construct
SEQUENCE: 114
MSWKVIIFS LLITPQHGLK ESYLEESCST ITEGYLSVLR TGWYTNVFTL EVGDVENLTC      60
SDCPSLIKTE LDLTKSALRE LKTVSADQLA REEQIEGGGG GGFVLGAIAL GVATAAAVTA    120
GVAIAKTIRL ESEVTAIKNC LKTTNECVST LGNGVRVLAT AVRELKDFVS KNLTSAINKN    180
KCDIDDLCMA VSFSQFNRRF LNVVRQFSDN AGITPAISLD LMTDAELARA VSNMPTSAGQ    240
IKLMLENRAM VRRKGFGILI GVYGSSVIYM VQLPIFGVID TPCWIIKAAP SCSEKKGNYA    300
CLLREDQGWY CQNAGSTVYY PNEKDCETRG DHVFCDTAAG INVAEQSKEC NINISTTNYP    360
CKVSTGRHPI SMVALSPLGA LVACYKGVSC SIGSNRVGII KQLNKGCSYI TNQDADTVTI    420
DNTVYQLSKV EGEQHVIKGR PVSSSFDPIK FPEDQFNVAL DQVFENIENS QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                 707

SEQ ID NO: 115           moltype = AA   length = 707
FEATURE                  Location/Qualifiers
REGION                   1..707
                         note = synthetic construct
source                   1..707
                         mol_type = protein
                         organism = synthetic construct
SEQUENCE: 115
MSWKVIIFS LLITPQHGLK ESYLEESCST ITEGYLSVLR TGWYTNVFTL EVGDVENLTC      60
ADCPSLIKTE LDLTKSALRE LRTVSADQLA REEQIEGGGG GGFVLGAIAL GVATAAAVTA    120
GVAIAKTIRL ESEVTAIKNC LKKTNECVST LGNGVRVLAT AVRELKDFVS KNLTRAINKN    180
KCDIADLCMA VSFSQFNRRF LNVVRQFSDN AGITPAISLD LMTDAELARA VSNMPTSAGQ    240
IKLMLENRAM VRRKGFGFLI GVYGSSVIYM VQLPIFGVID TPCWIVKAAP SCSEKKGNYA    300
CLLREDQGWY CQNAGSTVYY PNEKDCETRG DHVFCDTAAG INVAEQSKEC NINISTTNYP    360
CKVSTGRHPI SMVALSPLGA LVACYKGVSC SIGSNRVGII KQLNKGCSYI TNQDADTVTI    420
DNTVYQLSKV EGEQHVIKGR PVSSSFDPVC FPEDQFNVAL DQVFESIENC QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQA RKAVESGAEF IVSPHLDEEI SQFAKEKGVF    600
YMPGVMTPTE LVKAMKLGHT ILKLFPGEVV GPQFVKAMKG PFPNVKFVPT GGVNLDNVAE    660
WFKAGVLAVG VGSALVKGTP DEVREKAKAF VEKIRGATEL EHHHHHH                 707
```

```
SEQ ID NO: 116          moltype = AA   length = 707
FEATURE                 Location/Qualifiers
REGION                  1..707
                        note = synthetic construct
source                  1..707
                        mol_type = protein
                        organism = synthetic construct
SEQUENCE: 116
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIEGGGG GGFVLGAIAL GVATAAAVTA   120
GVAIAKTIRL ESEVTAIKNA LKKTNEAVST LGNGVRVLAT AVRELKDFVS KNLTRAINKN   180
KCDIADLCMA VSFSQFNRRF LNVVRQFSDN AGITPAISLD LMTDAELARA VSNMPTSAGQ   240
IKLMLENRAM VRRKGFGFLI GVYGSSVIYM VQLPIFGVID TPCWIVKAAP SCSEKKGNYA   300
CLLREDQGWY CQNAGSTVYY PNEKDCETRG DHVFCDTAAG INVAEQSKEC NINISTTNYP   360
CKVSTGRHPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQVFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH               707

SEQ ID NO: 117          moltype = AA   length = 707
FEATURE                 Location/Qualifiers
REGION                  1..707
                        note = synthetic construct
source                  1..707
                        mol_type = protein
                        organism = synthetic construct
SEQUENCE: 117
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIENPRR RRFVLGAIAL GVATAAAVTA   120
GVAIAKCIRL ESEVTAIKNA LKKTNEAVST LGCGVRVLAT AVRELKDFVS KNLTRAINKN   180
KCDIPDLKMA VSFSQFNRRF LNVVRQFSDN AGITPAISLD LMTDAELARA ISNMPTSAGQ   240
IKLMLENRAM VRRKGFGILI GVYGSSVIYM VQLPIFGVID TPCWIVKAAP SCSEKKGNYA   300
CLLREDQGWY CQNAGSTVYY PNEKDCETRG DHVFCDTAAG INVAEQSKEC NINISTTNYP   360
CKVSCGRNPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQVFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH               707

SEQ ID NO: 118          moltype = AA   length = 725
FEATURE                 Location/Qualifiers
REGION                  1..725
                        note = synthetic construct
source                  1..725
                        mol_type = protein
                        organism = synthetic construct
SEQUENCE: 118
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIENPRR RRFVLGAIAL GVATAAAVTA   120
GVAIAKCIRL ESEVTAIKNA LKKTNEAVST LGCGVRVLAT AVRELKDFVS KNLTRAINKN   180
KCDIPDLKMA VSFSQFNRRF LNVVRQFSDN AGITPAISLD LMTDAELARA ISNMPTSAGQ   240
IKLMLENRAM VRRKGFGILI GVYGSSVIYM VQLPIFGVID TPCWIVKAAP SCSEKKGNYA   300
CLLREDQGWY CQNAGSTVYY PNEKDCETRG DHVFCDTAAG INVAEQSKEC NINISTTNYP   360
CKVSCGRNPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQCFESIENS QALVDQSNRI   480
LSSAEKGNTG GSGGSGSGSG GSEKAAKAEE AARKMEELFK KHKIVAVLRA NSVEEAIEKA   540
VAVFAGGVHL IEITFTVPDA DTVIKALSVL KEKGAIIGAG TVTSVEQARK AVESGAEFIV   600
SPHLDEEISQ FAKEKGVFYM PGVMTPTELV KAMKLGHTIL KLFPGEVVGP QFVKAMKGPF   660
PNVKFVPTGG VNLDNVAEWF KAGVLAVGVG SALVKGTPDE VREKAKAFVE KIRGATELEH   720
HHHHH                                                              725

SEQ ID NO: 119          moltype = AA   length = 707
FEATURE                 Location/Qualifiers
REGION                  1..707
                        note = synthetic construct
source                  1..707
                        mol_type = protein
                        organism = synthetic construct
SEQUENCE: 119
MSWKVMIIIS LLITPQHGLK ESYLEESCST ITEGYLSVLR TGWYTNVFTL EVGDVENLTC    60
TDCPSLIKTE LDLTKSALRE LKTVSADQLA REEQIEGGGG GGFVLGAIAL GVATAAAVTA   120
GIAIAKTIRL ESEVNAIKGC LKTTNECVST LGNGVRVLAT AVRELKEFVS KNLTSAINKN   180
KCDIADLCMA VSFSQFNRRF LNVVRQFSDN AGITPAISLD LMTDAELARA VSYMPTSAGQ   240
IKLMLENRAM VRRKGFGILI GVYGSSVIYM VQLPIFGVID TPCWIIKAAP SCSEKDGNYA   300
CLLREDQGWY CKNAGSTVYY PNDKDCETRG DHVFCDTAAG INVAEQSREC NINISTTNYP   360
```

```
CKVSTGRHPI SMVALSPLGA LVACYKGVSC SIGSNRVGII KQLPKGCSYI TNQDADTVTI    420
DNTVYQLSKV EGEQHVIKGR PVSSSFDPIC FPEDQFNVAL DQVFESIENC QAGSGGSGSG    480
SGGSEKAAKA EEAARKMEEL FKKHKIVAVL RANSVEEAIE KAVAVFAGGV HLIEITFTVP    540
DADTVIKALS VLKEKGAIIG AGTVTSVEQC RKAVESGAEF IVSPHLDEEI SQFCKEKGVF    600
YMPGVMTPTE LVKAMKLGHT ILKLFPGEVV GPQFVKAMKG PFPNVKFVPT GGVNLDNVCE    660
WFKAGVLAVG VGSALVKGTP DEVREKAKAF VEKIRGCTEL EHHHHHH                 707

SEQ ID NO: 120          moltype = AA  length = 707
FEATURE                 Location/Qualifiers
REGION                  1..707
                        note = synthetic construct
source                  1..707
                        mol_type = protein
                        organism = synthetic construct
SEQUENCE: 120
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIENPRR RRFVLGAIAL GVATAAAVTA   120
GVAIAKCIRL ESEVTAIKNA LKKTNEAVST LGCGVRVLAT AVRELKDFVS KNLTRAINKN   180
KCDIPDLKMA VSFSQFNRRF LNVVRQFSDN AGITPAISKD LMTDAELARA ISNMPTSAGQ   240
IKLMLENRAM VRRKGFGILI GVYGSSVIYM VQLPIFGVID TPCWIVKAAP SCSEKKGNYA   300
CLLREDQGWY CQNAGSTVYY PNEKDCETRG DHVFCDTAAG INVAEQSKEC NINISTTNYP   360
CKVSCGRNPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQCFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQC RKAVESGAEF IVSPHLDEEI SQFCKEKGVF   600
YMPGVMTPTE LVKAMKLGHT ILKLFPGEVV GPQFVKAMKG PFPNVKFVPT GGVNLDNVCE   660
WFKAGVLAVG VGSALVKGTP DEVREKAKAF VEKIRGCTEL EHHHHHH                707

SEQ ID NO: 121          moltype = AA  length = 725
FEATURE                 Location/Qualifiers
REGION                  1..725
                        note = synthetic construct
source                  1..725
                        mol_type = protein
                        organism = synthetic construct
SEQUENCE: 121
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIENPRR RRFVLGAIAL GVATAAAVTA   120
GVAIAKCIRL ESEVTAIKNA LKKTNEAVST LGCGVRVLAT AVRELKDFVS KNLTRAINKN   180
KCDIPDLKMA VSFSQFNRRF LNVVRQFSDN AGITPAISKD LMTDAELARA ISNMPTSAGQ   240
IKLMLENRAM VRRKGFGILI GVYGSSVIYM VQLPIFGVID TPCWIVKAAP SCSEKKGNYA   300
CLLREDQGWY CQNAGSTVYY PNEKDCETRG DHVFCDTAAG INVAEQSKEC NINISTTNYP   360
CKVSCGRNPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQCFESIENS QALVDQSNRI   480
LSSAEKGNTG GSGGSGSGSG GSEKAAKAEE AARKMEELFK KHKIVAVLRA NSVEEAIEKA   540
VAVFAGGVHL IEITFTVPDA DTVIKALSVL KEKGAIIGAG TVTSVEQCRK AVESGAEFIV   600
SPHLDEEISQ FCKEKGVFYM PGVMTPTELV KAMKLGHTIL KLFPGEVVGP QFVKAMKGPF   660
PNVKFVPTGG VNLDNVCEWF KAGVLAVGVG SALVKGTPDE VREKAKAFVE KIRGCTELEH   720
HHHHH                                                              725

SEQ ID NO: 122          moltype = AA  length = 707
FEATURE                 Location/Qualifiers
REGION                  1..707
                        note = synthetic construct
source                  1..707
                        mol_type = protein
                        organism = synthetic construct
SEQUENCE: 122
MSWKVMIIIS LLITPQHGLK ESYLEESCST ITEGYLSVLR TGWYTNVFTL EVGDVENLTC    60
TDGPSLIKTE LDLTKSALRE LKTCSADQLA REEQIEGGGG GGFVLGAIAL GVATAAAVTA   120
GIAIAKTIRL ESEVNAIKGC LKTTNECVST LGNGVRVLAT AVRELKEFVS KNLTSAINKN   180
KCDIADLKMA VSFSQFNRRF LNVVRQFSDN AGITPAISLD LMTDAELARA VSYMPTSAGQ   240
IKLMLENRCM VRRKGFGILI GVYGSSVIYM VQLPIFGVID TPCWIIKAAP SCSEKDGNYA   300
CLLREDQGWY CKNAGSTVYY PNDKDCETRG DHVFCDTAAG INVAEQSREC NINISTTNYP   360
CKVSTGRHPI SMVALSPLGA LVACYKGVSC SIGSNRVGII KQLPKGCSYI TNQDADTVTI   420
DNTVYQLSKV EGEQHVIKGR PVSSSFDPIK FPEDQFNVAL DQVFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQC RKAVESGAEF IVSPHLDEEI SQFCKEKGVF   600
YMPGVMTPTE LVKAMKLGHT ILKLFPGEVV GPQFVKAMKG PFPNVKFVPT GGVNLDNVCE   660
WFKAGVLAVG VGSALVKGTP DEVREKAKAF VEKIRGCTEL EHHHHHH                707

SEQ ID NO: 123          moltype = AA  length = 707
FEATURE                 Location/Qualifiers
REGION                  1..707
                        note = synthetic construct
source                  1..707
                        mol_type = protein
                        organism = synthetic construct
```

```
SEQUENCE: 123
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIEGGGG GGFVLGAIAL GVATAAAVTA   120
GVAIAKCIRL ESEVTAIKNA LKKTNEAVST LGCGVRVLAT AVRELKDFVS KNLTRAINKN   180
KCDIPDLKMA VSFSQFNRRF LNVVRQFSDN AGITPAISKD LMTDAELARA ISNMPTSAGQ   240
IKLMLENRAM VRRKGFGILI GVYGSSVIYM VQLPIFGVID TPCWIVKAAP SCSEKKGNYA   300
CLLREDQGWY CQNAGSTVYY PNEKDCETRG DHVFCDTAAG INVAEQSKEC NINISTTNYP   360
CKVSCGRNPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQCFESIENS QAGSGGSGSG   480
SGGSEKAAKA EEAARKMEEL FKKHKIVAVL RANSVEEAIE KAVAVFAGGV HLIEITFTVP   540
DADTVIKALS VLKEKGAIIG AGTVTSVEQA RKAVESGAEF IVSPHLDEEI SQFAKEKGVF   600
YMPGVMTPTE LVKAMKLGHT ILKLFPGEVV GPQFVKAMKG PFPNVKFVPT GGVNLDNVAE   660
WFKAGVLAVG VGSALVKGTP DEVREKAKAF VEKIRGATEL EHHHHHH                707

SEQ ID NO: 124          moltype = AA  length = 725
FEATURE                 Location/Qualifiers
REGION                  1..725
                        note = synthetic construct
source                  1..725
                        mol_type = protein
                        organism = synthetic construct
SEQUENCE: 124
MSWKVVIIFS LLITPQHGLK ESYLEESCST ITEGYLSVLR TGWYTNVFTL EVGDVENLTC    60
ADGPSLIKTE LDLTKSALRE LRTVSADQLA REEQIEGGGG GGFVLGAIAL GVATAAAVTA   120
GVAIAKCIRL ESEVTAIKNA LKKTNEAVST LGCGVRVLAT AVRELKDFVS KNLTRAINKN   180
KCDIPDLKMA VSFSQFNRRF LNVVRQFSDN AGITPAISKD LMTDAELARA ISNMPTSAGQ   240
IKLMLENRAM VRRKGFGILI GVYGSSVIYM VQLPIFGVID TPCWIVKAAP SCSEKKGNYA   300
CLLREDQGWY CQNAGSTVYY PNEKDCETRG DHVFCDTAAG INVAEQSKEC NINISTTNYP   360
CKVSCGRNPI SMVALSPLGA LVACYKGVSC SIGSNRVGII KQLNKGCSYI TNQDADTVTI   420
DNTVYQLSKV EGEQHVIKGR PVSSSFDPVK FPEDQFNVAL DQCFESIENS QALVDQSNRI   480
LSSAEKGNTG GSGGSGSGSG GSEKAAKAEE AARKMEELFK KHKIVAVLRA NSVEEAIEKA   540
VAVFAGGVHL IEITFTVPDA DTVIKALSVL KEKGAIIGAG TVTSVEQARK AVESGAEFIV   600
SPHLDEEISQ FAKEKGVFYM PGVMTPTELV KAMKLGHTIL KLFPGEVVGP QFVKAMKGPF   660
PNVKFVPTGG VNLDNVAEWF KAGVLAVGVG SALVKGTPDE VREKAKAFVE KIRGATELEH   720
HHHHH                                                              725

SEQ ID NO: 125          moltype = AA  length = 12
FEATURE                 Location/Qualifiers
REGION                  1..12
                        note = foldon sequence
source                  1..12
                        mol_type = protein
                        organism = synthetic construct
SEQUENCE: 125
EKAAKAEEAA RK                                                       12

SEQ ID NO: 126          moltype = AA  length = 12
FEATURE                 Location/Qualifiers
REGION                  1..12
                        note = linker sequence
source                  1..12
                        mol_type = protein
                        organism = synthetic construct
SEQUENCE: 126
GSGGSGSGSG GS                                                       12

SEQ ID NO: 127          moltype = AA  length = 15
FEATURE                 Location/Qualifiers
REGION                  1..15
                        note = linker sequence
source                  1..15
                        mol_type = protein
                        organism = synthetic construct
SEQUENCE: 127
GSGGSGSGSG GSGSG                                                    15

SEQ ID NO: 128          moltype = AA  length = 8
FEATURE                 Location/Qualifiers
REGION                  1..8
                        note = linker sequence
source                  1..8
                        mol_type = protein
                        organism = synthetic construct
SEQUENCE: 128
GGSGGSGS                                                             8
```

```
SEQ ID NO: 129          moltype = AA   length = 8
FEATURE                 Location/Qualifiers
REGION                  1..8
                        note = linker sequence
source                  1..8
                        mol_type = protein
                        organism = synthetic construct
SEQUENCE: 129
GSGGSGSG                                                                    8

SEQ ID NO: 130          moltype = AA   length = 7
FEATURE                 Location/Qualifiers
REGION                  1..7
                        note = linker sequence
source                  1..7
                        mol_type = protein
                        organism = synthetic construct
SEQUENCE: 130
GSGSGSG                                                                     7

SEQ ID NO: 131          moltype = AA   length = 15
FEATURE                 Location/Qualifiers
REGION                  1..15
                        note = linker sequence
source                  1..15
                        mol_type = protein
                        organism = synthetic construct
SEQUENCE: 131
GSGSGSGSGS GSGSG                                                           15

SEQ ID NO: 132          moltype = AA   length = 203
FEATURE                 Location/Qualifiers
REGION                  1..203
                        note = synthetic construct
source                  1..203
                        mol_type = protein
                        organism = synthetic construct
SEQUENCE: 132
MEELFKKHKI VAVLRANSVE EAIEKAVAVF AGGVHLIEIT FTVPDADTVI KALSVLKEKG           60
AIIGAGTVTS VEQARKAVES GAEFIVSPHL DEEISQFAKE KGVFYMPGVM TPTELVKAMK          120
LGHTILKLFP GEVVGPQFVK AMKGPFPNVK FVPTGGVNLD NVAEWFKAGV LAVGVGSALV          180
KGTPDEVREK AKAFVEKIRG ATE                                                 203

SEQ ID NO: 133          moltype = AA   length = 19
FEATURE                 Location/Qualifiers
REGION                  1..19
                        note = signal peptide
source                  1..19
                        mol_type = protein
                        organism = synthetic construct
SEQUENCE: 133
MSWKVVIIFS LLITPQHGL                                                       19

SEQ ID NO: 134          moltype = AA   length = 19
FEATURE                 Location/Qualifiers
REGION                  1..19
                        note = signal peptide
source                  1..19
                        mol_type = protein
                        organism = synthetic construct
SEQUENCE: 134
MSWKVMIIIS LLITPQHGL                                                       19

SEQ ID NO: 135          moltype = AA   length = 119
FEATURE                 Location/Qualifiers
REGION                  1..119
                        note = synthetic construct
source                  1..119
                        mol_type = protein
                        organism = synthetic construct
SEQUENCE: 135
NLAEKMYKAG NAMYRKGQYT IAIIAYTLAL LKDPNNAEAW YNLGNAAYKK GEYDEAIEAY           60
QKALELDPNN AEAWYNLGNA YYKQGDYDEA IEYYKKALRL DPRNVDAIEN LIEAEEKQG          119
```

```
SEQ ID NO: 136          moltype = AA  length = 119
FEATURE                 Location/Qualifiers
REGION                  1..119
                        note = synthetic construct
source                  1..119
                        mol_type = protein
                        organism = synthetic construct
SEQUENCE: 136
EEAELAYLLG ELAYKLGEYR IAIRAYRIAL KRDPNNAEAW YNLGNAYYKQ GDYREAIRYY    60
LRALKLDPEN AEAWYNLGNA LYKQGKYDLA IIAYQAALEE DPNNAEAKQN LGNAKQKQG    119

SEQ ID NO: 137          moltype = AA  length = 119
FEATURE                 Location/Qualifiers
REGION                  1..119
                        note = synthetic construct
source                  1..119
                        mol_type = protein
                        organism = synthetic construct
SEQUENCE: 137
NSAEAMYKMG NAAYKQGDYI LAIIAYLLAL EKDPNNAEAW YNLGNAAYKQ GDYDEAIEYY    60
QKALELDPNN AEAWYNLGNA YYKQGDYDEA IEYYEKALEL DPNNAEALKN LLEAIAEQD    119

SEQ ID NO: 138          moltype = AA  length = 187
FEATURE                 Location/Qualifiers
REGION                  1..187
                        note = synthetic construct
source                  1..187
                        mol_type = protein
                        organism = synthetic construct
SEQUENCE: 138
TDPLAVILYI AILKAEKSIA RAKAAEALGK IGDERAVEPL IKALKDEDAL VRAAAADALG    60
QIGDERAVEP LIKALKDEEG LVRASAAIAL GQIGDERAVQ PLIKALTDER DLVRVAAAVA   120
LGRIGDEKAV RPLIIVLKDE EGEVREAAAI ALGSIGGERV RAAMEKLAER GTGFARKVAV   180
NYLETHK                                                             187

SEQ ID NO: 139          moltype = AA  length = 119
FEATURE                 Location/Qualifiers
REGION                  1..119
                        note = synthetic construct
source                  1..119
                        mol_type = protein
                        organism = synthetic construct
SEQUENCE: 139
EEAELAYLLG ELAYKLGEYR IAIRAYRIAL KRDPNNAEAW YNLGNAYYKQ GDYDEAIEYY    60
QKALELDPNN AEAWYNLGNA YYKQGDYDEA IEYYEKALEL DPENLEALQN LLNAMDKQG    119

SEQ ID NO: 140          moltype = AA  length = 279
FEATURE                 Location/Qualifiers
REGION                  1..279
                        note = synthetic construct
source                  1..279
                        mol_type = protein
                        organism = synthetic construct
SEQUENCE: 140
IEEVVAEMID ILAESSKKSI EELARAADNK TTEKAVAEAI EEIARLATAA IQLIEALAKN    60
LASEEFMARA ISAIAELAKK AIEAIYRLAD NHTTDTFMAR AIAAIANLAV TAILAIAALA   120
SNHTTEEFMA RAISAIAELA KKAIEAIYRL ADNHTTEKFM AAAIEAIALL ATLAILAIAL   180
LASNHTTEKF MARAIMAIAI LAAKAIEAIY RLADNHTSPT YIEKAIEAIE KIARKAIKAI   240
EMLAKNITTE EYKEKAKKII DIIRKLAKMA IKKLEDNRT                          279

SEQ ID NO: 141          moltype = AA  length = 153
FEATURE                 Location/Qualifiers
REGION                  1..153
                        note = synthetic construct
source                  1..153
                        mol_type = protein
                        organism = synthetic construct
SEQUENCE: 141
KYDGSKLRIG ILHARWNAEI ILALVLGALK RLQEFGVKRE NIIIETVPGS FELPYGSKLF    60
VEKQKRLGKP LDAIIPIGVL IKGSTMHFEY ICDSTTHQLM KLNFELGIPV IFGVLTCLTD   120
EQAEARAGLI EGKMHNHGED WGAAAVEMAT KFN                                153
```

```
SEQ ID NO: 142        moltype = AA  length = 119
FEATURE               Location/Qualifiers
REGION                1..119
                      note = synthetic construct
source                1..119
                      mol_type = protein
                      organism = synthetic construct
SEQUENCE: 142
EEAELAYLLG ELAYKLGEYR IAIRAYRIAL KRDPNNAEAW YNLGNAYYKQ GRYREAIEYY   60
QKALELDPNN AEAWYNLGNA YYERGEYEEA IEYYRKALRL DPNNADAMQN LLNAKMREE   119

SEQ ID NO: 143        moltype = AA  length = 6
FEATURE               Location/Qualifiers
REGION                1..6
                      note = poly-His tag
source                1..6
                      mol_type = protein
                      organism = synthetic construct
SEQUENCE: 143
HHHHHH                                                              6
```

What is claimed is:

1. A protein-based virus-like particle (VLP), comprising a first component and a second component;
   wherein the first component comprises a first protein, wherein the first protein is a fusion protein comprising a human metapneumovirus (hMPV) F protein ectodomain and a first multimerization domain sharing at least 90% identity to SEQ ID NO: 7; and
   wherein the second component comprises a second protein, the second protein comprising a second multimerization domain sharing at least 90% identity to SEQ ID NO: 8.

2. The VLP of claim 1, wherein the hMPV F protein ectodomain is in a prefusion state.

3. The VLP of claim 1, wherein the hMPV F protein ectodomain comprises, relative to SEQ ID NO: 56:
   a. the substitutions Q100R and S101R;
   b. the substitutions A185P, Q100R, and S101R;
   c. the substitutions A185P, T127C, N153C, Q100R, and S101R;
   d. the substitutions V84C, A140C, A147C, A249C, N97G, P98G, R99G, Q100G, S101G, and R102G;
   e. the substitutions A63C, A140C, A147C, K188C, K450C, S470C, N97G, P98G, R99G, Q100G, S101G, and R102G;
   f. the substitutions and deletion A63C, A140C, A147C, K188C, G106 deletion, N97G, P98G, R99G, Q100G, S101G, and R102G;
   g. the substitutions A113C, A120C, A339C, Q426C, T160F, I177L, Q100K, and S101A;
   h. the substitutions V84C, A140C, A147C, A249C, Q100R, and S101R;
   i. the substitutions A63C, A140C, A147C, K188C, K450C, S470C, Q100R, and S101R;
   j. the substitutions and deletion A63C, A140C, A147C, K188C, G106 deletion, Q100R, and S101R;
   k. substitutions A113C, A120C, A339C, Q426C, T160F, I177L, Q100R, and S101R;
   l. substitutions A185P, A113C, A339C, Q100R, and S101R;
   m. substitutions A185P, T160F, I177L, Q100R, and S101R;
   n. substitutions A185P, A113C, A339C, T160F, I177L, Q100R, and S101R;
   o. substitutions A63C, K188C, N97G, P98G, R99G, Q100G, S101G, and R102G;
   p. substitutions A63C, K188C, K450A, S470A, N97G, P98G, R99G, Q100G, S101G, and R102G;
   q. substitutions A63C, A140C, A147C, K188C, G294E, N97G, P98G, R99G, Q100G, S101G, and R102G;
   r. substitutions A63C, A140C, A147C, K188C, K450C, S470C, N97G, P98G, R99G, Q100G, S101G, R102G, and G294E;
   s. substitutions A63C, K188C, N97G, P98G, R99G, Q100G, S101G, R102G, and G294E;
   t. substitutions T127C, N153C, T365C, V463C, A185P, L219K, V231I, G294E, H368N, Q100R, and S101R;
   u. substitutions V84C, A140C, A147C, A249C, N97G, P98G, R99G, Q100G, S101G, and R102G; or
   v. substitutions T127C, N153C, T365C, V463C, A185P, L219K, V231I, G294E, N97G, P98G, R99G, Q100G, S101G, H368N, and R102G.

4. The VLP of claim 1, wherein the hMPV F protein ectodomain comprises, relative to SEQ ID NO: 56, the substitutions A63C, A140C, A147C, K188C, K450C, S470C, N97G, P98G, R99G, Q100G, S101G, and R102G.

5. The VLP of claim 1, wherein the hMPV F protein ectodomain comprises, relative to SEQ ID NO: 56, the substitutions and deletion A63C, A140C, A147C, K188C, N97G, P98G, R99G, Q100G, S101G, and R102G; and wherein the hMPV F protein ectodomain comprises a polypeptide sequence at least 90% identical to residues 472-488 of SEQ ID NO: 56.

6. The VLP of claim 1, wherein the hMPV F protein ectodomain comprises, relative to SEQ ID NO: 56, substitutions A63C, A140C, A147C, K188C, K450C, S470C, N97G, P98G, R99G, Q100G, S101G, R102G, and G294E.

7. The VLP of claim 1, wherein the hMPV F protein ectodomain comprises, relative to SEQ ID NO: 56, substitutions T127C, N153C, T365C, V463C, A185P, L219K, V231I, G294E, H368N, Q100R, and S101R.

8. The VLP of claim 1, wherein the hMPV F protein ectodomain comprises, relative to SEQ ID NO: 56, substitutions T127C, N153C, T365C, V463C, A185P, L219K, V231I, G294E, N97G, P98G, R99G, Q100G, S101G, H368N, and R102G.

9. The VLP of claim 1, wherein the hMPV F protein ectodomain comprises, relative to SEQ ID NO: 56, the substitutions A63C, A140C, A147C, K188C, K450C, and S470C.

10. The VLP of claim 1, wherein the hMPV F protein ectodomain comprises, relative to SEQ ID NO: 56, substitutions T127C, N153C, T365C, V463C, A185P, L219K, V231I, G294E, Q100R, and S101R.

11. The VLP of claim 1, wherein the hMPV F protein ectodomain comprises, relative to SEQ ID NO: 56, substitutions T127C, N153C, T365C, V463C, A185P, L219K, V231I, and G294E.

12. The VLP of claim 1, wherein the hMPV F protein ectodomain comprises a polypeptide sequence according to SEQ ID NO: 65.

13. The VLP of claim 1, wherein the hMPV F protein ectodomain comprises a polypeptide sequence according to SEQ ID NO: 89.

14. The VLP of claim 1, wherein the first multimerization domain comprises a polypeptide sequence according to SEQ ID NO: 7.

15. The VLP of claim 1, wherein the first multimerization domain comprises the amino acid substitutions C74A and C98A and the amino acid substitutions C163A and C201A relative to SEQ ID NO: 7.

16. The VLP of claim 15, wherein the first multimerization domain comprises a polypeptide sequence identical to SEQ ID NO: 132.

17. The VLP of claim 1, wherein the (hMPV) F protein ectodomain and the first multimerization domain are joined by a linker sequence comprising GSGGSGSGSGGS (SEQ ID NO: 126).

18. The VLP of claim 1, wherein the fusion protein comprises a polypeptide sequence at least 99% identical to a reference sequence according to SEQ ID NO: 99 without the N-terminal signal peptide MSWKVVIIFSLLITPQHGL (SEQ ID NO: 133) and without the C-terminal HHHHHH (SEQ ID NO: 143).

19. The VLP of claim 1, wherein the fusion protein comprises a polypeptide sequence at least 99% identical to a reference sequence according to SEQ ID NO: 117 without the N-terminal signal peptide MSWKVVIIFSLLITPQHGL (SEQ ID NO: 133) and without the C-terminal HHHHHH (SEQ ID NO: 143).

20. The VLP of claim 1, wherein the fusion protein comprises a polypeptide sequence at least 99% identical to a reference sequence according to SEQ ID NO: 123 without the N-terminal signal peptide MSWKVVIIFSLLITPQHGL (SEQ ID NO: 133) and without the C-terminal HHHHHH (SEQ ID NO: 143).

21. The VLP of claim 18, wherein the second protein comprises a polypeptide sequence according to SEQ ID NO: 8.

22. The VLP of claim 19, wherein the second protein comprises a polypeptide sequence according to SEQ ID NO: 8.

23. The VLP of claim 20, wherein the second protein comprises a polypeptide sequence according to SEQ ID NO: 8.

24. The VLP of claim 18, wherein the second protein comprises a polypeptide sequence according to SEQ ID NO: 34.

25. The VLP of claim 19, wherein the second protein comprises a polypeptide sequence according to SEQ ID NO: 34.

26. The VLP of claim 20, wherein the second protein comprises a polypeptide sequence according to SEQ ID NO: 34.

27. The VLP of claim 1, wherein the hMPV F protein ectodomain binds an antibody that preferentially binds the prefusion form of the hMPV F protein ectodomain.

28. The VLP of claim 1, wherein the first component is a trimeric assembly of the first protein and the second component is a pentameric assembly of the second protein, and wherein the VLP comprises 20 copies of the trimeric assembly and 12 copies of the pentameric assembly.

29. A polynucleotide encoding a protein-based virus-like particle (VLP), comprising a first component and a second component;
wherein the first component comprises a first protein, wherein the first protein is a fusion protein comprising a human metapneumovirus (hMPV) F protein ectodomain and a first multimerization domain sharing at least 90% identity to SEQ ID NO: 7; and
wherein the second component comprises a second protein, the second protein comprising a second multimerization domain sharing at least 90% identity to SEQ ID NO: 8.

30. A method of immunizing a subject against infection by human metapneumovirus, the method comprising administering a protein-based virus-like particle (VLP), comprising a first component and a second component;
wherein the first component comprises a first protein, wherein the first protein is a fusion protein comprising a human metapneumovirus (hMPV) F protein ectodomain and a first multimerization domain sharing at least 90% identity to SEQ ID NO: 7; and
wherein the second component comprises a second protein, the second protein comprising a second multimerization domain sharing at least 90% identity to SEQ ID NO: 8.

* * * * *